US010898565B2

(12) United States Patent
Livengood et al.

(10) Patent No.: US 10,898,565 B2
(45) **Date of Patent: *Jan. 26, 2021**

(54) COMPOSITIONS, METHODS AND USES FOR DENGUE VIRUS SEROTYPE-4 CONSTRUCTS

(71) Applicants: Takeda Vaccines, Inc, Cambridge, MA (US); THE UNITED STATES OF AMERICA AS REPRESENTED BY THE SECRETARY OF THE DEPT OF HEALTH AND HUMAN SERVICES, Atlanta, GA (US)

(72) Inventors: Jill A. Livengood, Fort Collins, CO (US); Claire Kinney, Fort Collins, CO (US); Timothy D. Powell, Fort Collins, CO (US); Dan T. Stinchcomb, Fort Collins, CO (US); Jorge Osorio, Mount Horeb, WI (US)

(73) Assignees: Takeda Vaccines, Inc., Cambridge, MA (US); The United States of America as Represented by the Secretary of the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/996,275

(22) Filed: Jun. 1, 2018

(65) Prior Publication Data

US 2019/0151433 A1 May 23, 2019

Related U.S. Application Data

(60) Continuation of application No. 15/195,820, filed on Jun. 28, 2016, now Pat. No. 10,052,374, which is a division of application No. 14/076,034, filed on Nov. 8, 2013, now Pat. No. 9,408,901.

(60) Provisional application No. 61/788,536, filed on Mar. 15, 2013, provisional application No. 61/724,190, filed on Nov. 8, 2012.

(51) Int. Cl.

| | |
|---|---|
| ***A61K 39/12*** | (2006.01) |
| ***C12N 7/00*** | (2006.01) |
| *A61K 39/00* | (2006.01) |

(52) U.S. Cl.

CPC ................ *A61K 39/12* (2013.01); *C12N 7/00* (2013.01); *A61K 2039/5254* (2013.01); *A61K 2039/5256* (2013.01); *A61K 2039/53* (2013.01); *A61K 2039/575* (2013.01); *A61K 2039/70* (2013.01); *C12N 2770/24121* (2013.01); *C12N 2770/24122* (2013.01); *C12N 2770/24134* (2013.01); *C12N 2770/24171* (2013.01); *Y02A 50/30* (2018.01)

(58) Field of Classification Search

None

See application file for complete search history.

(56) References Cited

U.S. PATENT DOCUMENTS

| | | | | |
|---|---|---|---|---|
| 9,408,901 | B2 * | 8/2016 | Livengood | C12N 7/00 |
| 10,052,374 | B2 * | 8/2018 | Livengood | A61K 39/12 |

FOREIGN PATENT DOCUMENTS

| | | | |
|---|---|---|---|
| WO | WO 01/60847 | A2 * | 8/2001 |

* cited by examiner

*Primary Examiner* — Stacy B Chen

(74) *Attorney, Agent, or Firm* — Nath, Goldberg & Meyer; Joshua B. Goldberg; Scott H. Blackman

(57) ABSTRACT

Embodiments herein report compositions, methods and uses for dengue-4 (DENV-4) virus constructs. Some embodiments concern a composition that includes, but is not limited to, DENV-4 virus constructs alone or in combination with other constructs, can be used in a vaccine composition to induce an immune response in a subject. In certain embodiments, compositions can include constructs of more than one serotypes of dengue virus, such as dengue-1 virus, dengue-2 virus, or dengue-3 virus in combination with DENV-4 virus constructs disclosed herein. In other embodiments, DENV-4 constructs disclosed herein can be combined in a composition with other flavivirus constructs to generate a vaccine against more than one flavivirus. Other embodiments provide methods and uses for DENV-4 virus constructs in vaccine compositions that when administered to a subject induce an immune response in the subject against DENV-4 that is improved by modified constructs compared to other vaccine compositions.

17 Claims, 23 Drawing Sheets

Specification includes a Sequence Listing.

| | ATTENUATED IN VITRO | REPLICATION IN MOSQUITO CELLS | SAFE/nABS IN MICE | SAFE/nABS IN PRIMATES |
|---|---|---|---|---|
| DENVax-1 | + | - | +/+ | +/+ |
| DENVax-3 | + | - | +/+ | +/+ |
| DENVax-4 | + | - | +/+ | +/+ |

Fig. 2

| Group | Schedule | Formulation |
|---|---|---|
| Group 1 | Prime 2 doses (0,0) | 1) High Dose DENVax [2e4, 5e4, 1e5, 3e5] |
| Group 2 | Prime 2 doses (0,0) | 2) High Dose w/$2^{nd}$ Gen. DEN-r (4b-P10) [2e4, 5e4, 1e5, 3e5] |

| | DENVax-4 | DENVax-4b | DENVax-4e | DENVax-4f | DENVax-4g | DENVax-4h | DENVax-4i | DENVax-4j | DENVax-4k |
|---|---|---|---|---|---|---|---|---|---|
| P1 | YES | YES | YES | YES | YES | YES | YES | YES | NO |
| PHENO-TYPE | | | LYTIC | | | LYTIC | LYTIC | | |
| IFU SIZE | 2mm | | 3mm | | | 3mm | 1mm | 2mm | |
| PEAK TITER IN VERO CELLS | 10E7 | | TBD | NACENT | NACENT | NACENT | NACENT | NACENT | |
| GROWTH IN C6/36 | NO | NO | NACENT | NACENT | NACENT | NACENT | NACENT | NACENT | |

Genetic variations among D2/4 chimeras (compared to wt D2 16681 and D4-1036)

| Genome | D2 | | | junction | D4 | | | |
|---|---|---|---|---|---|---|---|---|
| Genes | NCR | C | | prM | E | | | |
| Mutation types* | **PDK-53** | seed | Eng | MluI | seed | Marker | Eng | Eng |
| Genome NT position | C57T | A225T | A396C | A453G | C647G/C | A1401G | C2027T | A2275C |
| Protein-AA position | NCR | C-silent | C-R100S | prM-silent | prM-T79R/T | E-silent | E-A364V | E-M447L |
| D2-16681 | C | A | A (R) | A | | | | |
| D2-PDK-53 | **T** | - | - | | | | | |
| D4-1036 | | | | | G (T) | A | C (A) | A (M) |
| DENVax-4F: D24-VR2 | **T** | - | C (S) | g | G/C (R/T) | g | T (V) | C (L) |
| DENVax-4G: D24-VR5 | **Rev-C** | - | C (S) | g | - | g | T (V) | C (L) |
| DENVax-4J: D24-VR5 | **Rev-C** | - | C (S) | g | - | g | T (V) | C (L) |

| junction | D2 | | | | | | | | | | | |
|---|---|---|---|---|---|---|---|---|---|---|---|---|
| | NS1 | NS2A | | | NS3 | | | NS4A | | NS4B | NS5 | |
| NgoMIV | **PDK-53** | seed | seed | **PDK-53** | **PDK-53** | seed | **PDK-53** | seed | **PDK-53** | seed | **PDK-53** | seed |
| TG2380/1CC | G2579A | A3674G | A3773A/G | C4018T | A5270T | C5391T | T5547C | C6437T | G6599C | T7026C/T | C8571T* | A9750C |
| E-V482A | NS1-G53D | NS2A-D66G | NS2A-K99K/R | NS2A-L181F | NS3-E250V | NS3-siler | NS3-sile | NS4A-A21V | NS4A-G75A | NS4B-silent | NS5-silei | NS5-silent |
| TG (V) | G (G) | A (D) | A (K) | C (L) | A (E) | C | T | C (A) | G (G) | T | C | A |
| | **A (D)** | - | - | **T (F)** | T (V) | - | **c** | - | **C (A)** | - | **t** | - |
| CC (A) | **A (D)** | - | - | **Rev-C (L)** | T (V) | - | **c** | - | **Rev-G** | - | - | - |
| CC (A) | **A (D)** | - | - | **Rev-C (L)** | T (V) | - | **c** | - | **Rev-G** | - | - | - |
| CC (A) | **A (D)** | - | - | **T (F)** | T (V) | - | **c** | - | **C (A)** | - | - | - |

"-": same as wt D2 16681 or D4 1036; small nt letter: silent mutation in open reading region
*:PDK-53: D2-PDK-53 specific genotype (vs 16681), Red: major attenuation PDK-53 loci; Seed: mutations found only in specified virus seed and not in the original clone;
Eng: Engineered mutations for the D2/4 clones; Mlu and NgoMV: D2/4 junction engineered RE sites;
**: C8571T (PDK-53 silent mutation) was not included in most D2/4 chimeric clones
Rev: Engineered reversion back to wt nucleotide

Fig. 11

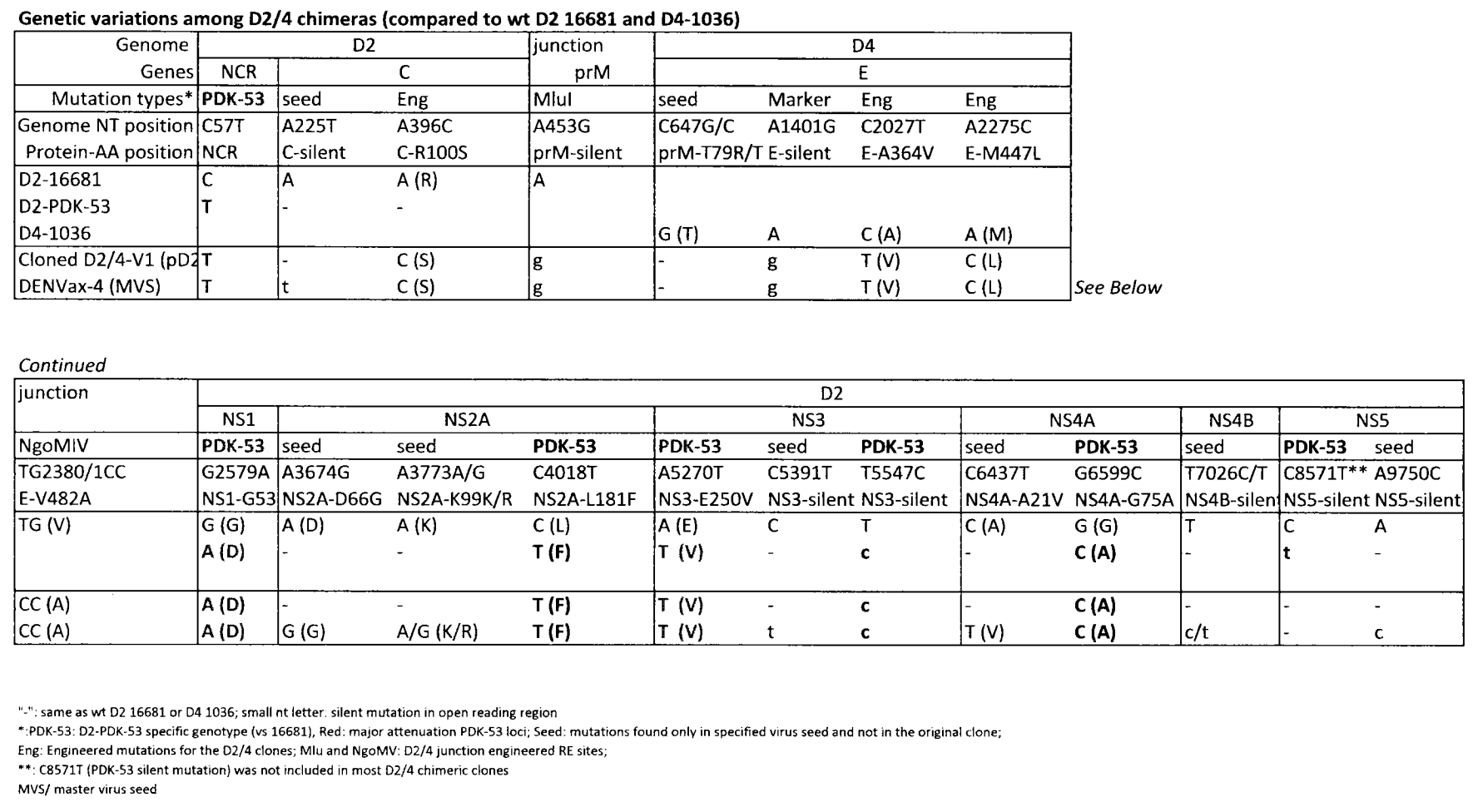

Genetic variations among D2/4 chimeras (compared to wt D2 16681 and D4-1036)

| Genome | D2 | | | junction | D4 | | | |
|---|---|---|---|---|---|---|---|---|
| Genes | NCR | C | | prM | E | | | |
| Mutation types* | **PDK-53** | seed | Eng | MluI | seed | Marker | Eng | Eng |
| Genome NT position | C57T | A225T | A396C | A453G | C647G/C | A1401G | C2027T | A2275C |
| Protein-AA position | NCR | C-silent | C-R100S | prM-silent | prM-T79R/T | E-silent | E-A364V | E-M447L |
| D2-16681 | C | A | A (R) | A | | | | |
| D2-PDK-53 | **T** | - | - | | | | | |
| D4-1036 | | | | | G (T) | A | C (A) | A (M) |
| Cloned D2/4-V1 (pD2 | **T** | - | C (S) | g | - | g | T (V) | C (L) |
| DENVax-4 (MVS) | T | t | C (S) | g | - | g | T (V) | C (L) |

*See Below*

*Continued*

| junction | D2 | | | | | | | | | | | |
|---|---|---|---|---|---|---|---|---|---|---|---|---|
| | NS1 | NS2A | | | NS3 | | | NS4A | | NS4B | NS5 | |
| NgoMIV | **PDK-53** | seed | seed | **PDK-53** | **PDK-53** | seed | **PDK-53** | seed | **PDK-53** | seed | **PDK-53** | seed |
| TG2380/1CC | G2579A | A3674G | A3773A/G | C4018T | A5270T | C5391T | T5547C | C6437T | G6599C | T7026C/T | C8571T** | A9750C |
| E-V482A | NS1-G53 | NS2A-D66G | NS2A-K99K/R | NS2A-L181F | NS3-E250V | NS3-silent | NS3-silent | NS4A-A21V | NS4A-G75A | NS4B-silen | NS5-silent | NS5-silent |
| TG (V) | G (G) | A (D) | A (K) | C (L) | A (E) | C | T | C (A) | G (G) | T | C | A |
| | **A (D)** | - | - | **T (F)** | **T (V)** | - | **c** | - | **C (A)** | - | **t** | - |
| CC (A) | **A (D)** | - | - | **T (F)** | **T (V)** | - | **c** | - | **C (A)** | - | - | - |
| CC (A) | **A (D)** | G (G) | A/G (K/R) | **T (F)** | **T (V)** | t | **c** | T (V) | **C (A)** | c/t | - | c |

"-": same as wt D2 16681 or D4 1036; small nt letter: silent mutation in open reading region

*:PDK-53: D2-PDK-53 specific genotype (vs 16681), Red: major attenuation PDK-53 loci; Seed: mutations found only in specified virus seed and not in the original clone;

Eng: Engineered mutations for the D2/4 clones; Mlu and NgoMV: D2/4 junction engineered RE sites;

**: C8571T (PDK-53 silent mutation) was not included in most D2/4 chimeric clones MVS/ master virus seed

- DEN-2 PDK53
- 9 attenuating mutations
  - 3 silent
  - 6 amino acid changes
    - 5 in PDK-53 backbone

- 5' NC C to T
- NS1-53 Gly-to-Asp
- NS3-250 Glu-to-Val

- *NS2A-181 Leu-to-Phe*
- *NS4A-75 Gly-to-Ala*

Fig. 13

Cloning of DENVax-4e, DENVax-4h, and DENVax-4i

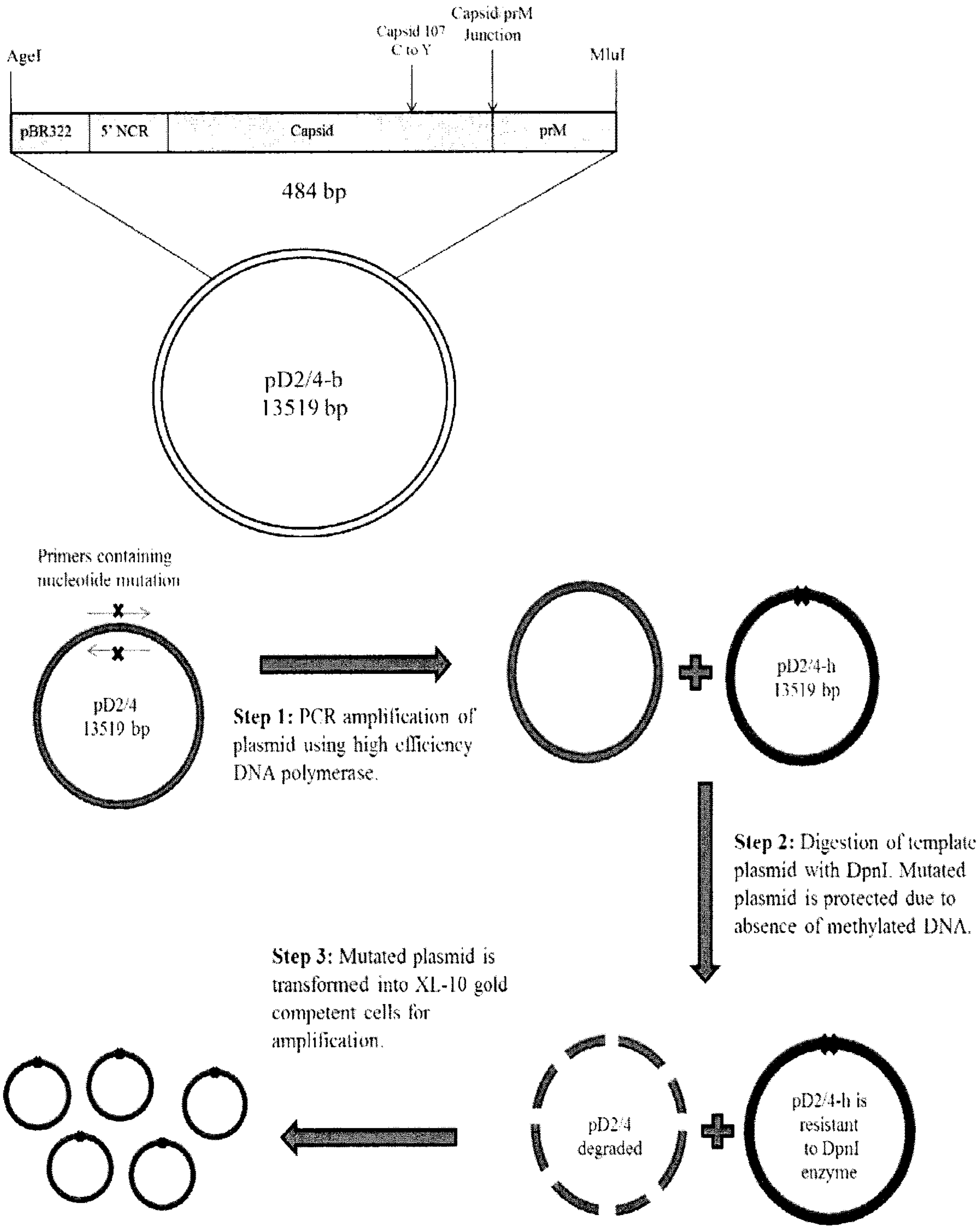

Fig. 13     Cloning of DENVax-4e, DENVax-4h, and DENVax-4i

AgeI     Capsid 107 C to Y     Capsid prM Junction     MluI

| pBR322 | 5' NCR | Capsid | prM |

484 bp pD2/4-h
13519 bp

Primers containing nucleotide mutation pD2/4
13519 bp

Step 1: PCR amplification of plasmid using high efficiency DNA polymerase.

pD2/4-h
13519 bp

Step 2: Digestion of template plasmid with DpnI. Mutated plasmid is protected due to absence of methylated DNA.

Step 3: Mutated plasmid is transformed into XL-10 gold competent cells for amplification.

pD2/4 degraded pD2/4-h is resistant to DpnI enzyme

COMPOSITIONS, METHODS AND USES FOR DENGUE VIRUS SEROTYPE-4 CONSTRUCTS

PRIORITY CLAIM

This application is a continuation of U.S. patent application Ser. No. 15/195,820, filed Jun. 28, 2016, now allowed, which is a divisional of U.S. patent application Ser. No. 14/076,034, filed Nov. 8, 2013, which issued on Aug. 9, 2016, as U.S. Pat. No. 9,408,901, which claims priority to U.S. Provisional Application No. 61/724,190 filed Nov. 8, 2012, and U.S. Provisional Application No. 61/788,536 filed Mar. 15, 2013. These applications are incorporated herein by reference in their entirety for all purposes.

FEDERALLY FUNDED RESEARCH

This invention was made with government support under grant number R43 AI084291 awarded by the National Institutes of Health. The government has certain rights in this invention.

FIELD

Embodiments herein report compositions, methods and uses for dengue-virus 4 (DENV-4) constructs. Some embodiments concern a composition that includes, but is not limited to, DENV-4 virus constructs that alone or in combination with other agents can be used in a vaccine composition. In certain embodiments, compositions can include chimera constructs of more than one serotypes of dengue virus, such as dengue-1 (DEN-1) virus, dengue-2 (DEN-2) virus, or dengue-3 (DEN-3) virus in combination with DENV-4 virus chimera constructs in di-, tri or tetravalent formulations. In other embodiments, DENV-4 chimera constructs (dengue-dengue chimeras) disclosed herein can be combined with other flavivirus constructs. Certain embodiments include DENV-4 chimeric constructs having components of other dengue serotypes, such as structural elements. Other embodiments provide methods and uses for DENV-4 virus chimera constructs in vaccine compositions that when administered to a subject induces an immune response in the subject against DENV-4 that is improved compared to other constructs.

BACKGROUND

Infection with dengue virus can lead to a painful fever of varying severity. To date, five serotypes of dengue virus have been identified: dengue-1 (DEN-1), dengue-2 (DEN-2), or dengue-3 (DEN-3), dengue-4 (DENV-4) and dengue-5 (DEN-5). Dengue fever is caused by infection of a dengue virus. Dengue virus serotypes 1-4 can also cause dengue hemorrhagic fever (DHF), and dengue shock syndrome (DSS). The most severe consequences of infection, DHF and DSS, can be life threatening. Dengue viruses cause 50-100 million cases of debilitating dengue fever, 500,000 cases of DHF/DSS, and more than 20,000 deaths each year. To date, there is no effective vaccine to protect against dengue fever and no drug treatment for the disease. Mosquito control efforts have been ineffective in preventing dengue outbreaks in endemic areas or in preventing further geographic spread of the disease. It is estimated that 3.5 billion people are threatened by infection with dengue virus. In addition, dengue virus is a leading cause of fever in travelers to endemic areas, such as Asia, Central and South America, and the Caribbean.

All four dengue virus serotypes are endemic throughout the tropical and subtropical regions of the world and constitute the most significant mosquito-borne viral threat to humans worldwide. Dengue viruses are transmitted to humans primarily by *Aedes aegypti* mosquitoes. Infection with one dengue virus serotype results in life-long protection from re-infection by that serotype, but does not prevent secondary infection by one of the other three dengue virus serotypes. In fact, previous infection with one dengue virus serotype can lead to an increased risk of severe disease (DHF/DSS) upon secondary infection with a different serotype. The development of an effective vaccine represents an important approach to the prevention and control of this global emerging disease.

SUMMARY

Embodiments herein concern compositions, methods and uses of DENV chimera constructs, for example DENV-4. In some embodiments, a composition can include DENV-4 virus chimera constructs alone or in combination with other dengue virus serotype constructs or live, attenuated dengue viruses of the same or other serotypes or other flavivirus constructs capable of inducing an immune response to a target virus (e.g. dengue virus). Other embodiments can include a composition of a live, attenuated virus construct against DENV-4 and optionally, one or more live, attenuated viral constructs against DEN-1, DEN-2 and DEN-3. In other embodiments, an immunogenic composition is provided that includes a DENV-4 live, attenuated chimeric virus construct with strong immunogenicity when introduced to a subject. In accordance with these embodiments, these live, attenuated viral constructs can be used alone or in combination with one or more other DEN-1, DEN-2 and DEN-3 constructs, and a pharmaceutically acceptable excipient to generate a vaccine formulation against dengue virus serotypes. In certain embodiments, monovalent, bivalent, trivalent or tetravalent pharmaceutically effective formulations against one or more dengue viruses are generated. In certain embodiments, an immunogenic composition can include one or more of DEN-1, DEN-2, DEN-3 dengue-dengue chimeric constructs in combination with a chimeric DENV-4 construct disclosed herein.

In certain embodiments, an immunogenic composition including a DENV-4 construct of the present invention in combination with one or more of DEN-1, DEN-2 and DEN-3 can be used to confer simultaneous protection against two or more dengue virus serotypes in a single vaccine administration. In other embodiments, an immunogenic composition including DEN-1, DEN-2, DEN-3 and modified or mutated DENV-4 constructs of embodiments disclosed herein can be administered to a subject to induce improved immunogenic responses against each dengue virus serotype and where immune response interference to DENV-4 is reduced.

In certain embodiments, DENV-4 constructs can include a dengue-dengue chimeric construct having adaptive mutations in the structural or non-structural regions of DENV-4. In other embodiments, DENV-4 constructs can include a backbone of another dengue virus serotype, DEN-1, DEN-2 or DEN-3. In yet other embodiments, a chimeric construct can include a DEN-2 backbone where DENV-4 structural or non-structural regions of DENV-4 are substituted for DEN-2 structural or non-structural regions. In accordance with these embodiments, a DEN-2 backbone can include any live attenuated DEN-2 virus. In other embodiments, a DEN-2 backbone can include live attenuated DEN-2 PDK-53 virus as a backbone where the live attenuated DEN-2 PDK virus further includes structural proteins of one or more of prM (premembrane) and E (envelope) structural proteins of DENV-4. In addition, a DEN-2 PDK-53 backbone can include additional mutations or reversions of mutations of DEN-2 PDK-53 generating a novel construct in order to enhance in vitro growth, or in vivo the immune response to DENV-4 in a subject upon administration.

In some embodiments, a current dengue chimeric construct denoted as DENVax-4 strain (SEQ ID NO:21) was modified to contain a capsid/PrM junction of the DEN-2 backbone to be more genetically similar to that of DENV-4 instead of DEN-2 in order to improve replication efficiency of the virus both in vitro for production and in vivo as a construct of use for inducing an immune response to DENV-4. The current strain of DENV-4, DENVax-4, has a capsid/PrM sequence that is identical to DEN-2 instead of DEN-4, possibly creating an inefficient transcription and translation from the genomic RNA, which is different than that of wild type DENV-4.

In some embodiments, structural protein genes can include prM and E genes of DENV-4 on another dengue virus backbone (e.g. dengue-2, DEN-2 PDK-53), making a dengue-dengue chimera. For example, a DENV-4 construct, in certain embodiments can include those construct termed DENVax-4e (Capsid 107 Cysteine to Tyrosine; DenVax-4b backbone, modifications at Capsid/prM junction), DENVax-4f (where the PDK-53 backbone NS2A and NS4A mutations are reverted to that of 16681) or DENVax-4h (Envelope 417 Glu to Lys) (see for example FIG. 4) where for certain constructs the DEN-2 PDK-53 backbone has one or more reversions to wild-type DEN-2 (e.g. in the non-coding region (NCR) or a non-structural region (NS2 etc.)) and one or more mutations in the DENV-4 structural region (e.g. prM or E), while encoding one or more structural proteins of DENV-4 (e.g. strain 1036). A modified DENV-4 construct disclosed herein can include a modified attenuated DEN-2 PDK-53 backbone, having one or more modified structural proteins of DENV-4 strain 1036. In some embodiments, one or more mutations present in live, attenuated DEN-2 PDK-53 virus can be reverted back to a wildtype nucleic acid (which may be a silent mutation) or another nucleic acid to produce constructs herein that generate a modified DEN-2/DENV-4 construct having increased replication ability and immunogenicity without affecting its attenuation or safety but may affect growth and/or replication of the DEN-4 virus. In certain embodiment, the reversions may lead to increased growth and/or replication.

In other embodiments, a modified DENV-4 construct can incorporate mutations introduced to one or more structural regions and/or non-structural regions of DENV-4 in order to generate constructs inducing an improved immunological response while maintaining safety and viral attenuation. For example, a modified or mutated dengue-dengue chimera of DEN-2/DENV-4 may contain mutations at one or more non-structural regions of a DEN-2 PDK-53 backbone, such as NS2A, and NS4A, and/or mutations at 5' non-coding region (5'NCR). In another embodiment, a modified DENV-4 chimera construct can include NS2A and NS4A of DEN-2 16681 by reverting mutations at NS2A and NS4A of PDK-53 (e.g. an M-L substitution at NS4A). Some embodiments include a modified DENV-4 chimera construct having 5'NCR, NS2A and NS4A of DEN-2 16681 by reverting corresponding mutations in the DEN-2 PDK-53 backbone of a target construct. Other embodiments can include a modified DENV-4 chimera construct having 5'NCR of DEN-2 16681 by reverting corresponding mutations in the DEN-2 PDK-53 backbone. A modified DEN-4 chimera construct can also include DEN-2 PDK-53 backbone, and encode one or more structural proteins of DEN-4 strain H241. It is contemplated that, to induce an immune response, any DEN-4 structural protein can be substituted for structural regions of a chimeric virus containing a dengue-2 serotype backbone (e.g. PDK-53 or modified PDK-53). In some embodiments, a modified DEN-4 construct contains live attenuated DEN-2 PDK-53 as a backbone, and DEN-4 structural proteins where mutations can be introduced to modify structural regions of a DEN-4 (e.g. strain 1036).

In other embodiments, mutations can be introduced to capsid/prM junction amino acid sequences of a DENV virus in order to increase immunogenicity of a construct containing such a mutation. For example, a mutation in DEN-4 can be a Cys-Tyr mutation at capsid position 107 of the DENV-4. In other embodiments, it is contemplated that the cysteine in position 107 can be mutated to any other aromatic amino acid with a hydrophobic side chain (see for example DENV-4e). Other DEN-2 PDK-53 reversion of a chimeric construct can be found in NS2A or NS4A. Yet other embodiments include a DENV-4 construct where a DEN-2 backbone comprises PDK-53 (MVS, SEQ ID NO:21) where amino acid positions 102-107 of the capsid region of PDK-53 are converted to a homologous DENV-4 counterpart amino acid to generate DENV-4b (see for example, FIG. 4). These backbone constructs can then further comprise a cysteine in the capsid region to aromatic amino acid in position (e.g. tyrosine, tryptophan etc). In certain embodiments, this construct is represented by SEQ ID NO:22 or SEQ ID NO:23.

Other DENV-4 constructs disclosed herein can include an amino acid substitution at Envelope position 417. For example, DENV-4 strain 1036 strain sequence or equivalent strain position thereof where a PDK-53 (MVS DEN2/4, SEQ ID NO:21) backbone of Dengue-2 with DENV-4 structural proteins is provided. Embodiments include further mutating Envelope position 417 from a negative to a positively charged side-chain amino acid (e.g. lysine). It is contemplated that any charged side chain will provide increased immunogenicity of the DENV-4 construct without affecting its safety or attenuation. In certain embodiments, this construct is represented by SEQ ID NO:24 or SEQ ID NO:25.

In certain embodiments, DEN-2 PDK-53 reversions of a chimeric DENV construct have the 5' NC, NS1 and NS3 mutations found in DEN-2 PDK-53 MVS while having other reversions or mutations. It has been demonstrated that these three mutations can be important for attenuation (e.g. small plaque size, reduced growth rate, lower titer, increased temperature sensitivity and decreased neurovirulence compared to a control).

In other embodiments, DEN-2 PDK-53 genome backbones can be used to generate chimeric constructs of DEN-1 and DEN-3, where one or more structural protein genes of DEN-2 PDK-53 genome can be replaced by one or more structural protein genes of DEN-1 and DEN-3. These constructs can include a combination of both DEN-1 and DEN-3 in a single chimera having a DEN-2 PDK-53 backbone. In some embodiments, a structural protein can be the C, prM or E protein of DEN-1 and/or DEN-3. In certain embodiments, structural protein genes include the prM and E genes of DEN-1 or DEN-3. These hybrid/chimeric viruses express the surface antigens of DEN-1, DEN-3 or DENV-4 while retaining the attenuation phenotypes of the parent DEN-2. In certain embodiments, these constructs can be represented by SEQ ID NO:15, DEN-2/DEN-1 and SEQ ID NO: 19, DEN-2/DEN-3 where these constructs can be used in di-, tri or tetravalent compositions disclosed herein.

In some embodiment, constructs disclosed herein can include chimeric constructs of DENV-4, DEN-2, DEN-1, and DEN-3 expressing surface antigens of DEN-1, DEN-3 and DENV-4 using attenuated DEN-2 PDK-53 virus as a backbone.

Some embodiments disclose methods for making modified or mutated DENV-4 constructs of use in any vaccine composition including, but not limited to, a single vaccine composition having only DENV-4 constructs, a mixture single vaccine composition capable of inducing an immune response against two or more dengue virus serotypes, a mixture single vaccine composition having chimeric (and non-chimeric) constructs disclosed herein in combination with other flavivirus constructs capable in inducing an immune response to a flavivirus as well as one or more dengue virus serotypes that include DENV-4.

BRIEF DESCRIPTION OF THE DRAWINGS

The following drawings form part of the present specification and are included to further demonstrate certain embodiments. Some embodiments may be better understood by reference to one or more of these drawings alone or in combination with the detailed description of specific embodiments presented.

FIG. 2 is a table that illustrates an exemplary experimental design for analyzing certain vaccines including DENV-4 chimeric constructs of some embodiments disclosed herein in non-human primates.

FIG. 5 is a table illustrating some exemplary data of analysis of plaque phenotypes, Vero cell titers and mosquito growth of some DENV-4 virus constructs of certain embodiments disclosed herein.

FIG. 10 illustrates an alignment of various DENV-4 chimeric constructs, illustrating common sequences and exemplary mutations and/or reversions.

FIG. 11 illustrates an alignment of various DENV-4 chimeric constructs, illustrating common sequences and exemplary mutations and/or reversions.

FIG. 13 illustrates an exemplary schematic of cloning of various DENV-4 constructs disclosed herein.

DEFINITIONS

Figure 1A:
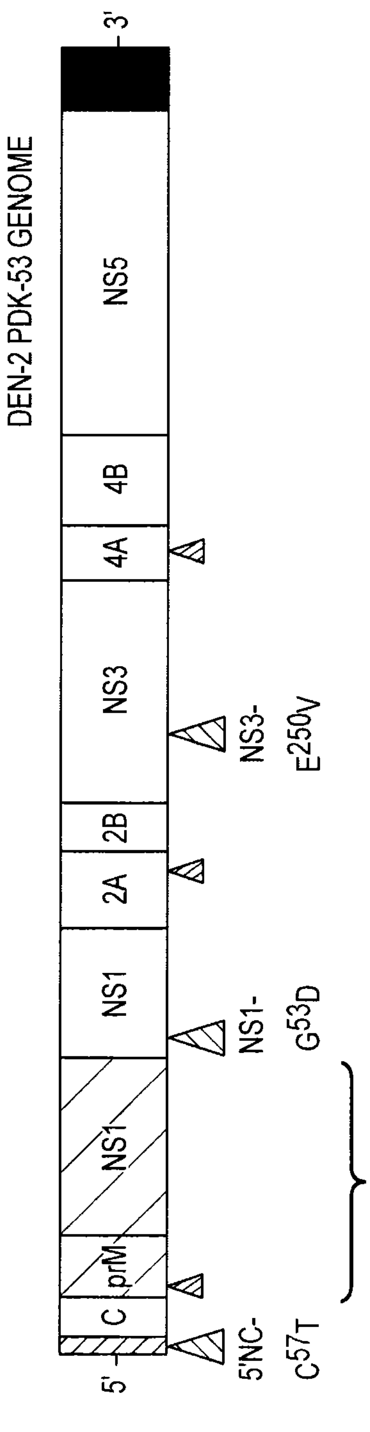
FIGS. 1A-1B illustrates (A) a representative schematic diagram of structural and non-structural genes of DEN-2 PDK-53, and (B) exemplary results of certain chimeric dengue virus constructs of some embodiments disclosed herein expressing structural proteins of different dengue virus serotypes respectively in the DEN-2 PDK-53 backbone.

As used herein, "a" or "an" may mean one or more than one of an item.

As used herein the specification, "subject" or "subjects" may include, but are not limited to, mammals such as humans (e.g. adults and juveniles) or mammals, domesticated or wild, for example dogs, cats, other household pets (e.g. hamster, guinea pig, mouse, rat), ferrets, rabbits, pigs, horses, cattle, prairie dogs, wild rodents, or zoo animals.

As used herein, the terms "chimeric construct," "virus chimera," "chimeric virus," "flavivirus chimera" and "chimeric flavivirus" can mean a construct comprising a portion of the nucleotide sequence of a dengue-2 virus and further nucleotide sequence that is not from dengue-2 virus or is from a different dengue virus serotype or a different flavivirus. A "dengue chimera" comprises at least two different dengue virus serotypes. Examples of other dengue viruses or flaviviruses include, but are not limited to, sequences from dengue-1 virus, dengue-3 virus, dengue-4 virus, West Nile virus, Japanese encephalitis virus, St. Louis encephalitis virus, tick-borne encephalitis virus, yellow fever virus and any combination thereof.

As used herein, "nucleic acid chimera" can mean a construct disclosed herein including nucleic acid sequences comprising a portion of the nucleotide sequence of a dengue-2 virus and further one or more nucleotide sequences are not of the same origin as the nucleotide sequence of the dengue-2 virus. Correspondingly, any chimeric flavivirus, any dengue chimera or flavivirus chimera disclosed herein can be recognized as an example of a nucleic acid chimera.

DESCRIPTION

In the following sections, various exemplary compositions and methods are described in order to detail various embodiments. It will be obvious to one skilled in the art that practicing the various embodiments does not require the employment of all or even some of the specific details outlined herein, but rather that concentrations, times and other specific details may be modified through routine experimentation. In some cases, well-known methods or components have not been included in the description.

In accordance with embodiments of the present invention, there may be employed conventional molecular biology, protein chemistry, microbiology, and recombinant DNA techniques within the skill of the art. Such techniques are explained fully in the literature. See, e.g., Sambrook, Fritsch & Maniatis, Molecular Cloning: A Laboratory Manual, Second Edition 1989, Cold Spring Harbor Laboratory Press, Cold Spring Harbor, N.Y.; Animal Cell Culture, R. I. Freshney, ed., 1986).

Embodiments herein concern compositions, methods and uses for inducing improved immune responses against DENV-4 alone or in combination with one or more agents for inducing immune responses against other dengue virus serotypes or flaviviruses in a subject. In accordance with these embodiments, live, attenuated dengue viruses and nucleic acid chimeras of DENV-4 are generated and used in immunogenic compositions disclosed herein. Some embodiments concern modified or mutated DENV-4 constructs. Some embodiments concern introducing mutations and/or reversions into DENV-4 chimeric constructs to modify the amino acid sequence of the chimeric construct. Some embodiments concern introducing mutations and/or reversions into the DEN-2 PDK-53 backbone constructs to modify the amino acid sequence or RNA sequence of the chimeric construct. In certain embodiments, mutations and/or reversions into DENV-4 chimeric constructs to modify the amino acid sequence of the chimeric construct can include mutations upstream of the C/prM cleavage site of a known chimeric construct referred to as DENVax-4 (SEQ ID NO: 21) by techniques including, but not limited to mutagenesis.

Embodiments herein concern compositions, methods and uses of DENV-4 virus chimera constructs. In some embodiments, a composition can include DENV-4 virus chimera constructs alone or in combination with other dengue virus serotype constructs or live, attenuated dengue viruses of the same or other serotypes or other flavivirus constructs capable of inducing an immune response to a target virus (e.g. dengue virus or other flavivirus). Other embodiments can include a composition of a live, attenuated virus construct against DENV-4 and optionally, one or more live, attenuated viral constructs against DEN-1, DEN-2 and DEN-3. In yet other embodiments, an immunogenic composition is provided that includes a DENV-4 live, attenuated chimeric virus constructs with increased immunogenicity compared to other known constructs when introduced to a subject. In accordance with these embodiments, these live, attenuated viral chimera constructs can be used alone or in combination with one or more other DEN-1, DEN-2 and DEN-3 constructs (e.g. live, attenuated viruses or chimeras), and a pharmaceutically acceptable excipient to generate a vaccine formulation against one or more dengue virus serotypes. In certain embodiments, monovalent, bivalent, trivalent or tetravalent pharmaceutically effective formulations against one or more dengue viruses are generated. In certain embodiments, an immunogenic composition can include one or more of DEN-1, DEN-2, DEN-3 dengue-dengue chimeric constructs or live, attenuated dengue virus in combination with a chimeric DENV-4 construct disclosed herein.

In certain embodiments, an immunogenic composition including a DENV-4 construct of the present invention in combination with one or more of DEN-1, DEN-2 and DEN-3 can be used to confer simultaneous protection against two or more dengue virus serotypes in a single vaccine administration. In other embodiments, an immunogenic composition including DEN-1, DEN-2, DEN-3 and modified or mutated DENV-4 constructs of embodiments disclosed herein can be administered to a subject to induce improved immunogenic responses against each dengue virus serotype and where immune response interference to DENV-4 is reduced.

In certain embodiments, DENV constructs can include a dengue-dengue chimeric construct having adaptive mutations in the structural or non-structural regions of the backbone (PDK-53) or structural regions of DEN-4. In other embodiments, DENV-4 constructs can include a backbone of another dengue virus serotype, DEN-1, DEN-2 or DEN-3. In yet other embodiments, a chimeric construct can include a DEN-2 backbone where DENV-4 structural or non-structural regions of DENV-4 are substituted for DEN-2 structural and/or non-structural regions. In accordance with these embodiments, a DEN-2 backbone can include any live, attenuated DEN-2 virus having safety and efficacy while inducing an immune response to DEN-2. In other embodiments, a DEN-2 backbone can include live, attenuated DEN-2 PDK-53 (53 passages in primary dog kidney cells (PDK)) or derived from DEN-16681 strain virus as a backbone where the live, attenuated DEN-2 PDK-53 virus further includes structural proteins of one or more of prM (premembrane) and E (envelope) structural proteins of DENV-4. In addition, a DEN-2 PDK-53 backbone can include additional mutations or reversions of mutations of DEN-2 PDK-53 in order to enhance the immune response to DENV-4 in a subject upon administration (see for example FIG. 4).

In some embodiments, structural protein genes can include prM and E genes of DENV-4 on another dengue virus backbone, making a dengue-dengue chimera. For example, a DENV-4 construct, in certain embodiments can include those construct termed DENVax-4e, DENVax-4f, or DENVax-4h (see for example FIG. 4) where the DEN-2 PDK-53 backbone has one or more reversions to wild-type DEN-2 amino acids (e.g. in the non-coding region (NCR) or a non-structural region (NS1 etc.)) and one or more mutations in the DENV-4 structural region (e.g. prM or E), while encoding one or more structural proteins of DENV-4 (e.g. strain 1036). A modified DENV-4 construct disclosed herein can include a modified attenuated DEN-2 PDK-53 backbone, having one or more modified structural regions of DENV-4 strain 1036. In some embodiments, one or more mutations present in live, attenuated DEN-2 PDK-53 virus can be reverted back to a control amino acid or another amino acid to produce constructs herein that generate a modified DEN-2/DENV-4 chimeric construct (when compared to MVS sequence SEQ ID. NO: 21) having increased immunogenicity without affecting its safety or attenuation but may affect in vitro growth and/or replication of the DEN-4 virus. In certain embodiment, the reversions may lead to increased growth and/or replication.

In other embodiments, a modified DENV-4 construct can incorporate mutations introduced to one or more structural regions and/or non-structural regions of DENV-4 in order to generate constructs inducing an improved immunological response while maintaining safety and viral attenuation. For example, a modified or mutated dengue-dengue chimera of DEN-2/DENV-4 may contain mutations at one or more non-structural regions of a DEN-2 PDK-53 backbone, such as NS2A, and NS4A, and/or mutations at 5' non-coding region (5'NCR). In another embodiment, a modified DENV-4 chimera construct can include NS2A and NS4A of DEN-2 16681 by reverting mutations at NS2A and NS4A of PDK-53 (e.g. an M-L substitution at NS4A). Some embodiments include a modified DENV-4 chimera construct having 5'NCR, NS2A and NS4A of DEN-2 16681 by reverting corresponding mutations in the DEN-2 PDK-53 backbone of a target construct. Other embodiments can include a modified DENV-4 chimera construct having 5'NCR of DEN-2 16681 by reverting corresponding mutations in the DEN-2 PDK-53 backbone. A modified DENV-4 chimera construct can also include DEN-2 PDK-53 backbone, and encode one or more structural proteins of DENV-4 strain H241.

It is contemplated that DENV-4 structural proteins can substitute for structural or non-structural regions of a dengue-2 serotype backbone (e.g. PDK-53 or modified PDK-53 identified herein) In some embodiments, a modified DENV-4 construct contains live attenuated modified DEN-2 PDK-53 as a backbone, and DENV-4 structural proteins where mutations can be introduced to modify structural regions of a DENV-4 (e.g. strain 1036). In some embodiments, mutations can be introduced to capsid/prM junction amino acid sequences of DENV-4 in order to increase replication and/or immunogenicity of a construct containing such a mutation. For example, a mutation in DENV-4 can be a C-Y mutation at capsid position 107 of the DENV-4 (see for example, DENVax-4e). In accordance with these embodiments, a cysteine can be mutated to an aromatic amino acid (e.g. tyrosine or other) on a modified PDK-53 backbone (DENV-4b). Other mutations can include an amino acid substitution at Envelope position 417 (glutamic acid, E) in a DENV-4 1036 strain sequence (see for example, DENVax-4h) or equivalent position thereof in another DENV-4, where a negative amino acid is replaced by a positive amino acid with a charged side chain (e.g. lysine, arginine, histidine etc.). Other DEN-2 PDK-53 reversion of a chimeric construct can be found in the NS2A or NS4A regions.

In other embodiments, DEN-2 PDK-53 genome backbones can be used to generate chimeric dengue virus constructs of DEN-1 and DEN-3, where one or more structural or non-structural protein genes of DEN-2 PDK-53 genome can be replaced by one or more structural protein or non-structural genes of DEN-1 and DEN-3. These constructs can include a combination of both DEN-1 and DEN-3 structural or non-structural genes in a single chimera having a DEN-2 PDK-53 backbone. In some embodiments, a structural protein can be the C, prM or E protein of DEN-1 and/or DEN-3. In certain embodiments, structural protein genes include the prM and E genes of DEN-1 or DEN-3 or a combination thereof. These hybrid/chimeric viruses can express surface antigens of DEN-1, DEN-3 or DENV-4 while retaining the attenuation phenotypes of the parent DEN-2.

In some embodiment, constructs disclosed herein can include chimeric constructs of DENV-4, DEN-2, DEN-1, and DEN-3 expressing surface antigens of DEN-1, DEN-3 and DENV-4 using attenuated DEN-2 PDK-53 or live, attenuated DEN-2 16681 virus (or a dengue-2 virus with one or more reversion of any of the mutations found in dengue-2 serotype PDK-53 back to its wildtype 16681 virus) as a backbone. In addition, constructs that are part of a pharmaceutical composition can include other agents such as other live, attenuated viruses (e.g. DEN-2, other flaviviruses). Further, other agents of use in these compositions can include other pharmaceutically acceptable anti-viral agents, adjuvants or stabilizing agents to reduce degradation of the live, attenuated viruses.

Some embodiments herein disclose methods for making modified or mutated DENV-4 constructs of use in any vaccine composition against DENV-4 including, but not limited to, a single vaccine composition having only DENV-4 constructs, a mixture of dengue virus constructs of a single vaccine composition capable of inducing an immune response against two or more dengue virus serotypes, a mixture in a single vaccine composition having chimeric (and non-chimeric) constructs disclosed herein in combination with other flavivirus constructs capable in inducing an immune response to a different flavivirus (e.g. yellow fever, West Nile, Japanese encephalitis etc.) as well as one or more dengue virus serotypes that include DENV-4.

In other embodiments, other combinations are contemplated of use with DENV-4 constructs disclosed herein. For example, a dengue virus serotype 1 wild-type virus passaged in PDK cells 13 times is designated as DEN-1 PDK-13 virus. Other vaccine candidates are DEN-2 PDK-53, DEN-3 PGMK-30/FRhL-3 (e.g. thirty passages in primary green monkey kidney cells, followed by three passages in fetal rhesus lung cells) and DENV-4 PDK-48. These four candidate vaccine viruses were derived by tissue culture passage of wild-type parental DEN-1 16007, DEN-2 16681, DEN-3 16562 and DENV-4 1036 viruses, respectively. Any of these existing live, attenuated dengue viruses are contemplated of use in combination with the DENV-4 chimeric virus constructs disclosed herein.

Previous human clinical trials with these attenuated viruses have indicated that DEN-2 PDK-53 has the lowest infectious dose (50% minimal infectious dose of 5 plaque forming units or PFU) in humans, is strongly immunogenic, and produces no apparent safety concerns. The DEN-1 PDK-13, DEN-3 PGMK-30/FRhL-3 and DENV-4 PDK-48 vaccine virus candidates have higher 50% minimal infectious doses of 10,000, 3500, and 150 PFU, respectively, in humans.

DEN-2 PDK-53 virus vaccine candidate, henceforth abbreviated PDK-53, has several measurable biological markers associated with attenuation, including temperature sensitivity, small plaque size, decreased replication in mosquito C6136 cell culture, decreased replication in intact mosquitoes, loss of neurovirulence for suckling mice and decreased incidence of viremia in monkeys. Clinical trials of the candidate PDK-53 vaccine have demonstrated its safety and immunogenicity in humans. Furthermore, the PDK-53 vaccine induces dengue virus-specific T-cell memory responses in human vaccine recipients.

In certain embodiments, a nucleic acid molecule can include a chimeric flavivirus construct having a nucleic acid sequences encoding nonstructural proteins and at least one or more structural proteins from a live, attenuated dengue-2 virus and at least encoding one or more structural proteins from a second flavivirus, wherein the chimeric construct further comprises one or more mutations comprising a mutation in the envelope (E) protein at a position synonymous to amino acid 417, a mutation in the capsid protein at a position synonymous to position 107, and a mutation in NS4A at a position synonymous to amino acid position 17. In other embodiments, a nucleic acid can further include a mutation in the envelope (E) protein at a position synonymous to amino acid 417 that changes the wild type glutamic acid to a lysine. Yet other nucleic acid molecules disclosed herein can further include a mutation in the capsid (C) protein at a position synonymous to amino acid 107 that changes a cysteine to a tyrosine. In other nucleic acid molecules, the mutation in the NS4A protein at a position synonymous to amino acid 17 changes methionine (e.g. wild type sequence) to a leucine. It is contemplated that the second flavivirus can be a DEN-1, DEN-3 or DENV-4. In certain embodiments, the nucleic acid molecule can include a second flavivirus that is DENV-4. In other embodiments, the nucleic acid molecules having a live attenuated dengue-2 backbone contains a mutation at position 57 in the 5'NCR, at position 53 of ns1 and position 250 of ns3. According to these embodiments, a live, attenuated dengue-2 virus contains a mutation at position 53 of ns1 and position 250 of ns1 plus a dengue-1, 3 or 4 substitution of one or more structural proteins. In certain embodiments, a nucleic acid construct can be DENV-4e (SEQ ID NO:22), DENV-4h (SEQ ID NO:24) or DENV-4i (SEQ ID NO:9) capable of inducing an immune response to dengue-4 virus in a subject. It is contemplated herein that the structural sequences of dengue virus serotype 4 can be substituted using dengue-virus 1 or 3 and further contain the above referenced mutations for increasing an immune response to the construct.

Some embodiments concern a nucleic acid molecule having a chimeric flavivirus construct including a nucleic acid sequences encoding nonstructural proteins and at least one or more structural proteins from a live, attenuated dengue-2 virus and at least encoding one or more structural proteins from a second flavivirus, wherein the attenuated dengue-2 contains a mutation at position 53 of ns1 and position 250 of ns3 but does not contain mutations in NS2A or NS4A. In certain embodiments, a nucleic acid construct can be DENV-4f (SEQ ID NO:30). In other embodiments, nucleotide position 674 can be mutated to C from its wild-type nucleotide of G of DENV-4f. In yet other embodiments, a mixture of DEN-2/DENV-4 constructs of the instant application can be combined in a pharmaceutically acceptable composition of use as an immunogenic agent against dengue virus infection.

In certain embodiments, an attenuated dengue-2 virus backbone of DEN-2/DENV-4 constructs can further include one or more mutations/substitutions at positions 102-107 to a wild-type dengue 4 sequence (e.g. 1086) in a DEN-2/DENV-4 construct. For example, one or more of TITLLC at respective positions 102-107 from dengue-4 can replace wild type dengue-2 virus one or more of AGMIIM, at synonymous positions 102-107, respectively. In accordance with these embodiments, a DEN-2/DENV-4 construct having a substitution in this region can further include a mutation of cysteine to an aromatic amino acid (e.g. tyrosine, tryptophan etc.).

In other embodiments, a DEN-2/DENV-4 construct of any immunogenic compositions disclosed herein can be DENV-4g (SEQ ID NO:28) or DENV-4j (SEQ ID NO:32).

Immunogenic flavivirus chimeras having a dengue-2 virus backbone and at least one structural protein of dengue-4 virus can be used for preparing the dengue virus chimeras and methods for producing the dengue virus or flavivirus chimeras are described. The immunogenic flavivirus chimeras are provided, alone or in combination, in a pharmaceutically acceptable carrier as immunogenic compositions to minimize, inhibit, or immunize individuals against infection by one or more dengue virus or flaviviral strains, such as dengue virus serotypes DENV-4, alone or in combination with DEN-2, DEN-3 and DEN-1. When combined, the immunogenic flavivirus chimeras may be used as multivalent vaccines to confer simultaneous protection against infection by more than one species or strain of flavivirus. In certain embodiments, the flavivirus chimeras are combined in an immunogenic composition useful as a bivalent, trivalent or tetravalent vaccine against the known dengue virus serotypes or confer immunity to other pathogenic flaviviruses by including nucleic acids encoding one or more proteins from a different flavivirus. The nucleic acid sequence for each of the DEN-1, DEN-2, DEN-3 and DENV-4 viruses can be used to generate a probe for use in detecting dengue virus in a biological sample in order, for example, to assess efficacy of the vaccine and/or level of a dengue virus infection.

In some embodiments, avirulent, immunogenic flavivirus chimeras provided herein contain the nonstructural protein genes of the attenuated dengue-2 virus (e.g. PDK-53), or the equivalent thereof, and one or more of the structural protein genes or immunogenic portions thereof of the flavivirus against which immunogenicity is to be induced in a subject. For example, some embodiments concern a chimera having attenuated dengue-2 virus PDK-53 genome as the viral backbone, and one or more structural protein genes encoding capsid, premembrane/membrane, or envelope of the PDK-53 genome, or combinations thereof, replaced with one or more corresponding structural protein genes from DENV-4 virus or other flavivirus to be protected against, such as a different flavivirus or a different dengue virus serotype. In accordance with these embodiments, the PDK-53 backbone is further mutated or reverted to increase immunogenicity of the construct. Further, a nucleic acid chimera disclosed herein can have functional properties of the attenuated dengue-2 virus and is avirulent, but expresses antigenic epitopes of the structural gene products of DENV-4 in addition to other flaviviruses and is immunogenic (e.g. induces an immune response to the gene products in a subject). The mutations and/or reversions do not affect the attenuation and/or safety of the chimeric construct.

In another embodiment, a nucleic acid chimera can be a nucleic acid chimera having, but not limited to, a first nucleotide sequence encoding nonstructural proteins from an attenuated dengue-2 virus, and a second nucleotide sequence encoding a structural protein from dengue-4 virus alone or in combination with another flavivirus. In other embodiments, the attenuated dengue-2 virus can be vaccine strain PDK-53 or 16681. Some embodiments include structural proteins of one or more of C, prM or E protein of a dengue or other flavivirus. Examples of flaviviruses from which the structural protein may be selected include, but are not limited to, DEN-1, DEN-2, DEN-3, West Nile virus, Japanese encephalitis virus, St. Louis encephalitis virus, yellow fever virus and tick-borne encephalitis virus in combination with the DENV-4 constructs disclosed herein. In other embodiments, the structural protein may be selected from non-flavivirus species that are closely related to the flaviviruses, such as hepatitis C virus.

Other aspects disclosed herein include that chimeric viruses can include nucleotide and amino acid substitutions, deletions or insertions for example, in the DEN-2 PDK-53; these changes can reduce interference with immunogenicity responses to DENV-4 virus. These modifications can be made in structural and nonstructural proteins alone or in combination with the example modifications disclosed herein.

Embodiments herein include structural and nonstructural proteins of a flavivirus that can be any protein including or any gene encoding the sequence of the complete protein, an epitope of the protein, or any fragment comprising, for example, five or more amino acid residues thereof.

Certain embodiments disclosed herein provide for method for making the chimeric viruses of this invention using recombinant techniques, by inserting the required substitutions into the appropriate backbone genome.

Flavivirus Chimeras

Dengue virus types 1-4 (DEN-1 to DENV-4) are mosquito-borne flavivirus pathogens. The flavivirus genome contains a 5'-noncoding region (5'-NC), followed by a capsid protein (C) encoding region, followed by a premembrane/membrane protein (prM) encoding region, followed by an envelope protein (E) encoding region, followed by the region encoding the nonstructural proteins (NS1-NS2A-NS2B-NS3-NS4A-NS4B-NS5) and finally a 3' noncoding region (3'NC) (See for example FIG. 1A). The viral structural proteins are C, prM and E, and the nonstructural proteins are NS1-NS5. The structural and nonstructural proteins are translated as a single polyprotein and processed by cellular and viral proteases.

Structure of Dengue Virus Genome

| 5'- | C | prM | E | NS1 | 2A | 2B | NS3 | 4A | 4B | NS5 | -3' |
|---|---|---|---|---|---|---|---|---|---|---|---|

Flavivirus chimeras can be constructs formed by fusing non-structural protein genes from one type, or serotype, of dengue virus or virus species of the flaviviridae, with protein genes, for example, structural protein genes, from a different type, or serotype, of dengue virus or virus species of the flaviviridae. Alternatively, a flavivirus chimera disclosed herein is a construct formed by fusing non-structural protein genes from one type, or serotype, of dengue virus or virus species of the flaviviridae, with further nucleotide sequences that direct the synthesis of polypeptides or proteins selected from other dengue virus serotypes or other viruses of the flaviviridae.

In other embodiments, avirulent, immunogenic flavivirus chimeras provided herein contain the nonstructural protein genes of the attenuated dengue-2 virus, or the equivalent thereof, and one or more of the structural protein genes, or antigenic portions thereof, of the flavivirus against which immunogenicity is to be conferred.

Other suitable flaviviruses for use in constructing the flavivirus chimeras can be wild-type, virulent DEN-1 16007, DEN-2 16681, DEN-3 16562 and DENV-4 1036 and attenuated, vaccine-strain DEN-1 PDK-13, DEN-2 PDK-53, DEN-3 PMK-30/FRhL-3 and DENV-4 PDK-48. Genetic differences between the DEN-1, DEN-2, DEN-3 and DENV-4 wild type/attenuated virus pairs are contemplated along with changes in the amino acid sequences encoded by the viral genomes. Any DENV-4 strain of use herein would contain synonymous mutations to the constructs contemplated and/or disclosed herein.

Sequence listings for DEN-2 PDK-53 correspond to the DEN-2 PDK-53-V variant, wherein genome nucleotide position 5270 is mutated from an A to a T and amino acid position 1725 of the polyprotein or amino acid position 250 of the NS3 protein contains a valine residue. The DEN-2 PDK-53 variant without this nucleotide mutation, DEN-2 PDK-53-E, differs from PDK-53-V only in this one position. DEN-2 PDK-53-E has an A at nucleotide position 5270 and a glutamate at polyprotein amino acid position 1725, NS3 protein amino acid position 250. It is understood that embodiments herein can include modified DEN-2 PDK-53 that include one or more reversions/mutations of these positions to the native derived sequence.

Sequence listings for DEN-3 16562 correspond to the variant wherein genome nucleotide position 1521 is a T and amino acid position 476 of the polyprotein or amino acid position 196 of the E protein contains a leucine. A second variant, present in DEN-3 16562 cultures has a T at nucleotide position 1521 and amino acid position 476 of the polyprotein or amino acid position 196 of the E protein contain a serine.

Sequence listings for DENV-4 PDK-48 correspond to the variant wherein genome nucleotide positions: 6957 is a T and amino acid position 2286 of the polyprotein and amino acid position 44 of NS4B protein is a phenylalanine, 7546 is a T and amino acid position 2366 of the polyprotein and amino acid position 240 of NS4B protein is a valine, and 7623 is a T and amino acid position 2508 of the polyprotein and amino acid position 21 of NS5 protein is a tyrosine.

In certain embodiments, designations of the chimeras are based on the DEN-2 virus-specific infectious clone backbones and the structural genes (prM-E or C-prM-E) insert of other flaviviruses. DEN-2 for the dengue-2 backbone, followed by the strain from which the structural genes are inserted. The particular backbone variant is reflected in next. The particular DEN-2 backbone variant from which the chimera was constructed is indicated by the following letter placed after a hyphen, parent 16681 (P), PDK-53-E (E), or PDK-53-V (V); the last letter indicates the C-prM-E structural genes from the parental (P) strain or its vaccine derivative (V) or the prM-E structural genes from the parental (P) or its vaccine derivative (V1). For example; DEN-2/1-VP denotes the chimera comprising the attenuated DEN-2 PDK-53V backbone comprising a valine at NS3-250 and the C-prM-E genes from wild-type DEN-1 16007; DEN-2/1-VV denotes the DEN-2 PDK-53V backbone with the vaccine strain of dengue-1, DEN-1 PDK-13; DEN-2/1-VP1 denotes the DEN-2 PDK-53V backbone and the prM-E genes from wild-type DEN-1 16007; DEN-2/3-VP1 denotes the DEN-2 PDK-53V backbone and the prM-E genes from wild-type DEN-3 16562; DEN-2/4VP1 denotes the DEN-2 PDK-53V backbone and the prM-E genes from wild-type DENV-4 1036; and DEN-2/WN-PP1 denotes the DEN-2 16681 backbone and the prM-E genes from West Nile NY99. Other chimeras disclosed herein are indicated by the same manner.

In one embodiment, chimeras disclosed herein contain attenuated DEN-2 virus PDK-53 genome as the viral backbone, in which the structural protein genes encoding C, prM and E proteins of the PDK-53 genome, or combinations thereof, are replaced with the corresponding structural protein genes from DENV-4 virus and optionally, another flavivirus to be protected against, such as a different flavivirus or a different dengue virus strain. Newly discovered flaviviruses or flavivirus pathogens can also be incorporated into the DEN-2 backbone.

In the nonstructural protein regions, a Gly-to-Asp (wild type-to-PDK-53) mutation was discovered at nonstructural protein NS1-53 (genome nucleotide position 2579); a Leu-to-Phe (wild type-to-PDK-53) mutation was discovered at nonstructural protein NS2A-181 (genome nucleotide position 4018); a Glu-to-Val (wild type-to-PDK-53) mutation was discovered at nonstructural protein NS3-250 (genome nucleotide position 5270); and a Gly-to-Ala mutation (wild type-to-PDK-53) was discovered at nonstructural protein NS4A-75 (genome nucleotide position 6599).

Attenuated PDK-53 virus strain has a mixed genotype at genome nt 5270. A significant portion (approximately 29%) of the virus population encodes the non-mutated NS3-250-Glu that is present in the wild type DEN-2 16681 virus rather than the NS3-250-Val mutation. As both genetic variants are avirulent, this mutation may not be necessary in an avirulent chimera.

Previously, it was discovered that avirulence of the attenuated PDK-53 virus strain can be attributed to mutations in the nucleotide sequence encoding nonstructural proteins and in the 5' noncoding region. For example, a single mutation at NS1-53, a double mutation at NS1-53 and at 5'NC-57, a double mutation at NS1-53 and at NS3-250 and a triple mutation at NS1-53, at 5'NC-57 and at NS3-250, result in attenuation of the DEN-2 virus. Therefore, the genome of any dengue-2 virus containing such non-conservative amino acid substitutions or nucleotide substitutions at these loci can be used as a base sequence for deriving the modified PDK-53 viruses disclosed herein. Another mutation in the stem of the stem/loop structure in the 5' noncoding region will provide additional avirulent phenotype stability, if desired. Mutations to this region disrupt potential secondary structures important for viral replication. A single mutation in this short (only 6 nucleotide residues in length) stem structure in both DEN and Venezuelan equine encephalitis viruses disrupts the formation of the hairpin structure. Further mutations in this stem structure decrease the possibility of reversion at this locus, while maintaining virus viability.

Mutations disclosed herein can be achieved by any method known in the art including, but not limited to, site-directed mutagenesis, direct synthesis, deletion, or other method using techniques known to those skilled in the art. It is understood by those skilled in the art that the virulence screening assays, as described herein and as are well known in the art, can be used to distinguish between virulent and avirulent backbone structures.

Construction of Flavivirus Chimeras

Flavivirus chimeras described herein can be produced by splicing one or more of the structural protein genes of the flavivirus against which immunity is desired into a PDK-53 dengue virus genome backbone, or other methods known in the art, using recombinant engineering to remove the corresponding PDK-53 gene and replace it with a dengue-4 virus gene or other gene known in the art.

Alternatively, nucleic acid sequences of any construct disclosed herein, nucleic acid molecules encoding the flavivirus proteins, may be synthesized using any known nucleic acid synthesis techniques and inserted into an appropriate vector. Avirulent, immunogenic viruses of embodiments herein can therefore be produced using recombinant engineering techniques known to those skilled in the art.

A target gene can be inserted into the backbone that encodes a flavivirus structural protein of interest for DENV-4, alone or in combination with another flavivirus. A flavivirus (e.g. dengue virus) gene to be inserted can be a gene encoding a C protein, a PrM protein and/or an E protein. For example, a sequence inserted into the dengue-2 backbone can encode both PrM and E structural proteins, or just a single structural protein. A sequence inserted into the dengue-2 backbone can encode all or one of C, prM and E structural proteins.

Suitable chimeric viruses or nucleic acid chimeras containing nucleotide sequences encoding structural proteins of other flaviviruses or dengue virus serotypes can be evaluated for usefulness as vaccines by screening them for phenotypic markers of attenuation that indicate avirulence and by screening them for immunogenicity. Antigenicity and immunogenicity can be evaluated using in vitro and/or in vivo reactivity with flavivirus antibodies or immunoreactive serum using routine screening procedures known to those skilled in the art.

Dengue Virus Vaccines

In certain embodiments, chimeric viruses and nucleic acid chimeras can provide live, attenuated viruses useful as immunogens or vaccines. Some embodiments include chimeras that exhibit high immunogenicity to dengue-4 virus while producing no dangerous pathogenic or lethal effects.

To reduce occurrence of DHF/DSS in subjects vaccinated against only one serotype of dengue virus, a di-, tri or tetravalent vaccine is needed to provide simultaneous immunity for two to all four serotypes of the virus. A tetravalent vaccine can be produced by combining live, attenuated dengue-2 (e.g. dengue-2 PDK-53) with dengue-2/1, dengue-2/3, and dengue-2/4 novel chimeras described herein in a suitable pharmaceutical carrier for administration as a multivalent vaccine against all four dengue virus serotypes. Other formulations can include divalent or trivalent formulations of the above where the formulation includes one or more novel DENV-4 chimeric construct.

Chimeric viruses or nucleic acid chimeras disclosed in certain embodiments herein can include structural genes of either wild-type or attenuated viruses in a virulent or an attenuated DEN-2 virus backbone. For example, the chimera may express the structural protein genes of wild-type DENV-4 1036 virus, and its candidate vaccine derivative in either DEN-2 PDK-53 backgrounds. In certain embodiments, pharmaceutical or experimental compositions disclosed herein can include one or more constructs having the designation of DENVax-4e, DENVax-4g, and/or DENVax-4h alone, or in combination with other flavivirus constructs. In certain examples, these constructs can be used in combination with one or more master virus seed (MVS) constructs disclosed herein (e.g. DEN-1/DEN-2). Other embodiments can include DENV-4 constructs disclosed herein in combination with other flavivirus chimeras such as those made on a Yellow Fever backbone or West Nile backbone or other flavivirus backbone where these flavivirus chimeras are capable of forming a chimeric construct with a dengue virus serotype that when introduced to a subject induces an immune response to the virus in the subject.

Viruses used in the chimeras described herein can be grown using techniques known in the art. Virus plaque titrations are then performed and plaques counted in order to assess the viability and phenotypic characteristics of the growing cultures. Wild type viruses are passaged through cultured cell lines to derive attenuated candidate starting materials.

Chimeric infectious clones can be constructed from the various dengue serotype clones available. The cloning of virus-specific cDNA fragments can also be accomplished, if desired. The cDNA fragments containing the structural protein or nonstructural protein genes can be amplified by reverse transcriptase-polymerase chain reaction (RT-PCR) from dengue virus RNA with various primers. Amplified fragments can be cloned into the cleavage sites of other intermediate clones. Intermediate, chimeric dengue virus clones can then be sequenced to verify the accuracy of the inserted dengue virus-specific cDNA.

In certain embodiments, full genome-length chimeric plasmids constructed by inserting the structural protein or nonstructural protein gene region of dengue serotype viruses into vectors are obtainable using recombinant techniques well known to those skilled in the art.

Nucleotide and Amino Acid Analysis

In certain embodiments, PDK-53 contains no amino acid mutations in the E protein relative to wild type dengue-2 virus; DEN-1, DEN-3 and DENV-4 attenuated viruses can have amino acid mutations in the E protein. Wild-type DEN-3 16562 has been demonstrated to comprise traces of a variant comprising a T at nucleotide position 1521 which directs incorporation of a leucine at polyprotein position 476, amino acid residue position 476 of the E protein. Each of the latter three viruses can possess a Glu-to-Lys (parent-to-vaccine) mutation in the E protein, although the mutation is located at a different amino acid residue in the E protein. This substitution causes a shift from a negatively charged amino acid to a positively charged one. The Glu-to-Lys substitution in the E protein of DENV-4 vaccine virus was the only mutation present in the E protein, while the E proteins of DEN-1 and DEN-3 vaccine viruses had five and three amino acid mutations, respectively.

In certain embodiments, an NS1-53 mutation occurs in the DEN-2 PDK-53 virus and is significant for the attenuated phenotype of this virus, because the NS1-53-Gly of the DEN-2 16681 virus is conserved in nearly all flaviviruses, including the tick-borne viruses, sequenced to date. DENV-4 virus constructs disclosed herein can contain an amino acid mutation in the NS1 protein at position 253. This locus, which is a Gln-to-His mutation in DENV-4 PDK-48 virus is Gln in all four wild serotypes of dengue virus. This Gln residue is unique to the dengue viruses within the flavivirus genus. The NS1 protein is a glycoprotein that is secreted from flavivirus-infected cells. It is present on the surface of the infected cell and NS1-specific antibodies are present in the serum of virus-infected individuals. Protection of animals immunized with NS1 protein or passively with NS1-specific antibody has been reported.

Certain mutations are found in NS2A, NS2B, NS4A, and NS4B proteins of the DEN-1, -2, -3 and -4 attenuated strains that are conservative in nature. The NS4A-75 and NS4A-95 mutations of DEN-2 and DENV-4 vaccine viruses, respectively, occurred at sites of amino acid conservation among dengue viruses, but not among flaviviruses in general.

Flaviviral NS3 protein possesses at least two recognized functions: the viral proteinase and RNA helicase/NTPase. The 698-aa long (DEN-2 virus) NS3 protein contains an amino-terminal serine protease domain (NS3-51-His, -75-Asp, -135-Ser catalytic triad) that is followed by sequence motifs for RNA helicase/NTPase functions (NS3-196-GAGKT), -284-DEAH, -459-GRIGR (SEQ ID NO:26), previously presented). None of the mutations in the NS3 proteins of DEN-1, DEN-2, or DEN-3 virus occur within a recognized motif. NS3-510 Tyr-to-Phe mutation in DEN-1 PDK-13 virus is a conservative mutation. Since the wild-type DEN-2, -3 and -4 viruses contain Phe at this position, it is unlikely that the Tyr-to-Phe mutation plays a role in the attenuation of DEN-1 virus. The NS3-182 Glu-to-Lys mutation in DEN-1 PDK-13 virus occurred at a position that is conserved as Asp or Glu in most mosquito-borne flaviviruses and it may play some role in attenuation. This mutation was located 15 amino acid residues upstream of the GAGKT (SEQ ID NO:27) helicase motif. In certain dengue-2 viruses, the NS3-250-Glu in DEN-2 16681 virus is conserved in all mosquito-borne flaviviruses except for yellow fever virus.

Nucleic acid probes of use in certain embodiments herein selectively hybridize with nucleic acid molecules encoding the DEN-1, DEN-3 and DENV-4 viruses or complementary sequences thereof. By “selective” or “selectively” is meant a sequence which does not hybridize with other nucleic acids to prevent adequate detection of the dengue virus. Therefore, in the design of hybridizing nucleic acids, selectivity will depend upon the other components present in a sample. Hybridizing nucleic acids should have at least 70% complementarity with the segment of the nucleic acid to which it hybridizes. As used herein to describe nucleic acids, the term “selectively hybridizes” excludes the occasional randomly hybridizing nucleic acids, and thus, has the same meaning as “specifically hybridizing.” The selectively hybridizing nucleic acids disclosed herein can have at least 70%, 80%, 85%, 90%, 95%, 97%, 98%, and 99% complementarity with the segment of the sequence to which it hybridizes, preferably 85% or more.

Sequences, probes and primers which selectively hybridize to the encoding nucleic acid or the complementary, or opposite, strand of the nucleic acid are contemplated. Specific hybridization with nucleic acid can occur with minor modifications or substitutions in the nucleic acid, so long as functional species-specific hybridization capability is maintained. By “probe” is meant nucleic acid sequences that can be used as probes or primers for selective hybridization with complementary nucleic acid sequences for their detection or amplification, which probes can vary in length from about 5 to 100 nucleotides, or preferably from about 10 to 50 nucleotides, or most preferably about 18-24 nucleotides.

If used as primers, the composition preferably includes at least two nucleic acid molecules which hybridize to different regions of the target molecule so as to amplify a desired region. Depending on the length of the probe or primer, the target region can range between 70% complementary bases and full complementarity and still hybridize under stringent conditions. For example, for the purpose of detecting the presence of the dengue virus, the degree of complementarity between the hybridizing nucleic acid (probe or primer) and the sequence to which it hybridizes is at least enough to distinguish hybridization with a nucleic acid from other organisms.

Nucleic acid sequences encoding the DENV-4, DEN-3 or DEN-1 virus can be inserted into a vector, such as a plasmid, and recombinantly expressed in a living organism to produce recombinant dengue virus peptides and/or polypeptides.

Nucleic Acid Detection Methods

A rapid genetic test that is diagnostic for each of the vaccine viruses described herein is provided by the current invention. This embodiment of the invention enhances analyses of viruses isolated from the serum of vaccinated humans who developed a viremia, as well as enhancing characterization of viremia in nonhuman primates immunized with the candidate vaccine viruses.

These sequences include a diagnostic TaqMan probe that serves to report the detection of the cDNA amplicon amplified from the viral genomic RNA template by using a reverse-transciptase/polymerase chain reaction (RT/PCR), as well as the forward and reverse amplimers that are designed to amplify the cDNA amplicon, as described below. In certain instances, one of the amplimers has been designed to contain a vaccine virus-specific mutation at the 3'-terminal end of the amplimer, which effectively makes the test even more specific for the vaccine strain because extension of the primer at the target site, and consequently amplification, will occur only if the viral RNA template contains that specific mutation.

Automated PCR-based nucleic acid sequence detection system can be used, which is becoming widely used in diagnostic laboratories. The TaqMan assay is a highly specific and sensitive assay that permits automated, real time visualization and quantitation of PCR-generated amplicons from a sample nucleic acid template. TaqMan can determine the presence or absence of a specific sequence. In this assay, a forward and a reverse primer are designed to anneal upstream and downstream of the target mutation site, respectively. A specific detector probe, which is designed to have a melting temperature of about 10° C., higher than either of the amplimers and containing the vaccine virus-specific nucleotide mutation or its complement (depending on the strand of RT/PCR amplicon that is being detected), constitutes the third primer component of this assay. A probe designed to specifically detect a mutated locus in one of the chimeric constructs can contain a specific nucleotide change for detecting any mutation.

One strategy for diagnostic genetic testing makes use of molecular beacons. The molecular beacon strategy also utilizes primers for RT/PCR amplification of amplicons, and detection of a specific sequence within the amplicon by a probe containing reporter and quencher dyes at the probe termini. In this assay, the probe forms a stem-loop structure. The 5'- and 3'-terminal reporter dye and quencher dye, respectively, are located at the termini of the short stem structure, which brings the quencher dye in close juxtaposition with the reporter dye. The stem-structure is melted during the denaturation step of the RT/PCR assay. If the target viral RNA contains the target sequence and is amplified by the forward and reverse amplimers, the opened loop of the probed hybridizes to the target sequence during the annealing step of the cycle. When the probe is annealed to either strand of the amplicon template, the quencher and reporter dyes are separated, and the fluorescence of the reporter dye is detected. This is a real-time identification and quantitation assay that is very similar to the TaqMan assay. The molecular beacons assay employs quencher and reporter dyes that differ from those used in the TaqMan assay.

Pharmaceutical Formulations

Any pharmaceutical formulation known in the art for a vaccine is contemplated herein. In certain embodiments, a formulation can contain, DENV-4 constructs alone or one or more additional DEN serotype (or other flavivirus compositions) in various ratios in combination with DENV-4 constructs disclosed herein, depending on predetermined exposure to or existence of dengue virus subtype prevalence in a region. It is contemplated that formulations can contain other agents of use in vaccination of a subject including, but not limited to other active or inactive ingredients or compositions known to one skilled in the art. In certain embodiments, an adjuvant may be included in a formulation disclosed herein.

Other aspects of the present invention can include modulating an immune response to a vaccine against dengue virus to a subject. Vaccines against dengue virus may include a composition comprising ratios of serotypes of dengue virus, live attenuated dengue virus, or fragments thereof such as proteins or nucleic acids derived or obtained from dengue virus serotypes. Ratios of various serotypes may be equal or certain serotypes may be represented more than others depending on need or exposure or potential exposure to the virus. In accordance with these embodiments, a ratio may be a 1:2, 1:3, 1:4, 1:10, 1:20; 1:1:1, 1:2:2, 1:2:1, 1:1:1:1, 1:2:1:2; 1:3:1:3, 2:3:3:3, 5:4:5:5, 4:4:4:5, 1:2:2, 4:4:5:5, 4:4:5:6 or any ratio for any of serotypes 1, 2, 3 in combination with the DENV-4 constructs disclosed herein, depending on for example, number of serotypes represented in the formulation, predetermined response and effect desired. The last number represents the amount of DENV-4 construct in a formulation. Each number represents the power of ten ($6=10^6$ PFU). It is contemplated that any dengue virus serotype formulation may be used to generate a vaccine (e.g. attenuated virus etc.) of use in administration to a subject in need thereof.

Embodiments herein provide for administration of compositions to subjects in a biologically compatible form suitable for pharmaceutical administration in vivo. By "biologically compatible form suitable for administration in vivo" is meant a form of the active agent (e.g. pharmaceutical protein, peptide, or gene etc. of the embodiments) to be administered in which any toxic effects are outweighed by the therapeutic effects of the active agent. Administration of a therapeutically active amount of the therapeutic compositions is defined as an amount effective, at dosages and for periods of time necessary to achieve the desired result. For example, a therapeutically active amount of a compound may vary according to factors such as the disease state, age, sex, and weight of the individual, and the ability of antibody to elicit a desired response in the individual. Dosage regimes may be adjusted to provide the optimum therapeutic response.

In one embodiment, the compound (e.g. pharmaceutical protein, peptide etc. of the embodiments) may be administered in a convenient manner such as subcutaneous, intravenous, intradermal, by oral administration, inhalation, transdermal application, intradermal, intravaginal application, topical application, intranasal or rectal administration. Depending on the route of administration, the active compound may be coated in a material to protect the compound from degradation by enzymes, acids and other natural conditions that may inactivate the compound. In one embodiment, the compound may be administered intranasally, such as inhalation.

A compound may be administered to a subject in an appropriate carrier or diluent, co-administered with enzyme inhibitors or in an appropriate carrier such as liposomes. The term "pharmaceutically acceptable carrier" as used herein is intended to include diluents such as saline and aqueous buffer solutions. It may be necessary to coat the compound with, or co-administer the compound with, a material to prevent its inactivation. The active agent may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use may be administered by means known in the art. For example, sterile aqueous solutions (where water soluble) or dispersions and sterile powders for the extemporaneous preparation of sterile injectable solutions or dispersion may be used. In all cases, the composition can be sterile and can be fluid to the extent that easy syringability exists. It might be stable under the conditions of manufacture and storage and may be preserved against the contaminating action of microorganisms such as bacteria and fungi. The pharmaceutically acceptable carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of microorganisms can be achieved by heating, exposing the agent to detergent, irradiation or adding various antibacterial or antifungal agents.

Sterile injectable solutions can be prepared by incorporating active compound in the required amount with one or a combination of ingredients enumerated above, as required.

Aqueous compositions can include an effective amount of a therapeutic compound, peptide, epitopic core region, stimulator, inhibitor, and the like, dissolved or dispersed in a pharmaceutically acceptable carrier or aqueous medium. Compounds and biological materials disclosed herein can be purified by means known in the art.

Upon formulation, solutions will be administered in a manner compatible with the dosage formulation and in such amount as is therapeutically effective. The formulations are easily administered in a variety of dosage forms, such as the type of injectable solutions described above. It is contemplated that slow release capsules, timed-release microparticles, and the like can also be employed. These particular aqueous solutions are especially suitable for intravenous, intramuscular, subcutaneous and intraperitoneal administration.

The active therapeutic agents may be formulated within a mixture to comprise about $10^2$ to about $5\times10^6$ PFU of each construct contemplated herein. Single dose or multiple doses can also be administered on an appropriate schedule for a predetermined condition. In certain embodiments, a dual dose on day 0 may be administered in single anatomical or multiple anatomical locations in order to induce an immune response with reduced interference or different lymph nodes. In certain embodiments, a mono-, bi-, tri- or tetravalent formulation of dengue virus constructs may be administered to a subject. Any of these formulations can be provided to a subject as a single or in multiple doses. In certain embodiments, one dose can be administered then a boost some time later may be provided.

In another embodiment, nasal solutions or sprays, aerosols or inhalants may be used to deliver the compound of interest. Additional formulations that are suitable for other modes of administration include suppositories and pessaries. A rectal pessary or suppository may also be used. In general, for suppositories, traditional binders and carriers may include, for example, polyalkylene glycols or triglycerides; such suppositories may be formed from mixtures containing the active ingredient in the range of 0.5% to 10%, preferably 1% 2%.

The pharmaceutical compositions containing the $\alpha$1-antitrypsin, analog thereof, or inhibitor of serine protease activity or a functional derivative thereof may be administered to individuals, particularly humans, for example by subcutaneously, intramuscularly, intranasally, orally, topically, transdermally, parenterally, gastrointestinally, transbronchially and transalveolarly.

In certain embodiments of the methods of the present invention, the subject may be a mammal such as a human or a veterinary and/or a domesticated animal.

In one embodiment of the present invention, methods provide for vaccinating a subject preparing to travel to a country with dengue virus. In other embodiments, a subject may be a resident in an endemic area. It is contemplated that a subject may be administered a single injection or dual injections on day 0, optionally followed by a boost less than 30 days, 2 months, 3 months, 6 months or as much as one year later.

Kits

Other embodiments concern kits of use with the methods (e.g. methods of application or administration of a vaccine) and compositions described herein. Some embodiments concern kits having vaccine compositions of use to prevent or treat subjects having, exposed or suspected of being exposed to one or more dengue viruses. In certain embodiments, a kit may contain one or more than one formulation of dengue virus serotype(s) (e.g. attenuated vaccines) at predetermined ratios. Kits can be portable, for example, able to be transported and used in remote areas such as military installations or remote villages. Other kits may be of use in a health facility to treat a subject having been exposed to one or more dengue viruses or suspected of being at risk of exposure to dengue virus.

Kits can also include a suitable container, for example, vials, tubes, mini- or microfuge tubes, test tube, flask, bottle, syringe or other container. Where an additional component or agent is provided, the kit can contain one or more additional containers into which this agent or component may be placed. Kits herein will also typically include a means for containing the agent, composition and any other reagent containers in close confinement for commercial sale. Such containers may include injection or blow-molded plastic containers into which the desired vials are retained. Optionally, one or more additional agents such as immunogenic agents or other anti-viral agents, anti-fungal or antibacterial agents may be needed for compositions described, for example, for compositions of use as a vaccine against one or more additional microorganisms.

Embodiments of the present invention are further illustrated by the following non-limiting examples, which are not to be construed in any way as imposing limitations upon the scope thereof. It should be appreciated by those of skill in the art that the techniques disclosed in the Examples which follow represent techniques discovered to function well in the practices disclosed herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope herein.

EXAMPLES

Example 1

In certain exemplary methods, DENV-4 chimera constructs are generated of use in pharmaceutically acceptable compositions.

Figure 1B:
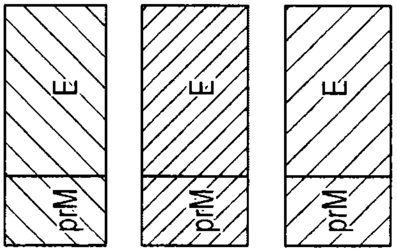

FIG. 1A illustrates an exemplary viral backbone of some embodiments disclosed herein referred to as DEN-2 PDK-53 genome (previously disclosed in PCT/US01/05142, U.S. application Ser. No. 10/204,252, each incorporated herein by reference in their entirety for all purposes) which can be used to generate modified DENV-4 constructs (also indicated as a second generation). As shown in FIG. 1A, specific amino acid substitution mutations in the nonstructural regions, such as NS1-G53D, NS3-E250V and a nucleotide substitution mutation in the 5' non-coding region, C57T in the DEN-2 PDK-53 genome have been identified. Original DEN-1, 3, and 4 constructs (also indicated as first generation) were generated by replacing the coding sequence of prM and E in the DEN-2 backbone with structural coding sequences of respective serotypes (FIG. 1B). To generate modified DENVax-4 constructs that can boost replication efficiency in vitro and in vivo, and improve immunogenicity in the host, point mutations were introduced to the non-coding region, structural protein coding sequences and/or non-structural regions of the original DENVax-4 construct. For example, modifications can be made to the amino acid sequence upstream of the current DENVax-4 C/prM cleavage site to mimic wild-type dengue-4 as opposed to dengue-2 (which DENVax-4 currently contains).

Some additional modifications in certain exemplary DENV-4 constructs are provided in Table 1. Illustrated below are sequences included in certain modified DENVax-4 constructs (DENVax-4b, DENVax-4c, and DENVax-4d) aligned to the wild type sequence of DENV-2, DENV-1 and original DENVax-4. The selected changes in these sequences are in bold and underlined:

| | C-100 Capsid --- | prM | |
|---|---|---|---|
| DEN-2: | NILNRRRRSAGMIIMLIPTVMA | FHLTTRN | SEQ ID NO: 1 |
| DENV-4 WT: | NILN**G**R**K**RS**TITLLC**LIPTVMA | FHL**S**TR**D** | SEQ ID NO: 2 |
| DENVax-4ori: | NILNRRR**S**SAGMIIMLIPTVMA | FHLTTR**D** | SEQ ID NO: 3 |
| DENVax-4b: | NILNRRR**S**S**TITLLC**LIPTVMA | FHL**S**TR**D** | SEQ ID NO: 4 |
| DENVax-4c: | NILN**G**R**K**RS**TITLLC**LIPTVMA | FHL**S**TR**D** | SEQ ID NO: 5 |
| DENVax-4d: | *ILN**G**R**K**RS**TITLLC**LIPTVMA | FHL**S**TR**D** | SEQ ID NO: 6 |

Figure 4:
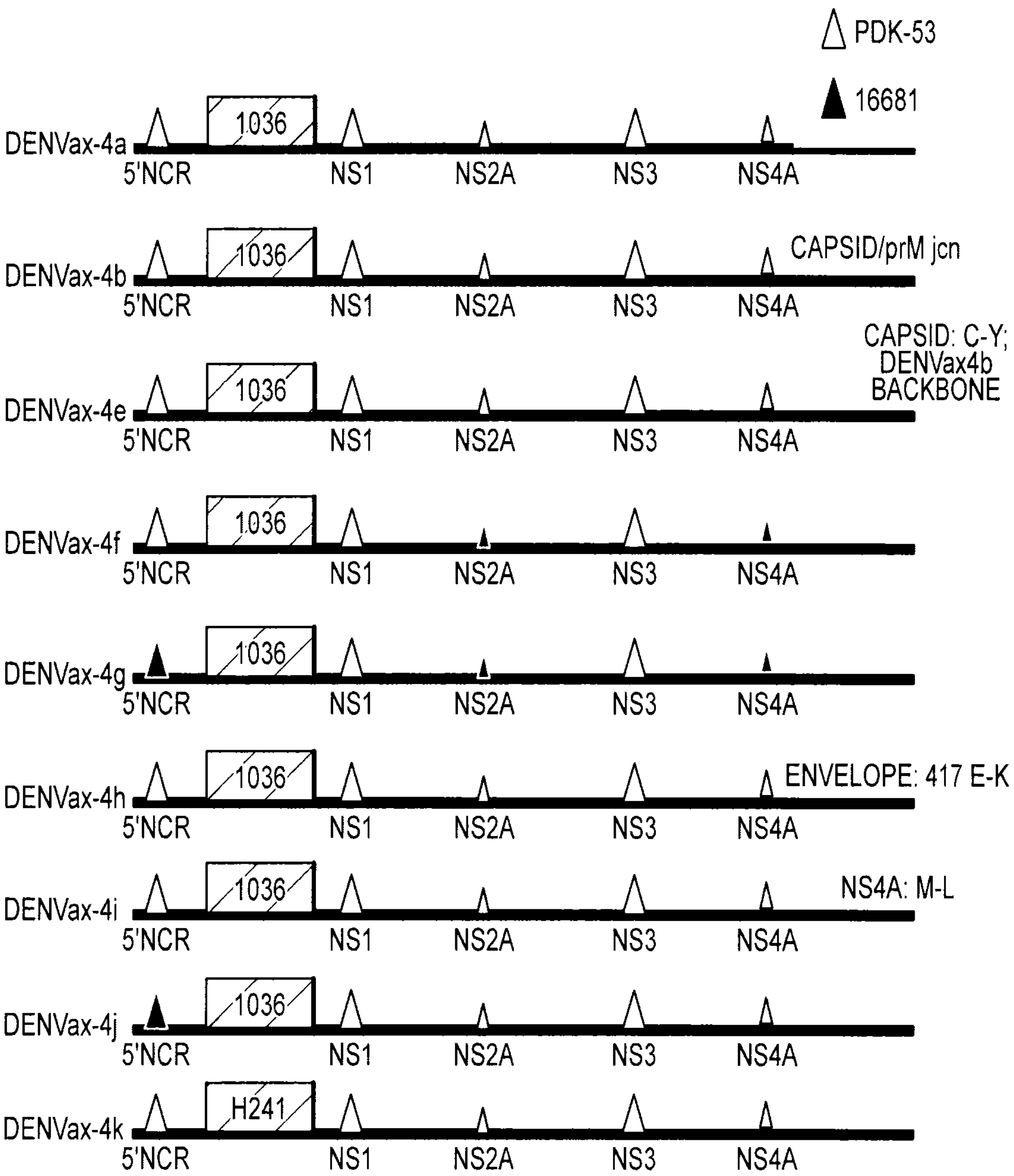
FIG. 4 represents a schematic of certain DENV-4 chimera constructs disclosed in some embodiments herein and used in vaccine formulations alone or in combination with other live, attenuated virus constructs.

FIG. 4 presents a schematic map of the original and modified DENV-4 constructs. DENVax-4e is generated using DENVax-4b sequence as a backbone, and further incorporates a C to Y mutation at amino acid 107 of Capsid protein. DENVax4f, DENVax4g and DENVax4j were built on the DENVax-4a backbone, but contain wild type reversions of the attenuating mutations of the PDK-53 sequence as indicated in FIG. 4: DENVax-4f contains wild type (DEN-2 16681) NS2A and NS4A; DENVax-4g contains wild type 5'NCR, NS2A and NS4A; and DENVax-4j contains wild type 5'NCR. DENVax4h has an E to K substitution at Envelope 417 in the DENV4 1036 sequence. DENVax4i has a methionine to leucine amino acid substitution at NS4A position 17 (synonymous position 6424 A to T of the genomic nucleic acid or amino acid position 2110 of the construct). DENVax4k has the PrM/E genes from DENV-4 H241 strain instead of 1036 strain (Table 1). Mutations constructed in DENVax4e, h, and i were based on sequence data from DENVax4 and DENVax-4b serial passages in Vero cells.

DENVax-4b contains 7 total amino acid changes, DENVax-4c contains 9 total amino acid changes, and DENVax-4d contains an amino acid deletion resulting in a frame shift of the sequence. RNA was transcribed and electroporated into Vero cells for amplification and virus rescue. DENVax-4b and DENVax-4c were tested for growth efficiency in Vero and C6/36 cells in a growth kinetics experiment, with DENVax4-P2, DENVax4-P8 and DENVax2-P2 used as controls. DENVax-4-P2 and DENVax-2-P2 are virus samples that have not been genotypically selected by viral plaque purification, a process in which individual viral plaques are picked from a DENVax-infected Vero cell monolayer, and then over-layed with agarose gel containing neutral red to visualize single plaques. DENVax-4-P8 had been selected by plaque purification to obtain a virus stock with a clonal DENVax-4 genotype. This procedure is done to generate a master seed virus (MVS) with no reverted attenuating mutations. DENVax-4c did not reach an adequate peak titer after growth in Vero cells, and had a slower initial growth rate than either DENVax-4 or DENVax-4b. There was no significant difference between the peak titers of DENVax-4 and DENVax-4b in the Vero growth curve, and both had similar initial growth rates. In the analysis C6/36 mosquito cells, growth of DENVax-4b and DENVax-4c both reached peak titers that were significantly less than wild type DENV-4, confirming their attenuation.

TABLE 1

Exemplary DENV-4 chimeric constructs: Differences in the constructs compared to DENV-4/DEN-2 PDK-53 previously disclosed

| Exemplary DENV-4 Constructs | Modifications |
|---|---|
| DENVax-4e | Capsid 107 C to Y mutation at position 416 with G mutated to A of DENVax-4b backbone |
| DENVax-4f | Attenuating mutations in NS2 and NS4 reverted to corresponding sequences of Dengue virus strain 16681 |
| DENVax-4g | Attenuating mutations in 5' NCR, NS2 and NS4 reverted to corresponding sequences of Dengue virus serotype 2 strain 16681 |
| DENVax-4h | Envelope 417 E to K mutation at position 2185 with G mutated to A of DENVax-4b backbone |
| DENVax-4i | NS4A 17 M to L mutation at position 6424 with A mutated to T of DENVax-4b backbone |
| DENVax-4j | Attenuating mutations in 5' NCR reverted to corresponding sequences of Dengue virus serotype 2 strain 16681 |
| DENVax-4k | Coding sequence of prM and E of DENV-2 backbone replaced with structural coding sequences of Dengue virus serotype 4 strain H241 |

Example 2

Generation of Full-Length Infectious cDNA Clones

To generate full-length infectious cDNA clones containing modified DENVax-4 construct sequences, a multi-step digestion/ligation scheme can be used. It can have the following steps: 1) insert the AgeI/MluI synthetic fragment including a modified nucleic acid sequence or a modified structural protein coding sequence (for example, b, c or d, or any of the above constructs) into pD2/3-PP1-5' to generate pD2/4i-b, c or d; 2) digest the pDENVax-4 full length cDNA clone to extract the MluI/NgoMIV fragment and insert it into the corresponding position of pD2/4i-b, c or d to obtain pD2/4i-b, c or d; 3) digest the pDENVax-4 full length cDNA clone to extract NgoMIV/XbaI fragment and insert it into the corresponding position of pD2/4i-b, c or d to generate the full length infectious clones containing modified sequences. The sequences of the final full-length infectious clones were confirmed by sequence analysis.

Virus Generation

The cDNA clones for each of the modified construct was transcribed into genomic viral RNA. The RNA was transformed into Vero cells by electroporation. The viruses were grown for 12 days while monitoring CPE, and harvested. This first harvest after electroporation was termed P1 (Passage 1). The subsequent amplifications and passages were called P2, P3, etc. There was limited CPE for the original DENVax-4, and DENVax-4b, and c, whereas DENVax-4d did not generate any noticeable CPE. Unlike other viruses when grown in vitro, the dengue viruses do not produce much CPE when grown in Vero cells. Although the DENVax-4d virus did not generate any CPE in vitro, it was amplified in parallel with the other strains. Amplified P1 viruses (for example, DENVax-4b, c, d P1) produced high enough titers to perform sequence analysis and growth curve experiments. DENVax-4d had no titer and therefore, no virus was made after electroporation.

The DENVax-4b and -4c viruses were fully sequenced. The DENVax-4b-P2 virus had two mutations. Nucleotide 416 was at the position of a modification engineered in the capsid (near the C/prM junction) of the DENVax-4b virus. Since this was a mixed population, the nt 416 was reverting back to the "A" nucleotide instead of the engineered "G" nucleotide, causing the expected amino acid arginine to instead be a lysine. The second mutation found in the DENVax-4b-P2 virus was at nucleotide 8769. This caused a change in the amino acid from the expected glutamine to a proline. This mutation was in the NS5 gene region of the infectious clone. The DENVax-4c-P2 virus had four mutations. They were all complete conversions, unlike the DENVax-4b virus that had mixed populations. The mutation at nucleotide 400 in the capsid region of the genome affected an engineered modification at the C/prM junction. This caused the expected amino acid at that position to be a proline instead of threonine. The other three mutations were in the nonstructural genes, two of which caused amino acid changes, and one that was a silent mutation.

Phenotypic and Genetic Characterization of the Viruses

Figures 6A, 6B, 6C, 6D, 6E, 6F:
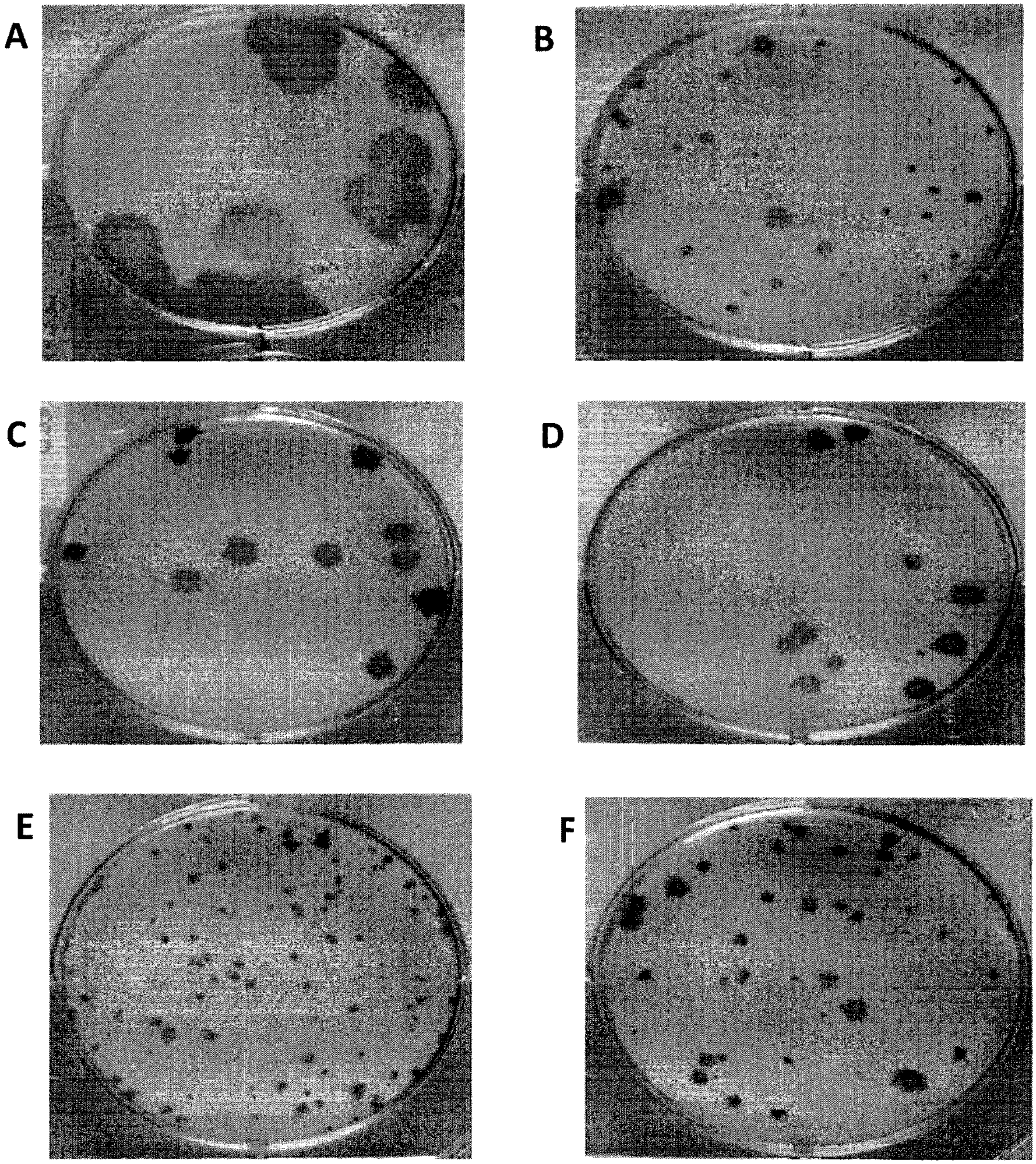
FIGS. 6A-6F are photographs providing exemplary phenotypes of ImmunoFoci (plaques) results of an exemplary experiment using certain DENV-4 chimera constructs including DENV-4 wild type (A), DENVax-4 (B), DENVax-4e (C), DENVax-4h (D), DENVax-4i (E), and DENVax-4j (F).

Phenotypic characterization of the viruses was performed in Vero cells and C6/36 (*Aedes albopictus*) cells. FIGS. 5-6 represent exemplary phenotypic character of the virus variants generated from the modified DENVax-4 constructs. Plaque size is an important attenuation marker, and was analyzed for each of the virus variants. As shown in FIG. 5, the plaque size of the DENVax-4b viruses was roughly 0.3 cm in diameter. The plaque size of the DENVax-4c viruses was about 0.1 cm in diameter. The plaque size of the DENVax-4h viruses was about 0.3 cm in diameter. The plaque size of the DENVax-4i viruses was about 0.1 cm in diameter. The plaque size of the DENVax-4c viruses was about 0.2 cm in diameter. Each of the sizes represents an average of 5-10 plaques. The plaques in the b and c candidate viruses, especially DENVax-4c were not homogenous. There was a mixed population of viruses with some small and some large plaques. The sequence variability of these small and large plaques can be characterized for possible nucleotide changes which would contribute to attenuation and fitness in vitro. If needed, these mutations could be engineered into further DENVax-4 variants. FIGS. 6A-6F present exemplary results of ImmunoFoci of the wild type DENV-4 virus (A) and each of the DENVax-4b-f virus variants (B-F).

In some exemplary methods, growth curves of DENV-4 constructs generated viruses were determined. Monolayers of Vero cells were infected at a MOI of 0.001 with various DENV-4 construct compositions (for example, DENVax-4b-j, and DENVax-4P1). In some exemplary experiments, samples were taken every other day through day 13, and aliquots were titrated. The DENVax-2-P2 virus reached peak titers more rapidly. The DENVax-4b virus was similar in peak titer and growth rate to the DENVax-4-P2 and P8 viruses. The DENVax-4c virus initially had a slower growth rate, but it finally reached a similar peak titer. The efficiency and peak titers of the DENVax-4b and DENVax-4c viruses were comparable to the original DENVax-4. In other exemplary experiments, samples were obtained every other day from day 2 through day 12. Harvested media was retained and stabilized at days 7, 9 and 11 for further study. Samples from day 2 to 12 were titered by IFA. The DENVax-4e-4h viruses showed similar peak titer to control DENVax-4 (FIG. 7).

To demonstrate attenuation, the replication efficiency of each vaccine virus should be decreased in C6/36 mosquito cells as compared to the wild-type virus. This phenotype is an essential safety feature of DENVax vaccine viruses, to ensure that there is no potential for transmission of the attenuated chimeric viruses in nature. In some exemplary methods, growth in C6/36 mosquito cells was conducted to compare the growth characteristics of the DENVax4b and DENVax-4c viruses to the wild-type dengue 4 virus (strain 1036). In other exemplary experiments, comparison was done between DENVax4e-4j and original DENVax4. Duplicate flasks of C6/36 cells were infected at a MOI of 0.001 with each of the P2 viruses (-b, -c, and wild-type) and grown for 14 days. The dengue 4 wild-type virus (WT D4 1036) replicated most efficiently and to the highest titer. The DENVax-4b virus replicated reasonably well in the C6/36 cells, reaching a peak titer of $2.7\times10^{6}$ pfu/mL by day 14. DENVax4c virus was very slow growing until after day 6 when growth was accelerated until day 14, and reaching a peak titer of $2.2\times10^{4}$ pfu/mL. At day 6, both DENVax-4b and DENVax4c were similarly attenuated for growth as compared to the wild-type in C6/36 cells, and had similar titers to the original DENVax-4. In other exemplary experiments, chimeric dengue viruses of certain embodiments herein were grown in C6/36 mosquito cells. Growth in the mosquito cells DENVax4e-4j was compared to a control DENVax4. Duplicate flasks of C6/36 cells were infected at a MOI of 0.001 with each of the P2 viruses and grown for 12 days. Samples were harvested on day 2 through day 12. Growth in the mosquito cells were compared to growth in Vero cell. Culture media was obtained and stabilized at days 7, 9 and 11. Samples from day 2 to 12 were titered by IFA and analyzed for virus production. Virus titer and growth of the constructs were compared to control DENVax4 (see FIG. 8).

Figure 7:
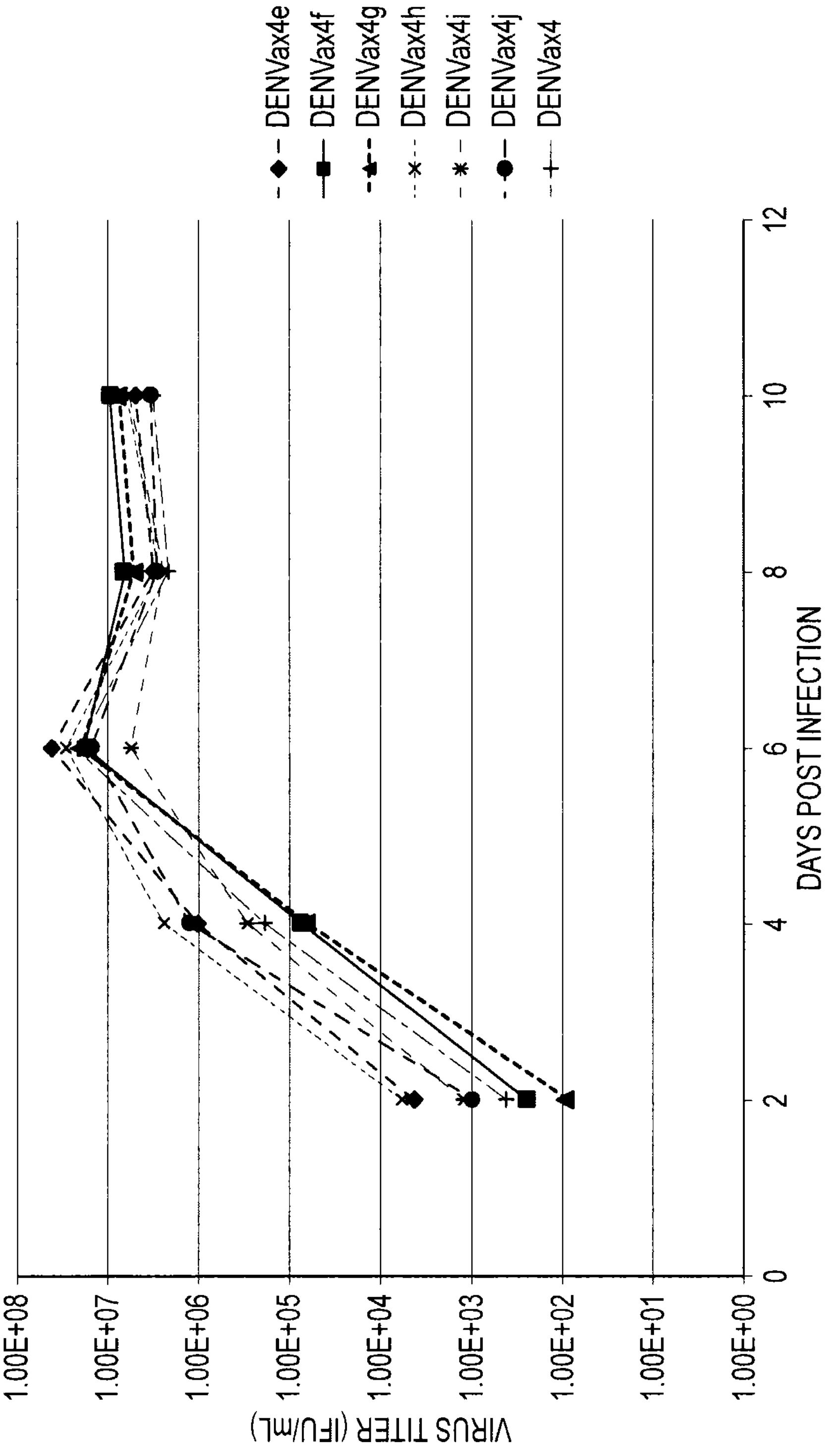
FIG. 7 is a graphic representation of viral titers over time of various DENV-4 chimeric constructs after growth in mammalian cells, illustrated as "Days Post Infection."
Figure 8:
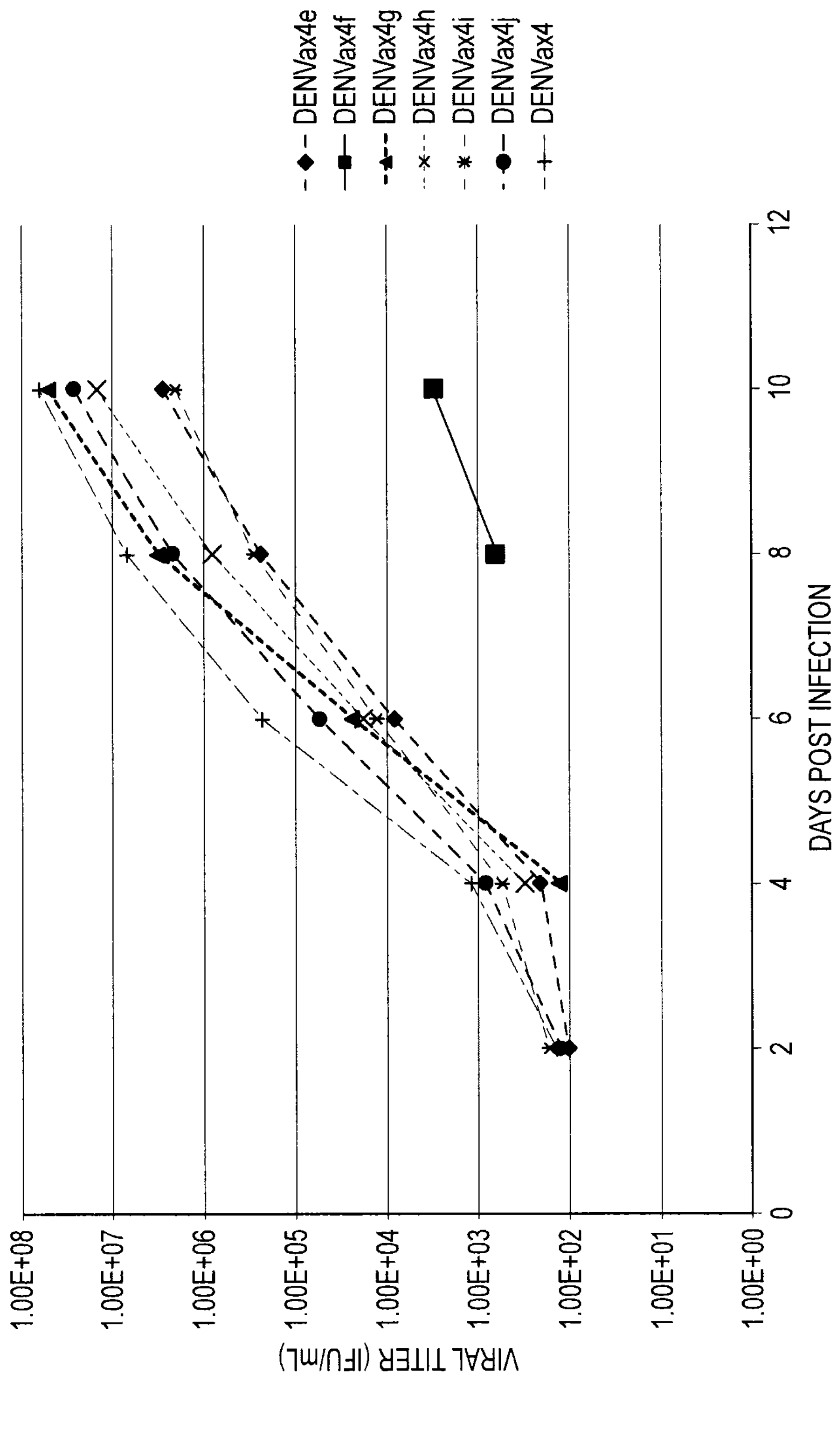
FIG. 8 is a graphic representation of viral titers over time of various DENV-4 chimeric constructs after growth in mosquito cells illustrated as "Days Post Infection."

FIGS. 7-8 represent exemplary graphs illustrating growth curves of viruses of various DENV4 constructs in Vero cells (FIG. 7) and in C6/36 mosquito cells (FIG. 8). Several novel DENVax4 constructs of certain embodiments herein produced higher titers in Vero cells (FIG. 7) than the control DENVax4 and lower titers in mosquito cells (FIG. 8) than control DENVax4, as desired for further assessment in animal models (see Table 2 below).

Safety and Efficacy of the Virus Variants in Mice

Studies were performed to analyze the immunogenicity of DENVax-4b, c or other variant viruses. Table 2 presents an exemplary study design. Groups of 10 AG129 mice were vaccinated intradermally (in the footpad) with $10^4$ PFU each of the original DENVax-4, and the separate variants. A control group was injected with excipient solution only. These mice received a booster dose after 42 days. Serum samples for serology were taken on days 42 and 56 post primary inoculation, and seroconversion was analyzed by PRNT. There was no significant improvement in the immunogenicity of DENVax-4 when using the second generation DENVax-4b and c variants as immunogens.

TABLE 2

Summary of Mouse Study Design

| Group | | Dose | Number of immunizations | Number of animals |
|---|---|---|---|---|
| 1 | DENVax-4 | $10^4$ PFU | 2 | 10 |
| 2 | DENVax-4b | $10^4$ PFU | 2 | 10 |
| 3 | DENVax-4c | $10^4$ PFU | 2 | 10 |
| 4 | TFA | NA | 2 | 10 |

included as a control. All mice received a booster injection on day 42 with the corresponding vaccine formulation, and mice were bled on days 0, 21, 41 and 56 post primary inoculation to assess the presence of neutralizing antibodies against all four DENV serotypes. On day 56, mice from groups 4, 5 and 6 were challenged with DEN-2 (NGC strain) to assess for survival (there is currently no mouse-adapted lethal DENV4 strain to use for efficacy analysis). As illustrated in Table 3, the first and second generation DENVax-4 vaccines have comparable immunogenic profile when administered alone. However, when they are given in the context of tetravalent dengue virus vaccine, immune responses to DENV-4 are diminished due to interference affecting only the second generation DENVax-4. Wild type DENV4 was highly immunogenic and in the context of tetravalent dengue virus vaccine it interferes and suppresses the neutralizing antibody responses elicited by the other three dengue virus vaccines. Wild type DENV4, the first generation and the second generation DENVax-4 provided partial protection against heterologous DEN-2 challenge.

Safety and Efficacy of Second Generation DENVax in NHP

TABLE 3

Mouse study #2 study design and PRNT results

| | Group | Dose | DENV1 | DENV2 | DENV3 | DENV4 |
|---|---|---|---|---|---|---|
| 1 | DENVax ($1^{st}$generation DENVax-4) | 4:3:4:5 | 1280 (320) | 640 (320) | >1280 (320) | 640 (160) |
| 2 | DENVax (DENVax-4 was replaced with wild type DENV-4) | 4:3:4:5 | 160 (320) | 160 (160) | 320 (160) | 640 (640) |
| 3 | DENVax (DENVax-4 was replaced with $2^{nd}$ generation DENVax-4) | 4:3:4:5 | >1280 (640) | 640 (320) | >1280 (640) | 80 (80) |
| 4 | DENVax-4 ($2^{nd}$ generation) | 10^5 | X | X | X | 320 (80) |
| 5 | Wild type DENV-4 | 10^5 | X | X | X | 640 (320) |
| 6 | DENVax-4 ($1^{st}$ generation) | 10^5 | X | X | X | 320 (80) |

To further modify and amplify the immunogenicity of DENVax-4b, this virus was adapted in vitro to Vero cell growth. This was performed by 10 blind passages in Vero cells, with the hypothesis that adaptation in mammalian cell culture would boost the replicative capacity of the virus and thus its immunogenicity. This "new" second generation DENVax-4 was termed DENVax-4b-P10 (Passage-10).

Figure 3:
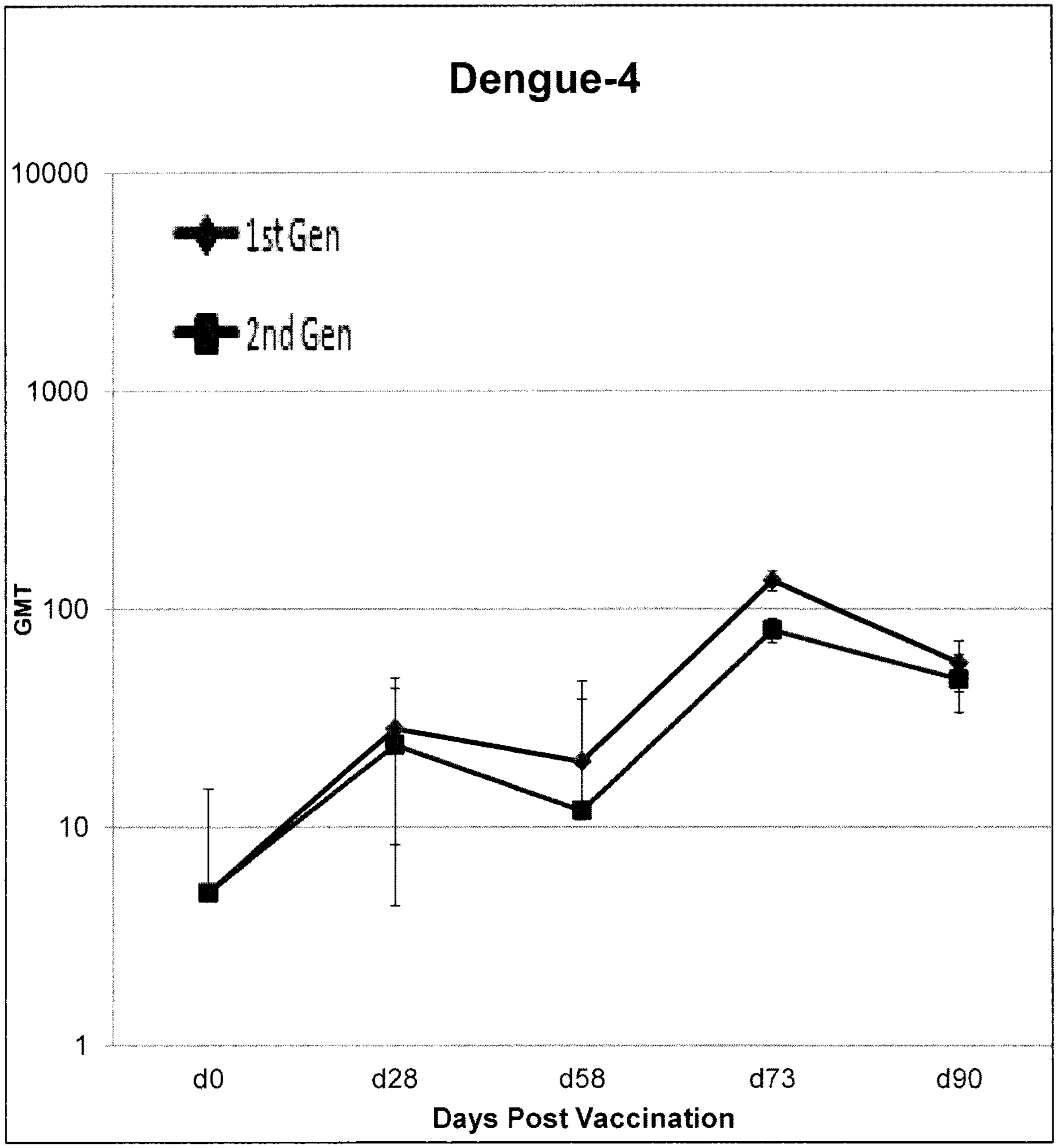
FIG. 3 represents an exemplary graph of an experiment related to production of DENV-4 neutralizing antibody titers produced by an animal model immunized with a vaccine composition having DENV-4 chimeric viral constructs of certain embodiments disclosed herein.

Another study was performed to evaluate different tetravalent formulations of dengue virus vaccine including three separate DEN4 viruses; first generation, second generation (4b construct) and the homologous wildtype DEN4 1036. Groups of 6 mice were injected intradermally with a tetravalent vaccine formulation containing $10^4$ PFU DENVax-1, $10^3$ PFU DENVax-2, $10^4$ PFU DENVax-3 and $10^5$ PFU DENVax 4 (4:3:4:5) in a 50 μL volume. Control mice were injected by the same route with $10^5$ PFU of $1^{st}$ generation, $2^{nd}$ generation or wildtype 1036 monovalent DENV4. A group of mice injected with diluent only was The immunogenicity of DENVax in groups of four Cynomologus macaques was evaluated after subcutaneous injection of each tetravalent DENVax formulation (Table 4 and FIG. 2) in 0.5 mL injection volume. The goal of this study was to evaluate the lead second generation DENVax-4 construct, as compared with the first generation DENVax-4. Additionally, different methods were explored to improve the neutralizing antibody responses to DENV-4 elicited by DENVax. These included testing a formulation which contained 10× the dose of DENVax-4 as used previously (termed "new formulation"), and also lowering the DENVax-2 component of the tetravalent mixture, as this vaccine is the most immunogenic of the four vaccine virus strains. Different dosing days were tested, and priming and boosting on the same day were compared (Day 0) to priming on Day 0 and boosting on Day 60. Samples for serology were taken on days 0, 28, 58, 73, and 90. The kinetics of neutralizing antibody titers against DENV-4 variant virus and the original was shown in FIG. 3 as an example, where comparable levels were observed.

TABLE 4

| NHP Study Design: | | | |
|---|---|---|---|
| Groups | Vaccine Source | Formulation | Treatment |
| 1 | DENVax Formulation (Clinical Stock) | 2e4, 5e4, 1e5, 3e5 | 2 dose (day 0) |
| 2 | DENVax Formulation (4b-P10) | 2e4, 5e4, 1e5, 3e5(46) | 2 dose (day 0) |
| 3 | DENVax Formulation (Clinical Stock) w/10x DENVax-4 | 2e4, 5e4, 1e5, 3e6 | 2 dose (day 0) |

TABLE 4-continued

| NHP Study Design: | | | |
|---|---|---|---|
| Groups | Vaccine Source | Formulation | Treatment |
| 4 | DENVax Formulation (Clinical Stock) w/10x DENVax-4 | 2e4, 5e4, 1e5, 3e6 | 2 dose (0, 60) |
| 5 | DENVax New formulation | 2e4, 1e4, 1e5, 3e6 | 2 dose (0, 60) |

Vaccine formulations for the NHP studies were prepared in bulk. Group 1 received vaccine which was cGMP manufactured and is identical to the vaccine which is currently being tested in human clinical trials. Vaccines were given to the NHPs and subsequently back-titrated to determine the actual dose. These results are presented in Table 5 below.

TABLE 5

| Vaccine Stocks - back titration results: | | | | | | | |
|---|---|---|---|---|---|---|---|
| DENVax | iFFU/dose GP1 | desired dose GP2 | back titradon | desired dose GP3 and 4 | back titration | desired dose GP5 | back titration |
| D1 | 2.00E+04 | 2.00E+04 | 1.90E+04 | 2.00E+04 | 1.80E+04 | 2.00E+04 | 1.80E+04 |
| D2 | 5.00E+04 | 5.00E+04 | 2.60E+04 | 5.00E+04 | 2.40E+04 | 1.00E+04 | 3.60E+03 |
| D3 | 1.00E+05 | 1.00E+05 | 1.80E+05 | 1.00E+05 | 1.40E+05 | 1.00E+05 | 1.70E+05 |
| D4 | 3.00E+05 | 300000 (4b) | 2.10E+05 | 3.00E+06 | 2.90E+06 | 3.00E+06 | 3.00E+06 |

Samples for viremia were taken after the primary dose on days −11 (baseline), 3, 5, 7, 9, 11, 13, 15, 17, 21, 28, 58, 62 and 66. RNA was extracted from the serum sample and virus titer was determined by tetraplex qRT-PCR assay. The only virus which gave any detectable viremia was DENVax-2, and this resolved by day 21 after primary vaccination. No virus was detected after the booster dose of vaccine was administered.

Serology was evaluated using a high throughput PRNT assay in a 96 well plate. Comparison of the first and second generation DENVax-4 (Group 1 compared to group 2) showed no significant difference in immunogenicity of these two viruses (Table 6).

TABLE 6

| Geometric Mean Titers of NHP study. | | | | | | | | | | |
|---|---|---|---|---|---|---|---|---|---|---|
| Group | DEN | d0 | d28 | d58 | d73 | d90 | d128 | d149 | d181 | d210 |
| 1 | 1 | 5 | 226.3 | 134.5 | 160.0 | 95.1 | 67.3 | 95.1 | 226.3 | 226.3 |
| 5455a | 2 | 5 | 1810.2 | 1280.0 | 905.1 | 905.1 | 761.1 | 761.1 | 761.1 | 380.5 |
| 0.0 | 3 | 5 | 226.3 | 190.3 | 320.0 | 226.3 | 95.1 | 134.5 | 226.3 | 160.0 |
| | 4 | 5 | 28.3 | 20.0 | 134.5 | 56.6 | 23.8 | 33.6 | 113.1 | 67.3 |
| 2 | 1 | 5 | 33.6 | 16.8 | 47.6 | 40.0 | 23.8 | 23.8 | 20.0 | 67.3 |
| 5455b | 2 | 5 | 1076.3 | 1280.0 | 905.1 | 1076.3 | 1076.3 | 1280.0 | 640.0 | 640.0 |
| 0.0 | 3 | 5 | 67.3 | 33.6 | 226.3 | 80.0 | 23.8 | 28.3 | 28.3 | 33.6 |
| | 4 | 5 | 23.8 | 11.9 | 80.0 | 47.6 | 23.8 | 33.6 | 23.8 | 20.0 |
| 3 | 1 | 5 | 80.0 | 47.6 | 56.6 | 67.3 | 40.0 | 33.6 | 134.5 | 134.5 |
| 5456 | 2 | 5 | 380.5 | 320.0 | 538.2 | 538.2 | 190.3 | 508.0 | 269.1 | 269.1 |
| 0.0 | 3 | 5 | 95.1 | 80.0 | 134.5 | 95.1 | 40.0 | 40.0 | 160.0 | 113.1 |
| | 4 | 5 | 95.1 | 134.5 | 160.0 | 160.0 | 134.5 | 134.5 | 320.0 | 226.3 |
| 4 | 1 | 5 | 16.8 | 16.8 | 80.0 | 56.6 | 23.8 | 23.8 | 16.8 | 20.0 |
| 5456 | 2 | 5 | 134.5 | 134.5 | 269.1 | 320.0 | 134.5 | 134.5 | 95.1 | 80.0 |
| 0.60 | 3 | 5 | 23.8 | 23.8 | 134.5 | 95.1 | 23.8 | 20.0 | 28.3 | 28.3 |
| | 4 | 5 | 23.8 | 20.0 | 134.5 | 113.1 | 56.6 | 80.0 | 28.3 | 28.3 |
| 5 | 1 | 5 | 20.0 | 11.9 | 134.5 | 134.5 | 33.6 | 20.0 | 28.3 | 14.1 |
| 5356 | 2 | 5 | 28.3 | 8.4 | 95.1 | 80.0 | 10.0 | 5.9 | 5.0 | 5.0 |
| 0.60 | 3 | 5 | 23.8 | 11.9 | 190.3 | 190.3 | 23.8 | 28.3 | 33.6 | 28.3 |
| | 4 | 5 | 33.6 | 33.6 | 269.1 | 134.5 | 113.1 | 56.6 | 80.0 | 67.3 |

Evaluating a higher dose of DENVax-4 (Group 3) revealed that a significant difference in the kinetics of DENV-4 neutralizing antibody responses could be obtained. The peak titers remained roughly equivalent (within a 2-fold dilution range) when comparing the two different vaccine formulations, but the rate in which the peak titer to DENV-4 was obtained was much earlier when the immunization was performed with a greater amount of DENVax-4. Further, when the amount of DENVax-2 was lowered in the formulation (Group 5), this had no marked difference in the kinetics or peak titer of DENV-4 in serum responses in this tetravalent DENVax vaccine.

Figure 9:
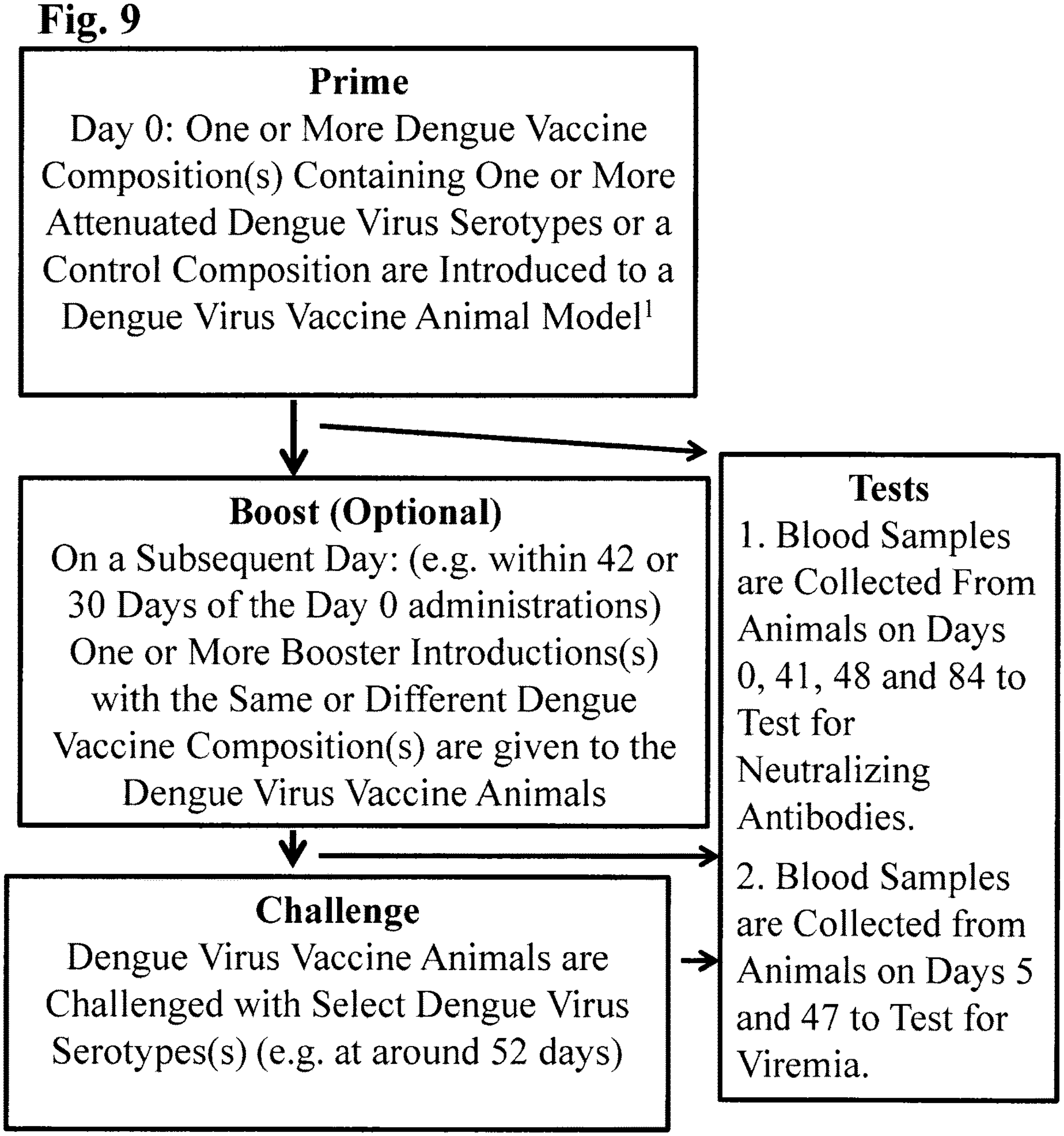
FIG. 9 is a flow chart representing an acceptable animal model used to test various DENV-4 chimeric constructs to induce an immune response to DENV-4 in the animal model.
Figure 12:
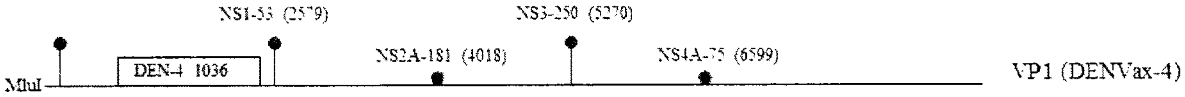
FIG. 12 illustrates a schematic representation of a live, attenuated virus construct of DEN-2 virus.
Figure 14:
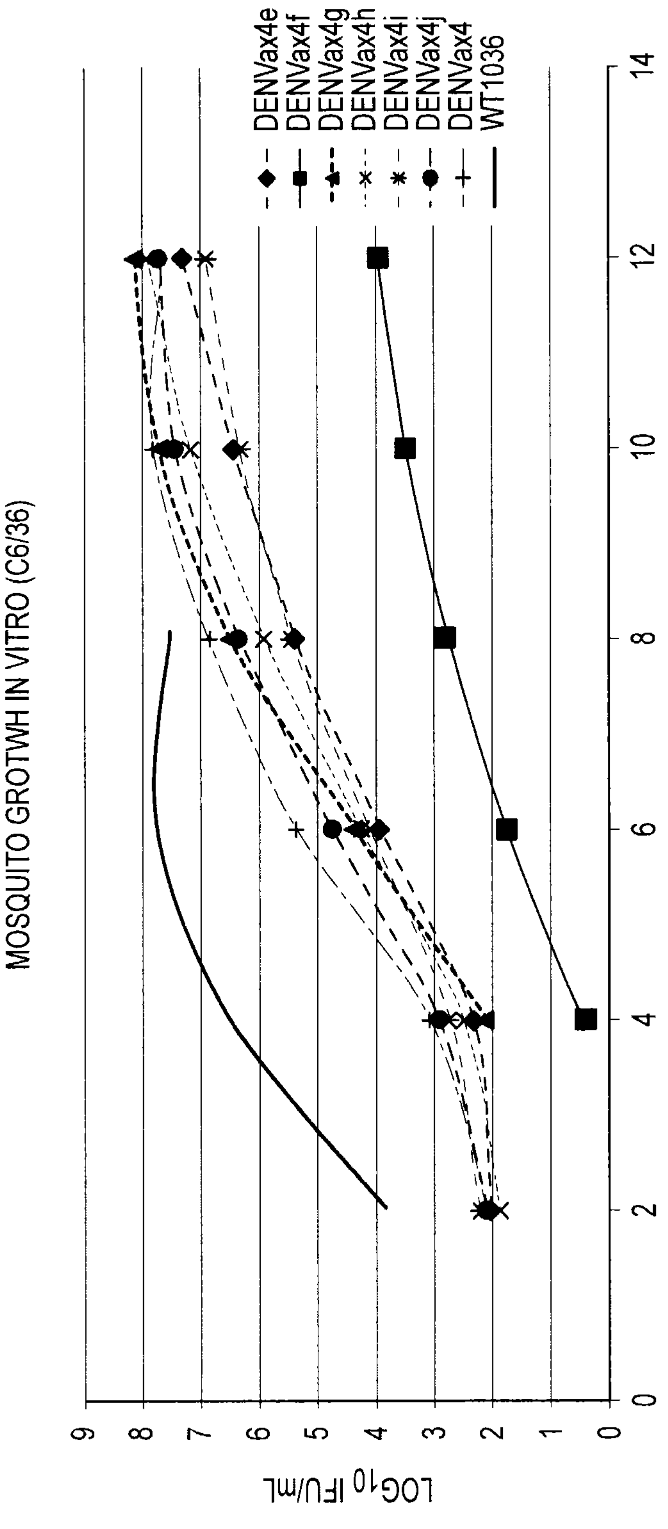
FIG. 14 represents a graph comparing various DENV-4 constructs growth in mosquito cells.
Figure 15:
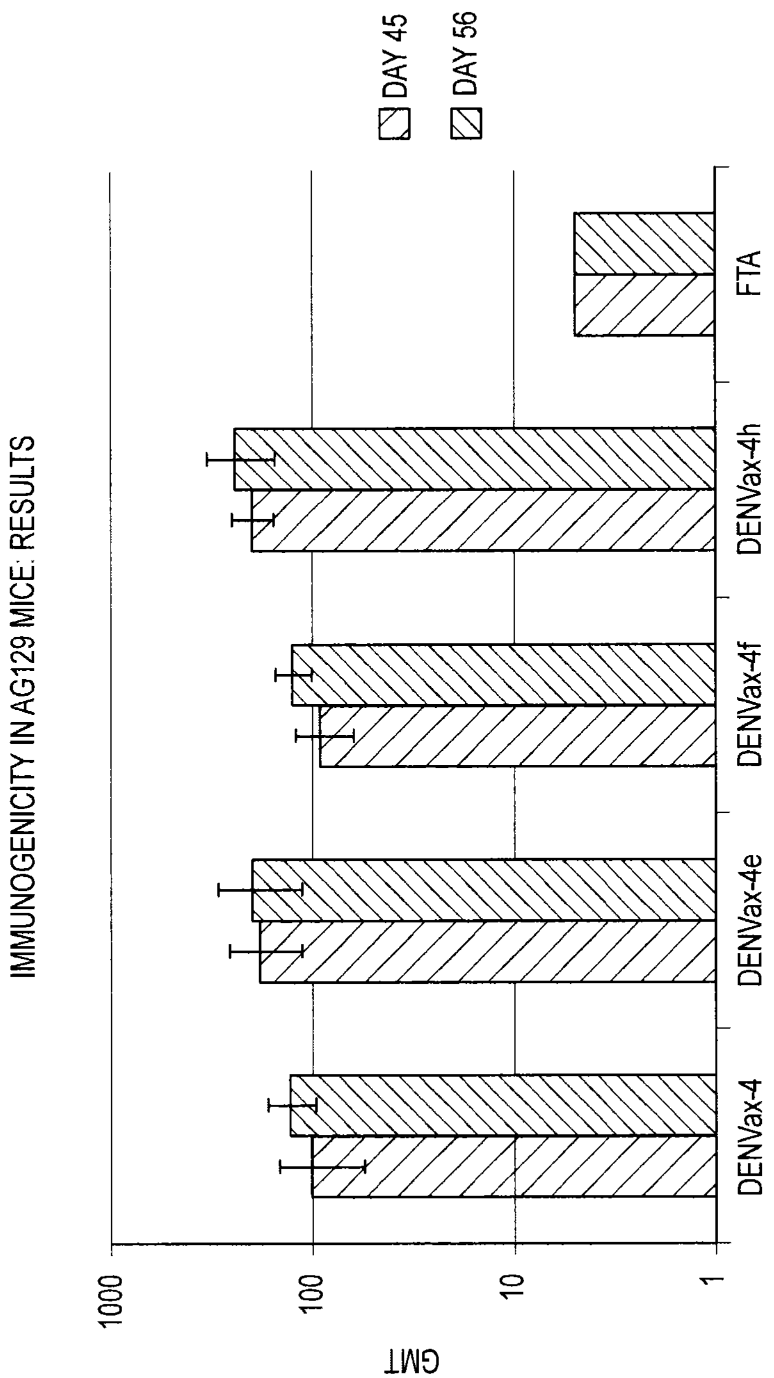
FIG. 15 represents an exemplary histogram plot comparing immunogenicity in mice of various DENV-4 constructs disclosed herein.
Figure 16:
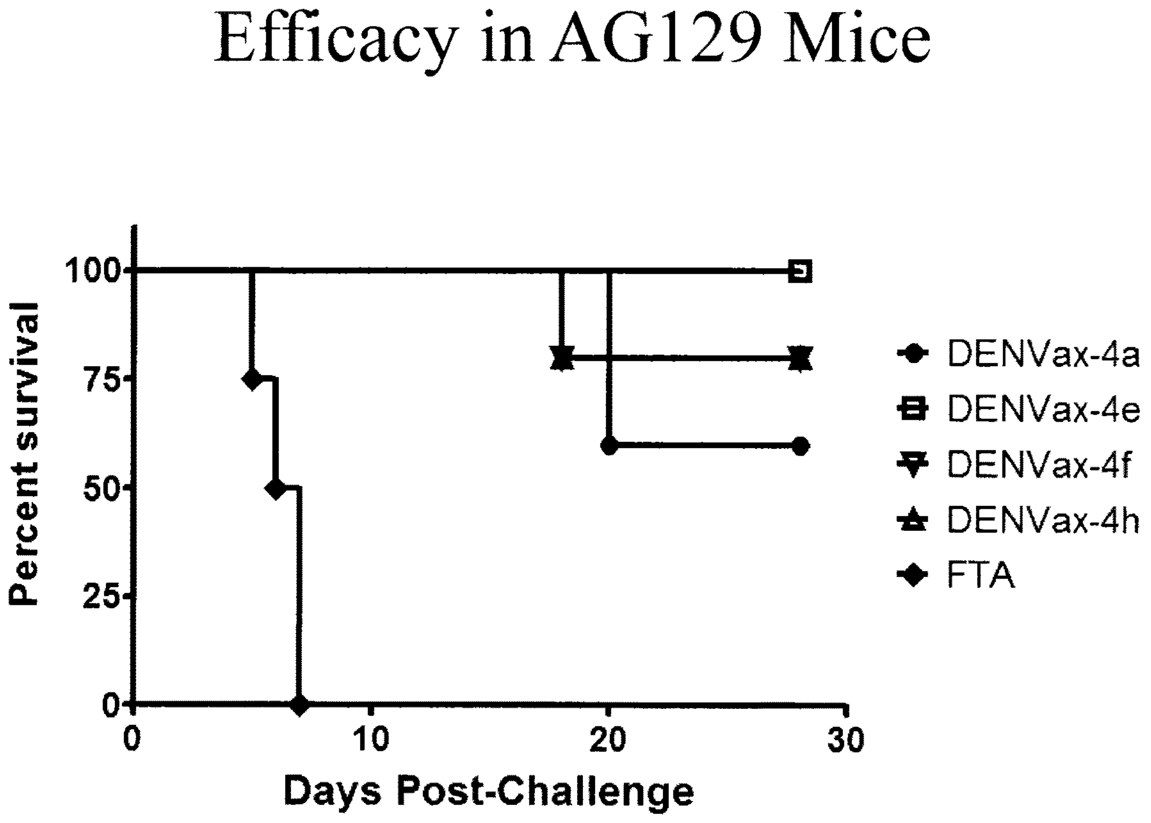
FIG. 16 represents an exemplary graph illustrating efficacy using various DEN-4 constructs in mice to protect immunized mice against challenge by wt-DENV, represented as survival.
Figure 17:
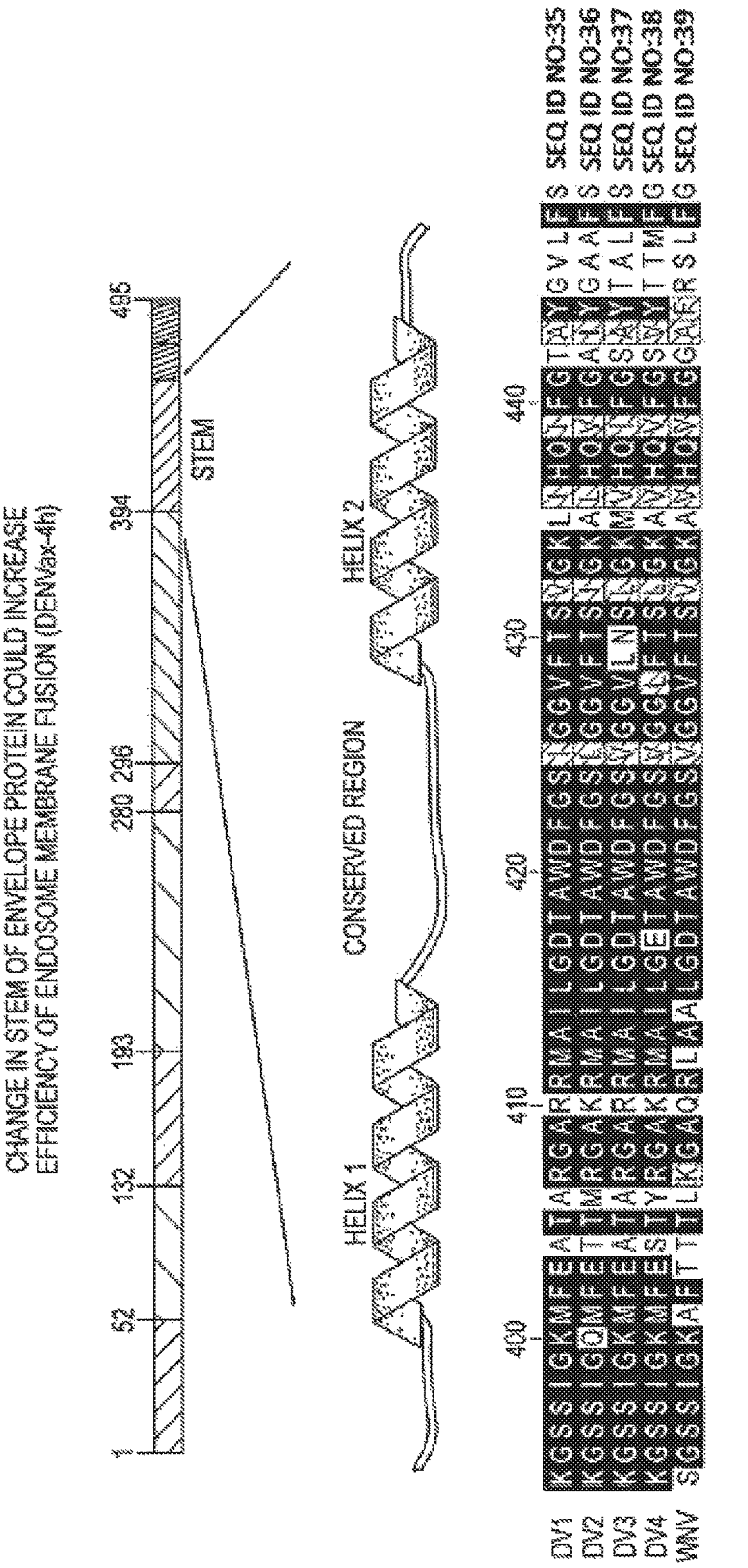
FIG. 17 represents an alignment of the flavivirus envelope protein.
Figure 18:
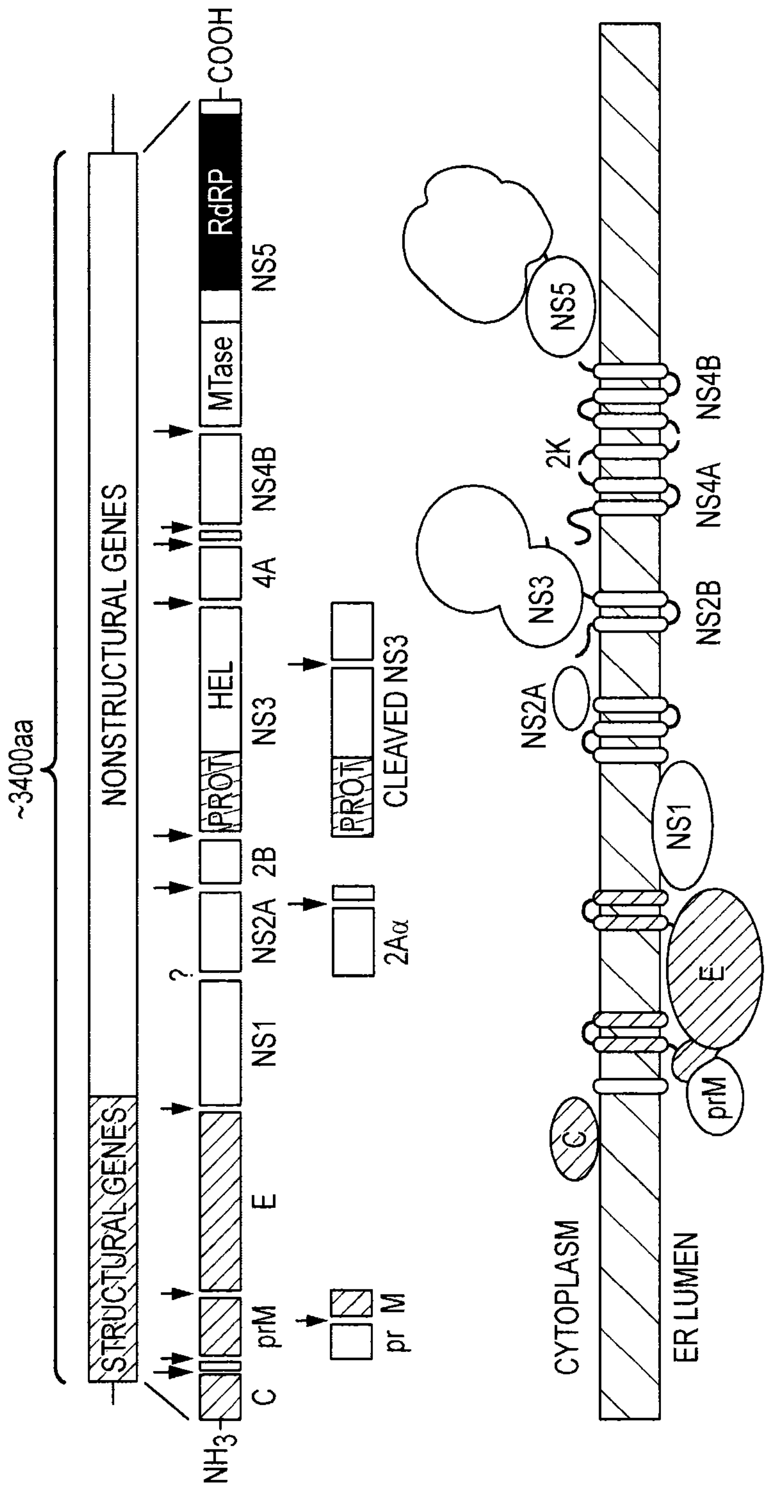
FIG. 18 represents a schematic of a DENV virus including open reading frames for proteins of DENV.

FIG. 9 represents a flow chart of one exemplary procedure for testing safety and efficacy of the virus construct disclosed herein in an animal model. For example, composition(s) that include one or more chimeric Dengue viruses of use as a vaccine, such as compositions of DENVax4e, DENVax4f or DENVax4h, or other chimeric constructs or a control composition can be tested in animal models, e.g. AG129. Animals can be primed on day 0, and subsequently boosted with the same or different Dengue virus vaccine compositions on or before day 30 or day 42 or other appropriate time. Then, the animals can be challenged with exposure to one or more Dengue virus serotypes to assess induction of an immune response to the challenge. Blood samples can be collected, for example, on days 0, 30, 41, 48, 52 or 84 or other appropriate day to test for neutralizing antibodies, and on other days such as 5 and 47 to test for viremia (or as deemed appropriate for the composition and administration protocol chosen).

Virus Cloning and Rescue to P1

Plasmid mutagenesis was used to create the new DENV-4 chimeric clones of use in vaccine compositions disclosed herein. Primers coding for point mutations were synthesized and used to amplify an entire new infectious clone. The template was digested by DpnI and the subsequent plasmid was sequenced. RNA was transcribed and electroporated into Vero cells to create a virus at passage level 0 (P0) and then amplified by a single passage in Vero cells (P1).

Modifications at the Capsid/PrM junction in the DENVax-4b clone did not appear to cause an increase in DENV-4 immunogenicity in NHP studies. Using the sequencing data from the blind serial passages of DENV-4 and DENVax-4b, 3 point mutations that may increase Vero cell adaptation were identified. In addition some attenuating mutations were reverted back to the wild-type sequence to increase immunogenicity in mice. As presented in FIG. 6, the larger IFU size and lytic phenotypes of DENVax-4e and DENVax-4h illustrates the potential that either of these clones may show an increase in immunogenicity in mice. Experiments to analyze the growth kinetics of each of the new DENVax-4 clones were conducted to determine whether the inserted modifications increase Vero cell adaptation. Test in A129 mice to analyze immunogenicity are also conducted.

Growth Kinetics

Serial passaging of Dengue vaccine strains in Vero cells is a classic method for selecting strains which are better fit to grow in vitro. In these exemplary growth experiments, DENVax-2 (FIG. 1) was included as a control and displayed the highest initial titer at day 2, followed by DENVax-4b-P10, DENVax-4, and DENVax-4b-P1. At the end of the growth period (day 12) DENVax-2 had the highest peak titer, followed by DENVax-4b-P10, DENVax-4b-P1, and DENVax-4.

Amino Acid Changes in Sequences

DENVax4-P10 genomic sequencing demonstrated mutations which corresponded to amino acids E-417 E-K (Glu-Lys) and NS4A-17 M-L. DENVax4b-P10 sequencing showed a mutation which corresponded to amino acid C-107 C-Y. The E-417 E-K mutation changes the amino acid residue so that an amine group (NH2) is substituted for a carbonyl hydroxyl group. However, the R group is still charged and remains hydrophilic. The NS4A-17 M-L mutation results in removal of a sulfate from the R group, but maintains non-polarity resulting in a hydrophobic amino acid. The C-107 C-Y mutation results in drastic change in the R group. Cysteine has an SH group that is capable of forming disulfide bonds, while tyrosine has a carbon benzene ring with a hydroxyl group. This causes the amino acid residue to become hydrophilic instead of hydrophobic, affecting its interaction with the other amino acid R groups.

Figure 19:
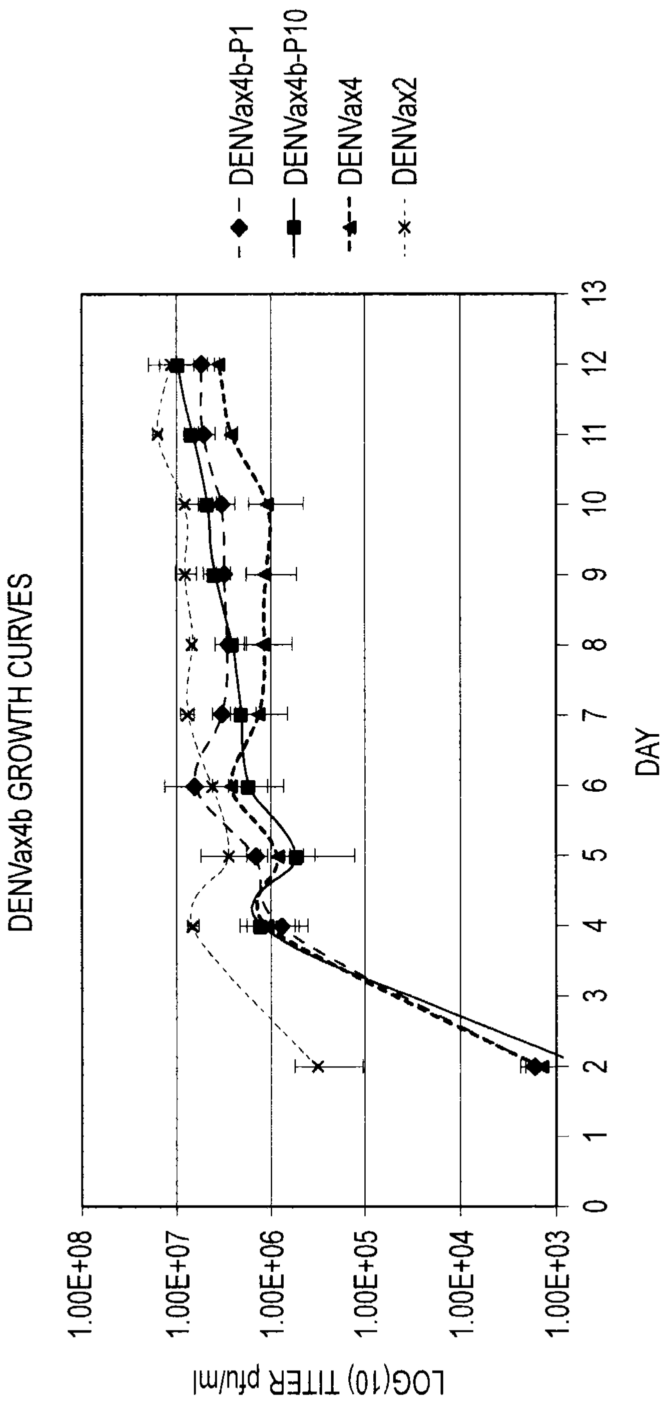
FIG. 19 represents a graphic illustration of titer achieved after growth of various DEN-4 constructs in a mammalian cell line contemplated of use herein.

FIG. 19 is a graphic representation of titers of DENVax-4 constructs during growth kinetics experiment. The day each sample was taken is plotted on the x-axis and the titer is plotted on the y-axis.

Neutralizing Antibodies in NHP Vaccinated with DENVax

Figure 20:
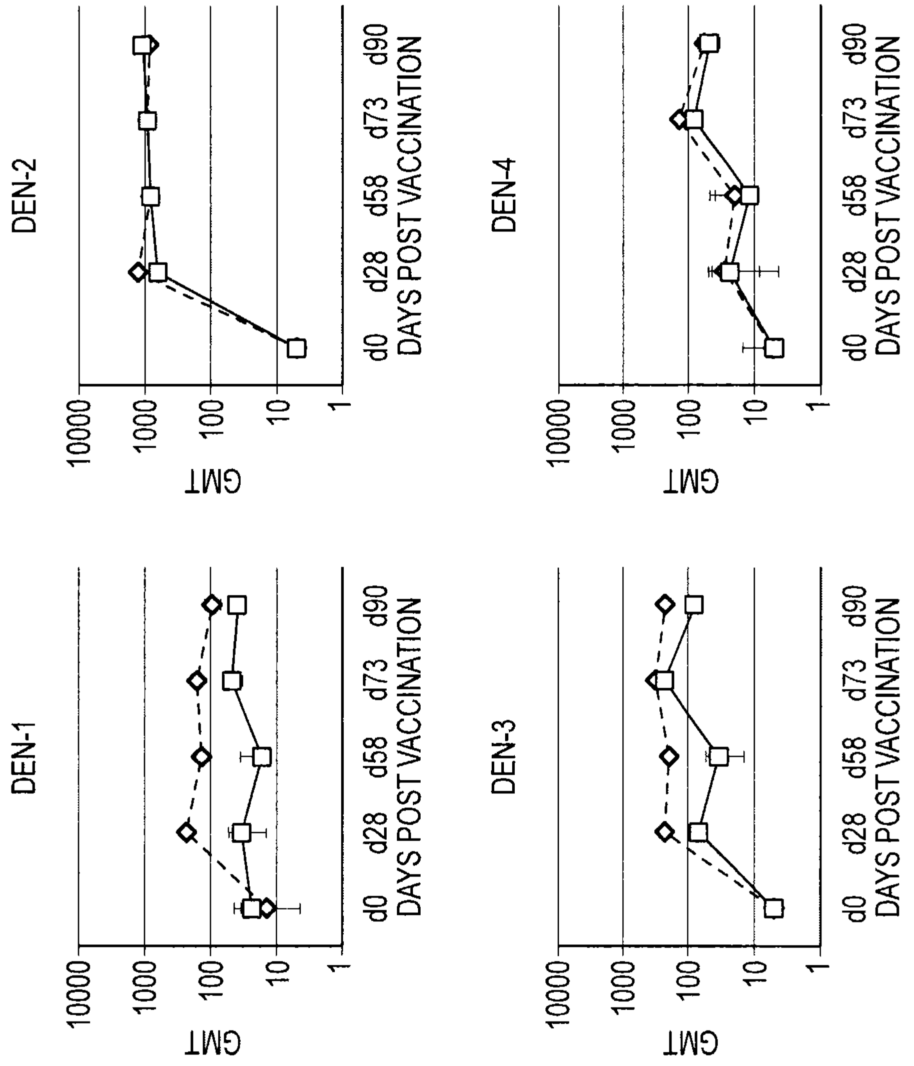
FIG. 20 represents various levels of neutralizing antibodies after vaccination with various dengue constructs in non-human primates post vaccination, represented as days post vaccination.

In certain methods, evaluation of the DENV-4 chimeric construct viruses took place with a larger study testing immunization regimens. The immunogenicity of DENVax-4b compared to that of DENVax-4a was tested. Groups 1 and 2 were vaccinated on Day 0 with 2 doses and given no booster vaccination. Equivalent titers of either DENVax-4 (diamonds) or DENVax-4b (squares) were used in all doses. No significant differences in geometric mean titers (GMT) of neutralizing antibodies were found between any of the serotypes including DENV-4. This suggests that using DENVax-4b in tetravalent DENVax does affect or increase the neutralizing antibody response against DENV-4. FIG. 20: GMT values comparing Groups 1 (DENVax-4, diamonds) and 2 (DENVax-4b, squares). GMT values are measurements of neutralizing antibody values from Plaque Reduction Neutralization Technique.

Figure 21:
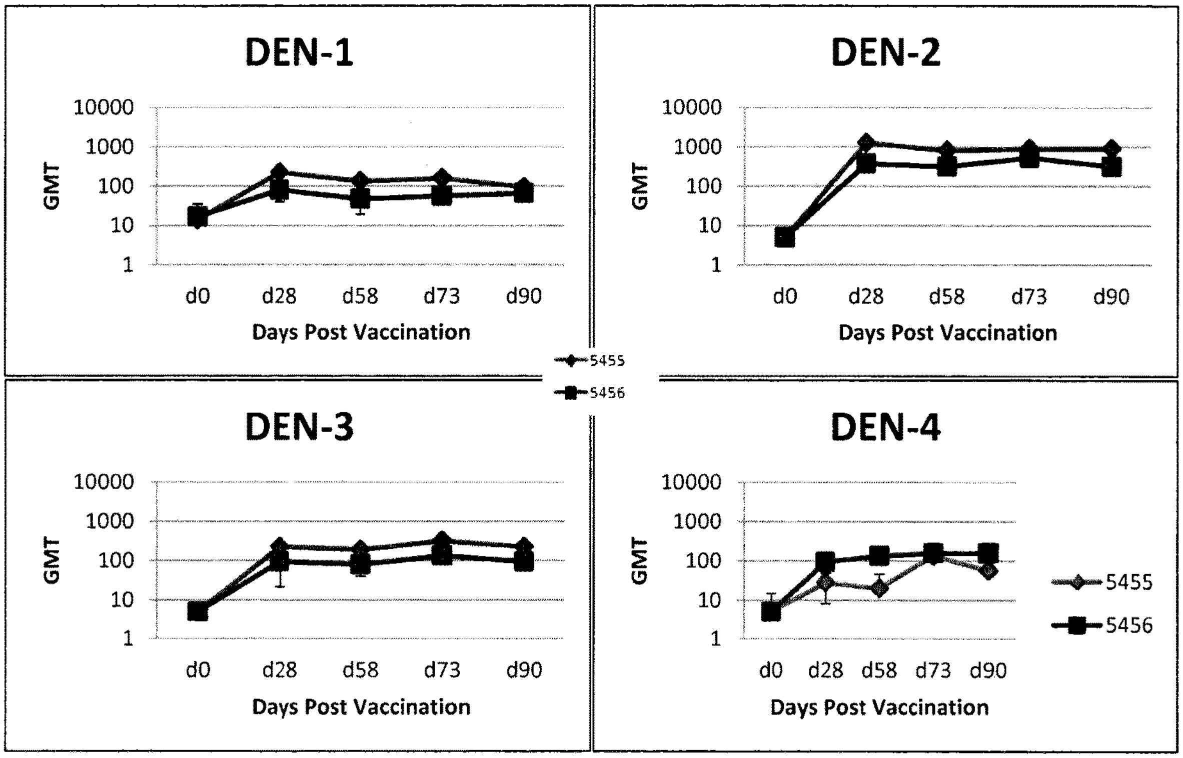
FIG. 21 represents various levels of neutralizing antibodies after vaccination with various dengue constructs in non-human primates post vaccination, represented as days post vaccination.

Neutralizing antibody responses in Groups 1 and 3 were compared to determine whether increasing the dose of DENVax-4 in tetravalent DENVax increased immunogenicity against DENV-4. Results demonstrated that primates immunized with a higher dose of DENVax-4 showed an increased in GMT of primary neutralizing antibodies detected in the first 60 days compared to those immunized with traditional tetravalent DENVax. There was no significant difference in GMT between the other DENV serotypes (FIG. 21). This suggests that a higher dose of DENVax-4 improves the neutralizing antibody response against DENV-4.

Figure 22:
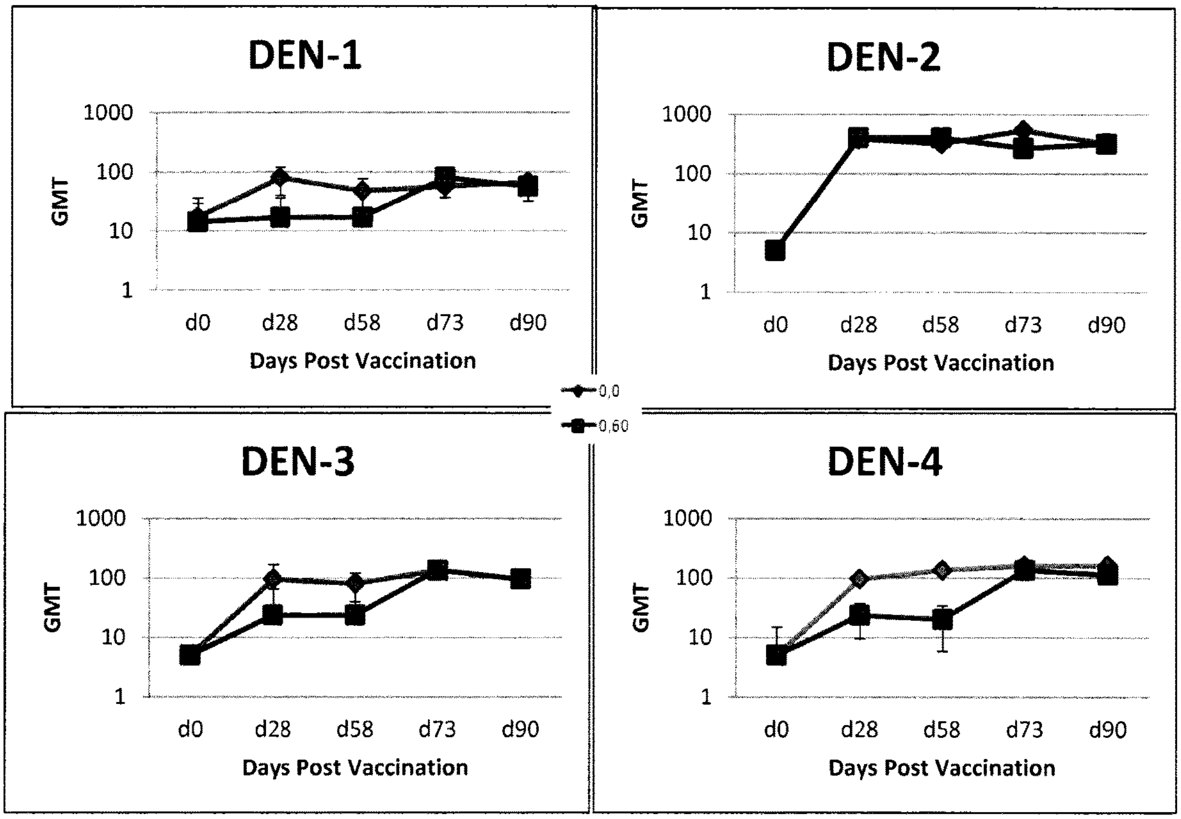
FIG. 22 represents various levels of dengue constructs in a mouse post vaccination, represented as days post vaccination.
Figure 23:
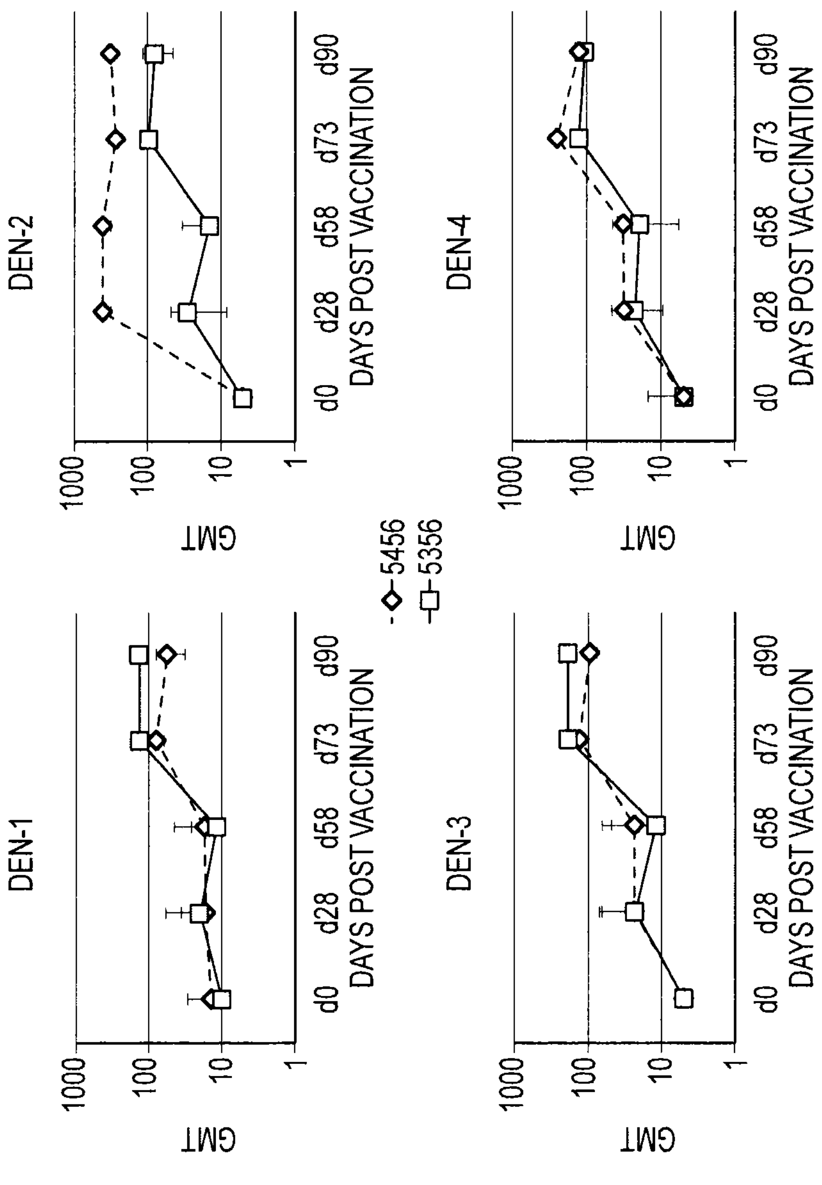
FIG. 23 represents various levels of dengue constructs in a mouse post vaccination, represented as days post vaccination.

Neutralizing antibody responses were compared in Groups 1 (diamonds) and 4 (squares) to test the effect of the immunization schedule on immunogenicity (FIG. 22). FIG. 22 illustrates GMT values demonstrating effect of vaccine schedule on neutralizing antibody response. This indicates that 2 doses on Day 0 and no boost has no adverse effects compared to 1 dose on Day 0 and 1 dose on Day 60. Finally, data from Groups 4 (diamonds) and 5 (squares) were compared to see if decreasing the dose of DENVax-2 had an effect on immunogenicity of DENVax-4. Results show no significant difference in GMT against DENV-4, but GMT against DENV-2 is significantly reduced in Group 5. This indicates that the antibody response elicited by the DENVax-2 dose does not have an adverse effect on the antibody response elicited by DENVax-4 (FIG. 23). FIG. 23 represents GMT values for Groups 4 (diamonds) and 5 (squares) for all DENV serotypes. Results were determined using Plaque Reduction Neutralization Technique.

The results of these experiments support that constructs disclosed herein improve DENV-4 neutralizing antibody responses. Increased DENVax-4 in the dose formulation does show a significant increase in neutralizing antibody production. The DENVax-2 dose also does not appear to have an impact on neutralizing antibody responses of DENVax-4. There may be little to no difference in antibody production between the prime 2 doses vaccination method and prime and boost vaccination method. Sufficient neutralizing antibody titers were produced against DENV-4 1036, the strain that is currently used in DENVax-4. A successful DENV-4 vaccine should be able to adequately neutralize multiple strains of wild type DENV-4 including newly evolved strains with genome modifications, different genotypes and different phenotypes During sequencing there were three point mutations identified between passage 1 and passage 10 in both constructs. These mutations were located in the capsid region of DENVax-4b and in the prM and envelope genes of DENVax-4 as previously discussed. Incorporating these mutations into the constructs may provide increased growth in Vero cells by decreasing the attenuation of the virus, which could improve immunogenicity. As disclosed herein DENVax-4h had a 2-fold increase in neutralizing antibody titers while DENVax-4e had a 1.5-fold increase in neutralizing antibody titers. In other methods, increased DENV-4 immunogenicity is tested and compared to other bivalent, trivalent and tetravalent construct compositions.

Materials and Methods

Cell Culture

Vero cells are mammalian cells derived from African Green Monkey kidney. The Vero cell line used in the in vitro experiments. Vero cells were grown at 37° C. in Dulbecco's Modification of Eagle's Medium (DMEM, Mediatech Inc., Manassas Va.) supplemented with 10% Fetal Bovine serum (FBS, Hyclone, Logan Utah), 2% L-glutamine (Hyclone), and 1% Penicillin-Streptomycin (Pen-Strep, Hyclone). To passage the cells Tryple Express solution (Life Technologies, Grand Island N.Y.) was used to remove the cells from the flask surface.

Viral Infection of Vero Monolayers

Vero cells were seeded on T-75 $cm^2$ flasks approximately 48 hours before infection. DMEM supplemented with 10% FBS, 2% L-glutamine, and 1% Penicillin-Streptomycin was used as cell growth medium. Upon cell confluency, 1 flask was trypsinized using 4 mL of a 0.25% trypsin solution diluted 1:5 in PBS. Cells were counted to establish an MOI. Two of the remaining flasks were infected at a predetermined MO1 in 1 mL of either DENVax-4-P2 ($1^{st}$ generation DENVax-4) or DENVax-4b-P3 or other construct and diluted in BA-1 diluent (Bovine serum albumin, 1×M199, 0.05M Tris-HCL, 1×L-glutamine, 7.5% Sodium bicarbonate, 1×Pen-strep, 1×Fungizone). Viruses were adsorbed onto Vero cells for 90 minutes with rocking every 10 minutes to prevent drying of cell monolayers. After adsorption 20 mL DMEM supplemented with 5% FBS was added to each flask. Flasks were incubated for 7 days at 37° C.

Viral Harvests and Subsequent Infections: Blind Passage

After a pre-determined period, the CPE was observed on each flask and viral supernatant was harvested and stabilized in 20% FBS for storage at −80° C. Previously seeded confluent T-75 $cm^2$ Vero flasks were infected with 1 mL of the viral supernatant from the preceding flask. Virus was adsorbed for 90 minutes with rocking every 10 minutes. After viral adsorption, 20 mL DMEM 5% FBS was added to each flask. New non-infected control flasks were plated every 7 days. This process was repeated every 7 days for 10 subsequent weeks, yielding 10 passages per virus denoted either DENVax-4-P2-P1 through P10 or DENVax-4b-P3-P1 through P10 or other indicated denotations for the various constructs.

Plaque Titration of Viruses

Samples from DENVax-4-P2 and DENVax-4b-P3 and other chimeric constructs were taken weeks 1, 5 and 10 were plaque titrated to measure titer. Virus samples were serially diluted $1\times10^{-1}$ to $1\times10^{-6}$ in BA-1 diluent. Samples were plaque titrated in triplicate, and 100 uL of each dilution was adsorbed to a pre-seeded 6-well plate of Vero cells for 90 minutes with rocking every 8 minutes. After adsorption, wells were overlayed with 4 mL of BSS/Agar (NaCl, KCl, $NaH_2PO_4$—$H_2O$, glucose, $CaCl_2$—$2H_2O$, $MgSO_4$-$7H_2O$) solution and incubated for 4 days at 37° C. On day 4 wells were over-layed with 2 mL BSS/Agar/Neutral Red solution and incubated overnight at 37° C. Plaques were counted on Days 5, 6 and 7.

Growth Curve Analysis

Growth kinetics of the adapted strains was analyzed by performing a growth curve on Vero cells. Vero flasks were seeded as previously described. On day 0 a confluent flask of Vero cells was counted to calculate the virus PFU needed to infect the flasks at an MOI of 0.001. Flasks were infected with 1 mL of DENVax-4, DENVax-4b-P1, DENVax-4b-P10, or DENVax-2 or other chimeric construct (e.g. DENVax-4e, 4h etc.). Viruses were adsorbed to the monolayers for 90 minutes with rocking every 8 minutes. After adsorption, 10 mL cDMEM without FBS supplemented with 1% F-127 was added to each flask and the samples were incubated at 37° C. with 5% $CO_2$. Samples were collected from the supernatant from each flask on Day 2 and Days 4-12. Vaccines were harvested by collecting the entire amount of the supernatant in the flask, and the growth media was replaced with fresh cDMEM-F127 on Day 4 and Days 6-12. Flasks were washed 3 times with PBS during media changes. Samples were stabilized in 1×FTA (FTA:15% trehalose, 1% F-127, 0.1% human serum albumin, PBS) and plaque titrated as previously described to determine titer.

After DENVax-4 and DENVax-4b were both blindly passaged 10 times in Vero cells, each passage was sequenced to identify mutations between P1 and P10. Sequencing reactions were done on DENVax-4-P2-P1 and P10 and DENVax-4b-P3-P1 and P10 at the CDC. Viral RNA was isolated from virus stocks using a QIAmp viral RNA kit. Reverse transcriptase PCR (RT-PCR) was used to transcribe the RNA into DNA, using primers previously designed by the CDC. The primers are designed from the sequences of DENV-2 16681 and DENV-4 1036. Approximately 7-9 PCR fragments per construct were amplified by RT-PCR. The DNA fragments were then sequenced by Beckman Coulter using an automated sequencing reaction, and aligned for comparison.

Sequencing

After the various constructs are passaged 10 or more times in Vero cells, each passage was sequenced to identify mutations. Sequencing reactions were performed on each sample. Viral RNA was isolated from virus stocks using a QIAmp viral RNA kit. Reverse transcriptase PCR (RT-PCR) was used to transcribe the RNA into DNA, using primers previously designed by the CDC. The primers are designed from the sequences of DENV-2 16681 and DENV-4 1036. Approximately 7-9 PCR fragments per construct were amplified by RT-PCR. The DNA fragments were then sequenced by Beckman Coulter using an automated sequencing reaction, and aligned for comparison.

Non-Human Primate Study

Cynomolgus macaques are place in different study groups and vaccinated with doses of tetravalent DENVax having various DENV-4 constructs. One formulation per group can be tested. Formulation 1 can contained a high dose of DENVax with DENVax-4 $1^{st}$ generation, and primates in Group 1 are primed with 2 doses on Day 0 and given no boost. Formulation 2 contained a high dose of DENVax with a DENV-4 construct included and primates in Group 2 can be primed with 2 doses on Day 0 and given no boost. A vaccine can be administered sub-cutaneous or ID or by other method using a needle or needleless system and syringe. Samples to test for serology can be taken on days 0, 28, 58, 73, 90, 128 or other appropriate timing. Neutralizing antibody responses in sera are measured by plaque reduction neutralization technique.

Plaque Reduction Neutralization Technique

To test for neutralizing antibody production in sera samples, a plaque reduction neutralization assay can be used. Vero 6-well plates are seeded 2 days before inoculation to ensure monolayer confluency. Sera samples were diluted serially two-fold in BA-1 diluent in a 96-well plate and incubated with dengue virus for approximately 20 hours at 4° C. After incubation Vero wells are inoculated with prepared virus/sera dilutions. Samples are adsorbed for 90 minutes with rocking every 8 minutes to prevent drying of the monolayers. After adsorption wells are over-layed with 1:1 solution of BSS and agarose, and incubated at 37° C. for 4 days. On Day 4 cells can be over-layed with a 1:1 ratio of BSS supplemented with neutral red solution and agarose. Plaques visible on wells are counted on for example, Days 5, 6, and 7. A GMT value refers to the average dilution of sera that can neutralize 50% of the virus. This is measured by determining the number of plaques formed in the absence of sera, dividing that value by 2 (to account for dilution), and noting which dilution of sera caused plaque formation equal to or less than that amount.

The higher immunogenicity of DENVax-4h (envelope mutation) compared to DENVax-4e (capsid mutation) suggest that the DENVax-4 envelope protein could be optimized. The envelope protein provides epitopes for the generation of neutralizing antibodies, and modifying the sequence to optimize epitope sites for eliciting a strong antibody response may increase antibody titer. The envelope mutation in DENVax-4h at position 417 is in the conserved portion in the stem region. DENV-4 has a different amino acid in this position compared to other flaviviruses. The stem region is in domain III of the E protein where the strongest neutralizing epitope sites exist. Antibodies that bind and neutralize this site prevent the stem region from fusing with the endosomal membrane after endocytosis. In fact, position 417 is conserved among the flavivirus family including DENV-1, -2, -3, and WNV. A reversion from E to K may change the secondary structure to favor a more robust immune response. A further mutation would be to revert back to the conserved charged Aspartic Acid (D) as seen in the other flaviviruses.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed:

1. A tetravalent dengue virus composition comprising:

live, attenuated dengue viruses comprising a dengue-2/4 chimera, wherein the dengue-2/4 chimera comprises a live, attenuated dengue-2 virus backbone having one or more structural proteins from a dengue-4 virus, and wherein a nucleic acid construct encoding the live, attenuated dengue-2/4 chimera further comprises one or more mutations, the one or more mutations comprising:

a mutation in an envelope (E) protein at an amino acid position synonymous to amino acid 417 of dengue-4 when the E protein is from dengue-4, wherein the mutation in the E protein at the position synonymous to amino acid 417 changes glutamic acid to a positively charged amino acid residue;

a mutation in the capsid (C) protein at an amino acid position synonymous to amino acid 107 in the live, attenuated dengue-2 virus backbone, wherein the mutation in the C protein at the position synonymous to amino acid 107 changes cysteine to an aromatic amino acid residue in dengue-2 virus backbone; and a mutation in nonstructural protein 4A (NS4A) at an amino acid position synonymous to amino acid 17 in the dengue-2 virus backbone; and one or more live, attenuated flaviviruses or one or more flavivirus chimeras, wherein the composition comprises all four dengue virus serotypes, dengue-1, dengue-2, dengue-3 and dengue-4.

2. The composition of claim 1, wherein the one or more flavivirus chimeras comprise at least one of dengue-2/1, dengue-2/3 chimeras.

3. The composition of claim 1, wherein the position synonymous to amino acid 417 of dengue-2/4 chimera is a lysine instead of the glutamic acid residue.

4. The composition of claim 1, wherein the aromatic amino acid at the position synonymous to amino acid 107 in the dengue-2 virus backbone of the dengue-2/4 chimera is a tyrosine.

5. The composition of claim 1, wherein the mutation in the NS4A protein at the position synonymous to amino acid 17 in the dengue-2 virus backbone of the dengue-2/4 chimera changes methionine to a basic amino acid.

6. The composition of claim 1, wherein the mutation in the NS4A protein at the position synonymous to amino acid 17 in the dengue-2 virus backbone of the dengue-2/4 chimera changes methionine to a leucine.

7. The composition of claim 1, wherein the dengue-2 virus backbone of the dengue-2/4 chimera contains a mutation at position 57 in the 5'NCR, a mutation at position 53 of NS1 and a mutation at position 250 of NS3.

8. The composition of claim 1, wherein the dengue-2 virus backbone of the dengue-2/4 chimera contains a mutation at position 53 of NS1 and a mutation at position 250 of NS3.

9. The composition of claim 1, wherein amino acid positions 102-106 of the dengue-2 virus backbone of the dengue-2/4 chimera are substituted with synonymous amino acids of a dengue-4 virus at these positions.

10. The composition of claim 1, wherein the dengue-2/4 chimera construct comprises DENVax4e, DENVax4i or DENVax4h.

11. The composition of claim 10, wherein the DENVax4e, DENVax4i and DENVax4h are represented by SEQ ID NO:22, SEQ ID NO:9, or SEQ ID NO:24, respectively.

12. The composition of claim 1, wherein the dengue-4 virus originates from strain 1036.

13. The composition of claim 1, wherein the one or more flavivirus chimeras comprise dengue virus in combination with another flavivirus.

14. The composition of claim 13, wherein the non-dengue flavivirus is selected from the group consisting of West Nile virus, Japanese encephalitis virus, St. Louis encephalitis virus, tickborne encephalitis virus, and yellow fever virus.

15. The composition of claim 13, wherein the flavivirus chimera comprises a dengue-yellow fever flavivirus.

16. The composition of claim 1, wherein the composition comprises a pharmaceutical composition further comprising a pharmaceutically acceptable carrier.

17. A method of inducing an immune response to dengue virus in a subject comprising administering the composition of claim 16 to the subject.

* * * * *

SEQUENCE LISTING

```
<160> NUMBER OF SEQ ID NOS: 39

<210> SEQ ID NO 1
<211> LENGTH: 29
<212> TYPE: PRT
<213> ORGANISM: Artificial
<220> FEATURE:
<223> OTHER INFORMATION: Derived from Dengue virus serotype 2 (DENV-2)

<400> SEQUENCE: 1

Asn Ile Leu Asn Arg Arg Arg Arg Ser Ala Gly Met Ile Ile Met Leu
1               5                   10                  15

Ile Pro Thr Val Met Ala Phe His Leu Thr Thr Arg Asn
            20                  25


<210> SEQ ID NO 2
<211> LENGTH: 29
<212> TYPE: PRT
<213> ORGANISM: Artificial
<220> FEATURE:
<223> OTHER INFORMATION: Derived from Dengue virus serotype 4
      (DENV-4 WT)

<400> SEQUENCE: 2

Asn Ile Leu Asn Gly Arg Lys Arg Ser Thr Ile Thr Leu Leu Cys Leu
1               5                   10                  15
```

Ile Pro Thr Val Met Ala Phe His Leu Ser Thr Arg Asp
20 25

<210> SEQ ID NO 3
<211> LENGTH: 29
<212> TYPE: PRT
<213> ORGANISM: Artificial
<220> FEATURE:
<223> OTHER INFORMATION: Derived from Dengue virus seroptype 4 (DENVax-4ori)

<400> SEQUENCE: 3

Asn Ile Leu Asn Arg Arg Arg Ser Ser Ala Gly Met Ile Ile Met Leu
1 5 10 15

Ile Pro Thr Val Met Ala Phe His Leu Thr Thr Arg Asp
20 25

<210> SEQ ID NO 4
<211> LENGTH: 29
<212> TYPE: PRT
<213> ORGANISM: Artificial
<220> FEATURE:
<223> OTHER INFORMATION: Derived from Dengue virus serotype 4 (DENVax-4b)

<400> SEQUENCE: 4

Asn Ile Leu Asn Arg Arg Arg Ser Ser Thr Ile Thr Leu Leu Cys Leu
1 5 10 15

Ile Pro Thr Val Met Ala Phe His Leu Ser Thr Arg Asp
20 25

<210> SEQ ID NO 5
<211> LENGTH: 29
<212> TYPE: PRT
<213> ORGANISM: Artificial
<220> FEATURE:
<223> OTHER INFORMATION: Derived from Dengue virus serotype 4 (DENVax-4c)

<400> SEQUENCE: 5

Asn Ile Leu Asn Gly Arg Lys Arg Ser Thr Ile Thr Leu Leu Cys Leu
1 5 10 15

Ile Pro Thr Val Met Ala Phe His Leu Ser Thr Arg Asp
20 25

<210> SEQ ID NO 6
<211> LENGTH: 28
<212> TYPE: PRT
<213> ORGANISM: Artificial
<220> FEATURE:
<223> OTHER INFORMATION: Derived from Dengue virus serotype 4 (DENVax-4d)

<400> SEQUENCE: 6

Ile Leu Asn Gly Arg Lys Arg Ser Thr Ile Thr Leu Leu Cys Leu Ile
1 5 10 15

Pro Thr Val Met Ala Phe His Leu Ser Thr Arg Asp
20 25

<210> SEQ ID NO 7
<211> LENGTH: 10722
<212> TYPE: DNA
<213> ORGANISM: Artificial
<220> FEATURE:
<223> OTHER INFORMATION: Dengue virus chimeric construct DENVax-4e -continued

<400> SEQUENCE: 7

```
agttgttagt ctacgtggac cgacaaagac agattctttg agggagctaa gctcaatgta     60
gttctaacag ttttttaatt agagagcaga tctctgatga ataaccaacg gaaaaaggcg    120
aaaaacacgc ctttcaatat gctgaaacgc gagagaaacc gcgtgtcgac tgtgcaacag    180
ctgacaaaga gattctcact tggaatgctg cagggacgag gaccattaaa actgttcatg    240
gccctggtgg cgttccttcg tttcctaaca atcccaccaa cagcagggat attgaagaga    300
tggggaacaa ttaaaaaatc aaaagctatt aatgttttga gagggttcag gaaagagatt    360
ggaaggatgc tgaacatctt gaataggaga cgcagctcaa cgataacatt gctgtacttg    420
attcccaccg taatggcgtt tcacttgtca acgcgtgatg gcgaacccct catgatagtg    480
gcaaaacatg aaagggggag acctctcttg tttaagacaa cagaggggat caacaaatgc    540
actctcattg ccatggactt gggtgaaatg tgtgaggaca ctgtcacgta taaatgcccc    600
ttactggtca ataccgaacc tgaagacatt gattgctggt gcaatctcac gtctacctgg    660
gtcatgtatg ggacatgcac ccagagcgga gaacggagac gagagaagcg ctcagtagct    720
ttaacaccac attcaggaat gggattggaa acaagagctg agacatggat gtcatcggaa    780
ggggcttgga agcatgctca gagagtagag agctggatac tcagaaaccc aggattcgcg    840
ctcttggcag gatttatggc ttatatgatt gggcaaacag gaatccagcg aactgtcttc    900
tttgtcctaa tgatgctggt cgccccatcc tacggaatgc gatgcgtagg agtaggaaac    960
agagactttg tggaaggagt ctcaggtgga gcatgggtcg atctggtgct agaacatgga   1020
ggatgcgtca caaccatggc ccagggaaaa ccaaccttgg attttgaact gactaagaca   1080
acagccaagg aagtggctct gttaagaacc tattgcattg aagcctcaat atcaaacata   1140
accacggcaa caagatgtcc aacgcaagga gagccttatc taaaagagga acaagaccaa   1200
cagtacattt gccggagaga tgtggtagac agagggtggg gcaatggctg tggcttgttt   1260
ggaaaaggag gagttgtgac atgtgcgaag ttttcatgtt cggggaagat aacaggcaat   1320
ttggtccaaa ttgagaacct tgaatacaca gtggttgtaa cagtccacaa tggagacacc   1380
catgcagtag gaaatgacac gtccaatcat ggagttacag ccacgataac tcccaggtca   1440
ccatcggtgg aagtcaaatt gccggactat ggagaactaa cactcgattg tgaacccagg   1500
tctggaattg actttaatga gatgattctg atgaaaatga aaaagaaaac atggcttgtg   1560
cataagcaat ggtttttgga tctacctcta ccatggacag caggagcaga cacatcagag   1620
gttcactgga attacaaaga gagaatggtg acatttaagg ttcctcatgc caagagacag   1680
gatgtgacag tgctgggatc tcaggaagga gccatgcatt ctgccctcgc tggagccaca   1740
gaagtggact ccggtgatgg aaatcacatg tttgcaggac atctcaagtg caaagtccgt   1800
atggagaaat tgagaatcaa gggaatgtca tacacgatgt gttcaggaaa gttctcaatt   1860
gacaaagaga tggcagaaac acagcatggg acaacagtgg tgaaagtcaa gtatgaaggt   1920
gctggagctc cgtgtaaagt ccccatagag ataagagatg tgaacaagga aaaagtggtt   1980
gggcgtatca tctcatccac ccctttggct gagaatacca acagtgtaac caacatagag   2040
ttagaacccc cctttgggga cagctacata gtgataggtg ttggaaacag tgcattaaca   2100
ctccattggt tcaggaaagg gagttccatt ggcaagatgt ttgagtccac atacagaggt   2160
gcaaaacgaa tggccattct aggtgaaaca gcttgggatt ttggttccgt tggtggactg   2220
ttcacatcat tgggaaaggc tgtgcaccag gtttttggaa gtgtgtatac aaccctgttt   2280
ggaggagtct catggatgat tagaatccta attgggttcc tagtgttgtg gattggcacg   2340
```

-continued

```
aactcaagga acacttcaat ggctatgacg tgcatagctg ccggcattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgttc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
```

-continued

```
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct tttattcttg gatgagcgca   6600
aggggcatag ggaagatgac cctgggaatg tgctgcataa tcacggctag catcctccta   6660
tggtacgcac aaatacagcc acactggata gcagcttcaa taatactgga gtttttctc   6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
```

-continued

```
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag    8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
```

```
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agaagcagga  10260
gttctgtggt agaaagcaaa actaacatga aacaaggcta gaagtcaggt cggattaagc  10320
catagtacgg aaaaaactat gctacctgtg agccccgtcc aaggacgtta aaagaagtca  10380
ggccatcata aatgccatag cttgagtaaa ctatgcagcc tgtagctcca cctgagaagg  10440
tgtaaaaaat ccgggaggcc acaaaccatg gaagctgtac gcatggcgta gtggactagc  10500
ggttagagga gacccctccc ttacaaatcg cagcaacaat gggggcccaa ggcgagatga  10560
agctgtagtc tcgctggaag gactagaggt tagaggagac ccccccgaaa caaaaaacag  10620
catattgacg ctgggaaaga ccagagatcc tgctgtctcc tcagcatcat tccaggcaca  10680
gaacgccaga aaatggaatg gtgctgttga atcaacaggt tc                     10722
```

```
<210> SEQ ID NO 8
<211> LENGTH: 10722
<212> TYPE: DNA
<213> ORGANISM: Artificial
<220> FEATURE:
<223> OTHER INFORMATION: Dengue virus chimeric construct DENVax-4h

<400> SEQUENCE: 8
```

```
agttgttagt ctacgtggac cgacaaagac agattctttg agggagctaa gctcaatgta     60
gttctaacag tttttttaatt agagagcaga tctctgatga ataaccaacg gaaaaaggcg    120
aaaaacacgc ctttcaatat gctgaaacgc gagagaaacc gcgtgtcgac tgtgcaacag    180
ctgacaaaga gattctcact tggaatgctg cagggacgag gaccattaaa actgttcatg    240
gccctggtgg cgttccttcg tttcctaaca atcccaccaa cagcagggat attgaagaga    300
tggggaacaa ttaaaaaatc aaaagctatt aatgttttga gagggttcag gaaagagatt    360
ggaaggatgc tgaacatctt gaataggaga cgcagctctg caggcatgat cattatgctg    420
attccaacag tgatggcgtt ccatttaacc acgcgtgatg gcgaacccct catgatagtg    480
gcaaaacatg aaagggggag acctctcttg tttaagacaa cagaggggat caacaaatgc    540
actctcattg ccatggactt gggtgaaatg tgtgaggaca ctgtcacgta taaatgcccc    600
ttactggtca ataccgaacc tgaagacatt gattgctggt gcaatctcac gtctacctgg    660
gtcatgtatg ggacatgcac ccagagcgga gaacggagac gagagaagcg ctcagtagct    720
ttaacaccac attcaggaat gggattggaa acaagagctg agacatggat gtcatcggaa    780
```

-continued

```
ggggcttgga agcatgctca gagagtagag agctggatac tcagaaaccc aggattcgcg    840
ctcttggcag gatttatggc ttatatgatt gggcaaacag gaatccagcg aactgtcttc    900
tttgtcctaa tgatgctggt cgccccatcc tacggaatgc gatgcgtagg agtaggaaac    960
agagactttg tggaaggagt ctcaggtgga gcatgggtcg atctggtgct agaacatgga   1020
ggatgcgtca caaccatggc ccagggaaaa ccaaccttgg attttgaact gactaagaca   1080
acagccaagg aagtggctct gttaagaacc tattgcattg aagcctcaat atcaaacata   1140
accacggcaa caagatgtcc aacgcaagga gagccttatc taaaagagga acaagaccaa   1200
cagtacattt gccggagaga tgtggtagac agagggtggg gcaatggctg tggcttgttt   1260
ggaaaaggag gagttgtgac atgtgcgaag ttttcatgtt cggggaagat aacaggcaat   1320
ttggtccaaa ttgagaacct tgaatacaca gtggttgtaa cagtccacaa tggagacacc   1380
catgcagtag gaaatgacac gtccaatcat ggagttacag ccacgataac tcccaggtca   1440
ccatcggtgg aagtcaaatt gccggactat ggagaactaa cactcgattg tgaacccagg   1500
tctggaattg actttaatga gatgattctg atgaaaatga aaaagaaaac atggcttgtg   1560
cataagcaat ggtttttgga tctacctcta ccatggacag caggagcaga cacatcagag   1620
gttcactgga attacaaaga gagaatggtg acatttaagg ttcctcatgc caagagacag   1680
gatgtgacag tgctgggatc tcaggaagga gccatgcatt ctgccctcgc tggagccaca   1740
gaagtggact ccggtgatgg aaatcacatg tttgcaggac atctcaagtg caaagtccgt   1800
atggagaaat tgagaatcaa gggaatgtca tacacgatgt gttcaggaaa gttctcaatt   1860
gacaaagaga tggcagaaac acagcatggg acaacagtgg tgaaagtcaa gtatgaaggt   1920
gctggagctc cgtgtaaagt ccccatagag ataagagatg tgaacaagga aaaagtggtt   1980
gggcgtatca tctcatccac cccttttggct gagaatacca acagtgtaac caacatagag   2040
ttagaacccc cctttgggga cagctacata gtgataggtg ttggaaacag tgcattaaca   2100
ctccattggt tcaggaaagg gagttccatt ggcaagatgt ttgagtccac atacagaggt   2160
gcaaaacgaa tggccattct aggtaaaaca gcttgggatt ttggttccgt tggtggactg   2220
ttcacatcat tgggaaaggc tgtgcaccag gtttttggaa gtgtgtatac aaccctgttt   2280
ggaggagtct catggatgat tagaatccta attgggttcc tagtgttgtg gattggcacg   2340
aactcaagga acacttcaat ggctatgacg tgcatagctg ccggcattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
```

-continued

```
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgttc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
```

-continued

```
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct tttattctt gatgagcgca    6600
aggggcatag ggaagatgac cctgggaatg tgctgcataa tcacggctag catcctccta   6660
tggtacgcac aaatacagcc acactggata gcagcttcaa taatactgga gtttttctc    6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
```

-continued

```
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agaagcagga  10260
```

gttctgtggt agaaagcaaa actaacatga aacaaggcta gaagtcaggt cggattaagc 10320
catagtacgg aaaaaactat gctacctgtg agccccgtcc aaggacgtta aaagaagtca 10380
ggccatcata aatgccatag cttgagtaaa ctatgcagcc tgtagctcca cctgagaagg 10440
tgtaaaaaat ccgggaggcc acaaaccatg gaagctgtac gcatggcgta gtggactagc 10500
ggttagagga gacccctccc ttacaaatcg cagcaacaat gggggcccaa ggcgagatga 10560
agctgtagtc tcgctggaag gactagaggt tagaggagac ccccccgaaa caaaaaacag 10620
catattgacg ctgggaaaga ccagagatcc tgctgtctcc tcagcatcat tccaggcaca 10680
gaacgccaga aaatggaatg gtgctgttga atcaacaggt tc 10722

<210> SEQ ID NO 9
<211> LENGTH: 10722
<212> TYPE: DNA
<213> ORGANISM: Artificial
<220> FEATURE:
<223> OTHER INFORMATION: Dengue virus chimeric construct DENVax-4i

<400> SEQUENCE: 9
agttgttagt ctacgtggac cgacaaagac agattctttg agggagctaa gctcaatgta 60
gttctaacag ttttttaatt agagagcaga tctctgatga ataaccaacg gaaaaaggcg 120
aaaaacacgc ctttcaatat gctgaaacgc gagagaaacc gcgtgtcgac tgtgcaacag 180
ctgacaaaga gattctcact tggaatgctg cagggacgag gaccattaaa actgttcatg 240
gccctggtgg cgttccttcg tttcctaaca atcccaccaa cagcagggat attgaagaga 300
tggggaacaa ttaaaaaatc aaaagctatt aatgttttga gagggttcag gaaagagatt 360
ggaaggatgc tgaacatctt gaataggaga cgcagctctg caggcatgat cattatgctg 420
attccaacag tgatggcgtt ccatttaacc acgcgtgatg gcgaacccct catgatagtg 480
gcaaaacatg aaagggggag acctctcttg tttaagacaa cagaggggat caacaaatgc 540
actctcattg ccatggactt gggtgaaatg tgtgaggaca ctgtcacgta taaatgcccc 600
ttactggtca ataccgaacc tgaagacatt gattgctggt gcaatctcac gtctacctgg 660
gtcatgtatg ggacatgcac ccagagcgga gaacggagac gagagaagcg ctcagtagct 720
ttaacaccac attcaggaat gggattggaa acaagagctg agacatggat gtcatcggaa 780
ggggcttgga agcatgctca gagagtagag agctggatac tcagaaaccc aggattcgcg 840
ctcttggcag gatttatggc ttatatgatt gggcaaacag gaatccagcg aactgtcttc 900
tttgtcctaa tgatgctggt cgccccatcc tacggaatgc gatgcgtagg agtaggaaac 960
agagactttg tggaaggagt ctcaggtgga gcatgggtcg atctggtgct agaacatgga 1020
ggatgcgtca caaccatggc ccagggaaaa ccaaccttgg attttgaact gactaagaca 1080
acagccaagg aagtggctct gttaagaacc tattgcattg aagcctcaat atcaaacata 1140
accacggcaa caagatgtcc aacgcaagga gagccttatc taaaagagga acaagaccaa 1200
cagtacattt gccggagaga tgtggtagac agagggtggg gcaatggctg tggcttgttt 1260
ggaaaaggag gagttgtgac atgtgcgaag ttttcatgtt cggggaagat aacaggcaat 1320
ttggtccaaa ttgagaacct tgaatacaca gtggttgtaa cagtccacaa tggagacacc 1380
catgcagtag gaaatgacac gtccaatcat ggagttacag ccacgataac tcccaggtca 1440
ccatcggtgg aagtcaaatt gccggactat ggagaactaa cactcgattg tgaacccagg 1500
tctggaattg actttaatga gatgattctg atgaaaatga aaaagaaaac atggcttgtg 1560

-continued

```
cataagcaat ggtttttgga tctacctcta ccatggacag caggagcaga cacatcagag   1620
gttcactgga attacaaaga gagaatggtg acatttaagg ttcctcatgc caagagacag   1680
gatgtgacag tgctgggatc tcaggaagga gccatgcatt ctgccctcgc tggagccaca   1740
gaagtggact ccggtgatgg aaatcacatg tttgcaggac atctcaagtg caaagtccgt   1800
atggagaaat tgagaatcaa gggaatgtca tacacgatgt gttcaggaaa gttctcaatt   1860
gacaaagaga tggcagaaac acagcatggg acaacagtgg tgaaagtcaa gtatgaaggt   1920
gctggagctc cgtgtaaagt ccccatagag ataagagatg tgaacaagga aaaagtggtt   1980
gggcgtatca tctcatccac ccctttggct gagaatacca acagtgtaac caacatagag   2040
ttagaacccc cctttgggga cagctacata gtgataggtg ttggaaacag tgcattaaca   2100
ctccattggt tcaggaaagg gagttccatt ggcaagatgt ttgagtccac atacagaggt   2160
gcaaaacgaa tggccattct aggtgaaaca gcttgggatt ttggttccgt tggtggactg   2220
ttcacatcat tgggaaaggc tgtgcaccag gtttttggaa gtgtgtatac aaccctgttt   2280
ggaggagtct catggatgat tagaatccta attgggttcc tagtgttgtg gattggcacg   2340
aactcaagga acacttcaat ggctatgacg tgcatagctg ccggcattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
```

-continued

```
caaaacgcat ggaaagtgag ttgcacaata ttggcagtgg tgtccgtttc cccactgttc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
```

-continued

```
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcttgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct ttttattctt gatgagcgca   6600
aggggcatag ggaagatgac cctgggaatg tgctgcataa tcacggctag catcctccta   6660
tggtacgcac aaatacagcc acactggata gcagcttcaa taatactgga gtttttctc    6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag    8640
aaagtggaca cgagaaccca agaaccgaaa gaaggcacga agaaactaat gaaaataaca   8700
```

gcagagtggc tttggaaaga attagggaag aaaaagacac ccaggatgtg caccagagaa 8760
gaattcacaa gaaaggtgag aagcaatgca gccttggggg ccatattcac tgatgagaac 8820
aagtggaagt cggcacgtga ggctgttgaa gatagtaggt tttgggagct ggttgacaag 8880
gaaaggaatc tccatcttga aggaaagtgt gaaacatgtg tgtacaacat gatgggaaaa 8940
agagagaaga agctagggga attcggcaag gcaaaaggca gcagagccat atggtacatg 9000
tggcttggag cacgcttctt agagtttgaa gccctaggat tcttaaatga agatcactgg 9060
ttctccagag agaactccct gagtggagtg gaaggagaag ggctgcacaa gctaggttac 9120
attctaagag acgtgagcaa gaaagaggga ggagcaatgt atgccgatga caccgcagga 9180
tgggatacaa gaatcacact agaagaccta aaaaatgaag aaatggtaac aaaccacatg 9240
gaaggagaac acaagaaact agccgaggcc attttcaaac taacgtacca aaacaaggtg 9300
gtgcgtgtgc aaagaccaac accaagaggc acagtaatgg acatcatatc gagaagagac 9360
caaagaggta gtggacaagt tggcacctat ggactcaata ctttcaccaa tatggaagcc 9420
caactaatca gacagatgga gggagaagga gtctttaaaa gcattcagca cctaacaatc 9480
acagaagaaa tcgctgtgca aaactggtta gcaagagtgg ggcgcgaaag gttatcaaga 9540
atggccatca gtggagatga ttgtgttgtg aaacctttag atgacaggtt cgcaagcgct 9600
ttaacagctc taaatgacat gggaaagatt aggaaagaca tacaacaatg ggaaccttca 9660
agaggatgga atgattggac acaagtgccc ttctgttcac accatttcca tgagttaatc 9720
atgaaagacg gtcgcgtact cgttgttcca tgtagaaacc aagatgaact gattggcaga 9780
gcccgaatct cccaaggagc agggtggtct ttgcgggaga cggcctgttt ggggaagtct 9840
tacgcccaaa tgtggagctt gatgtacttc cacagacgcg acctcaggct ggcggcaaat 9900
gctatttgct cggcagtacc atcacattgg gttccaacaa gtcgaacaac ctggtccata 9960
catgctaaac atgaatggat gacaacggaa gacatgctga cagtctggaa cagggtgtgg 10020
attcaagaaa acccatggat ggaagacaaa actccagtgg aatcatggga ggaaatccca 10080
tacttgggga aaagagaaga ccaatggtgc ggctcattga ttgggttaac aagcagggcc 10140
acctgggcaa agaacatcca agcagcaata aatcaagtta gatcccttat aggcaatgaa 10200
gaatacacag attacatgcc atccatgaaa agattcagaa gagaagagga agaagcagga 10260
gttctgtggt agaaagcaaa actaacatga aacaaggcta gaagtcaggt cggattaagc 10320
catagtacgg aaaaaactat gctacctgtg agccccgtcc aaggacgtta aaagaagtca 10380
ggccatcata aatgccatag cttgagtaaa ctatgcagcc tgtagctcca cctgagaagg 10440
tgtaaaaaat ccgggaggcc acaaaccatg gaagctgtac gcatggcgta gtggactagc 10500
ggttagagga gacccctccc ttacaaatcg cagcaacaat gggggcccaa ggcgagatga 10560
agctgtagtc tcgctggaag gactagaggt tagaggagac ccccccgaaa caaaaaacag 10620
catattgacg ctgggaaaga ccagagatcc tgctgtctcc tcagcatcat tccaggcaca 10680
gaacgccaga aaatggaatg gtgctgttga atcaacaggt tc 10722

<210> SEQ ID NO 10
<211> LENGTH: 10699
<212> TYPE: DNA
<213> ORGANISM: Artificial
<220> FEATURE:
<223> OTHER INFORMATION: Synthetic construct

<400> SEQUENCE: 10

-continued

```
agttgttagt ctacgtggac cgacaagaac agtttcgact cggaagcttg cttaacgtag     60
tgctgacagt tttttattag agagcagatc tctgatgaac aaccaacgga aaaagacggg    120
aaaaccgtct atcaatatgc tgaaacgcgt gagaaaccgt gtgtcaactg gatcacagtt    180
ggcgaagaga ttctcaagag gattgctgaa cggccaagga ccaatgaaat tggttatggc    240
atttatagct ttcctcagat ttctagccat tccaccgaca gcaggagtct tggctagatg    300
gggtaccttt aagaagtcgg gggctattaa ggtcttaaaa ggcttcaaga aggagatctc    360
aaacatgctg agcattatca acaaacggaa aaagacatcg ctctgtctca tgatgatgtt    420
accagcaaca cttgctttcc acttaacttc acgagatgga gagccgcgca tgattgtggg    480
gaagaatgaa agaggaaaat ccctactttt caagacagcc tctggaatca acatgtgcac    540
actcatagcc atggatctgg gagagatgtg tgatgacacg gtcacttaca aatgccccca    600
cattaccgaa gtggagcctg aagacattga ctgctggtgc aaccttacat cgacatgggt    660
gacttatgga acatgcaatc aagctggaga gcatagacgc gataagagat cagtggcgtt    720
agctccccat gttggcatgg gactggacac acgcactcaa acctggatgt cggctgaagg    780
agcttggaga caagtcgaga aggtagagac atgggccctt aggcacccag ggtttaccat    840
actagcccta tttcttgccc attacatagg cacttccttg acccagaaag tggttatttt    900
tatactatta atgctggtta ccccatccat gacaatgaga tgtgtaggag taggaaacag    960
agattttgtg gaaggcctat cgggagctac gtgggttgac gtggtgctcg agcacggtgg   1020
gtgtgtgact accatggcta agaacaagcc cacgctggac atagagcttc agaagaccga   1080
ggccacccaa ctggcgaccc taaggaagct atgcattgag ggaaaaatta ccaacataac   1140
aaccgactca agatgtccca cccaagggga agcgatttta cctgaggagc aggaccagaa   1200
ctacgtgtgt aagcatacat acgtggacag aggctgggga aacggttgtg gtttgtttgg   1260
caagggaagc ttggtgacat gcgcgaaatt tcaatgttta gaatcaatag agggaaaagt   1320
ggtgcaacat gagaacctca aatacaccgt catcatcaca gtgcacacag gagaccaaca   1380
ccaggtggga aatgaaacgc agggagtcac ggctgagata acaccccagg catcaaccgc   1440
tgaagccatt ttacctgaat atggaaccct cgggctagaa tgctcaccac ggacaggttt   1500
ggatttcaat gaaatgatct cattgacaat gaagaacaaa gcatggatgg tacatagaca   1560
atggttcttt gacttacccc taccatggac atcaggagct acagcagaaa caccaacttg   1620
gaacaggaaa gagcttcttg tgacatttaa aaatgcacat gcaaaaaagc aagaagtagt   1680
tgttcttgga tcacaagagg gagcaatgca tacagcactg acaggagcta cagagatcca   1740
aacctcagga ggcacaagta tctttgcggg gcacttaaaa tgtagactca agatggacaa   1800
attggaactc aaggggatga gctatgcaat gtgcttgagt agctttgtgt tgaagaaaga   1860
agtctccgaa acgcagcatg ggacaatact cattaaggtt gagtacaaag gggaagatgc   1920
accctgcaag attcctttct ccacggagga tggacaagga aaagctcaca atggcagact   1980
gatcacagcc aatccagtgg tgaccaagaa ggaggagcct gtcaacattg aggctgaacc   2040
tccttttgga gaaagtaaca tagtaattgg aattggagac aaagccctga aaatcaactg   2100
gtacaagaag ggaagctcga ttgggaagat gttcgaggcc actgccagag gtgcaaggcg   2160
catggccatc ttgggagaca cagcctggga ctttggatca gtgggtggtg ttttgaattc   2220
attagggaaa atggtccacc aaatatttgg gagtgcttac acagccctat ttggtggagt   2280
ctcctggatg atgaaaattg gaataggtgt cctcttaacc tggatagggt tgaactcaaa   2340
aaatacttct atgtcatttt catgcatcgc gataggaatc attacactct atctgggagc   2400
```

```
cgtggtgcaa gctgacatgg ggtgtgtcat aaactggaaa ggcaaagaac tcaaatgtgg   2460
aagtggaatt ttcgtcacta atgaggtcca cacctggaca gagcaataca aatttcaagc   2520
agactccccc aagagactgg caacagccat tgcaggcgct tgggaaaatg gagtgtgcgg   2580
aattaggtca acaaccagaa tggagaacct cttgtggaag caaatagcca atgaactgaa   2640
ttacatatta tgggaaaaca acattaaatt aacggtagtt gtaggcgaca taactggggt   2700
cttagagcaa gggaaaagaa cactaacacc acaacccatg gagctaaaat attcttggaa   2760
aacatgggga aaggcaaaaa tagtgacagc tgaaacacaa aattcctctt tcataataga   2820
tgggccaagc acaccggagt gtccaagtgc ctcaagagca tggaatgtgt gggaggtgga   2880
ggattacggg ttcggagttt tcacaaccaa catatggctg aaactccgag aggtgtacac   2940
ccaactatgt gaccataggc taatgtcggc agccgtcaag gatgagaggg ctgtacatgc   3000
cgacatgggc tattggatag aaagccaaaa gaatgggagt tggaagctag aaaaagcatc   3060
cttcatagag gtgaaaacct gcacatggcc aaaatcacac actctctgga gcaatggtgt   3120
gctagagagt gacatgatta tcccaaagag tctagctggt cccatttcgc aacacaacca   3180
caggcccggg taccacaccc aaacggcagg accctggcac ttaggaaaat tggagctgga   3240
cttcaactat tgtgaaggaa caacagttgt catctcagaa aactgtggga caagaggccc   3300
atcattgaga acaacaacgg tgtcagggaa gttgatacac gaatggtgct gccgctcgtg   3360
cacacttcct cccctacgat acatgggaga agacggctgc tggtatggca tggaaatcag   3420
acccattaat gagaaagaag agaatatggt aaagtctcta gcctcagcag ggagtggaaa   3480
ggtggacaac ttcacaatgg gtgtcttgtg tttggcaatc ctctttgaag aggtgatgag   3540
aggaaaattt gggaaaaaac acatgattgc aggggttctc ttcacgtttg tgctcctcct   3600
ctcagggcaa ataacatgga gagacatggc gcacacactc ataatgattg ggtccaacgc   3660
ctctgacaga atggggatgg gcgtcactta cctagctcta attgcaacat ttaaaattca   3720
gccattcctg gctttgggat tcttcctgag gaaactgaca tctagagaaa atttattgct   3780
gggagttggg ttggccatgg cagcaacgtt acgactgcca gaggacattg aacagatggc   3840
gaatggaatt gctttggggc tcatggctct taaactgata acacaatttg aaacatacca   3900
actatggacg gcattagttt ccctaacgtg ttcaaataca attttcacgt tgactgttgc   3960
ctggagaaca gccactctga ttttagccgg aatttcgctt ttgccagtgt gccagtcttc   4020
gagcatgagg aaaacagatt ggctcccaat gactgtggca gctatgggag ctcaacccct   4080
accacttttt attttcagtc tgaaagatac actcaaaagg agaagctggc cactgaatga   4140
gggggtgatg gcagttggac ttgtgagcat tctagctagt tctctcctta ggaatgatgt   4200
gcctatggct ggaccattag tggctggggg cttgctgata gcgtgctacg tcataactgg   4260
cacgtcagca gacctcactg tagaaaaagc agcagatgta acatgggagg aagaggccga   4320
gcaaacagga gtgtcccaca atttaatggt cacagttgat gatgatggaa caatgagaat   4380
aaaagatgac gagactgaga acatcttaac agtgctttta aaaacagcac tactaatagt   4440
atcaggcatc tttccatact ccatacccgc aacactgttg gtctggcata cttggcaaaa   4500
gcaaacccaa agatccggcg tcctatggga cgtacccagc cccccagaga cacagaaagc   4560
ggaactggaa gaaggggtct ataggatcaa acagcaagga atttttggga aaacccaagt   4620
gggggttgga gtacagaaag aaggagtttt ccacaccatg tggcatgtca caagaggggc   4680
agtgttgaca cacaatggga aaagactgga accaaactgg gctagcgtga aaaaagatct   4740
```

-continued

```
gatttcatac ggaggaggat ggagattgag tgcacaatgg caaaaggggg aggaggtgca   4800
ggttattgcc gtagagcctg ggaagaaccc aaagaacttt caaaccatgc caggcatttt   4860
tcagacaaca acaggggaaa taggagcaat tgcactggat ttcaagcctg gaacttcagg   4920
atctcccatc ataaacagag agggaaaggt agtgggactg tatggcaatg gagtggttac   4980
aaagaatgga ggctatgtca gtggaatagc gcaaacaaat gcagaaccag atggaccgac   5040
accagagttg gaagaagaga tgttcaaaaa gcgaaatcta accataatgg atctccatcc   5100
tgggtcagga aagacgcgga aatatcttcc agctattgtt agagaggcaa tcaagagacg   5160
cttaaggact ctaattttgg caccaacaag ggtagttgca gctgagatgg aagaagcatt   5220
gaaagggctc ccaataaggt atcaaacaac tgcaacaaaa tctgaacaca caggaagaga   5280
gattgttgat ctaatgtgtc acgcaacgtt cacaatgcgc ttgctgtcac cagtcagggt   5340
tccaaactac aacttgataa taatggatga ggcccatttc acagacccag ccagtatagc   5400
ggctagaggg tacatatcaa ctcgtgtagg aatgggagag gcagccgcaa ttttcatgac   5460
agcaacaccc cctggaacag ctgatgcctt tcctcagagc aacgctccaa ttcaagatga   5520
agagagagac ataccggaac gctcatggaa ttcaggcaat gaatggatta ctgactttgt   5580
tgggaagaca gtgtggtttg tccctagcat caaagccgga aatgacatag caaactgctt   5640
gcggaaaaat ggaaaaaagg ttattcaact cagcaggaag acctttgaca cagaatatca   5700
aaagaccaaa ctgaatgatt gggactttgt ggtgacaaca gacatttcag aaatgggagc   5760
caatttcaaa gcagatagag tgatcgaccc aagaagatgt ctcaagccgg tgattttgac   5820
agatggaccc gagcgggtga tcctggctgg accaatgcca gtcaccgtag cgagcgctgc   5880
gcaaaggaga gggagagttg gcaggaaccc acaaaaagaa aatgaccagt acatattcat   5940
gggccagcct ctcaacaatg atgaagacca tgctcactgg acagaagcaa aaatgctgct   6000
ggacaacatc aacacaccag aagggattat accagctctc tttgaaccag aaagggagaa   6060
gtcagccgcc atagacggcg aataccgcct gaagggtgag tccaggaaga ctttcgtgga   6120
actcatgagg aggggtgacc tcccagtttg gctagcccat aaagtagcat cagaagggat   6180
caaatataca gatagaaaat ggtgctttga tggagaacgt aataatcaaa ttttagagga   6240
gaatatggat gtggaaatct ggacaaagga aggagaaaag aaaaaactga gacctaggtg   6300
gcttgatgcc cgcacttatt cagatccttt agcactcaaa gaattcaagg attttgcagc   6360
tggcagaaag tcaatcgccc ttgatcttgt gacagaaata ggaagagtgc cttcacactt   6420
agcccacaga acgagaaacg ccctggataa tttggtgatg ctgcacacgt cagaacatgg   6480
cggtagggcc tacaggcatg cagtggagga actaccagaa acgatggaaa cactcttact   6540
cctgggactg atgatcttgt taacaggtgg agcaatgctc ttcttgatat caggtaaagg   6600
gattggaaag acttcaatag gactcatttg tgtaattgct tccagcggca tgttatggat   6660
ggctgatgtc ccactccaat ggatcgcatc ggctatagtc ctggagtttt ttatgatggt   6720
gttgctcata ccagaaccag aaaagcagag aactccccaa gacaaccaac tcgcatatgt   6780
cgtgataggc atacttacat tggctgcaat agtagcggcc aatgaaatgg gactgttgga   6840
aactacaaag agagatttag gaatgtctaa agaaccaggt gttgtttctc caaccagcta   6900
tttggatgtg gacttgcacc cagcatcagc ctggacattg tacgccgtgg ccacaacagt   6960
aataacacca atgttgagac acaccataga gaattccaca gcaaatgtgt ctctggcagc   7020
catagctaac caggcagtgg tcctgatggg tttagacaaa ggatggccga tatcgaaaat   7080
ggacttgggc gtaccactat tggcactggg ttgctattca caagtgaacc cactaactct   7140
```

```
tgcagcggca gtacttttgc tagtcacaca ttatgcaatt ataggtccag gattgcaggc   7200
aaaagccacc cgtgaagctc agaaaaggac agctgctgga ataatgaaga atccaacggt   7260
ggatggaata atgacaatag acctagatcc tgtaatatat gattcaaaat ttgaaaagca   7320
actaggacag gtcatgctcc tggttctgtg tgcagtccaa cttttattga tgagaacatc   7380
atgggccttg tgtgaagttc taaccctagc cacaggacca ataacaacac tctgggaagg   7440
atcacctggg aagttctgga acaccacgat agctgtttcc atggcgaaca tctttagagg   7500
gagctattta gcaggagctg ggcttgcttt ttctatcatg aaatcagttg gaacaggaaa   7560
gagaggaaca gggtcacaag gtgaaacctt aggagaaaag tggaaaaaga aattaaatca   7620
gttatcccgg aaagagtttg acctttacaa gaaatccgga atcaccgaag tggatagaac   7680
agaagccaaa gaagggttaa aaagaggaga aataacacac catgccgtgt ccagaggcag   7740
cgcaaaactt caatggttcg tggagagaaa catggtcatt cctgaaggaa gagtcataga   7800
cctaggctgt ggaagaggag gctggtcata ttactgtgca ggactgaaaa aagttacaga   7860
agtgcgagga tacacaaaag gcggcccagg acacgaagaa ccagtaccta tgtctacata   7920
cggatggaac atagtcaagt taatgagtgg aaaggatgtt ttttatctgc cacctgaaaa   7980
gtgtgatacc ctattgtgtg acattggaga atcttcacca agcccaacag tggaagaaag   8040
cagaaccata agagttttga agatggttga accatggcta aagaacaacc agttttgcat   8100
taaagtattg aacccataca tgccaactgt gattgagcac ttagaaagac tacaaaggaa   8160
acatggagga atgcttgtga gaaatccact ctcacgaaac tccacgcacg aaatgtattg   8220
gatatccaat ggtacaggca atatcgtctc ttcagtcaac atggtatcca gattgctact   8280
gaacagattc acaatgacac acaggagacc caccatagag aaagatgtgg atctaggagc   8340
aggaacccga catgtcaatg cggaaccaga aacacccaac atggatgtca ttggggaaag   8400
aataaaaagg atcaaagagg agcatagttc aacatggcac tatgatgatg aaaatcctta   8460
caaaacgtgg gcttaccatg gatcctatga agtaaaagcc acaggctcag cctcctccat   8520
gataaatgga gtcgtgaaac tcctcacaaa accatgggat gtggtgccca tggtgacaca   8580
gatggcaatg acagatacaa ctccattcgg ccagcaaaga gtttttaaag agaaagtgga   8640
caccaggaca cctaggccca tgccaggaac aagaaaggtt atggagatca cagcggagtg   8700
gctttggagg accctgggaa ggaacaaaag acccagatta tgcacaaggg aggaattcac   8760
aaagaaggtc agaaccaacg cagctatggg cgctgtcttc acagaagaga accaatggga   8820
cagtgcgaga gctgctgttg aggacgaaga attttggaaa cttgtggaca gagaacgtga   8880
actccacaaa ctgggcaagt gtggaagctg cgtttacaac atgatgggca agagagagaa   8940
aaaacttgga gagtttggta aagcaaaagg cagtagggct atatggtaca tgtggttggg   9000
agccaggtac cttgagttcg aggcgctcgg attcctcaat gaagaccact ggttctcgcg   9060
tgaaaactct tacagtggag tagaaggaga aggactgcac aagctgggat acatcttgag   9120
agatatttcc aagatacccg gaggagccat gtatgctgat gacacagccg gttgggacac   9180
aagaataaca gaagatgacc tgcacaatga ggaaaaaatc acacagcaga tggaccctga   9240
acacaggcag ctagcgaacg ctatattcaa gctcacatac caaaacaaag tggtcaaagt   9300
ccaacgacca actccaaagg gcacggtaat ggacatcata tctaggaaag accaaagagg   9360
cagtggacag gtgggaactt atggtctgaa cacattcacc aacatggaag cccagctaat   9420
cagacaaatg gaaggagaag gcgtgttgtc aaaggcagac ctcgagaacc cccatccgct   9480
```

```
agagaagaaa attacacaat ggttggaaac taaaggagtg gaaaggttaa aaagaatggc   9540
catcagcggg gatgattgcg ttgtgaaacc aatcgacgac agattcgcca atgccctgct   9600
tgccctgaac gatatgggaa aggttagaaa ggacatacct caatggcagc catcaaaggg   9660
atggcatgat tggcaacagg tccccttctg ctcccaccac tttcatgaat tgatcatgaa   9720
agatggaaga aagttggtag ttccctgcag accccaggac gaactaatag gaagagcgag   9780
aatctcccaa ggagcaggat ggagccttag agaaactgca tgtctaggga aagcctacgc   9840
tcaaatgtgg gctctcatgt attttcacag aagagatctt agactagcat ccaacgccat   9900
atgttcagca gtaccagtcc actgggtccc cacgagcaga acgacatggt ctattcatgc   9960
tcaccatcag tggatgacta cagaagacat gcttactgtc tggaacaggg tgtggataga  10020
ggacaatcca tggatggaag acaaaactcc agtcacaacg tgggaagatg ttccatatct  10080
agggaagaga gaagaccaat ggtgcggatc actcataggt ctcacttcca gagcaacctg  10140
ggcccagaac atactcacag caatccaaca ggtgagaagc ctcataggca atgaagagtt  10200
tctggactac atgccttcga tgaagagatt caggaaggag gaggagtcag agggagccat  10260
ttggtaaaag caggaggtaa actgtcaggc cacattaagc cacagtacgg aagaagctgt  10320
gcagcctgtg agccccgtcc aaggacgtta aaagaagaag tcaggcccaa aagccacggt  10380
ttgagcaaac cgtgctgcct gtagctccgt cgtggggacg taaagcctgg gaggctgcaa  10440
accgtggaag ctgtacgcac ggtgtagcag actagtggtt agaggagacc cctcccatga  10500
cacaacgcag cagcggggcc cgagcactga gggaagctgt acctccttgc aaaggactag  10560
aggttagagg agaccccccg caaacaaaaa cagcatattg acgctgggag agaccagaga  10620
tcctgctgtc tcctcagcat cattccaggc acagaacgcc agaaaatgga atggtgctgt  10680
tgaatcaaca ggttctagt                                               10699
```

<210> SEQ ID NO 11
<211> LENGTH: 3390
<212> TYPE: PRT
<213> ORGANISM: Artificial
<220> FEATURE:
<223> OTHER INFORMATION: Synthetic construct

<400> SEQUENCE: 11

```
Met Asn Asn Gln Arg Lys Lys Thr Gly Lys Pro Ser Ile Asn Met Leu
1               5                   10                  15

Lys Arg Val Arg Asn Arg Val Ser Thr Gly Ser Gln Leu Ala Lys Arg
            20                  25                  30

Phe Ser Arg Gly Leu Leu Asn Gly Gln Gly Pro Met Lys Leu Val Met
        35                  40                  45

Ala Phe Ile Ala Phe Leu Arg Phe Leu Ala Ile Pro Pro Thr Ala Gly
    50                  55                  60

Val Leu Ala Arg Trp Gly Thr Phe Lys Lys Ser Gly Ala Ile Lys Val
65                  70                  75                  80

Leu Lys Gly Phe Lys Lys Glu Ile Ser Asn Met Leu Ser Ile Ile Asn
                85                  90                  95

Lys Arg Lys Lys Thr Ser Leu Cys Leu Met Met Met Leu Pro Ala Thr
            100                 105                 110

Leu Ala Phe His Leu Thr Ser Arg Asp Gly Glu Pro Arg Met Ile Val
        115                 120                 125

Gly Lys Asn Glu Arg Gly Lys Ser Leu Leu Phe Lys Thr Ala Ser Gly
    130                 135                 140
```

-continued

Ile Asn Met Cys Thr Leu Ile Ala Met Asp Leu Gly Glu Met Cys Asp
145 150 155 160

Asp Thr Val Thr Tyr Lys Cys Pro His Ile Thr Glu Val Glu Pro Glu
165 170 175

Asp Ile Asp Cys Trp Cys Asn Leu Thr Ser Thr Trp Val Thr Tyr Gly
180 185 190

Thr Cys Asn Gln Ala Gly Glu His Arg Arg Asp Lys Arg Ser Val Ala
195 200 205

Leu Ala Pro His Val Gly Met Gly Leu Asp Thr Arg Thr Gln Thr Trp
210 215 220

Met Ser Ala Glu Gly Ala Trp Arg Gln Val Glu Lys Val Glu Thr Trp
225 230 235 240

Ala Leu Arg His Pro Gly Phe Thr Ile Leu Ala Leu Phe Leu Ala His
245 250 255

Tyr Ile Gly Thr Ser Leu Thr Gln Lys Val Val Ile Phe Ile Leu Leu
260 265 270

Met Leu Val Thr Pro Ser Met Thr Met Arg Cys Val Gly Val Gly Asn
275 280 285

Arg Asp Phe Val Glu Gly Leu Ser Gly Ala Thr Trp Val Asp Val Val
290 295 300

Leu Glu His Gly Gly Cys Val Thr Thr Met Ala Lys Asn Lys Pro Thr
305 310 315 320

Leu Asp Ile Glu Leu Gln Lys Thr Glu Ala Thr Gln Leu Ala Thr Leu
325 330 335

Arg Lys Leu Cys Ile Glu Gly Lys Ile Thr Asn Ile Thr Thr Asp Ser
340 345 350

Arg Cys Pro Thr Gln Gly Glu Ala Ile Leu Pro Glu Glu Gln Asp Gln
355 360 365

Asn Tyr Val Cys Lys His Thr Tyr Val Asp Arg Gly Trp Gly Asn Gly
370 375 380

Cys Gly Leu Phe Gly Lys Gly Ser Leu Val Thr Cys Ala Lys Phe Gln
385 390 395 400

Cys Leu Glu Ser Ile Glu Gly Lys Val Val Gln His Glu Asn Leu Lys
405 410 415

Tyr Thr Val Ile Ile Thr Val His Thr Gly Asp Gln His Gln Val Gly
420 425 430

Asn Glu Thr Gln Gly Val Thr Ala Glu Ile Thr Pro Gln Ala Ser Thr
435 440 445

Ala Glu Ala Ile Leu Pro Glu Tyr Gly Thr Leu Gly Leu Glu Cys Ser
450 455 460

Pro Arg Thr Gly Leu Asp Phe Asn Glu Met Ile Ser Leu Thr Met Lys
465 470 475 480

Asn Lys Ala Trp Met Val His Arg Gln Trp Phe Phe Asp Leu Pro Leu
485 490 495

Pro Trp Thr Ser Gly Ala Thr Ala Glu Thr Pro Thr Trp Asn Arg Lys
500 505 510

Glu Leu Leu Val Thr Phe Lys Asn Ala His Ala Lys Lys Gln Glu Val
515 520 525

Val Val Leu Gly Ser Gln Glu Gly Ala Met His Thr Ala Leu Thr Gly
530 535 540

Ala Thr Glu Ile Gln Thr Ser Gly Gly Thr Ser Ile Phe Ala Gly His
545 550 555 560

Leu Lys Cys Arg Leu Lys Met Asp Lys Leu Glu Leu Lys Gly Met Ser

-continued

```
                565                 570                 575

Tyr Ala Met Cys Leu Ser Ser Phe Val Leu Lys Lys Glu Val Ser Glu
            580                 585                 590

Thr Gln His Gly Thr Ile Leu Ile Lys Val Glu Tyr Lys Gly Glu Asp
        595                 600                 605

Ala Pro Cys Lys Ile Pro Phe Ser Thr Glu Asp Gly Gln Gly Lys Ala
    610                 615                 620

His Asn Gly Arg Leu Ile Thr Ala Asn Pro Val Val Thr Lys Lys Glu
625                 630                 635                 640

Glu Pro Val Asn Ile Glu Ala Glu Pro Pro Phe Gly Glu Ser Asn Ile
                645                 650                 655

Val Ile Gly Ile Gly Asp Lys Ala Leu Lys Ile Asn Trp Tyr Lys Lys
            660                 665                 670

Gly Ser Ser Ile Gly Lys Met Phe Glu Ala Thr Ala Arg Gly Ala Arg
        675                 680                 685

Arg Met Ala Ile Leu Gly Asp Thr Ala Trp Asp Phe Gly Ser Val Gly
    690                 695                 700

Gly Val Leu Asn Ser Leu Gly Lys Met Val His Gln Ile Phe Gly Ser
705                 710                 715                 720

Ala Tyr Thr Ala Leu Phe Gly Gly Val Ser Trp Met Met Lys Ile Gly
                725                 730                 735

Ile Gly Val Leu Leu Thr Trp Ile Gly Leu Asn Ser Lys Asn Thr Ser
            740                 745                 750

Met Ser Phe Ser Cys Ile Ala Ile Gly Ile Ile Thr Leu Tyr Leu Gly
        755                 760                 765

Ala Val Val Gln Ala Asp Met Gly Cys Val Ile Asn Trp Lys Gly Lys
    770                 775                 780

Glu Leu Lys Cys Gly Ser Gly Ile Phe Val Thr Asn Glu Val His Thr
785                 790                 795                 800

Trp Thr Glu Gln Tyr Lys Phe Gln Ala Asp Ser Pro Lys Arg Leu Ala
                805                 810                 815

Thr Ala Ile Ala Gly Ala Trp Glu Asn Gly Val Cys Gly Ile Arg Ser
            820                 825                 830

Thr Thr Arg Met Glu Asn Leu Leu Trp Lys Gln Ile Ala Asn Glu Leu
        835                 840                 845

Asn Tyr Ile Leu Trp Glu Asn Asn Ile Lys Leu Thr Val Val Val Gly
    850                 855                 860

Asp Ile Thr Gly Val Leu Glu Gln Gly Lys Arg Thr Leu Thr Pro Gln
865                 870                 875                 880

Pro Met Glu Leu Lys Tyr Ser Trp Lys Thr Trp Gly Lys Ala Lys Ile
                885                 890                 895

Val Thr Ala Glu Thr Gln Asn Ser Ser Phe Ile Ile Asp Gly Pro Ser
            900                 905                 910

Thr Pro Glu Cys Pro Ser Ala Ser Arg Ala Trp Asn Val Trp Glu Val
        915                 920                 925

Glu Asp Tyr Gly Phe Gly Val Phe Thr Thr Asn Ile Trp Leu Lys Leu
    930                 935                 940

Arg Glu Val Tyr Thr Gln Leu Cys Asp His Arg Leu Met Ser Ala Ala
945                 950                 955                 960

Val Lys Asp Glu Arg Ala Val His Ala Asp Met Gly Tyr Trp Ile Glu
                965                 970                 975

Ser Gln Lys Asn Gly Ser Trp Lys Leu Glu Lys Ala Ser Phe Ile Glu
            980                 985                 990
```

```
Val Lys Thr Cys Thr Trp Pro Lys  Ser His Thr Leu Trp  Ser Asn Gly
        995                 1000                1005

Val Leu  Glu Ser Asp Met Ile  Ile Pro Lys Ser Leu  Ala Gly Pro
    1010                 1015                 1020

Ile Ser  Gln His Asn His Arg  Pro Gly Tyr His Thr  Gln Thr Ala
    1025                 1030                 1035

Gly Pro  Trp His Leu Gly Lys  Leu Glu Leu Asp Phe  Asn Tyr Cys
    1040                 1045                 1050

Glu Gly  Thr Thr Val Val Ile  Ser Glu Asn Cys Gly  Thr Arg Gly
    1055                 1060                 1065

Pro Ser  Leu Arg Thr Thr Thr  Val Ser Gly Lys Leu  Ile His Glu
    1070                 1075                 1080

Trp Cys  Cys Arg Ser Cys Thr  Leu Pro Pro Leu Arg  Tyr Met Gly
    1085                 1090                 1095

Glu Asp  Gly Cys Trp Tyr Gly  Met Glu Ile Arg Pro  Ile Asn Glu
    1100                 1105                 1110

Lys Glu  Glu Asn Met Val Lys  Ser Leu Ala Ser Ala  Gly Ser Gly
    1115                 1120                 1125

Lys Val  Asp Asn Phe Thr Met  Gly Val Leu Cys Leu  Ala Ile Leu
    1130                 1135                 1140

Phe Glu  Glu Val Met Arg Gly  Lys Phe Gly Lys Lys  His Met Ile
    1145                 1150                 1155

Ala Gly  Val Leu Phe Thr Phe  Val Leu Leu Leu Ser  Gly Gln Ile
    1160                 1165                 1170

Thr Trp  Arg Asp Met Ala His  Thr Leu Ile Met Ile  Gly Ser Asn
    1175                 1180                 1185

Ala Ser  Asp Arg Met Gly Met  Gly Val Thr Tyr Leu  Ala Leu Ile
    1190                 1195                 1200

Ala Thr  Phe Lys Ile Gln Pro  Phe Leu Ala Leu Gly  Phe Phe Leu
    1205                 1210                 1215

Arg Lys  Leu Thr Ser Arg Glu  Asn Leu Leu Leu Gly  Val Gly Leu
    1220                 1225                 1230

Ala Met  Ala Ala Thr Leu Arg  Leu Pro Glu Asp Ile  Glu Gln Met
    1235                 1240                 1245

Ala Asn  Gly Ile Ala Leu Gly  Leu Met Ala Leu Lys  Leu Ile Thr
    1250                 1255                 1260

Gln Phe  Glu Thr Tyr Gln Leu  Trp Thr Ala Leu Val  Ser Leu Thr
    1265                 1270                 1275

Cys Ser  Asn Thr Ile Phe Thr  Leu Thr Val Ala Trp  Arg Thr Ala
    1280                 1285                 1290

Thr Leu  Ile Leu Ala Gly Ile  Ser Leu Leu Pro Val  Cys Gln Ser
    1295                 1300                 1305

Ser Ser  Met Arg Lys Thr Asp  Trp Leu Pro Met Thr  Val Ala Ala
    1310                 1315                 1320

Met Gly  Ala Gln Pro Leu Pro  Leu Phe Ile Phe Ser  Leu Lys Asp
    1325                 1330                 1335

Thr Leu  Lys Arg Arg Ser Trp  Pro Leu Asn Glu Gly  Val Met Ala
    1340                 1345                 1350

Val Gly  Leu Val Ser Ile Leu  Ala Ser Ser Leu Leu  Arg Asn Asp
    1355                 1360                 1365

Val Pro  Met Ala Gly Pro Leu  Val Ala Gly Gly Leu  Leu Ile Ala
    1370                 1375                 1380
```

-continued

```
Cys Tyr Val Ile Thr Gly Thr Ser Ala Asp Leu Thr Val Glu Lys
    1385                1390                1395

Ala Ala Asp Val Thr Trp Glu Glu Glu Ala Glu Gln Thr Gly Val
    1400                1405                1410

Ser His Asn Leu Met Val Thr Val Asp Asp Asp Gly Thr Met Arg
    1415                1420                1425

Ile Lys Asp Asp Glu Thr Glu Asn Ile Leu Thr Val Leu Leu Lys
    1430                1435                1440

Thr Ala Leu Leu Ile Val Ser Gly Ile Phe Pro Tyr Ser Ile Pro
    1445                1450                1455

Ala Thr Leu Leu Val Trp His Thr Trp Gln Lys Gln Thr Gln Arg
    1460                1465                1470

Ser Gly Val Leu Trp Asp Val Pro Ser Pro Pro Glu Thr Gln Lys
    1475                1480                1485

Ala Glu Leu Glu Glu Gly Val Tyr Arg Ile Lys Gln Gln Gly Ile
    1490                1495                1500

Phe Gly Lys Thr Gln Val Gly Val Gly Val Gln Lys Glu Gly Val
    1505                1510                1515

Phe His Thr Met Trp His Val Thr Arg Gly Ala Val Leu Thr His
    1520                1525                1530

Asn Gly Lys Arg Leu Glu Pro Asn Trp Ala Ser Val Lys Lys Asp
    1535                1540                1545

Leu Ile Ser Tyr Gly Gly Gly Trp Arg Leu Ser Ala Gln Trp Gln
    1550                1555                1560

Lys Gly Glu Glu Val Gln Val Ile Ala Val Glu Pro Gly Lys Asn
    1565                1570                1575

Pro Lys Asn Phe Gln Thr Met Pro Gly Ile Phe Gln Thr Thr Thr
    1580                1585                1590

Gly Glu Ile Gly Ala Ile Ala Leu Asp Phe Lys Pro Gly Thr Ser
    1595                1600                1605

Gly Ser Pro Ile Ile Asn Arg Glu Gly Lys Val Val Gly Leu Tyr
    1610                1615                1620

Gly Asn Gly Val Val Thr Lys Asn Gly Gly Tyr Val Ser Gly Ile
    1625                1630                1635

Ala Gln Thr Asn Ala Glu Pro Asp Gly Pro Thr Pro Glu Leu Glu
    1640                1645                1650

Glu Glu Met Phe Lys Lys Arg Asn Leu Thr Ile Met Asp Leu His
    1655                1660                1665

Pro Gly Ser Gly Lys Thr Arg Lys Tyr Leu Pro Ala Ile Val Arg
    1670                1675                1680

Glu Ala Ile Lys Arg Arg Leu Arg Thr Leu Ile Leu Ala Pro Thr
    1685                1690                1695

Arg Val Val Ala Ala Glu Met Glu Glu Ala Leu Lys Gly Leu Pro
    1700                1705                1710

Ile Arg Tyr Gln Thr Thr Ala Thr Lys Ser Glu His Thr Gly Arg
    1715                1720                1725

Glu Ile Val Asp Leu Met Cys His Ala Thr Phe Thr Met Arg Leu
    1730                1735                1740

Leu Ser Pro Val Arg Val Pro Asn Tyr Asn Leu Ile Ile Met Asp
    1745                1750                1755

Glu Ala His Phe Thr Asp Pro Ala Ser Ile Ala Ala Arg Gly Tyr
    1760                1765                1770

Ile Ser Thr Arg Val Gly Met Gly Glu Ala Ala Ala Ile Phe Met
```

```
    1775                1780                1785

Thr Ala  Thr Pro Pro Gly Thr  Ala Asp Ala Phe Pro  Gln Ser Asn
    1790                1795                1800

Ala Pro  Ile Gln Asp Glu Glu  Arg Asp Ile Pro Glu  Arg Ser Trp
    1805                1810                1815

Asn Ser  Gly Asn Glu Trp Ile  Thr Asp Phe Val Gly  Lys Thr Val
    1820                1825                1830

Trp Phe  Val Pro Ser Ile Lys  Ala Gly Asn Asp Ile  Ala Asn Cys
    1835                1840                1845

Leu Arg  Lys Asn Gly Lys Lys  Val Ile Gln Leu Ser  Arg Lys Thr
    1850                1855                1860

Phe Asp  Thr Glu Tyr Gln Lys  Thr Lys Leu Asn Asp  Trp Asp Phe
    1865                1870                1875

Val Val  Thr Thr Asp Ile Ser  Glu Met Gly Ala Asn  Phe Lys Ala
    1880                1885                1890

Asp Arg  Val Ile Asp Pro Arg  Arg Cys Leu Lys Pro  Val Ile Leu
    1895                1900                1905

Thr Asp  Gly Pro Glu Arg Val  Ile Leu Ala Gly Pro  Met Pro Val
    1910                1915                1920

Thr Val  Ala Ser Ala Ala Gln  Arg Arg Gly Arg Val  Gly Arg Asn
    1925                1930                1935

Pro Gln  Lys Glu Asn Asp Gln  Tyr Ile Phe Met Gly  Gln Pro Leu
    1940                1945                1950

Asn Asn  Asp Glu Asp His Ala  His Trp Thr Glu Ala  Lys Met Leu
    1955                1960                1965

Leu Asp  Asn Ile Asn Thr Pro  Glu Gly Ile Ile Pro  Ala Leu Phe
    1970                1975                1980

Glu Pro  Glu Arg Glu Lys Ser  Ala Ala Ile Asp Gly  Glu Tyr Arg
    1985                1990                1995

Leu Lys  Gly Glu Ser Arg Lys  Thr Phe Val Glu Leu  Met Arg Arg
    2000                2005                2010

Gly Asp  Leu Pro Val Trp Leu  Ala His Lys Val Ala  Ser Glu Gly
    2015                2020                2025

Ile Lys  Tyr Thr Asp Arg Lys  Trp Cys Phe Asp Gly  Glu Arg Asn
    2030                2035                2040

Asn Gln  Ile Leu Glu Glu Asn  Met Asp Val Glu Ile  Trp Thr Lys
    2045                2050                2055

Glu Gly  Glu Lys Lys Lys Leu  Arg Pro Arg Trp Leu  Asp Ala Arg
    2060                2065                2070

Thr Tyr  Ser Asp Pro Leu Ala  Leu Lys Glu Phe Lys  Asp Phe Ala
    2075                2080                2085

Ala Gly  Arg Lys Ser Ile Ala  Leu Asp Leu Val Thr  Glu Ile Gly
    2090                2095                2100

Arg Val  Pro Ser His Leu Ala  His Arg Thr Arg Asn  Ala Leu Asp
    2105                2110                2115

Asn Leu  Val Met Leu His Thr  Ser Glu His Gly Gly  Arg Ala Tyr
    2120                2125                2130

Arg His  Ala Val Glu Glu Leu  Pro Glu Thr Met Glu  Thr Leu Leu
    2135                2140                2145

Leu Leu  Gly Leu Met Ile Leu  Leu Thr Gly Gly Ala  Met Leu Phe
    2150                2155                2160

Leu Ile  Ser Gly Lys Gly Ile  Gly Lys Thr Ser Ile  Gly Leu Ile
    2165                2170                2175
```

```
Cys Val  Ile Ala Ser Ser Gly  Met Leu Trp Met Ala  Asp Val Pro
    2180                 2185                 2190

Leu Gln  Trp Ile Ala Ser Ala  Ile Val Leu Glu Phe  Phe Met Met
    2195                 2200                 2205

Val Leu  Leu Ile Pro Glu Pro  Glu Lys Gln Arg Thr  Pro Gln Asp
    2210                 2215                 2220

Asn Gln  Leu Ala Tyr Val Val  Ile Gly Ile Leu Thr  Leu Ala Ala
    2225                 2230                 2235

Ile Val  Ala Ala Asn Glu Met  Gly Leu Leu Glu Thr  Thr Lys Arg
    2240                 2245                 2250

Asp Leu  Gly Met Ser Lys Glu  Pro Gly Val Val Ser  Pro Thr Ser
    2255                 2260                 2265

Tyr Leu  Asp Val Asp Leu His  Pro Ala Ser Ala Trp  Thr Leu Tyr
    2270                 2275                 2280

Ala Val  Ala Thr Thr Val Ile  Thr Pro Met Leu Arg  His Thr Ile
    2285                 2290                 2295

Glu Asn  Ser Thr Ala Asn Val  Ser Leu Ala Ala Ile  Ala Asn Gln
    2300                 2305                 2310

Ala Val  Val Leu Met Gly Leu  Asp Lys Gly Trp Pro  Ile Ser Lys
    2315                 2320                 2325

Met Asp  Leu Gly Val Pro Leu  Leu Ala Leu Gly Cys  Tyr Ser Gln
    2330                 2335                 2340

Val Asn  Pro Leu Thr Leu Ala  Ala Ala Val Leu Leu  Leu Val Thr
    2345                 2350                 2355

His Tyr  Ala Ile Ile Gly Pro  Gly Leu Gln Ala Lys  Ala Thr Arg
    2360                 2365                 2370

Glu Ala  Gln Lys Arg Thr Ala  Ala Gly Ile Met Lys  Asn Pro Thr
    2375                 2380                 2385

Val Asp  Gly Ile Met Thr Ile  Asp Leu Asp Pro Val  Ile Tyr Asp
    2390                 2395                 2400

Ser Lys  Phe Glu Lys Gln Leu  Gly Gln Val Met Leu  Leu Val Leu
    2405                 2410                 2415

Cys Ala  Val Gln Leu Leu Leu  Met Arg Thr Ser Trp  Ala Leu Cys
    2420                 2425                 2430

Glu Val  Leu Thr Leu Ala Thr  Gly Pro Ile Thr Thr  Leu Trp Glu
    2435                 2440                 2445

Gly Ser  Pro Gly Lys Phe Trp  Asn Thr Thr Ile Ala  Val Ser Met
    2450                 2455                 2460

Ala Asn  Ile Phe Arg Gly Ser  Tyr Leu Ala Gly Ala  Gly Leu Ala
    2465                 2470                 2475

Phe Ser  Ile Met Lys Ser Val  Gly Thr Gly Lys Arg  Gly Thr Gly
    2480                 2485                 2490

Ser Gln  Gly Glu Thr Leu Gly  Glu Lys Trp Lys Lys  Lys Leu Asn
    2495                 2500                 2505

Gln Leu  Ser Arg Lys Glu Phe  Asp Leu Tyr Lys Lys  Ser Gly Ile
    2510                 2515                 2520

Thr Glu  Val Asp Arg Thr Glu  Ala Lys Glu Gly Leu  Lys Arg Gly
    2525                 2530                 2535

Glu Ile  Thr His His Ala Val  Ser Arg Gly Ser Ala  Lys Leu Gln
    2540                 2545                 2550

Trp Phe  Val Glu Arg Asn Met  Val Ile Pro Glu Gly  Arg Val Ile
    2555                 2560                 2565
```

-continued

```
Asp Leu  Gly Cys Gly Arg Gly  Gly Trp Ser Tyr Tyr  Cys Ala Gly
    2570                 2575                 2580

Leu Lys  Lys Val Thr Glu Val  Arg Gly Tyr Thr Lys  Gly Gly Pro
    2585                 2590                 2595

Gly His  Glu Glu Pro Val Pro  Met Ser Thr Tyr Gly  Trp Asn Ile
    2600                 2605                 2610

Val Lys  Leu Met Ser Gly Lys  Asp Val Phe Tyr Leu  Pro Pro Glu
    2615                 2620                 2625

Lys Cys  Asp Thr Leu Leu Cys  Asp Ile Gly Glu Ser  Ser Pro Ser
    2630                 2635                 2640

Pro Thr  Val Glu Glu Ser Arg  Thr Ile Arg Val Leu  Lys Met Val
    2645                 2650                 2655

Glu Pro  Trp Leu Lys Asn Asn  Gln Phe Cys Ile Lys  Val Leu Asn
    2660                 2665                 2670

Pro Tyr  Met Pro Thr Val Ile  Glu His Leu Glu Arg  Leu Gln Arg
    2675                 2680                 2685

Lys His  Gly Gly Met Leu Val  Arg Asn Pro Leu Ser  Arg Asn Ser
    2690                 2695                 2700

Thr His  Glu Met Tyr Trp Ile  Ser Asn Gly Thr Gly  Asn Ile Val
    2705                 2710                 2715

Ser Ser  Val Asn Met Val Ser  Arg Leu Leu Leu Asn  Arg Phe Thr
    2720                 2725                 2730

Met Thr  His Arg Arg Pro Thr  Ile Glu Lys Asp Val  Asp Leu Gly
    2735                 2740                 2745

Ala Gly  Thr Arg His Val Asn  Ala Glu Pro Glu Thr  Pro Asn Met
    2750                 2755                 2760

Asp Val  Ile Gly Glu Arg Ile  Lys Arg Ile Lys Glu  Glu His Ser
    2765                 2770                 2775

Ser Thr  Trp His Tyr Asp Asp  Glu Asn Pro Tyr Lys  Thr Trp Ala
    2780                 2785                 2790

Tyr His  Gly Ser Tyr Glu Val  Lys Ala Thr Gly Ser  Ala Ser Ser
    2795                 2800                 2805

Met Ile  Asn Gly Val Val Lys  Leu Leu Thr Lys Pro  Trp Asp Val
    2810                 2815                 2820

Val Pro  Met Val Thr Gln Met  Ala Met Thr Asp Thr  Thr Pro Phe
    2825                 2830                 2835

Gly Gln  Gln Arg Val Phe Lys  Glu Lys Val Asp Thr  Arg Thr Pro
    2840                 2845                 2850

Arg Pro  Met Pro Gly Thr Arg  Lys Val Met Glu Ile  Thr Ala Glu
    2855                 2860                 2865

Trp Leu  Trp Arg Thr Leu Gly  Arg Asn Lys Arg Pro  Arg Leu Cys
    2870                 2875                 2880

Thr Arg  Glu Glu Phe Thr Lys  Lys Val Arg Thr Asn  Ala Ala Met
    2885                 2890                 2895

Gly Ala  Val Phe Thr Glu Glu  Asn Gln Trp Asp Ser  Ala Arg Ala
    2900                 2905                 2910

Ala Val  Glu Asp Glu Glu Phe  Trp Lys Leu Val Asp  Arg Glu Arg
    2915                 2920                 2925

Glu Leu  His Lys Leu Gly Lys  Cys Gly Ser Cys Val  Tyr Asn Met
    2930                 2935                 2940

Met Gly  Lys Arg Glu Lys Lys  Leu Gly Glu Phe Gly  Lys Ala Lys
    2945                 2950                 2955

Gly Ser  Arg Ala Ile Trp Tyr  Met Trp Leu Gly Ala  Arg Tyr Leu
```

```
    2960                2965                2970

Glu Phe  Glu Ala Leu Gly Phe  Leu Asn Glu Asp His  Trp Phe Ser
    2975                2980                2985

Arg Glu  Asn Ser Tyr Ser Gly  Val Glu Gly Glu Gly  Leu His Lys
    2990                2995                3000

Leu Gly  Tyr Ile Leu Arg Asp  Ile Ser Lys Ile Pro  Gly Gly Ala
    3005                3010                3015

Met Tyr  Ala Asp Asp Thr Ala  Gly Trp Asp Thr Arg  Ile Thr Glu
    3020                3025                3030

Asp Asp  Leu His Asn Glu Glu  Lys Ile Thr Gln Gln  Met Asp Pro
    3035                3040                3045

Glu His  Arg Gln Leu Ala Asn  Ala Ile Phe Lys Leu  Thr Tyr Gln
    3050                3055                3060

Asn Lys  Val Val Lys Val Gln  Arg Pro Thr Pro Lys  Gly Thr Val
    3065                3070                3075

Met Asp  Ile Ile Ser Arg Lys  Asp Gln Arg Gly Ser  Gly Gln Val
    3080                3085                3090

Gly Thr  Tyr Gly Leu Asn Thr  Phe Thr Asn Met Glu  Ala Gln Leu
    3095                3100                3105

Ile Arg  Gln Met Glu Gly Glu  Gly Val Leu Ser Lys  Ala Asp Leu
    3110                3115                3120

Glu Asn  Pro His Pro Leu Glu  Lys Lys Ile Thr Gln  Trp Leu Glu
    3125                3130                3135

Thr Lys  Gly Val Glu Arg Leu  Lys Arg Met Ala Ile  Ser Gly Asp
    3140                3145                3150

Asp Cys  Val Val Lys Pro Ile  Asp Asp Arg Phe Ala  Asn Ala Leu
    3155                3160                3165

Leu Ala  Leu Asn Asp Met Gly  Lys Val Arg Lys Asp  Ile Pro Gln
    3170                3175                3180

Trp Gln  Pro Ser Lys Gly Trp  His Asp Trp Gln Gln  Val Pro Phe
    3185                3190                3195

Cys Ser  His His Phe His Glu  Leu Ile Met Lys Asp  Gly Arg Lys
    3200                3205                3210

Leu Val  Val Pro Cys Arg Pro  Gln Asp Glu Leu Ile  Gly Arg Ala
    3215                3220                3225

Arg Ile  Ser Gln Gly Ala Gly  Trp Ser Leu Arg Glu  Thr Ala Cys
    3230                3235                3240

Leu Gly  Lys Ala Tyr Ala Gln  Met Trp Ala Leu Met  Tyr Phe His
    3245                3250                3255

Arg Arg  Asp Leu Arg Leu Ala  Ser Asn Ala Ile Cys  Ser Ala Val
    3260                3265                3270

Pro Val  His Trp Val Pro Thr  Ser Arg Thr Thr Trp  Ser Ile His
    3275                3280                3285

Ala His  His Gln Trp Met Thr  Thr Glu Asp Met Leu  Thr Val Trp
    3290                3295                3300

Asn Arg  Val Trp Ile Glu Asp  Asn Pro Trp Met Glu  Asp Lys Thr
    3305                3310                3315

Pro Val  Thr Thr Trp Glu Asp  Val Pro Tyr Leu Gly  Lys Arg Glu
    3320                3325                3330

Asp Gln  Trp Cys Gly Ser Leu  Ile Gly Leu Thr Ser  Arg Ala Thr
    3335                3340                3345

Trp Ala  Gln Asn Ile Leu Thr  Ala Ile Gln Gln Val  Arg Ser Leu
    3350                3355                3360
```

```
Ile Gly  Asn Glu Glu Phe Leu  Asp Tyr Met Pro Ser  Met Lys Arg
    3365                 3370                 3375

Phe Arg  Lys Glu Glu Glu Ser  Glu Gly Ala Ile Trp
    3380                 3385                 3390
```

<210> SEQ ID NO 12
<211> LENGTH: 5
<212> TYPE: PRT
<213> ORGANISM: Artificial
<220> FEATURE:
<223> OTHER INFORMATION: Synthetic construct

<400> SEQUENCE: 12

```
Gly Ala Gly Lys Thr
1               5
```

<210> SEQ ID NO 13
<211> LENGTH: 5
<212> TYPE: PRT
<213> ORGANISM: Artificial
<220> FEATURE:
<223> OTHER INFORMATION: Synthetic construct

<400> SEQUENCE: 13

```
Gly Arg Ile Gly Arg
1               5
```

<210> SEQ ID NO 14
<211> LENGTH: 10723
<212> TYPE: DNA
<213> ORGANISM: Artificial Sequence
<220> FEATURE:
<223> OTHER INFORMATION: Derived from Dengue virus serotype 2/Dengue virus serotype 1, MVS

<400> SEQUENCE: 14

```
agttgttagt ctacgtggac cgacaaagac agattctttg agggagctaa gctcaatgta     60

gttctaacag tttttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagatctg caggcatgat cattatgctg    420

attccaacag tgatggcgtt ccatttaacc acgcgtgggg gagagccgca tatgatagtt    480

agcaagcagg aaagaggaaa gtcacttttg ttcaagacct ctgcaggtgt caacatgtgc    540

accctcattg cgatggattt gggagagttg tgtgaggaca cgatgaccta caaatgcccc    600

cggatcactg aggcggaacc agatgacgtt gactgttggt gcaatgccac ggacacatgg    660

gtgacctatg gaacgtgctc tcaaactggc gaacaccgac gagacaaacg ttccgtcgca    720

ttggccccac acgtggggct tggcctagaa acaagagccg aaacgtggat gtcctctgaa    780

ggtgcttgga aacagataca aaaagtagag acttgggctc tgagacatcc aggattcacg    840

gtgatagccc tttttctagc acatgccata ggaacatcca tcacccagaa agggatcatt    900

ttcattttgc tgatgctggt aacaccatct atggccatgc gatgcgtggg aataggcaac    960

agagacttcg tggaaggact gtcaggagca acatgggtgg atgtggtact ggagcatgga   1020

agttgcgtca ccaccatggc aaaaaacaaa ccaacactgg acattgaact cttgaagacg   1080
```

gaggtcacaa accctgcagt tctgcgtaaa ttgtgcattg aagctaaaat atcaaacacc 1140
accaccgatt cgagatgtcc aacacaagga gaagccacac tggtggaaga acaagacgcg 1200
aactttgtgt gccgacgaac gttcgtggac agaggctggg gcaatggctg tgggctattc 1260
ggaaaaggta gtctaataac gtgtgccaag tttaagtgtg tgacaaaact agaaggaaag 1320
atagttcaat atgaaaacct aaaatattca gtgatagtca ccgtccacac tggagatcag 1380
caccaggtgg gaaatgagac tacagaacat ggaacaactg caaccataac acctcaagct 1440
cctacgtcgg aaatacagct gaccgactac ggaaccctta cattagattg ttcacctagg 1500
acagggctag attttaacga gatggtgttg ctgacaatga aagaaagatc atggcttgtc 1560
cacaaacaat ggttcctaga cttaccactg ccttggacct ctggggcttc aacatcccaa 1620
gagacttgga acagacaaga tttactggtc acatttaaga cagctcatgc aaagaagcag 1680
gaagtagtcg tactaggatc acaagaagga gcaatgcaca ctgcgctgac tggagcgaca 1740
gaaatccaaa cgtcaggaac gacaacaatt ttcgcaggac acctaaaatg cagactaaaa 1800
atggacaaac taactttaaa agggatgtca tatgtgatgt gcacaggctc attcaagtta 1860
gagaaagaag tggctgagac ccagcatgga actgttctgg tgcaggttaa atatgaagga 1920
acagacgcac catgcaagat tccctttcg acccaagatg agaaaggagc aacccagaat 1980
gggagattaa taacagccaa ccccatagtc actgacaaag aaaaaccagt caatattgag 2040
gcagaaccac cctttggtga gagctacatc gtggtaggag caggtgaaaa agctttgaaa 2100
ctaagctggt tcaagaaagg aagcagcata gggaaaatgt ttgaagcaac tgcccgagga 2160
gcacgaagga tggccattct gggagacacc gcatgggact tcggttctat aggaggagtg 2220
ttcacgtcta tgggaaaact ggtacaccag gtttttggaa ctgcatatgg agttttgttt 2280
agcggagttt cttggaccat gaaaatagga atagggattc tgctgacatg gctaggatta 2340
aattcaagga acacgtccct ttcgatgatg tgcatcgcag ccggcattgt gacactgtat 2400
ttgggagtca tggtgcaggc cgatagtggt tgcgttgtga gctggaaaaa caaagaactg 2460
aaatgtggca gtgggatttt catcacagac aacgtgcaca catggacaga acaatacaag 2520
ttccaaccag aatccccttc aaaactagct tcagctatcc agaaagccca tgaagaggac 2580
atttgtggaa tccgctcagt aacaagactg gagaatctga tgtggaaaca aataacacca 2640
gaattgaatc acattctatc agaaaatgag gtgaagttaa ctattatgac aggagacatc 2700
aaaggaatca tgcaggcagg aaaacgatct ctgcggcctc agcccactga gctgaagtat 2760
tcatggaaaa catggggcaa agcaaaaatg ctctctacag agtctcataa ccagaccttt 2820
ctcattgatg gccccgaaac agcagaatgc cccaacacaa atagagcttg gaattcgttg 2880
gaagttgaag actatggctt tggagtattc accaccaata tatggctaaa attgaaagaa 2940
aaacaggatg tattctgcga ctcaaaactc atgtcagcgg ccataaaaga caacagagcc 3000
gtccatgccg atatgggtta ttggatagaa agtgcactca atgacacatg gaagatagag 3060
aaagcctctt tcattgaagt taaaaactgc cactggccaa aatcacacac cctctggagc 3120
aatggagtgc tagaaagtga gatgataatt ccaaagaatc tcgctggacc agtgtctcaa 3180
cacaactata gaccaggcta ccatacacaa ataacaggac catggcatct aggtaagctt 3240
gagatggact ttgatttctg tgatggaaca acagtggtag tgactgagga ctgcggaaat 3300
agaggaccct ctttgagaac aaccactgcc tctggaaaac tcataacaga atggtgctgc 3360
cgatcttgca cattaccacc gctaagatac agaggtgagg atgggtgctg gtacgggatg 3420

```
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccctaccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgttc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagatcaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
```

ctaacagatg gtgaagagcg ggtgattctg gcaggaccta tgccagtgac ccactctagt 5880
gcagcacaaa gaagagggag aataggaaga aatccaaaaa atgagaatga ccagtacata 5940
tacatggggg aacctctgga aaatgatgaa gactgtgcac actggaaaga agctaaaatg 6000
ctcctagata acatcaacac gccagaagga atcattccta gcatgttcga accagagcgt 6060
gaaaaggtgg atgccattga tggcgaatac cgcttgagag gagaagcaag gaaaaccttt 6120
gtagacttaa tgagaagagg agacctacca gtctggttgg cctacagagt ggcagctgaa 6180
ggcatcaact acgcagacag aaggtggtgt tttgatggag tcaagaacaa ccaaatccta 6240
gaagaaaacg tggaagttga aatctggaca aaagaagggg aaaggaagaa attgaaaccc 6300
agatggttgg atgctaggat ctattctgac ccactggcgc taaaagaatt taaggaattt 6360
gcagccggaa gaaagtctct gaccctgaac ctaatcacag aaatgggtag gctcccaacc 6420
ttcatgactc agaaggcaag agacgcactg gacaacttag cagtgctgca cacggctgag 6480
gcaggtggaa gggcgtacaa ccatgctctc agtgaactgc cggagaccct ggagacattg 6540
cttttactga cacttctggc tacagtcacg ggagggatct tttattctt gatgagcgca 6600
aggggcatag ggaagatgac cctgggaatg tgctgcataa tcacggctag catcctccta 6660
tggtacgcac aaatacagcc acactggata gcagcttcaa taatactgga gtttttctc 6720
atagttttgc ttattccaga acctgaaaaa cagagaacac cccaagacaa ccaactgacc 6780
tacgttgtca tagccatcct cacagtggtg gccgcaacca tggcaaacga gatgggtttc 6840
ctagaaaaaa cgaagaaaga tctcggattg ggaagcattg caacccagca acccgagagc 6900
aacatcctgg acatagatct acgtcctgca tcagcatgga cgctgtatgc cgtggccaca 6960
acatttgtta caccaatgtt gagacatagc attgaaaatt cctcagtgaa tgtgtcccta 7020
acagctatag ccaaccaagc cacagtgtta atgggtctcg ggaaaggatg gccattgtca 7080
aagatggaca tcggagttcc ccttctcgcc attggatgct actcacaagt caaccccata 7140
actctcacag cagctctttt cttattggta gcacattatg ccatcatagg gccaggactc 7200
caagcaaaag caaccagaga agctcagaaa agagcagcgg cgggcatcat gaaaaaccca 7260
actgtcgatg gaataacagt gattgaccta gatccaatac cttatgatcc gaagtttgaa 7320
aagcagttgg gacaagtaat gctcctagtc ctctgcgtga ctcaagtatt gatgatgagg 7380
actacatggg ctctgtgtga ggctttaacc ttagctaccg ggcccatctc cacattgtgg 7440
gaaggaaatc cagggaggtt ttggaacact accattgcgg tgtcaatggc taacattttt 7500
agagggagtt acttggccgg agctggactt ctcttttcta ttatgaagaa cacaaccaac 7560
acaagaaggg gaactggcaa cataggagag acgcttggag agaaatggaa aagccgattg 7620
aacgcattgg gaaaaagtga attccagatc tacaagaaaa gtggaatcca ggaagtggat 7680
agaaccttag caaaagaagg cattaaaaga ggagaaacgg accatcacgc tgtgtcgcga 7740
ggctcagcaa aactgagatg gttcgttgag agaaacatgg tcacaccaga agggaaagta 7800
gtggacctcg gttgtggcag aggaggctgg tcatactatt gtggaggact aaagaatgta 7860
agagaagtca aaggcctaac aaaaggagga ccaggacacg aagaacccat ccccatgtca 7920
acatatgggt ggaatctagt gcgtcttcaa agtggagttg acgttttctt catcccgcca 7980
gaaaagtgtg acacattatt gtgtgacata ggggagtcat caccaaatcc cacagtggaa 8040
gcaggacgaa cactcagagt ccttaactta gtagaaaatt ggttgaacaa caacactcaa 8100
ttttgcataa aggttctcaa cccatatatg ccctcagtca tagaaaaaat ggaagcacta 8160

-continued

```
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttttaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agaagcagga  10260
gttctgtggt agaaagcaaa actaacatga aacaaggcta gaagtcaggt cggattaagc  10320
catagtacgg aaaaaactat gctacctgtg agccccgtcc aaggacgtta aaagaagtca  10380
ggccatcata aatgccatag cttgagtaaa ctatgcagcc tgtagctcca cctgagaagg  10440
tgtaaaaaat ccgggaggcc acaaaccatg gaagctgtac gcatggcgta gtggactagc  10500
ggttagagga gacccctccc ttacaaatcg cagcaacaat gggggcccaa ggcgagatga  10560
```

agctgtagtc tcgctggaag gactagaggt tagaggagac ccccccgaaa caaaaaacag 10620
catattgacg ctgggaaaga ccagagatcc tgctgtctcc tcagcatcat tccaggcaca 10680
gaacgccaga aaatggaatg gtgctgttga atcaacaggt tct 10723

<210> SEQ ID NO 15
<211> LENGTH: 3391
<212> TYPE: PRT
<213> ORGANISM: Artificial Sequence
<220> FEATURE:
<223> OTHER INFORMATION: Polypeptide, Derived from Dengue virus serotype 2/Dengue virus serotype 1, MVS

<400> SEQUENCE: 15

Met Asn Asn Gln Arg Lys Lys Ala Lys Asn Thr Pro Phe Asn Met Leu
1 5 10 15

Lys Arg Glu Arg Asn Arg Val Ser Thr Val Gln Gln Leu Thr Lys Arg
20 25 30

Phe Ser Leu Gly Met Leu Gln Gly Arg Gly Pro Leu Lys Leu Phe Met
35 40 45

Ala Leu Val Ala Phe Leu Arg Phe Leu Thr Ile Pro Pro Thr Ala Gly
50 55 60

Ile Leu Lys Arg Trp Gly Thr Ile Lys Lys Ser Lys Ala Ile Asn Val
65 70 75 80

Leu Arg Gly Phe Arg Lys Glu Ile Gly Arg Met Leu Asn Ile Leu Asn
85 90 95

Arg Arg Arg Arg Ser Ala Gly Met Ile Ile Met Leu Ile Pro Thr Val
100 105 110

Met Ala Phe His Leu Thr Thr Arg Gly Gly Glu Pro His Met Ile Val
115 120 125

Ser Lys Gln Glu Arg Gly Lys Ser Leu Leu Phe Lys Thr Ser Ala Gly
130 135 140

Val Asn Met Cys Thr Leu Ile Ala Met Asp Leu Gly Glu Leu Cys Glu
145 150 155 160

Asp Thr Met Thr Tyr Lys Cys Pro Arg Ile Thr Glu Ala Glu Pro Asp
165 170 175

Asp Val Asp Cys Trp Cys Asn Ala Thr Asp Thr Trp Val Thr Tyr Gly
180 185 190

Thr Cys Ser Gln Thr Gly Glu His Arg Arg Asp Lys Arg Ser Val Ala
195 200 205

Leu Ala Pro His Val Gly Leu Gly Leu Glu Thr Arg Ala Glu Thr Trp
210 215 220

Met Ser Ser Glu Gly Ala Trp Lys Gln Ile Gln Lys Val Glu Thr Trp
225 230 235 240

Ala Leu Arg His Pro Gly Phe Thr Val Ile Ala Leu Phe Leu Ala His
245 250 255

Ala Ile Gly Thr Ser Ile Thr Gln Lys Gly Ile Ile Phe Ile Leu Leu
260 265 270

Met Leu Val Thr Pro Ser Met Ala Met Arg Cys Val Gly Ile Gly Asn
275 280 285

Arg Asp Phe Val Glu Gly Leu Ser Gly Ala Thr Trp Val Asp Val Val
290 295 300

Leu Glu His Gly Ser Cys Val Thr Thr Met Ala Lys Asn Lys Pro Thr
305 310 315 320

Leu Asp Ile Glu Leu Leu Lys Thr Glu Val Thr Asn Pro Ala Val Leu

-continued

```
                325                 330                 335

Arg Lys Leu Cys Ile Glu Ala Lys Ile Ser Asn Thr Thr Thr Asp Ser
            340                 345                 350

Arg Cys Pro Thr Gln Gly Glu Ala Thr Leu Val Glu Glu Gln Asp Ala
        355                 360                 365

Asn Phe Val Cys Arg Arg Thr Phe Val Asp Arg Gly Trp Gly Asn Gly
    370                 375                 380

Cys Gly Leu Phe Gly Lys Gly Ser Leu Ile Thr Cys Ala Lys Phe Lys
385                 390                 395                 400

Cys Val Thr Lys Leu Glu Gly Lys Ile Val Gln Tyr Glu Asn Leu Lys
                405                 410                 415

Tyr Ser Val Ile Val Thr Val His Thr Gly Asp Gln His Gln Val Gly
            420                 425                 430

Asn Glu Thr Thr Glu His Gly Thr Thr Ala Thr Ile Thr Pro Gln Ala
        435                 440                 445

Pro Thr Ser Glu Ile Gln Leu Thr Asp Tyr Gly Thr Leu Thr Leu Asp
    450                 455                 460

Cys Ser Pro Arg Thr Gly Leu Asp Phe Asn Glu Met Val Leu Leu Thr
465                 470                 475                 480

Met Lys Glu Arg Ser Trp Leu Val His Lys Gln Trp Phe Leu Asp Leu
                485                 490                 495

Pro Leu Pro Trp Thr Ser Gly Ala Ser Thr Ser Gln Glu Thr Trp Asn
            500                 505                 510

Arg Gln Asp Leu Leu Val Thr Phe Lys Thr Ala His Ala Lys Lys Gln
        515                 520                 525

Glu Val Val Val Leu Gly Ser Gln Glu Gly Ala Met His Thr Ala Leu
    530                 535                 540

Thr Gly Ala Thr Glu Ile Gln Thr Ser Gly Thr Thr Thr Ile Phe Ala
545                 550                 555                 560

Gly His Leu Lys Cys Arg Leu Lys Met Asp Lys Leu Thr Leu Lys Gly
                565                 570                 575

Met Ser Tyr Val Met Cys Thr Gly Ser Phe Lys Leu Glu Lys Glu Val
            580                 585                 590

Ala Glu Thr Gln His Gly Thr Val Leu Val Gln Val Lys Tyr Glu Gly
        595                 600                 605

Thr Asp Ala Pro Cys Lys Ile Pro Phe Ser Thr Gln Asp Glu Lys Gly
    610                 615                 620

Ala Thr Gln Asn Gly Arg Leu Ile Thr Ala Asn Pro Ile Val Thr Asp
625                 630                 635                 640

Lys Glu Lys Pro Val Asn Ile Glu Ala Glu Pro Pro Phe Gly Glu Ser
                645                 650                 655

Tyr Ile Val Val Gly Ala Gly Glu Lys Ala Leu Lys Leu Ser Trp Phe
            660                 665                 670

Lys Lys Gly Ser Ser Ile Gly Lys Met Phe Glu Ala Thr Ala Arg Gly
        675                 680                 685

Ala Arg Arg Met Ala Ile Leu Gly Asp Thr Ala Trp Asp Phe Gly Ser
    690                 695                 700

Ile Gly Gly Val Phe Thr Ser Met Gly Lys Leu Val His Gln Val Phe
705                 710                 715                 720

Gly Thr Ala Tyr Gly Val Leu Phe Ser Gly Val Ser Trp Thr Met Lys
                725                 730                 735

Ile Gly Ile Gly Ile Leu Leu Thr Trp Leu Gly Leu Asn Ser Arg Asn
            740                 745                 750
```

```
Thr Ser Leu Ser Met Met Cys Ile Ala Ala Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
        995                 1000                1005

Asn Gly  Val Leu Glu Ser Glu  Met Ile Ile Pro Lys  Asn Leu Ala
    1010                1015                1020

Gly Pro  Val Ser Gln His Asn  Tyr Arg Pro Gly Tyr  His Thr Gln
    1025                1030                1035

Ile Thr  Gly Pro Trp His Leu  Gly Lys Leu Glu Met  Asp Phe Asp
    1040                1045                1050

Phe Cys  Asp Gly Thr Thr Val  Val Val Thr Glu Asp  Cys Gly Asn
    1055                1060                1065

Arg Gly  Pro Ser Leu Arg Thr  Thr Thr Ala Ser Gly  Lys Leu Ile
    1070                1075                1080

Thr Glu  Trp Cys Cys Arg Ser  Cys Thr Leu Pro Pro  Leu Arg Tyr
    1085                1090                1095

Arg Gly  Glu Asp Gly Cys Trp  Tyr Gly Met Glu Ile  Arg Pro Leu
    1100                1105                1110

Lys Glu  Lys Glu Glu Asn Leu  Val Asn Ser Leu Val  Thr Ala Gly
    1115                1120                1125

His Gly  Gln Val Asp Asn Phe  Ser Leu Gly Val Leu  Gly Met Ala
    1130                1135                1140

Leu Phe  Leu Glu Glu Met Leu  Arg Thr Arg Val Gly  Thr Lys His
    1145                1150                1155
```

-continued

```
Ala Ile  Leu Leu Val Ala Val  Ser Phe Val Thr Leu  Ile Thr Gly
    1160                 1165                 1170

Asn Met  Ser Phe Arg Asp Leu  Gly Arg Val Met Val  Met Val Gly
    1175                 1180                 1185

Ala Thr  Met Thr Asp Asp Ile  Gly Met Gly Val Thr  Tyr Leu Ala
    1190                 1195                 1200

Leu Leu  Ala Ala Phe Lys Val  Arg Pro Thr Phe Ala  Ala Gly Leu
    1205                 1210                 1215

Leu Leu  Arg Lys Leu Thr Ser  Lys Glu Leu Met Met  Thr Thr Ile
    1220                 1225                 1230

Gly Ile  Val Leu Leu Ser Gln  Ser Thr Leu Pro Glu  Thr Ile Leu
    1235                 1240                 1245

Glu Leu  Thr Asp Ala Leu Ala  Leu Gly Met Met Val  Leu Lys Met
    1250                 1255                 1260

Val Arg  Asn Met Glu Lys Tyr  Gln Leu Ala Val Thr  Ile Met Ala
    1265                 1270                 1275

Ile Leu  Cys Val Pro Asn Ala  Val Ile Leu Gln Asn  Ala Trp Lys
    1280                 1285                 1290

Val Ser  Cys Thr Ile Leu Ala  Val Val Ser Val Ser  Pro Leu Phe
    1295                 1300                 1305

Leu Thr  Ser Ser Gln Gln Lys  Thr Asp Trp Ile Pro  Leu Ala Leu
    1310                 1315                 1320

Thr Ile  Lys Gly Leu Asn Pro  Thr Ala Ile Phe Leu  Thr Thr Leu
    1325                 1330                 1335

Ser Arg  Thr Ser Lys Lys Arg  Ser Trp Pro Leu Asn  Glu Ala Ile
    1340                 1345                 1350

Met Ala  Val Gly Met Val Ser  Ile Leu Ala Ser Ser  Leu Leu Lys
    1355                 1360                 1365

Asn Asp  Ile Pro Met Thr Gly  Pro Leu Val Ala Gly  Gly Leu Leu
    1370                 1375                 1380

Thr Val  Cys Tyr Val Leu Thr  Gly Arg Ser Ala Asp  Leu Glu Leu
    1385                 1390                 1395

Glu Arg  Ala Ala Asp Val Lys  Trp Glu Asp Gln Ala  Glu Ile Ser
    1400                 1405                 1410

Gly Ser  Ser Pro Ile Leu Ser  Ile Thr Ile Ser Glu  Asp Gly Ser
    1415                 1420                 1425

Met Ser  Ile Lys Asn Glu Glu  Glu Asp Gln Thr Leu  Thr Ile Leu
    1430                 1435                 1440

Ile Arg  Thr Gly Leu Leu Val  Ile Ser Gly Leu Phe  Pro Val Ser
    1445                 1450                 1455

Ile Pro  Ile Thr Ala Ala Ala  Trp Tyr Leu Trp Glu  Val Lys Lys
    1460                 1465                 1470

Gln Arg  Ala Gly Val Leu Trp  Asp Val Pro Ser Pro  Pro Pro Met
    1475                 1480                 1485

Gly Lys  Ala Glu Leu Glu Asp  Gly Ala Tyr Arg Ile  Lys Gln Lys
    1490                 1495                 1500

Gly Ile  Leu Gly Tyr Ser Gln  Ile Gly Ala Gly Val  Tyr Lys Glu
    1505                 1510                 1515

Gly Thr  Phe His Thr Met Trp  His Val Thr Arg Gly  Ala Val Leu
    1520                 1525                 1530

Met His  Lys Gly Lys Arg Ile  Glu Pro Ser Trp Ala  Asp Val Lys
    1535                 1540                 1545

Lys Asp  Leu Ile Ser Tyr Gly  Gly Gly Trp Lys Leu  Glu Gly Glu
```

-continued

```
    1550                1555                1560

Trp Lys  Glu Gly Glu Glu Val  Gln Val Leu Ala Leu  Glu Pro Gly
    1565                1570                1575

Lys Asn  Pro Arg Ala Val Gln  Thr Lys Pro Gly Leu  Phe Lys Thr
    1580                1585                1590

Asn Ala  Gly Thr Ile Gly Ala  Val Ser Leu Asp Phe  Ser Pro Gly
    1595                1600                1605

Thr Ser  Gly Ser Pro Ile Ile  Asp Lys Lys Gly Lys  Val Val Gly
    1610                1615                1620

Leu Tyr  Gly Asn Gly Val Val  Thr Arg Ser Gly Ala  Tyr Val Ser
    1625                1630                1635

Ala Ile  Ala Gln Thr Glu Lys  Ser Ile Glu Asp Asn  Pro Glu Ile
    1640                1645                1650

Glu Asp  Asp Ile Phe Arg Lys  Arg Arg Leu Thr Ile  Met Asp Leu
    1655                1660                1665

His Pro  Gly Ala Gly Lys Thr  Lys Arg Tyr Leu Pro  Ala Ile Val
    1670                1675                1680

Arg Glu  Ala Ile Lys Arg Gly  Leu Arg Thr Leu Ile  Leu Ala Pro
    1685                1690                1695

Thr Arg  Val Val Ala Ala Glu  Met Glu Glu Ala Leu  Arg Gly Leu
    1700                1705                1710

Pro Ile  Arg Tyr Gln Thr Pro  Ala Ile Arg Ala Val  His Thr Gly
    1715                1720                1725

Arg Glu  Ile Val Asp Leu Met  Cys His Ala Thr Phe  Thr Met Arg
    1730                1735                1740

Leu Leu  Ser Pro Val Arg Val  Pro Asn Tyr Asn Leu  Ile Ile Met
    1745                1750                1755

Asp Glu  Ala His Phe Thr Asp  Pro Ala Ser Ile Ala  Ala Arg Gly
    1760                1765                1770

Tyr Ile  Ser Thr Arg Val Glu  Met Gly Glu Ala Ala  Gly Ile Phe
    1775                1780                1785

Met Thr  Ala Thr Pro Pro Gly  Ser Arg Asp Pro Phe  Pro Gln Ser
    1790                1795                1800

Asn Ala  Pro Ile Ile Asp Glu  Glu Arg Glu Ile Pro  Glu Arg Ser
    1805                1810                1815

Trp Asn  Ser Gly His Glu Trp  Val Thr Asp Phe Lys  Gly Lys Thr
    1820                1825                1830

Val Trp  Phe Val Pro Ser Ile  Lys Ala Gly Asn Asp  Ile Ala Ala
    1835                1840                1845

Cys Leu  Arg Lys Asn Gly Lys  Lys Val Ile Gln Leu  Ser Arg Lys
    1850                1855                1860

Thr Phe  Asp Ser Glu Tyr Val  Lys Thr Arg Thr Asn  Asp Trp Asp
    1865                1870                1875

Phe Val  Val Thr Thr Asp Ile  Ser Glu Met Gly Ala  Asn Phe Lys
    1880                1885                1890

Ala Glu  Arg Val Ile Asp Pro  Arg Arg Cys Met Lys  Pro Val Ile
    1895                1900                1905

Leu Thr  Asp Gly Glu Glu Arg  Val Ile Leu Ala Gly  Pro Met Pro
    1910                1915                1920

Val Thr  His Ser Ser Ala Ala  Gln Arg Arg Gly Arg  Ile Gly Arg
    1925                1930                1935

Asn Pro  Lys Asn Glu Asn Asp  Gln Tyr Ile Tyr Met  Gly Glu Pro
    1940                1945                1950
```

-continued

```
Leu Glu  Asn Asp Glu Asp Cys  Ala His Trp Lys Glu  Ala Lys Met
    1955                 1960                 1965

Leu Leu  Asp Asn Ile Asn Thr  Pro Glu Gly Ile Ile  Pro Ser Met
    1970                 1975                 1980

Phe Glu  Pro Glu Arg Glu Lys  Val Asp Ala Ile Asp  Gly Glu Tyr
    1985                 1990                 1995

Arg Leu  Arg Gly Glu Ala Arg  Lys Thr Phe Val Asp  Leu Met Arg
    2000                 2005                 2010

Arg Gly  Asp Leu Pro Val Trp  Leu Ala Tyr Arg Val  Ala Ala Glu
    2015                 2020                 2025

Gly Ile  Asn Tyr Ala Asp Arg  Arg Trp Cys Phe Asp  Gly Val Lys
    2030                 2035                 2040

Asn Asn  Gln Ile Leu Glu Glu  Asn Val Glu Val Glu  Ile Trp Thr
    2045                 2050                 2055

Lys Glu  Gly Glu Arg Lys Lys  Leu Lys Pro Arg Trp  Leu Asp Ala
    2060                 2065                 2070

Arg Ile  Tyr Ser Asp Pro Leu  Ala Leu Lys Glu Phe  Lys Glu Phe
    2075                 2080                 2085

Ala Ala  Gly Arg Lys Ser Leu  Thr Leu Asn Leu Ile  Thr Glu Met
    2090                 2095                 2100

Gly Arg  Leu Pro Thr Phe Met  Thr Gln Lys Ala Arg  Asp Ala Leu
    2105                 2110                 2115

Asp Asn  Leu Ala Val Leu His  Thr Ala Glu Ala Gly  Gly Arg Ala
    2120                 2125                 2130

Tyr Asn  His Ala Leu Ser Glu  Leu Pro Glu Thr Leu  Glu Thr Leu
    2135                 2140                 2145

Leu Leu  Leu Thr Leu Leu Ala  Thr Val Thr Gly Gly  Ile Phe Leu
    2150                 2155                 2160

Phe Leu  Met Ser Ala Arg Gly  Ile Gly Lys Met Thr  Leu Gly Met
    2165                 2170                 2175

Cys Cys  Ile Ile Thr Ala Ser  Ile Leu Leu Trp Tyr  Ala Gln Ile
    2180                 2185                 2190

Gln Pro  His Trp Ile Ala Ala  Ser Ile Ile Leu Glu  Phe Phe Leu
    2195                 2200                 2205

Ile Val  Leu Leu Ile Pro Glu  Pro Glu Lys Gln Arg  Thr Pro Gln
    2210                 2215                 2220

Asp Asn  Gln Leu Thr Tyr Val  Val Ile Ala Ile Leu  Thr Val Val
    2225                 2230                 2235

Ala Ala  Thr Met Ala Asn Glu  Met Gly Phe Leu Glu  Lys Thr Lys
    2240                 2245                 2250

Lys Asp  Leu Gly Leu Gly Ser  Ile Ala Thr Gln Gln  Pro Glu Ser
    2255                 2260                 2265

Asn Ile  Leu Asp Ile Asp Leu  Arg Pro Ala Ser Ala  Trp Thr Leu
    2270                 2275                 2280

Tyr Ala  Val Ala Thr Thr Phe  Val Thr Pro Met Leu  Arg His Ser
    2285                 2290                 2295

Ile Glu  Asn Ser Ser Val Asn  Val Ser Leu Thr Ala  Ile Ala Asn
    2300                 2305                 2310

Gln Ala  Thr Val Leu Met Gly  Leu Gly Lys Gly Trp  Pro Leu Ser
    2315                 2320                 2325

Lys Met  Asp Ile Gly Val Pro  Leu Leu Ala Ile Gly  Cys Tyr Ser
    2330                 2335                 2340
```

-continued

```
Gln Val  Asn Pro Ile Thr Leu  Thr Ala Ala Leu Phe  Leu Leu Val
    2345                 2350                 2355

Ala His  Tyr Ala Ile Ile Gly  Pro Gly Leu Gln Ala  Lys Ala Thr
    2360                 2365                 2370

Arg Glu  Ala Gln Lys Arg Ala  Ala Ala Gly Ile Met  Lys Asn Pro
    2375                 2380                 2385

Thr Val  Asp Gly Ile Thr Val  Ile Asp Leu Asp Pro  Ile Pro Tyr
    2390                 2395                 2400

Asp Pro  Lys Phe Glu Lys Gln  Leu Gly Gln Val Met  Leu Leu Val
    2405                 2410                 2415

Leu Cys  Val Thr Gln Val Leu  Met Met Arg Thr Thr  Trp Ala Leu
    2420                 2425                 2430

Cys Glu  Ala Leu Thr Leu Ala  Thr Gly Pro Ile Ser  Thr Leu Trp
    2435                 2440                 2445

Glu Gly  Asn Pro Gly Arg Phe  Trp Asn Thr Thr Ile  Ala Val Ser
    2450                 2455                 2460

Met Ala  Asn Ile Phe Arg Gly  Ser Tyr Leu Ala Gly  Ala Gly Leu
    2465                 2470                 2475

Leu Phe  Ser Ile Met Lys Asn  Thr Thr Asn Thr Arg  Arg Gly Thr
    2480                 2485                 2490

Gly Asn  Ile Gly Glu Thr Leu  Gly Glu Lys Trp Lys  Ser Arg Leu
    2495                 2500                 2505

Asn Ala  Leu Gly Lys Ser Glu  Phe Gln Ile Tyr Lys  Lys Ser Gly
    2510                 2515                 2520

Ile Gln  Glu Val Asp Arg Thr  Leu Ala Lys Glu Gly  Ile Lys Arg
    2525                 2530                 2535

Gly Glu  Thr Asp His His Ala  Val Ser Arg Gly Ser  Ala Lys Leu
    2540                 2545                 2550

Arg Trp  Phe Val Glu Arg Asn  Met Val Thr Pro Glu  Gly Lys Val
    2555                 2560                 2565

Val Asp  Leu Gly Cys Gly Arg  Gly Gly Trp Ser Tyr  Tyr Cys Gly
    2570                 2575                 2580

Gly Leu  Lys Asn Val Arg Glu  Val Lys Gly Leu Thr  Lys Gly Gly
    2585                 2590                 2595

Pro Gly  His Glu Glu Pro Ile  Pro Met Ser Thr Tyr  Gly Trp Asn
    2600                 2605                 2610

Leu Val  Arg Leu Gln Ser Gly  Val Asp Val Phe Phe  Ile Pro Pro
    2615                 2620                 2625

Glu Lys  Cys Asp Thr Leu Leu  Cys Asp Ile Gly Glu  Ser Ser Pro
    2630                 2635                 2640

Asn Pro  Thr Val Glu Ala Gly  Arg Thr Leu Arg Val  Leu Asn Leu
    2645                 2650                 2655

Val Glu  Asn Trp Leu Asn Asn  Asn Thr Gln Phe Cys  Ile Lys Val
    2660                 2665                 2670

Leu Asn  Pro Tyr Met Pro Ser  Val Ile Glu Lys Met  Glu Ala Leu
    2675                 2680                 2685

Gln Arg  Lys Tyr Gly Gly Ala  Leu Val Arg Asn Pro  Leu Ser Arg
    2690                 2695                 2700

Asn Ser  Thr His Glu Met Tyr  Trp Val Ser Asn Ala  Ser Gly Asn
    2705                 2710                 2715

Ile Val  Ser Ser Val Asn Met  Ile Ser Arg Met Leu  Ile Asn Arg
    2720                 2725                 2730

Phe Thr  Met Arg Tyr Lys Lys  Ala Thr Tyr Glu Pro  Asp Val Asp
```

2735 2740 2745

Leu Gly Ser Gly Thr Arg Asn Ile Gly Ile Glu Ser Glu Ile Pro
2750 2755 2760

Asn Leu Asp Ile Ile Gly Lys Arg Ile Glu Lys Ile Lys Gln Glu
2765 2770 2775

His Glu Thr Ser Trp His Tyr Asp Gln Asp His Pro Tyr Lys Thr
2780 2785 2790

Trp Ala Tyr His Gly Ser Tyr Glu Thr Lys Gln Thr Gly Ser Ala
2795 2800 2805

Ser Ser Met Val Asn Gly Val Val Arg Leu Leu Thr Lys Pro Trp
2810 2815 2820

Asp Val Val Pro Met Val Thr Gln Met Ala Met Thr Asp Thr Thr
2825 2830 2835

Pro Phe Gly Gln Gln Arg Val Phe Lys Glu Lys Val Asp Thr Arg
2840 2845 2850

Thr Gln Glu Pro Lys Glu Gly Thr Lys Lys Leu Met Lys Ile Thr
2855 2860 2865

Ala Glu Trp Leu Trp Lys Glu Leu Gly Lys Lys Lys Thr Pro Arg
2870 2875 2880

Met Cys Thr Arg Glu Glu Phe Thr Arg Lys Val Arg Ser Asn Ala
2885 2890 2895

Ala Leu Gly Ala Ile Phe Thr Asp Glu Asn Lys Trp Lys Ser Ala
2900 2905 2910

Arg Glu Ala Val Glu Asp Ser Arg Phe Trp Glu Leu Val Asp Lys
2915 2920 2925

Glu Arg Asn Leu His Leu Glu Gly Lys Cys Glu Thr Cys Val Tyr
2930 2935 2940

Asn Met Met Gly Lys Arg Glu Lys Lys Leu Gly Glu Phe Gly Lys
2945 2950 2955

Ala Lys Gly Ser Arg Ala Ile Trp Tyr Met Trp Leu Gly Ala Arg
2960 2965 2970

Phe Leu Glu Phe Glu Ala Leu Gly Phe Leu Asn Glu Asp His Trp
2975 2980 2985

Phe Ser Arg Glu Asn Ser Leu Ser Gly Val Glu Gly Glu Gly Leu
2990 2995 3000

His Lys Leu Gly Tyr Ile Leu Arg Asp Val Ser Lys Lys Glu Gly
3005 3010 3015

Gly Ala Met Tyr Ala Asp Asp Thr Ala Gly Trp Asp Thr Arg Ile
3020 3025 3030

Thr Leu Glu Asp Leu Lys Asn Glu Glu Met Val Thr Asn His Met
3035 3040 3045

Glu Gly Glu His Lys Lys Leu Ala Glu Ala Ile Phe Lys Leu Thr
3050 3055 3060

Tyr Gln Asn Lys Val Val Arg Val Gln Arg Pro Thr Pro Arg Gly
3065 3070 3075

Thr Val Met Asp Ile Ile Ser Arg Arg Asp Gln Arg Gly Ser Gly
3080 3085 3090

Gln Val Gly Thr Tyr Gly Leu Asn Thr Phe Thr Asn Met Glu Ala
3095 3100 3105

Gln Leu Ile Arg Gln Met Glu Gly Glu Gly Val Phe Lys Ser Ile
3110 3115 3120

Gln His Leu Thr Ile Thr Glu Glu Ile Ala Val Gln Asn Trp Leu
3125 3130 3135

```
Ala Arg  Val Gly Arg Glu Arg  Leu Ser Arg Met Ala  Ile Ser Gly
    3140                 3145                 3150

Asp Asp  Cys Val Val Lys Pro  Leu Asp Asp Arg Phe  Ala Ser Ala
    3155                 3160                 3165

Leu Thr  Ala Leu Asn Asp Met  Gly Lys Ile Arg Lys  Asp Ile Gln
    3170                 3175                 3180

Gln Trp  Glu Pro Ser Arg Gly  Trp Asn Asp Trp Thr  Gln Val Pro
    3185                 3190                 3195

Phe Cys  Ser His His Phe His  Glu Leu Ile Met Lys  Asp Gly Arg
    3200                 3205                 3210

Val Leu  Val Val Pro Cys Arg  Asn Gln Asp Glu Leu  Ile Gly Arg
    3215                 3220                 3225

Ala Arg  Ile Ser Gln Gly Ala  Gly Trp Ser Leu Arg  Glu Thr Ala
    3230                 3235                 3240

Cys Leu  Gly Lys Ser Tyr Ala  Gln Met Trp Ser Leu  Met Tyr Phe
    3245                 3250                 3255

His Arg  Arg Asp Leu Arg Leu  Ala Ala Asn Ala Ile  Cys Ser Ala
    3260                 3265                 3270

Val Pro  Ser His Trp Val Pro  Thr Ser Arg Thr Thr  Trp Ser Ile
    3275                 3280                 3285

His Ala  Lys His Glu Trp Met  Thr Thr Glu Asp Met  Leu Thr Val
    3290                 3295                 3300

Trp Asn  Arg Val Trp Ile Gln  Glu Asn Pro Trp Met  Glu Asp Lys
    3305                 3310                 3315

Thr Pro  Val Glu Ser Trp Glu  Glu Ile Pro Tyr Leu  Gly Lys Arg
    3320                 3325                 3330

Glu Asp  Gln Trp Cys Gly Ser  Leu Ile Gly Leu Thr  Ser Arg Ala
    3335                 3340                 3345

Thr Trp  Ala Lys Asn Ile Gln  Ala Ala Ile Asn Gln  Val Arg Ser
    3350                 3355                 3360

Leu Ile  Gly Asn Glu Glu Tyr  Thr Asp Tyr Met Pro  Ser Met Lys
    3365                 3370                 3375

Arg Phe  Arg Arg Glu Glu Glu  Glu Ala Gly Val Leu  Trp
    3380                 3385                 3390
```

<210> SEQ ID NO 16
<211> LENGTH: 10723
<212> TYPE: DNA
<213> ORGANISM: Artificial Sequence
<220> FEATURE:
<223> OTHER INFORMATION: Derived from Dengue virus serotype 2, PDK-53 derivative, MVS

<400> SEQUENCE: 16

```
agttgttagt ctacgtggac cgacaaagac agattctttg agggagctaa gctcaatgta     60

gttctaacag ttttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagatctg caggcatgat cattatgctg    420

attccaacag tgatggcgtt ccatttaacc acacgtaacg gagaaccaca catgatcgtc    480
```

-continued

```
agcagacaag agaaagggaa aagtcttctg tttaaaacag aggttggcgt gaacatgtgt    540
accctcatgg ccatggacct tggtgaattg tgtgaagaca caatcacgta cgagtgtccc    600
cttctcaggc agaatgagcc agaagacata gactgttggt gcaactctac gtccacgtgg    660
gtaacttatg ggacgtgtac caccatggga gaacatagaa gagaaaaaag atcagtggca    720
ctcgttccac atgtgggaat gggactggag acacgaactg aaacatggat gtcatcagaa    780
ggggcctgga aacatgtcca gagaattgaa acttggatct tgagacatcc aggcttcacc    840
atgatggcag caatcctggc atacaccata ggaacgacac atttccaaag agccctgatc    900
ttcatcttac tgacagctgt cactccttca atgacaatgc gttgcatagg aatgtcaaat    960
agagactttg tggaaggggt ttcaggagga agctgggttg acatagtctt agaacatgga   1020
agctgtgtga cgacgatggc aaaaaacaaa ccaacattgg attttgaact gataaaaaca   1080
gaagccaaac agcctgccac cctaaggaag tactgtatag aggcaaagct aaccaacaca   1140
acaacagaat ctcgctgccc aacacaaggg gaacccagcc taaatgaaga gcaggacaaa   1200
aggttcgtct gcaaacactc catggtagac agaggatggg gaaatggatg tggactattt   1260
ggaaagggag gcattgtgac ctgtgctatg ttcagatgca aaaagaacat ggaaggaaaa   1320
gttgtgcaac cagaaaactt ggaatacacc attgtgataa cacctcactc aggggaagag   1380
catgcagtcg gaaatgacac aggaaaacat ggcaaggaaa tcaaaataac accacagagt   1440
tccatcacag aagcagaatt gacaggttat ggcactgtca caatggagtg ctctccaaga   1500
acgggcctcg acttcaatga gatggtgttg ctgcagatgg aaaataaagc ttggctggtg   1560
cacaggcaat ggttcctaga cctgccgtta ccatggttgc ccggagcgga cacacaaggg   1620
tcaaattgga tacagaaaga gacattggtc actttcaaaa atccccatgc gaagaaacag   1680
gatgttgttg ttttaggatc ccaagaaggg gccatgcaca cagcacttac aggggccaca   1740
gaaatccaaa tgtcatcagg aaacttactc ttcacaggac atctcaagtg caggctgaga   1800
atggacaagc tacagctcaa aggaatgtca tactctatgt gcacaggaaa gtttaaagtt   1860
gtgaaggaaa tagcagaaac acaacatgga acaatagtta tcagagtgca atatgaaggg   1920
gacggctctc catgcaagat ccctttttgag ataatggatt tggaaaaaag acatgtctta   1980
ggtcgcctga ttacagtcaa cccaattgtg acagaaaaag atagcccagt caacatagaa   2040
gcagaacctc catttggaga cagctacatc atcataggag tagagccggg acaactgaag   2100
ctcaactggt ttaagaaagg aagttctatc ggccaaatgt ttgagacaac aatgaggggg   2160
gcgaagagaa tggccatttt aggtgacaca gcctgggatt ttggatcctt gggaggagtg   2220
tttacatcta taggaaaggc tctccaccaa gtctttggag caatctatgg agctgccttc   2280
agtggggttt catggactat gaaaatcctc ataggagtca ttatcacatg gataggaatg   2340
aattcacgca gcacctcact gtctgtgaca ctagtattgg tgggaattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc ccccaacacaa atagagcttg gaattcgttg   2880
```

gaagttgaag actatggctt tggagtattc accaccaata tatggctaaa attgaaagaa 2940
aaacaggatg tattctgcga ctcaaaactc atgtcagcgg ccataaaaga caacagagcc 3000
gtccatgccg atatgggtta ttggatagaa agtgcactca atgacacatg gaagatagag 3060
aaagcctctt tcattgaagt taaaaactgc cactggccaa aatcacacac cctctggagc 3120
aatggagtgc tagaaagtga gatgataatt ccaaagaatc tcgctggacc agtgtctcaa 3180
cacaactata gaccaggcta ccatacacaa ataacaggac catggcatct aggtaagctt 3240
gagatggact ttgatttctg tgatggaaca acagtggtag tgactgagga ctgcggaaat 3300
agaggaccct ctttgagaac aaccactgcc tctggaaaac tcataacaga atggtgctgc 3360
cgatcttgca cattaccacc gctaagatac agaggtgagg atgggtgctg gtacgggatg 3420
gaaatcagac cattgaagga gaaagaagag aatttggtca actccttggt cacagctgga 3480
catgggcagg tcgacaactt ttcactagga gtcttgggaa tggcattgtt cctggaggaa 3540
atgcttagga cccgagtagg aacgaaacat gcaatactac tagttgcagt ttcttttgtg 3600
acattgatca cagggaacat gtcctttaga gacctgggaa gagtgatggt tatggtaggc 3660
gccactatga cggatgacat aggtatgggc gtgacttatc ttgccctact agcagccttc 3720
aaagtcagac caacttttgc agctggacta ctcttgagaa agctgacctc caaggaattg 3780
atgatgacta ctataggaat tgtactcctc tcccagagca ccataccaga gaccattctt 3840
gagttgactg atgcgttagc cttaggcatg atggtcctca aaatggtgag aaatatggaa 3900
aagtatcaat tggcagtgac tatcatggct atcttgtgcg tcccaaacgc agtgatatta 3960
caaaacgcat ggaaagtgag ttgcacaata ttggcagtgg tgtccgtttc cccactgttc 4020
ttaacatcct cacagcaaaa aacagattgg ataccattag cattgacgat caaaggtctc 4080
aatccaacag ctatttttct aacaaccctc tcaagaacca gcaagaaaag gagctggcca 4140
ttaaatgagg ctatcatggc agtcgggatg gtgagcattt tagccagttc tctcctaaaa 4200
aatgatattc ccatgacagg accattagtg gctggagggc tcctcactgt gtgctacgtg 4260
ctcactggac gatcggccga tttggaactg gagagagcag ccgatgtcaa atgggaagac 4320
caggcagaga tatcaggaag cagtccaatc ctgtcaataa caatatcaga agatggtagc 4380
atgtcgataa aaaatgaaga ggaagaacaa acactgacca tactcattag aacaggattg 4440
ctggtgatct caggactttt tcctgtatca ataccaatca cggcagcagc atggtacctg 4500
tgggaagtga agaaacaacg ggccggagta ttgtgggatg ttccttcacc cccacccatg 4560
ggaaaggctg aactggaaga tggagcctat agaattaagc aaaaagggat tcttggatat 4620
tcccagatcg gagccggagt ttacaaagaa ggaacattcc atacaatgtg gcatgtcaca 4680
cgtggcgctg ttctaatgca taaaggaaag aggattgaac catcatgggc ggacgtcaag 4740
aaagacctaa tatcatatgg aggaggctgg aagttagaag gagaatggaa ggaaggagaa 4800
gaagtccagg tattggcact ggagcctgga aaaaatccaa gagccgtcca aacgaaacct 4860
ggtcttttca aaaccaacgc cggaacaata ggtgctgtat ctctggactt ttctcctgga 4920
acgtcaggat ctccaattat cgacaaaaaa ggaaaagttg tgggtcttta tggtaatggt 4980
gttgttacaa ggagtggagc atatgtgagt gctatagccc agactgaaaa aagcattgaa 5040
gacaacccag agatcgaaga tgacattttc cgaaagagaa gactgaccat catggacctc 5100
cacccaggag cgggaaagac gaagagatac cttccggcca tagtcagaga agctataaaa 5160
cggggtttga gaacattaat cttggccccc actagagttg tggcagctga aatggaggaa 5220

```
gcccttagag gacttccaat aagataccag accccagcca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct tttattctt gatgagcgca    6600
aggggcatag ggaagatgac cctgggaatg tgctgcataa tcacggctag catcctccta   6660
tggtacgcac aaatacagcc acactggata gcagcttcaa taatactgga gtttttctc    6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
```

aacgcattgg gaaaaagtga attccagatc tacaagaaaa gtggaatcca ggaagtggat 7680
agaaccttag caaaagaagg cattaaaaga ggagaaacgg accatcacgc tgtgtcgcga 7740
ggctcagcaa aactgagatg gttcgttgag agaaacatgg tcacaccaga agggaaagta 7800
gtggacctcg gttgtggcag aggaggctgg tcatactatt gtggaggact aaagaatgta 7860
agagaagtca aaggcctaac aaaaggagga ccaggacacg aagaacccat ccccatgtca 7920
acatatgggt ggaatctagt gcgtcttcaa agtggagttg acgttttctt catcccgcca 7980
gaaaagtgtg acacattatt gtgtgacata ggggagtcat caccaaatcc cacagtggaa 8040
gcaggacgaa cactcagagt ccttaactta gtagaaaatt ggttgaacaa caacactcaa 8100
ttttgcataa aggttctcaa cccatatatg ccctcagtca tagaaaaaat ggaagcacta 8160
caaaggaaat atggaggagc cttagtgagg aatccactct cacgaaactc cacacatgag 8220
atgtactggg tatccaatgc ttccgggaac atagtgtcat cagtgaacat gatttcaagg 8280
atgttgatca acagatttac aatgagatac aagaaagcca cttacgagcc ggatgttgac 8340
ctcggaagcg gaacccgtaa catcgggatt gaaagtgaga taccaaacct agatataatt 8400
gggaaaagaa tagaaaaaat aaagcaagag catgaaacat catggcacta tgaccaagac 8460
cacccataca aaacgtgggc ataccatggt agctatgaaa caaaacagac tggatcagca 8520
tcatccatgg tcaacggagt ggtcaggctg ctgacaaaac cttgggacgt cgtccccatg 8580
gtgacacaga tggcaatgac agacacgact ccatttggac aacagcgcgt tttaaagag 8640
aaagtggaca cgagaaccca agaaccgaaa gaaggcacga agaaactaat gaaaataaca 8700
gcagagtggc tttggaaaga attagggaag aaaaagacac ccaggatgtg caccagagaa 8760
gaattcacaa gaaaggtgag aagcaatgca gccttggggg ccgtattcac tgatgagaac 8820
aagtggaagt cggcacgtga ggctgttgaa gatagtaggt tttgggagct ggttgacaag 8880
gaaaggaatc tccatcttga aggaaagtgt gaaacatgtg tgtacaacat gatgggaaaa 8940
agagagaaga agctagggga attcggcaag gcaaaaggca gcagagccat atggtacatg 9000
tggcttggag cacgcttctt agagtttgaa gccctaggat tcttaaatga agatcactgg 9060
ttctccagag agaactccct gagtggagtg gaaggagaag ggctgcacaa gctaggttac 9120
attctaagag acgtgagcaa gaaagaggga ggagcaatgt atgccgatga caccgcagga 9180
tgggatacaa gaatcacact agaagaccta aaaaatgaag aaatggtaac aaaccacatg 9240
gaaggagaac acaagaaact agccgaggcc attttcaaac taacgtacca aaacaaggtg 9300
gtgcgtgtgc aaagaccaac accaagaggc acagtaatgg acatcatatc gagaagagac 9360
caaagaggta gtggacaagt tggcacctat ggactcaata ctttcaccaa tatggaagcc 9420
caactaatca gacagatgga gggagaagga gtctttaaaa gcattcagca cctaacaatc 9480
acagaagaaa tcgctgtgca aaactggtta gcaagagtgg ggcgcgaaag gttatcaaga 9540
atggccatca gtggagatga ttgtgttgtg aaacctttag atgacaggtt cgcaagcgct 9600
ttaacagctc taaatgacat gggaaagatt aggaaagaca tacaacaatg ggaaccttca 9660
agaggatgga atgattggac acaagtgccc ttctgttcac accatttcca tgagttaatc 9720
atgaaagacg gtcgcgtact cgttgttcca tgtagaaacc aagatgaact gattggcaga 9780
gcccgaatct cccaaggagc agggtggtct ttgcgggaga cggcctgttt ggggaagtct 9840
tacgcccaaa tgtggagctt gatgtacttc cacagacgcg acctcaggct ggcggcaaat 9900
gctatttgct cggcagtacc atcacattgg gttccaacaa gtcgaacaac ctggtccata 9960

```
catgctaaac atgaatggat gacaacggaa gacatgctga cagtctggaa cagggtgtgg  10020

attcaagaaa acccatggat ggaagacaaa actccagtgg aatcatggga ggaaatccca  10080

tacttgggga aaagagaaga ccaatggtgc ggctcattga ttgggttaac aagcagggcc  10140

acctgggcaa agaacatcca agcagcaata aatcaagtta gatcccttat aggcaatgaa  10200

gaatacacag attacatgcc atccatgaaa agattcagaa gagaagagga agaagcagga  10260

gttctgtggt agaaagcaaa actaacatga aacaaggcta gaagtcaggt cggattaagc  10320

catagtacgg aaaaaactat gctacctgtg agccccgtcc aaggacgtta aaagaagtca  10380

ggccatcata aatgccatag cttgagtaaa ctatgcagcc tgtagctcca cctgagaagg  10440

tgtaaaaaat ccgggaggcc acaaaccatg gaagctgtac gcatggcgta gtggactagc  10500

ggttagagga gacccctccc ttacaaatcg cagcaacaat gggggcccaa ggcgagatga  10560

agctgtagtc tcgctggaag gactagaggt tagaggagac ccccccgaaa caaaaaacag  10620

catattgacg ctgggaaaga ccagagatcc tgctgtctcc tcagcatcat tccaggcaca  10680

gaacgccaga aaatggaatg gtgctgttga atcaacaggt tct                    10723
```

<210> SEQ ID NO 17
<211> LENGTH: 3391
<212> TYPE: PRT
<213> ORGANISM: Artificial Sequence
<220> FEATURE:
<223> OTHER INFORMATION: Derived from Dengue virus serotype 2, PDK-53 derivative, MVS

<400> SEQUENCE: 17

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Glu Val Gly
    130                 135                 140

Val Asn Met Cys Thr Leu Met Ala Met Asp Leu Gly Glu Leu Cys Glu
145                 150                 155                 160

Asp Thr Ile Thr Tyr Glu Cys Pro Leu Leu Arg Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Met Gly Glu His Arg Arg Glu Lys Arg Ser Val Ala
        195                 200                 205

Leu Val Pro His Val Gly Met Gly Leu Glu Thr Arg Thr Glu Thr Trp
    210                 215                 220
```

-continued

```
Met Ser Ser Glu Gly Ala Trp Lys His Val Gln Arg Ile Glu Thr Trp
225                 230                 235                 240

Ile Leu Arg His Pro Gly Phe Thr Met Met Ala Ala Ile Leu Ala Tyr
                245                 250                 255

Thr Ile Gly Thr Thr His Phe Gln Arg Ala Leu Ile Phe Ile Leu Leu
            260                 265                 270

Thr Ala Val Thr Pro Ser Met Thr Met Arg Cys Ile Gly Met Ser Asn
        275                 280                 285

Arg Asp Phe Val Glu Gly Val Ser Gly Gly Ser Trp Val Asp Ile Val
    290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Glu Ser
            340                 345                 350

Arg Cys Pro Thr Gln Gly Glu Pro Ser Leu Asn Glu Glu Gln Asp Lys
        355                 360                 365

Arg Phe Val Cys Lys His Ser Met Val Asp Arg Gly Trp Gly Asn Gly
    370                 375                 380

Cys Gly Leu Phe Gly Lys Gly Gly Ile Val Thr Cys Ala Met Phe Arg
385                 390                 395                 400

Cys Lys Lys Asn Met Glu Gly Lys Val Val Gln Pro Glu Asn Leu Glu
                405                 410                 415

Tyr Thr Ile Val Ile Thr Pro His Ser Gly Glu Glu His Ala Val Gly
            420                 425                 430

Asn Asp Thr Gly Lys His Gly Lys Glu Ile Lys Ile Thr Pro Gln Ser
        435                 440                 445

Ser Ile Thr Glu Ala Glu Leu Thr Gly Tyr Gly Thr Val Thr Met Glu
    450                 455                 460

Cys Ser Pro Arg Thr Gly Leu Asp Phe Asn Glu Met Val Leu Leu Gln
465                 470                 475                 480

Met Glu Asn Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
            500                 505                 510

Gln Lys Glu Thr Leu Val Thr Phe Lys Asn Pro His Ala Lys Lys Gln
        515                 520                 525

Asp Val Val Val Leu Gly Ser Gln Glu Gly Ala Met His Thr Ala Leu
    530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575

Met Ser Tyr Ser Met Cys Thr Gly Lys Phe Lys Val Val Lys Glu Ile
            580                 585                 590

Ala Glu Thr Gln His Gly Thr Ile Val Ile Arg Val Gln Tyr Glu Gly
        595                 600                 605

Asp Gly Ser Pro Cys Lys Ile Pro Phe Glu Ile Met Asp Leu Glu Lys
    610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
```

-continued

```
                645                 650                 655

Tyr Ile Ile Ile Gly Val Glu Pro Gly Gln Leu Lys Leu Asn Trp Phe
            660                 665                 670

Lys Lys Gly Ser Ser Ile Gly Gln Met Phe Glu Thr Thr Met Arg Gly
        675                 680                 685

Ala Lys Arg Met Ala Ile Leu Gly Asp Thr Ala Trp Asp Phe Gly Ser
    690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Ser
            740                 745                 750

Thr Ser Leu Ser Val Thr Leu Val Leu Val Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
        995                 1000                1005

Asn Gly  Val Leu Glu Ser Glu  Met Ile Ile Pro Lys  Asn Leu Ala
    1010                1015                1020

Gly Pro  Val Ser Gln His Asn  Tyr Arg Pro Gly Tyr  His Thr Gln
    1025                1030                1035

Ile Thr  Gly Pro Trp His Leu  Gly Lys Leu Glu Met  Asp Phe Asp
    1040                1045                1050

Phe Cys  Asp Gly Thr Thr Val  Val Val Thr Glu Asp  Cys Gly Asn
    1055                1060                1065
```

```
Arg Gly  Pro Ser Leu Arg Thr  Thr Thr Ala Ser Gly  Lys Leu Ile
    1070                 1075                 1080

Thr Glu  Trp Cys Cys Arg Ser  Cys Thr Leu Pro Pro  Leu Arg Tyr
    1085                 1090                 1095

Arg Gly  Glu Asp Gly Cys Trp  Tyr Gly Met Glu Ile  Arg Pro Leu
    1100                 1105                 1110

Lys Glu  Lys Glu Glu Asn Leu  Val Asn Ser Leu Val  Thr Ala Gly
    1115                 1120                 1125

His Gly  Gln Val Asp Asn Phe  Ser Leu Gly Val Leu  Gly Met Ala
    1130                 1135                 1140

Leu Phe  Leu Glu Glu Met Leu  Arg Thr Arg Val Gly  Thr Lys His
    1145                 1150                 1155

Ala Ile  Leu Leu Val Ala Val  Ser Phe Val Thr Leu  Ile Thr Gly
    1160                 1165                 1170

Asn Met  Ser Phe Arg Asp Leu  Gly Arg Val Met Val  Met Val Gly
    1175                 1180                 1185

Ala Thr  Met Thr Asp Asp Ile  Gly Met Gly Val Thr  Tyr Leu Ala
    1190                 1195                 1200

Leu Leu  Ala Ala Phe Lys Val  Arg Pro Thr Phe Ala  Ala Gly Leu
    1205                 1210                 1215

Leu Leu  Arg Lys Leu Thr Ser  Lys Glu Leu Met Met  Thr Thr Ile
    1220                 1225                 1230

Gly Ile  Val Leu Leu Ser Gln  Ser Thr Ile Pro Glu  Thr Ile Leu
    1235                 1240                 1245

Glu Leu  Thr Asp Ala Leu Ala  Leu Gly Met Met Val  Leu Lys Met
    1250                 1255                 1260

Val Arg  Asn Met Glu Lys Tyr  Gln Leu Ala Val Thr  Ile Met Ala
    1265                 1270                 1275

Ile Leu  Cys Val Pro Asn Ala  Val Ile Leu Gln Asn  Ala Trp Lys
    1280                 1285                 1290

Val Ser  Cys Thr Ile Leu Ala  Val Val Ser Val Ser  Pro Leu Phe
    1295                 1300                 1305

Leu Thr  Ser Ser Gln Gln Lys  Thr Asp Trp Ile Pro  Leu Ala Leu
    1310                 1315                 1320

Thr Ile  Lys Gly Leu Asn Pro  Thr Ala Ile Phe Leu  Thr Thr Leu
    1325                 1330                 1335

Ser Arg  Thr Ser Lys Lys Arg  Ser Trp Pro Leu Asn  Glu Ala Ile
    1340                 1345                 1350

Met Ala  Val Gly Met Val Ser  Ile Leu Ala Ser Ser  Leu Leu Lys
    1355                 1360                 1365

Asn Asp  Ile Pro Met Thr Gly  Pro Leu Val Ala Gly  Gly Leu Leu
    1370                 1375                 1380

Thr Val  Cys Tyr Val Leu Thr  Gly Arg Ser Ala Asp  Leu Glu Leu
    1385                 1390                 1395

Glu Arg  Ala Ala Asp Val Lys  Trp Glu Asp Gln Ala  Glu Ile Ser
    1400                 1405                 1410

Gly Ser  Ser Pro Ile Leu Ser  Ile Thr Ile Ser Glu  Asp Gly Ser
    1415                 1420                 1425

Met Ser  Ile Lys Asn Glu Glu  Glu Glu Gln Thr Leu  Thr Ile Leu
    1430                 1435                 1440

Ile Arg  Thr Gly Leu Leu Val  Ile Ser Gly Leu Phe  Pro Val Ser
    1445                 1450                 1455
```

```
Ile Pro  Ile Thr Ala Ala Ala  Trp Tyr Leu Trp Glu  Val Lys Lys
    1460                 1465                 1470

Gln Arg  Ala Gly Val Leu Trp  Asp Val Pro Ser Pro  Pro Pro Met
    1475                 1480                 1485

Gly Lys  Ala Glu Leu Glu Asp  Gly Ala Tyr Arg Ile  Lys Gln Lys
    1490                 1495                 1500

Gly Ile  Leu Gly Tyr Ser Gln  Ile Gly Ala Gly Val  Tyr Lys Glu
    1505                 1510                 1515

Gly Thr  Phe His Thr Met Trp  His Val Thr Arg Gly  Ala Val Leu
    1520                 1525                 1530

Met His  Lys Gly Lys Arg Ile  Glu Pro Ser Trp Ala  Asp Val Lys
    1535                 1540                 1545

Lys Asp  Leu Ile Ser Tyr Gly  Gly Gly Trp Lys Leu  Glu Gly Glu
    1550                 1555                 1560

Trp Lys  Glu Gly Glu Glu Val  Gln Val Leu Ala Leu  Glu Pro Gly
    1565                 1570                 1575

Lys Asn  Pro Arg Ala Val Gln  Thr Lys Pro Gly Leu  Phe Lys Thr
    1580                 1585                 1590

Asn Ala  Gly Thr Ile Gly Ala  Val Ser Leu Asp Phe  Ser Pro Gly
    1595                 1600                 1605

Thr Ser  Gly Ser Pro Ile Ile  Asp Lys Lys Gly Lys  Val Val Gly
    1610                 1615                 1620

Leu Tyr  Gly Asn Gly Val Val  Thr Arg Ser Gly Ala  Tyr Val Ser
    1625                 1630                 1635

Ala Ile  Ala Gln Thr Glu Lys  Ser Ile Glu Asp Asn  Pro Glu Ile
    1640                 1645                 1650

Glu Asp  Asp Ile Phe Arg Lys  Arg Arg Leu Thr Ile  Met Asp Leu
    1655                 1660                 1665

His Pro  Gly Ala Gly Lys Thr  Lys Arg Tyr Leu Pro  Ala Ile Val
    1670                 1675                 1680

Arg Glu  Ala Ile Lys Arg Gly  Leu Arg Thr Leu Ile  Leu Ala Pro
    1685                 1690                 1695

Thr Arg  Val Val Ala Ala Glu  Met Glu Glu Ala Leu  Arg Gly Leu
    1700                 1705                 1710

Pro Ile  Arg Tyr Gln Thr Pro  Ala Ile Arg Ala Val  His Thr Gly
    1715                 1720                 1725

Arg Glu  Ile Val Asp Leu Met  Cys His Ala Thr Phe  Thr Met Arg
    1730                 1735                 1740

Leu Leu  Ser Pro Val Arg Val  Pro Asn Tyr Asn Leu  Ile Ile Met
    1745                 1750                 1755

Asp Glu  Ala His Phe Thr Asp  Pro Ala Ser Ile Ala  Ala Arg Gly
    1760                 1765                 1770

Tyr Ile  Ser Thr Arg Val Glu  Met Gly Glu Ala Ala  Gly Ile Phe
    1775                 1780                 1785

Met Thr  Ala Thr Pro Pro Gly  Ser Arg Asp Pro Phe  Pro Gln Ser
    1790                 1795                 1800

Asn Ala  Pro Ile Ile Asp Glu  Glu Arg Glu Ile Pro  Glu Arg Ser
    1805                 1810                 1815

Trp Asn  Ser Gly His Glu Trp  Val Thr Asp Phe Lys  Gly Lys Thr
    1820                 1825                 1830

Val Trp  Phe Val Pro Ser Ile  Lys Ala Gly Asn Asp  Ile Ala Ala
    1835                 1840                 1845

Cys Leu  Arg Lys Asn Gly Lys  Lys Val Ile Gln Leu  Ser Arg Lys
```

```
    1850                1855                1860

Thr Phe  Asp Ser Glu Tyr Val  Lys Thr Arg Thr Asn  Asp Trp Asp
    1865                1870                1875

Phe Val  Val Thr Thr Asp Ile  Ser Glu Met Gly Ala  Asn Phe Lys
    1880                1885                1890

Ala Glu  Arg Val Ile Asp Pro  Arg Arg Cys Met Lys  Pro Val Ile
    1895                1900                1905

Leu Thr  Asp Gly Glu Glu Arg  Val Ile Leu Ala Gly  Pro Met Pro
    1910                1915                1920

Val Thr  His Ser Ser Ala Ala  Gln Arg Arg Gly Arg  Ile Gly Arg
    1925                1930                1935

Asn Pro  Lys Asn Glu Asn Asp  Gln Tyr Ile Tyr Met  Gly Glu Pro
    1940                1945                1950

Leu Glu  Asn Asp Glu Asp Cys  Ala His Trp Lys Glu  Ala Lys Met
    1955                1960                1965

Leu Leu  Asp Asn Ile Asn Thr  Pro Glu Gly Ile Ile  Pro Ser Met
    1970                1975                1980

Phe Glu  Pro Glu Arg Glu Lys  Val Asp Ala Ile Asp  Gly Glu Tyr
    1985                1990                1995

Arg Leu  Arg Gly Glu Ala Arg  Lys Thr Phe Val Asp  Leu Met Arg
    2000                2005                2010

Arg Gly  Asp Leu Pro Val Trp  Leu Ala Tyr Arg Val  Ala Ala Glu
    2015                2020                2025

Gly Ile  Asn Tyr Ala Asp Arg  Arg Trp Cys Phe Asp  Gly Val Lys
    2030                2035                2040

Asn Asn  Gln Ile Leu Glu Glu  Asn Val Glu Val Glu  Ile Trp Thr
    2045                2050                2055

Lys Glu  Gly Glu Arg Lys Lys  Leu Lys Pro Arg Trp  Leu Asp Ala
    2060                2065                2070

Arg Ile  Tyr Ser Asp Pro Leu  Ala Leu Lys Glu Phe  Lys Glu Phe
    2075                2080                2085

Ala Ala  Gly Arg Lys Ser Leu  Thr Leu Asn Leu Ile  Thr Glu Met
    2090                2095                2100

Gly Arg  Leu Pro Thr Phe Met  Thr Gln Lys Ala Arg  Asp Ala Leu
    2105                2110                2115

Asp Asn  Leu Ala Val Leu His  Thr Ala Glu Ala Gly  Gly Arg Ala
    2120                2125                2130

Tyr Asn  His Ala Leu Ser Glu  Leu Pro Glu Thr Leu  Glu Thr Leu
    2135                2140                2145

Leu Leu  Leu Thr Leu Leu Ala  Thr Val Thr Gly Gly  Ile Phe Leu
    2150                2155                2160

Phe Leu  Met Ser Ala Arg Gly  Ile Gly Lys Met Thr  Leu Gly Met
    2165                2170                2175

Cys Cys  Ile Ile Thr Ala Ser  Ile Leu Leu Trp Tyr  Ala Gln Ile
    2180                2185                2190

Gln Pro  His Trp Ile Ala Ala  Ser Ile Ile Leu Glu  Phe Phe Leu
    2195                2200                2205

Ile Val  Leu Leu Ile Pro Glu  Pro Glu Lys Gln Arg  Thr Pro Gln
    2210                2215                2220

Asp Asn  Gln Leu Thr Tyr Val  Val Ile Ala Ile Leu  Thr Val Val
    2225                2230                2235

Ala Ala  Thr Met Ala Asn Glu  Met Gly Phe Leu Glu  Lys Thr Lys
    2240                2245                2250
```

-continued

Lys Asp Leu Gly Leu Gly Ser Ile Ala Thr Gln Gln Pro Glu Ser
2255 2260 2265

Asn Ile Leu Asp Ile Asp Leu Arg Pro Ala Ser Ala Trp Thr Leu
2270 2275 2280

Tyr Ala Val Ala Thr Thr Phe Val Thr Pro Met Leu Arg His Ser
2285 2290 2295

Ile Glu Asn Ser Ser Val Asn Val Ser Leu Thr Ala Ile Ala Asn
2300 2305 2310

Gln Ala Thr Val Leu Met Gly Leu Gly Lys Gly Trp Pro Leu Ser
2315 2320 2325

Lys Met Asp Ile Gly Val Pro Leu Leu Ala Ile Gly Cys Tyr Ser
2330 2335 2340

Gln Val Asn Pro Ile Thr Leu Thr Ala Ala Leu Phe Leu Leu Val
2345 2350 2355

Ala His Tyr Ala Ile Ile Gly Pro Gly Leu Gln Ala Lys Ala Thr
2360 2365 2370

Arg Glu Ala Gln Lys Arg Ala Ala Ala Gly Ile Met Lys Asn Pro
2375 2380 2385

Thr Val Asp Gly Ile Thr Val Ile Asp Leu Asp Pro Ile Pro Tyr
2390 2395 2400

Asp Pro Lys Phe Glu Lys Gln Leu Gly Gln Val Met Leu Leu Val
2405 2410 2415

Leu Cys Val Thr Gln Val Leu Met Met Arg Thr Thr Trp Ala Leu
2420 2425 2430

Cys Glu Ala Leu Thr Leu Ala Thr Gly Pro Ile Ser Thr Leu Trp
2435 2440 2445

Glu Gly Asn Pro Gly Arg Phe Trp Asn Thr Thr Ile Ala Val Ser
2450 2455 2460

Met Ala Asn Ile Phe Arg Gly Ser Tyr Leu Ala Gly Ala Gly Leu
2465 2470 2475

Leu Phe Ser Ile Met Lys Asn Thr Thr Asn Thr Arg Arg Gly Thr
2480 2485 2490

Gly Asn Ile Gly Glu Thr Leu Gly Glu Lys Trp Lys Ser Arg Leu
2495 2500 2505

Asn Ala Leu Gly Lys Ser Glu Phe Gln Ile Tyr Lys Lys Ser Gly
2510 2515 2520

Ile Gln Glu Val Asp Arg Thr Leu Ala Lys Glu Gly Ile Lys Arg
2525 2530 2535

Gly Glu Thr Asp His His Ala Val Ser Arg Gly Ser Ala Lys Leu
2540 2545 2550

Arg Trp Phe Val Glu Arg Asn Met Val Thr Pro Glu Gly Lys Val
2555 2560 2565

Val Asp Leu Gly Cys Gly Arg Gly Gly Trp Ser Tyr Tyr Cys Gly
2570 2575 2580

Gly Leu Lys Asn Val Arg Glu Val Lys Gly Leu Thr Lys Gly Gly
2585 2590 2595

Pro Gly His Glu Glu Pro Ile Pro Met Ser Thr Tyr Gly Trp Asn
2600 2605 2610

Leu Val Arg Leu Gln Ser Gly Val Asp Val Phe Phe Ile Pro Pro
2615 2620 2625

Glu Lys Cys Asp Thr Leu Leu Cys Asp Ile Gly Glu Ser Ser Pro
2630 2635 2640

Asn Pro Thr Val Glu Ala Gly Arg Thr Leu Arg Val Leu Asn Leu
2645 2650 2655

Val Glu Asn Trp Leu Asn Asn Asn Thr Gln Phe Cys Ile Lys Val
2660 2665 2670

Leu Asn Pro Tyr Met Pro Ser Val Ile Glu Lys Met Glu Ala Leu
2675 2680 2685

Gln Arg Lys Tyr Gly Gly Ala Leu Val Arg Asn Pro Leu Ser Arg
2690 2695 2700

Asn Ser Thr His Glu Met Tyr Trp Val Ser Asn Ala Ser Gly Asn
2705 2710 2715

Ile Val Ser Ser Val Asn Met Ile Ser Arg Met Leu Ile Asn Arg
2720 2725 2730

Phe Thr Met Arg Tyr Lys Lys Ala Thr Tyr Glu Pro Asp Val Asp
2735 2740 2745

Leu Gly Ser Gly Thr Arg Asn Ile Gly Ile Glu Ser Glu Ile Pro
2750 2755 2760

Asn Leu Asp Ile Ile Gly Lys Arg Ile Glu Lys Ile Lys Gln Glu
2765 2770 2775

His Glu Thr Ser Trp His Tyr Asp Gln Asp His Pro Tyr Lys Thr
2780 2785 2790

Trp Ala Tyr His Gly Ser Tyr Glu Thr Lys Gln Thr Gly Ser Ala
2795 2800 2805

Ser Ser Met Val Asn Gly Val Val Arg Leu Leu Thr Lys Pro Trp
2810 2815 2820

Asp Val Val Pro Met Val Thr Gln Met Ala Met Thr Asp Thr Thr
2825 2830 2835

Pro Phe Gly Gln Gln Arg Val Phe Lys Glu Lys Val Asp Thr Arg
2840 2845 2850

Thr Gln Glu Pro Lys Glu Gly Thr Lys Lys Leu Met Lys Ile Thr
2855 2860 2865

Ala Glu Trp Leu Trp Lys Glu Leu Gly Lys Lys Lys Thr Pro Arg
2870 2875 2880

Met Cys Thr Arg Glu Glu Phe Thr Arg Lys Val Arg Ser Asn Ala
2885 2890 2895

Ala Leu Gly Ala Val Phe Thr Asp Glu Asn Lys Trp Lys Ser Ala
2900 2905 2910

Arg Glu Ala Val Glu Asp Ser Arg Phe Trp Glu Leu Val Asp Lys
2915 2920 2925

Glu Arg Asn Leu His Leu Glu Gly Lys Cys Glu Thr Cys Val Tyr
2930 2935 2940

Asn Met Met Gly Lys Arg Glu Lys Lys Leu Gly Glu Phe Gly Lys
2945 2950 2955

Ala Lys Gly Ser Arg Ala Ile Trp Tyr Met Trp Leu Gly Ala Arg
2960 2965 2970

Phe Leu Glu Phe Glu Ala Leu Gly Phe Leu Asn Glu Asp His Trp
2975 2980 2985

Phe Ser Arg Glu Asn Ser Leu Ser Gly Val Glu Gly Glu Gly Leu
2990 2995 3000

His Lys Leu Gly Tyr Ile Leu Arg Asp Val Ser Lys Lys Glu Gly
3005 3010 3015

Gly Ala Met Tyr Ala Asp Asp Thr Ala Gly Trp Asp Thr Arg Ile
3020 3025 3030

Thr Leu Glu Asp Leu Lys Asn Glu Glu Met Val Thr Asn His Met

```
    3035                3040                3045

Glu Gly  Glu His Lys Lys Leu  Ala Glu Ala Ile Phe  Lys Leu Thr
    3050                3055                3060

Tyr Gln  Asn Lys Val Val Arg  Val Gln Arg Pro Thr  Pro Arg Gly
    3065                3070                3075

Thr Val  Met Asp Ile Ile Ser  Arg Arg Asp Gln Arg  Gly Ser Gly
    3080                3085                3090

Gln Val  Gly Thr Tyr Gly Leu  Asn Thr Phe Thr Asn  Met Glu Ala
    3095                3100                3105

Gln Leu  Ile Arg Gln Met Glu  Gly Glu Gly Val Phe  Lys Ser Ile
    3110                3115                3120

Gln His  Leu Thr Ile Thr Glu  Glu Ile Ala Val Gln  Asn Trp Leu
    3125                3130                3135

Ala Arg  Val Gly Arg Glu Arg  Leu Ser Arg Met Ala  Ile Ser Gly
    3140                3145                3150

Asp Asp  Cys Val Val Lys Pro  Leu Asp Asp Arg Phe  Ala Ser Ala
    3155                3160                3165

Leu Thr  Ala Leu Asn Asp Met  Gly Lys Ile Arg Lys  Asp Ile Gln
    3170                3175                3180

Gln Trp  Glu Pro Ser Arg Gly  Trp Asn Asp Trp Thr  Gln Val Pro
    3185                3190                3195

Phe Cys  Ser His His Phe His  Glu Leu Ile Met Lys  Asp Gly Arg
    3200                3205                3210

Val Leu  Val Val Pro Cys Arg  Asn Gln Asp Glu Leu  Ile Gly Arg
    3215                3220                3225

Ala Arg  Ile Ser Gln Gly Ala  Gly Trp Ser Leu Arg  Glu Thr Ala
    3230                3235                3240

Cys Leu  Gly Lys Ser Tyr Ala  Gln Met Trp Ser Leu  Met Tyr Phe
    3245                3250                3255

His Arg  Arg Asp Leu Arg Leu  Ala Ala Asn Ala Ile  Cys Ser Ala
    3260                3265                3270

Val Pro  Ser His Trp Val Pro  Thr Ser Arg Thr Thr  Trp Ser Ile
    3275                3280                3285

His Ala  Lys His Glu Trp Met  Thr Thr Glu Asp Met  Leu Thr Val
    3290                3295                3300

Trp Asn  Arg Val Trp Ile Gln  Glu Asn Pro Trp Met  Glu Asp Lys
    3305                3310                3315

Thr Pro  Val Glu Ser Trp Glu  Glu Ile Pro Tyr Leu  Gly Lys Arg
    3320                3325                3330

Glu Asp  Gln Trp Cys Gly Ser  Leu Ile Gly Leu Thr  Ser Arg Ala
    3335                3340                3345

Thr Trp  Ala Lys Asn Ile Gln  Ala Ala Ile Asn Gln  Val Arg Ser
    3350                3355                3360

Leu Ile  Gly Asn Glu Glu Tyr  Thr Asp Tyr Met Pro  Ser Met Lys
    3365                3370                3375

Arg Phe  Arg Arg Glu Glu Glu  Glu Ala Gly Val Leu  Trp
    3380                3385                3390
```

<210> SEQ ID NO 18
<211> LENGTH: 10717
<212> TYPE: DNA
<213> ORGANISM: Artificial Sequence
<220> FEATURE:
<223> OTHER INFORMATION: Derived from Dengue virus serotype 2/Dengue
      virus serotype 3, MVS -continued

<400> SEQUENCE: 18

```
agttgttagt ctacgtggac cgacaaagac agattctttg agggagctaa gctcaatgta     60
gttctaacag tttttttaatt agagagcaga tctctgatga ataaccaacg gaaaaaggcg    120
aaaaacacgc ctttcaatat gctgaaacgc gagagaaacc gcgtgtcgac tgtgcaacag    180
ctgacaaaga gattctcact tggaatgctg cagggacgag gaccattaaa actgttcatg    240
gccctggtgg cgttccttcg tttcctaaca atcccaccaa cagcagggat attgaagaga    300
tggggaacaa ttaaaaaatc aaaagctatt aatgttttga gagggttcag gaaagagatt    360
ggaaggatgc tgaacatctt gaataggaga cgcagatctg caggcatgat cattatgctg    420
attccaacag tgatggcgtt ccatttaacc acgcgtgatg gagagccgcg catgattgtg    480
gggaagaatg aaagaggaaa atccctactt ttcaagacag cctctggaat caacatgtgc    540
acactcatag ctatggatct gggagagatg tgtgatgaca cggtcactta caaatgcccc    600
cacattaccg aagtggagcc tgaagacatt gactgctggt gcaaccttac atcgacatgg    660
gtgacttatg gaacatgcaa tcaagctgga gagcatagac gcgataagag atcagtggcg    720
ttagctcccc atgttggcat gggactggac acacgcactc aaacctggat gtcggctgaa    780
ggagcttgga gacaagtcga gaaggtagag acatgggccc ttaggcaccc agggtttacc    840
atactagccc tatttcttgc ccattacata ggcacttcct tgacccagaa agtggttatt    900
tttatactat taatgctggt taccccatcc atgacaatga gatgtgtagg agtaggaaac    960
agagattttg tggaaggcct atcgggagct acgtgggttg acgtggtgct cgagcacggt   1020
gggtgtgtga ctaccatggc taagaacaag cccacgctgg acatagagct tcagaagacc   1080
gaggccaccc aactggcgac cctaaggaag ctatgcattg agggaaaaat taccaacata   1140
acaaccgact caagatgtcc cacccaaggg gaagcgattt tacctgagga gcaggaccag   1200
aactacgtgt gtaagcatac atacgtggac agaggctggg gaaacggttg tggtttgttt   1260
ggcaagggaa gcttggtgac atgcgcgaaa tttcaatgtt tagaatcaat agagggaaaa   1320
gtggtgcaac atgagaacct caaatacacc gtcatcatca cagtgcacac aggagaccaa   1380
caccaggtgg gaaatgaaac gcagggagtc acggctgaga taacacccca ggcatcaacc   1440
gctgaagcca ttttacctga atatggaacc ctcgggctag aatgctcacc acggacaggt   1500
ttggatttca atgaaatgat ctcattgaca atgaagaaca aagcatggat ggtacataga   1560
caatggttct ttgacttacc cctaccatgg acatcaggag cttcagcaga aacaccaact   1620
tggaacagga aagagcttct tgtgacattt aaaaatgcac atgcaaaaaa gcaagaagta   1680
gttgttcttg gatcacaaga gggagcaatg catacagcac tgacaggagc tacagagatc   1740
caaacctcag gaggcacaag tatctttgcg gggcacttaa aatgtagact caagatggac   1800
aaattggaac tcaaggggat gagctatgca atgtgcttga gtagctttgt gttgaagaaa   1860
gaagtctccg aaacgcagca tgggacaata ctcattaagg ttgagtacaa aggggaagat   1920
gcaccctgca agattccttt ctccacggag gatggacaag gaaaagctct caatggcaga   1980
ctgatcacag ccaatccagt ggtgaccaag aaggaggagc ctgtcaacat tgaggctgaa   2040
cctccttttg gagaaagtaa catagtaatt ggaattggag acaaagccct gaaaatcaac   2100
tggtacaaga agggaagctc gattgggaag atgttcgagg ccactgccag aggtgcaagg   2160
cgcatggcca tcttgggaga cacagcctgg gactttggat cagtgggtgg tgttttgaat   2220
tcattaggga aaatggtcca ccaaatattt gggagtgctt acacagccct atttggtgga   2280
```

-continued

```
gtctcctgga tgatgaaaat tggaataggt gtcctcttaa cctggatagg gttgaactca   2340
aaaaatactt ctatgtcatt ttcatgcatc gcggccggca ttgtgacact gtatttggga   2400
gtcatggtgc aggccgatag tggttgcgtt gtgagctgga aaaacaaaga actgaaatgt   2460
ggcagtggga ttttcatcac agacaacgtg cacacatgga cagaacaata caagttccaa   2520
ccagaatccc cttcaaaact agcttcagct atccagaaag cccatgaaga ggacatttgt   2580
ggaatccgct cagtaacaag actggagaat ctgatgtgga aacaaataac accagaattg   2640
aatcacattc tatcagaaaa tgaggtgaag ttaactatta tgacaggaga catcaaagga   2700
atcatgcagg caggaaaacg atctctgcgg cctcagccca ctgagctgaa gtattcatgg   2760
aaaacatggg gcaaagcaaa aatgctctct acagagtctc ataaccagac ctttctcatt   2820
gatggccccg aaacagcaga atgccccaac acaaatagag cttggaattc gttggaagtt   2880
gaagactatg gctttggagt attcaccacc aatatatggc taaaattgaa agaaaaacag   2940
gatgtattct gcgactcaaa actcatgtca gcggccataa aagacaacag agccgtccat   3000
gccgatatgg gttattggat agaaagtgca ctcaatgaca catggaagat agagaaagcc   3060
tctttcattg aagttaaaaa ctgccactgg ccaaaatcac acaccctctg gagcaatgga   3120
gtgctagaaa gtgagatgat aattccaaag aatctcgctg gaccagtgtc tcaacacaac   3180
tatagaccag gctaccatac acaaataaca ggaccatggc atctaggtaa gcttgagatg   3240
gactttgatt tctgtgatgg aacaacagtg gtagtgactg aggactgcgg aaatagagga   3300
ccctctttga gaacaaccac tgcctctgga aaactcataa cagaatggtg ctgccgatct   3360
tgcacattac caccgctaag atacagaggt gaggatgggt gctggtacgg gatggaaatc   3420
agaccattga aggagaaaga agagaatttg gtcaactcct tggtcacagc tggacatggg   3480
caggtcgaca acttttcact aggagtcttg ggaatggcat tgttcctgga ggaaatgctt   3540
aggacccgag taggaacgaa acatgcaata ctactagttg cagtttcttt tgtgacattg   3600
atcacaggga acatgtcctt tagagacctg ggaagagtga tggttatggt aggcgccact   3660
atgacggatg acataggtat gggcgtgact tatcttgccc tactagcagc cttcaaagtc   3720
agaccaactt ttgcagctgg actactcttg agaaagctga cctccaagga attgatgatg   3780
actactatag gaattgtact cctctcccag agcaccatac cagagaccat tcttgagttg   3840
actgatgcgt tagccttagg catgatggtc ctcaaaatgg tgagaaatat ggaaaagtat   3900
caattggcag tgactatcat ggctatcttg tgcgtcccaa acgcagtgat attacaaaac   3960
gcatggaaag tgagttgcac aatattggca gtggtgtccg tttccccact gttcttaaca   4020
tcctcacagc aaaaaacaga ttggatacca ttagcattga cgatcaaagg tctcaatcca   4080
acagctattt ttctaacaac cctctcaaga accagcaaga aaaggagctg gccattaaat   4140
gaggctatca tggcagtcgg gatggtgagc attttagcca gttctctcct aaaaaatgat   4200
attcccatga caggaccatt agtggctgga gggctcctca ctgtgtgcta cgtgctcact   4260
ggacgatcgg ccgatttgga actggagaga gcagccgatg tcaaatggga agaccaggca   4320
gagatatcag gaagcagtcc aatcctgtca ataacaatat cagaagatgg tagcatgtcg   4380
ataaaaaatg aagaggaaga acaaacactg accatactca ttagaacagg attgctggtg   4440
atctcaggac tttttcctgt atcaatacca atcacggcag cagcatggta cctgtgggaa   4500
gtgaagaaac aacgggccgg agtattgtgg gatgttcctt cacccccacc catgggaaag   4560
gctgaactgg aagatggagc ctatagaatt aagcaaaaag ggattcttgg atattcccag   4620
atcggagccg gagtttacaa agaaggaaca ttccatacaa tgtggcatgt cacacgtggc   4680
```

gctgttctaa tgcataaagg aaagaggatt gaaccatcat gggcggacgt caagaaagac 4740
ctaatatcat atggaggagg ctggaagtta gaaggagaat ggaaggaagg agaagaagtc 4800
caggtattgg cactggagcc tggaaaaaat ccaagagccg tccaaacgaa acctggtctt 4860
ttcaaaacca acgccggaac aataggtgct gtatctctgg acttttctcc tggaacgtca 4920
ggatctccaa ttatcgacaa aaaaggaaaa gttgtgggtc tttatggtaa tggtgttgtt 4980
acaaggagtg gagcatatgt gagtgctata gcccagactg aaaaaagcat tgaagacaac 5040
ccagagatcg aagatgacat tttccgaaag agaagactga ccatcatgga cctccaccca 5100
ggagcgggaa agacgaagag ataccttccg gccatagtca gagaagctat aaaacggggt 5160
ttgagaacat taatcttggc ccccactaga gttgtggcag ctgaaatgga ggaagccctt 5220
agaggacttc caataagata ccagacccca gccatcagag ctgtgcacac cgggcgggag 5280
attgtggacc taatgtgtca tgccacattt accatgaggc tgctatcacc agttagagtg 5340
ccaaactaca acctgattat catggacgaa gcccatttca cagacccagc aagtatagca 5400
gctagaggat acatctcaac tcgagtggag atgggtgagg cagctgggat tttatgaca 5460
gccactcccc cgggaagcag agacccattt cctcagagca atgcaccaat catagatgaa 5520
gaaagagaaa tccctgaacg ctcgtggaat tccggacatg aatgggtcac ggattttaaa 5580
gggaagactg tttggttcgt tccaagtata aaagcaggaa atgatatagc agcttgcctg 5640
aggaaaaatg gaaagaaagt gatacaactc agtaggaaga cctttgattc tgagtatgtc 5700
aagactagaa ccaatgattg ggacttcgtg gttacaactg acatttcaga aatgggtgcc 5760
aatttcaagg ctgagagggt tatagacccc agacgctgca tgaaaccagt catactaaca 5820
gatggtgaag agcgggtgat tctggcagga cctatgccag tgacccactc tagtgcagca 5880
caaagaagag ggagaatagg aagaaatcca aaaaatgaga atgaccagta catatacatg 5940
ggggaacctc tggaaaatga tgaagactgt gcacactgga aagaagctaa aatgctccta 6000
gataacatca acacgccaga aggaatcatt cctagcatgt tcgaaccaga gcgtgaaaag 6060
gtggatgcca ttgatggcga ataccgcttg agaggagaag caaggaaaac ctttgtagac 6120
ttaatgagaa gaggagacct accagtctgg ttggcctaca gagtggcagc tgaaggcatc 6180
aactacgcag acagaaggtg gtgttttgat ggagtcaaga acaaccaaat cctagaagaa 6240
aacgtggaag ttgaaatctg gacaaaagaa ggggaaagga agaaattgaa acccagatgg 6300
ttggatgcta ggatctattc tgacccactg gcgctaaaag aatttaagga atttgcagcc 6360
ggaagaaagt ctctgaccct gaacctaatc acagaaatgg gtaggctccc aaccttcatg 6420
actcagaagg caagagacgc actggacaac ttagcagtgc tgcacacggc tgaggcaggt 6480
ggaagggcgt acaaccatgc tctcagtgaa ctgccggaga ccctggagac attgctttta 6540
ctgacacttc tggctacagt cacgggaggg atctttttat tcttgatgag cgcaaggggc 6600
atagggaaga tgaccctggg aatgtgctgc ataatcacgg ctagcatcct cctatggtac 6660
gcacaaatac agccacactg gatagcagct tcaataatac tggagttttt tctcatagtt 6720
ttgcttattc cagaacctga aaaacagaga acaccccaag acaaccaact gacctacgtt 6780
gtcatagcca tcctcacagt ggtggccgca accatggcaa acgagatggg tttcctagaa 6840
aaaacgaaga aagatctcgg attgggaagc attgcaaccc agcaacccga gagcaacatc 6900
ctggacatag atctacgtcc tgcatcagca tggacgctgt atgccgtggc cacaacattt 6960
gttacaccaa tgttgagaca tagcattgaa aattcctcag tgaatgtgtc cctaacagct 7020

-continued

```
atagccaacc aagccacagt gttaatgggt ctcgggaaag gatggccatt gtcaaagatg   7080
gacatcggag ttccccttct cgccattgga tgctactcac aagtcaaccc cataactctc   7140
acagcagctc ttttcttatt ggtagcacat tatgccatca tagggccagg actccaagca   7200
aaagcaacca gagaagctca gaaaagagca gcggcgggca tcatgaaaaa cccaactgtc   7260
gatggaataa cagtgattga cctagatcca ataccttatg atccaaagtt tgaaaagcag   7320
ttgggacaag taatgctcct agtcctctgc gtgactcaag tattgatgat gaggactaca   7380
tgggctctgt gtgaggcttt aaccttagct accgggccca tctccacatt gtgggaagga   7440
aatccaggga ggttttggaa cactaccatt gcggtgtcaa tggctaacat tttagagggg   7500
agttacttgg ccggagctgg acttctcttt tctattatga agaacacaac caacacaaga   7560
aggggaactg gcaacatagg agagacgctt ggagagaaat ggaaaagccg attgaacgcg   7620
ttgggaaaaa gtgaattcca gatctacaag aaaagtggaa tccaggaagt ggatagaacc   7680
ttagcaaaag aaggcattaa aagaggagaa acggaccatc acgctgtgtc gcgaggctca   7740
gcaaaactga gatggttcgt tgagagaaac atggtcacac cagaagggaa agtagtggac   7800
ctcggttgtg gcagaggagg ctggtcatac tattgtggag gactaaagaa tgtaagagaa   7860
gtcaaaggcc taacaaaagg aggaccagga cacgaagaac ccatccccat gtcaacatat   7920
gggtggaatc tagtgcgtct tcaaagtgga gttgacgttt tcttcatccc gccagaaaag   7980
tgtgacacat tattgtgtga catagggggag tcatcaccaa atcccacagt ggaagcagga   8040
cgaacactca gagtccttaa cttagtagaa aattggttga acaacaacac tcaattttgc   8100
ataaaggttc tcaacccata tatgccctca gtcatagaaa aaatggaagc actacaaagg   8160
aaatatggag gagccttagt gaggaatcca ctctcacgaa actccacaca tgagatgtac   8220
tgggtatcca atgcttccgg gaacatagtg tcatcagtga acatgatttc aaggatgttg   8280
atcaacagat ttacaatgag atacaagaaa gccacttacg agccggatgt tgacctcgga   8340
agcggaaccc gtaacatcgg gattgaaagt gagataccaa acctagatat aattgggaaa   8400
agaatagaaa aaataaagca agagcatgaa acatcatggc actatgacca agaccaccca   8460
tacaaaacgt gggcatacca tggtagctat gaaacaaaac agactggatc agcatcatcc   8520
atggtcaacg gagtggtcag gctgctgaca aaaccttggg acgtcgtccc catggtgaca   8580
cagatggcaa tgacagacac gactccattt ggacaacagc gcgtttttaa agagaaagtg   8640
gacacgagaa cccaagaacc gaaagaaggc acgaagaaac taatgaaaat aacagcagag   8700
tggctttgga aagaattagg gaagaaaaag acacccagga tgtgcaccag agaagaattc   8760
acaagaaagg tgagaagcaa tgcagccttg gggggccatat tcactgatga gaacaagtgg   8820
aagtcggcac gtgaggctgt tgaagatagt aggttttggg agctggttga caaggaaagg   8880
aatctccatc ttgaaggaaa gtgtgaaaca tgtgtgtaca acatgatggg aaaaagagag   8940
aagaagctag gggaattcgg caaggcaaaa ggcagcagag ccatatggta catgtggctt   9000
ggagcacgct tcttagagtt tgaagcccta ggattcttaa atgaagatca ctggttctcc   9060
agagagaact ccctgagtgg agtggaagga gaagggctgc acaagctagg ttacattcta   9120
agagacgtga gcaagaaaga gggaggagca atgtatgccg atgacaccgc aggatgggat   9180
acaagaatca cactagaaga cctaaaaaat gaagaaatgg taacaaacca catggaagga   9240
gaacacaaga aactagccga ggccattttc aaactaacgt accaaaacaa ggtggtgcgt   9300
gtgcaaagac caacaccaag aggcacagta atggacatca tatcgagaag agaccaaaga   9360
ggtagtggac aagttggcac ctatggactc aatactttca ccaatatgga agcccaacta   9420
```

atcagacaga tggagggaga aggagtcttt aaaagcattc agcacctaac aatcacagaa 9480
gaaatcgctg tgcaaaactg gttagcaaga gtggggcgcg aaaggttatc aagaatggcc 9540
atcagtggag atgattgtgt tgtgaaacct ttagatgaca ggttcgcaag cgctttaaca 9600
gctctaaatg acatgggaaa gattaggaaa gacatacaac aatgggaacc ttcaagagga 9660
tggaatgatt ggacacaagt gcccttctgt tcacaccatt tccatgagtt aatcatgaaa 9720
gacggtcgcg tactcgttgt tccatgtaga aaccaagatg aactgattgg cagagcccga 9780
atctcccaag gagcagggtg gtctttgcgg gagacggcct gtttggggaa gtcttacgcc 9840
caaatgtgga gcttgatgta cttccacaga cgcgacctca ggctggcggc aaatgctatt 9900
tgctcggcag taccatcaca ttgggttcca acaagtcgaa caacctggtc catacatgct 9960
aaacatgaat ggatgacaac ggaagacatg ctgacagtct ggaacagggt gtggattcaa 10020
gaaaacccat ggatggaaga caaaactcca gtggaatcat gggaggaaat cccatacttg 10080
gggaaaagag aagaccaatg gtgcggctca ttgattgggt taacaagcag ggccacctgg 10140
gcaaagaaca tccaagcagc aataaatcaa gttagatccc ttataggcaa tgaagaatac 10200
acagattaca tgccatccat gaaaagattc agaagagaag aggaagaagc aggagttctg 10260
tggtagaaag caaaactaac atgaaacaag gctagaagtc aggtcggatt aagccatagt 10320
acggaaaaaa ctatgctacc tgtgagcccc gtccaaggac gttaaaagaa gtcaggccat 10380
cataaatgcc atagcttgag taaactatgc agcctgtagc tccacctgag aaggtgtaaa 10440
aaatccggga ggccacaaac catggaagct gtacgcatgg cgtagtggac tagcggttag 10500
aggagacccc tcccttacaa atcgcagcaa caatgggggc ccaaggcgag atgaagctgt 10560
agtctcgctg gaaggactag aggttagagg agaccccccc gaaacaaaaa acagcatatt 10620
gacgctggga aagaccagag atcctgctgt ctcctcagca tcattccagg cacagaacgc 10680
cagaaaatgg aatggtgctg ttgaatcaac aggttct 10717

<210> SEQ ID NO 19
<211> LENGTH: 3389
<212> TYPE: PRT
<213> ORGANISM: Artificial Sequence
<220> FEATURE:
<223> OTHER INFORMATION: Derived from Dengue virus serotype 2/Dengue virus serotype 3, MVS

<400> SEQUENCE: 19

Met Asn Asn Gln Arg Lys Lys Ala Lys Asn Thr Pro Phe Asn Met Leu
1 5 10 15

Lys Arg Glu Arg Asn Arg Val Ser Thr Val Gln Gln Leu Thr Lys Arg
20 25 30

Phe Ser Leu Gly Met Leu Gln Gly Arg Gly Pro Leu Lys Leu Phe Met
35 40 45

Ala Leu Val Ala Phe Leu Arg Phe Leu Thr Ile Pro Pro Thr Ala Gly
50 55 60

Ile Leu Lys Arg Trp Gly Thr Ile Lys Lys Ser Lys Ala Ile Asn Val
65 70 75 80

Leu Arg Gly Phe Arg Lys Glu Ile Gly Arg Met Leu Asn Ile Leu Asn
85 90 95

Arg Arg Arg Arg Ser Ala Gly Met Ile Ile Met Leu Ile Pro Thr Val
100 105 110

Met Ala Phe His Leu Thr Thr Arg Asp Gly Glu Pro Arg Met Ile Val
115 120 125

-continued

```
Gly Lys Asn Glu Arg Gly Lys Ser Leu Leu Phe Lys Thr Ala Ser Gly
    130                 135                 140

Ile Asn Met Cys Thr Leu Ile Ala Met Asp Leu Gly Glu Met Cys Asp
145                 150                 155                 160

Asp Thr Val Thr Tyr Lys Cys Pro His Ile Thr Glu Val Glu Pro Glu
                165                 170                 175

Asp Ile Asp Cys Trp Cys Asn Leu Thr Ser Thr Trp Val Thr Tyr Gly
            180                 185                 190

Thr Cys Asn Gln Ala Gly Glu His Arg Arg Asp Lys Arg Ser Val Ala
        195                 200                 205

Leu Ala Pro His Val Gly Met Gly Leu Asp Thr Arg Thr Gln Thr Trp
    210                 215                 220

Met Ser Ala Glu Gly Ala Trp Arg Gln Val Glu Lys Val Glu Thr Trp
225                 230                 235                 240

Ala Leu Arg His Pro Gly Phe Thr Ile Leu Ala Leu Phe Leu Ala His
                245                 250                 255

Tyr Ile Gly Thr Ser Leu Thr Gln Lys Val Val Ile Phe Ile Leu Leu
            260                 265                 270

Met Leu Val Thr Pro Ser Met Thr Met Arg Cys Val Gly Val Gly Asn
        275                 280                 285

Arg Asp Phe Val Glu Gly Leu Ser Gly Ala Thr Trp Val Asp Val Val
    290                 295                 300

Leu Glu His Gly Gly Cys Val Thr Thr Met Ala Lys Asn Lys Pro Thr
305                 310                 315                 320

Leu Asp Ile Glu Leu Gln Lys Thr Glu Ala Thr Gln Leu Ala Thr Leu
                325                 330                 335

Arg Lys Leu Cys Ile Glu Gly Lys Ile Thr Asn Ile Thr Thr Asp Ser
            340                 345                 350

Arg Cys Pro Thr Gln Gly Glu Ala Ile Leu Pro Glu Glu Gln Asp Gln
        355                 360                 365

Asn Tyr Val Cys Lys His Thr Tyr Val Asp Arg Gly Trp Gly Asn Gly
    370                 375                 380

Cys Gly Leu Phe Gly Lys Gly Ser Leu Val Thr Cys Ala Lys Phe Gln
385                 390                 395                 400

Cys Leu Glu Ser Ile Glu Gly Lys Val Val Gln His Glu Asn Leu Lys
                405                 410                 415

Tyr Thr Val Ile Ile Thr Val His Thr Gly Asp Gln His Gln Val Gly
            420                 425                 430

Asn Glu Thr Gln Gly Val Thr Ala Glu Ile Thr Pro Gln Ala Ser Thr
        435                 440                 445

Ala Glu Ala Ile Leu Pro Glu Tyr Gly Thr Leu Gly Leu Glu Cys Ser
    450                 455                 460

Pro Arg Thr Gly Leu Asp Phe Asn Glu Met Ile Ser Leu Thr Met Lys
465                 470                 475                 480

Asn Lys Ala Trp Met Val His Arg Gln Trp Phe Phe Asp Leu Pro Leu
                485                 490                 495

Pro Trp Thr Ser Gly Ala Ser Ala Glu Thr Pro Thr Trp Asn Arg Lys
            500                 505                 510

Glu Leu Leu Val Thr Phe Lys Asn Ala His Ala Lys Lys Gln Glu Val
        515                 520                 525

Val Val Leu Gly Ser Gln Glu Gly Ala Met His Thr Ala Leu Thr Gly
    530                 535                 540
```

-continued

```
Ala Thr Glu Ile Gln Thr Ser Gly Gly Thr Ser Ile Phe Ala Gly His
545                 550                 555                 560

Leu Lys Cys Arg Leu Lys Met Asp Lys Leu Glu Leu Lys Gly Met Ser
                565                 570                 575

Tyr Ala Met Cys Leu Ser Ser Phe Val Leu Lys Lys Glu Val Ser Glu
            580                 585                 590

Thr Gln His Gly Thr Ile Leu Ile Lys Val Glu Tyr Lys Gly Glu Asp
        595                 600                 605

Ala Pro Cys Lys Ile Pro Phe Ser Thr Glu Asp Gly Gln Gly Lys Ala
    610                 615                 620

Leu Asn Gly Arg Leu Ile Thr Ala Asn Pro Val Val Thr Lys Lys Glu
625                 630                 635                 640

Glu Pro Val Asn Ile Glu Ala Glu Pro Pro Phe Gly Glu Ser Asn Ile
                645                 650                 655

Val Ile Gly Ile Gly Asp Lys Ala Leu Lys Ile Asn Trp Tyr Lys Lys
            660                 665                 670

Gly Ser Ser Ile Gly Lys Met Phe Glu Ala Thr Ala Arg Gly Ala Arg
        675                 680                 685

Arg Met Ala Ile Leu Gly Asp Thr Ala Trp Asp Phe Gly Ser Val Gly
    690                 695                 700

Gly Val Leu Asn Ser Leu Gly Lys Met Val His Gln Ile Phe Gly Ser
705                 710                 715                 720

Ala Tyr Thr Ala Leu Phe Gly Gly Val Ser Trp Met Met Lys Ile Gly
                725                 730                 735

Ile Gly Val Leu Leu Thr Trp Ile Gly Leu Asn Ser Lys Asn Thr Ser
            740                 745                 750

Met Ser Phe Ser Cys Ile Ala Ala Gly Ile Val Thr Leu Tyr Leu Gly
        755                 760                 765

Val Met Val Gln Ala Asp Ser Gly Cys Val Val Ser Trp Lys Asn Lys
    770                 775                 780

Glu Leu Lys Cys Gly Ser Gly Ile Phe Ile Thr Asp Asn Val His Thr
785                 790                 795                 800

Trp Thr Glu Gln Tyr Lys Phe Gln Pro Glu Ser Pro Ser Lys Leu Ala
                805                 810                 815

Ser Ala Ile Gln Lys Ala His Glu Glu Asp Ile Cys Gly Ile Arg Ser
            820                 825                 830

Val Thr Arg Leu Glu Asn Leu Met Trp Lys Gln Ile Thr Pro Glu Leu
        835                 840                 845

Asn His Ile Leu Ser Glu Asn Glu Val Lys Leu Thr Ile Met Thr Gly
    850                 855                 860

Asp Ile Lys Gly Ile Met Gln Ala Gly Lys Arg Ser Leu Arg Pro Gln
865                 870                 875                 880

Pro Thr Glu Leu Lys Tyr Ser Trp Lys Thr Trp Gly Lys Ala Lys Met
                885                 890                 895

Leu Ser Thr Glu Ser His Asn Gln Thr Phe Leu Ile Asp Gly Pro Glu
            900                 905                 910

Thr Ala Glu Cys Pro Asn Thr Asn Arg Ala Trp Asn Ser Leu Glu Val
        915                 920                 925

Glu Asp Tyr Gly Phe Gly Val Phe Thr Thr Asn Ile Trp Leu Lys Leu
    930                 935                 940

Lys Glu Lys Gln Asp Val Phe Cys Asp Ser Lys Leu Met Ser Ala Ala
945                 950                 955                 960

Ile Lys Asp Asn Arg Ala Val His Ala Asp Met Gly Tyr Trp Ile Glu
```

-continued

```
                965                 970                 975

Ser Ala Leu Asn Asp Thr Trp Lys Ile Glu Lys Ala Ser Phe Ile Glu
            980                 985                 990

Val Lys Asn Cys His Trp Pro Lys  Ser His Thr Leu Trp  Ser Asn Gly
        995                 1000                1005

Val Leu  Glu Ser Glu Met Ile  Ile Pro Lys Asn Leu  Ala Gly Pro
    1010                 1015                 1020

Val Ser  Gln His Asn Tyr Arg  Pro Gly Tyr His Thr  Gln Ile Thr
    1025                 1030                 1035

Gly Pro  Trp His Leu Gly Lys  Leu Glu Met Asp Phe  Asp Phe Cys
    1040                 1045                 1050

Asp Gly  Thr Thr Val Val Val  Thr Glu Asp Cys Gly  Asn Arg Gly
    1055                 1060                 1065

Pro Ser  Leu Arg Thr Thr Thr  Ala Ser Gly Lys Leu  Ile Thr Glu
    1070                 1075                 1080

Trp Cys  Cys Arg Ser Cys Thr  Leu Pro Pro Leu Arg  Tyr Arg Gly
    1085                 1090                 1095

Glu Asp  Gly Cys Trp Tyr Gly  Met Glu Ile Arg Pro  Leu Lys Glu
    1100                 1105                 1110

Lys Glu  Glu Asn Leu Val Asn  Ser Leu Val Thr Ala  Gly His Gly
    1115                 1120                 1125

Gln Val  Asp Asn Phe Ser Leu  Gly Val Leu Gly Met  Ala Leu Phe
    1130                 1135                 1140

Leu Glu  Glu Met Leu Arg Thr  Arg Val Gly Thr Lys  His Ala Ile
    1145                 1150                 1155

Leu Leu  Val Ala Val Ser Phe  Val Thr Leu Ile Thr  Gly Asn Met
    1160                 1165                 1170

Ser Phe  Arg Asp Leu Gly Arg  Val Met Val Met Val  Gly Ala Thr
    1175                 1180                 1185

Met Thr  Asp Asp Ile Gly Met  Gly Val Thr Tyr Leu  Ala Leu Leu
    1190                 1195                 1200

Ala Ala  Phe Lys Val Arg Pro  Thr Phe Ala Ala Gly  Leu Leu Leu
    1205                 1210                 1215

Arg Lys  Leu Thr Ser Lys Glu  Leu Met Met Thr Thr  Ile Gly Ile
    1220                 1225                 1230

Val Leu  Leu Ser Gln Ser Thr  Ile Pro Glu Thr Ile  Leu Glu Leu
    1235                 1240                 1245

Thr Asp  Ala Leu Ala Leu Gly  Met Met Val Leu Lys  Met Val Arg
    1250                 1255                 1260

Asn Met  Glu Lys Tyr Gln Leu  Ala Val Thr Ile Met  Ala Ile Leu
    1265                 1270                 1275

Cys Val  Pro Asn Ala Val Ile  Leu Gln Asn Ala Trp  Lys Val Ser
    1280                 1285                 1290

Cys Thr  Ile Leu Ala Val Val  Ser Val Ser Pro Leu  Phe Leu Thr
    1295                 1300                 1305

Ser Ser  Gln Gln Lys Thr Asp  Trp Ile Pro Leu Ala  Leu Thr Ile
    1310                 1315                 1320

Lys Gly  Leu Asn Pro Thr Ala  Ile Phe Leu Thr Thr  Leu Ser Arg
    1325                 1330                 1335

Thr Ser  Lys Lys Arg Ser Trp  Pro Leu Asn Glu Ala  Ile Met Ala
    1340                 1345                 1350

Val Gly  Met Val Ser Ile Leu  Ala Ser Ser Leu Leu  Lys Asn Asp
    1355                 1360                 1365
```

-continued

```
Ile Pro  Met Thr Gly Pro Leu  Val Ala Gly Gly Leu  Leu Thr Val
    1370                 1375                 1380

Cys Tyr  Val Leu Thr Gly Arg  Ser Ala Asp Leu Glu  Leu Glu Arg
    1385                 1390                 1395

Ala Ala  Asp Val Lys Trp Glu  Asp Gln Ala Glu Ile  Ser Gly Ser
    1400                 1405                 1410

Ser Pro  Ile Leu Ser Ile Thr  Ile Ser Glu Asp Gly  Ser Met Ser
    1415                 1420                 1425

Ile Lys  Asn Glu Glu Glu Glu  Gln Thr Leu Thr Ile  Leu Ile Arg
    1430                 1435                 1440

Thr Gly  Leu Leu Val Ile Ser  Gly Leu Phe Pro Val  Ser Ile Pro
    1445                 1450                 1455

Ile Thr  Ala Ala Ala Trp Tyr  Leu Trp Glu Val Lys  Lys Gln Arg
    1460                 1465                 1470

Ala Gly  Val Leu Trp Asp Val  Pro Ser Pro Pro Pro  Met Gly Lys
    1475                 1480                 1485

Ala Glu  Leu Glu Asp Gly Ala  Tyr Arg Ile Lys Gln  Lys Gly Ile
    1490                 1495                 1500

Leu Gly  Tyr Ser Gln Ile Gly  Ala Gly Val Tyr Lys  Glu Gly Thr
    1505                 1510                 1515

Phe His  Thr Met Trp His Val  Thr Arg Gly Ala Val  Leu Met His
    1520                 1525                 1530

Lys Gly  Lys Arg Ile Glu Pro  Ser Trp Ala Asp Val  Lys Lys Asp
    1535                 1540                 1545

Leu Ile  Ser Tyr Gly Gly Gly  Trp Lys Leu Glu Gly  Glu Trp Lys
    1550                 1555                 1560

Glu Gly  Glu Glu Val Gln Val  Leu Ala Leu Glu Pro  Gly Lys Asn
    1565                 1570                 1575

Pro Arg  Ala Val Gln Thr Lys  Pro Gly Leu Phe Lys  Thr Asn Ala
    1580                 1585                 1590

Gly Thr  Ile Gly Ala Val Ser  Leu Asp Phe Ser Pro  Gly Thr Ser
    1595                 1600                 1605

Gly Ser  Pro Ile Ile Asp Lys  Lys Gly Lys Val Val  Gly Leu Tyr
    1610                 1615                 1620

Gly Asn  Gly Val Val Thr Arg  Ser Gly Ala Tyr Val  Ser Ala Ile
    1625                 1630                 1635

Ala Gln  Thr Glu Lys Ser Ile  Glu Asp Asn Pro Glu  Ile Glu Asp
    1640                 1645                 1650

Asp Ile  Phe Arg Lys Arg Arg  Leu Thr Ile Met Asp  Leu His Pro
    1655                 1660                 1665

Gly Ala  Gly Lys Thr Lys Arg  Tyr Leu Pro Ala Ile  Val Arg Glu
    1670                 1675                 1680

Ala Ile  Lys Arg Gly Leu Arg  Thr Leu Ile Leu Ala  Pro Thr Arg
    1685                 1690                 1695

Val Val  Ala Ala Glu Met Glu  Glu Ala Leu Arg Gly  Leu Pro Ile
    1700                 1705                 1710

Arg Tyr  Gln Thr Pro Ala Ile  Arg Ala Val His Thr  Gly Arg Glu
    1715                 1720                 1725

Ile Val  Asp Leu Met Cys His  Ala Thr Phe Thr Met  Arg Leu Leu
    1730                 1735                 1740

Ser Pro  Val Arg Val Pro Asn  Tyr Asn Leu Ile Ile  Met Asp Glu
    1745                 1750                 1755
```

-continued

```
Ala His  Phe Thr Asp Pro Ala  Ser Ile Ala Ala Arg  Gly Tyr Ile
    1760                 1765                 1770

Ser Thr  Arg Val Glu Met Gly  Glu Ala Ala Gly Ile  Phe Met Thr
    1775                 1780                 1785

Ala Thr  Pro Pro Gly Ser Arg  Asp Pro Phe Pro Gln  Ser Asn Ala
    1790                 1795                 1800

Pro Ile  Ile Asp Glu Glu Arg  Glu Ile Pro Glu Arg  Ser Trp Asn
    1805                 1810                 1815

Ser Gly  His Glu Trp Val Thr  Asp Phe Lys Gly Lys  Thr Val Trp
    1820                 1825                 1830

Phe Val  Pro Ser Ile Lys Ala  Gly Asn Asp Ile Ala  Ala Cys Leu
    1835                 1840                 1845

Arg Lys  Asn Gly Lys Lys Val  Ile Gln Leu Ser Arg  Lys Thr Phe
    1850                 1855                 1860

Asp Ser  Glu Tyr Val Lys Thr  Arg Thr Asn Asp Trp  Asp Phe Val
    1865                 1870                 1875

Val Thr  Thr Asp Ile Ser Glu  Met Gly Ala Asn Phe  Lys Ala Glu
    1880                 1885                 1890

Arg Val  Ile Asp Pro Arg Arg  Cys Met Lys Pro Val  Ile Leu Thr
    1895                 1900                 1905

Asp Gly  Glu Glu Arg Val Ile  Leu Ala Gly Pro Met  Pro Val Thr
    1910                 1915                 1920

His Ser  Ser Ala Ala Gln Arg  Arg Gly Arg Ile Gly  Arg Asn Pro
    1925                 1930                 1935

Lys Asn  Glu Asn Asp Gln Tyr  Ile Tyr Met Gly Glu  Pro Leu Glu
    1940                 1945                 1950

Asn Asp  Glu Asp Cys Ala His  Trp Lys Glu Ala Lys  Met Leu Leu
    1955                 1960                 1965

Asp Asn  Ile Asn Thr Pro Glu  Gly Ile Ile Pro Ser  Met Phe Glu
    1970                 1975                 1980

Pro Glu  Arg Glu Lys Val Asp  Ala Ile Asp Gly Glu  Tyr Arg Leu
    1985                 1990                 1995

Arg Gly  Glu Ala Arg Lys Thr  Phe Val Asp Leu Met  Arg Arg Gly
    2000                 2005                 2010

Asp Leu  Pro Val Trp Leu Ala  Tyr Arg Val Ala Ala  Glu Gly Ile
    2015                 2020                 2025

Asn Tyr  Ala Asp Arg Arg Trp  Cys Phe Asp Gly Val  Lys Asn Asn
    2030                 2035                 2040

Gln Ile  Leu Glu Glu Asn Val  Glu Val Glu Ile Trp  Thr Lys Glu
    2045                 2050                 2055

Gly Glu  Arg Lys Lys Leu Lys  Pro Arg Trp Leu Asp  Ala Arg Ile
    2060                 2065                 2070

Tyr Ser  Asp Pro Leu Ala Leu  Lys Glu Phe Lys Glu  Phe Ala Ala
    2075                 2080                 2085

Gly Arg  Lys Ser Leu Thr Leu  Asn Leu Ile Thr Glu  Met Gly Arg
    2090                 2095                 2100

Leu Pro  Thr Phe Met Thr Gln  Lys Ala Arg Asp Ala  Leu Asp Asn
    2105                 2110                 2115

Leu Ala  Val Leu His Thr Ala  Glu Ala Gly Gly Arg  Ala Tyr Asn
    2120                 2125                 2130

His Ala  Leu Ser Glu Leu Pro  Glu Thr Leu Glu Thr  Leu Leu Leu
    2135                 2140                 2145

Leu Thr  Leu Leu Ala Thr Val  Thr Gly Gly Ile Phe  Leu Phe Leu
```

```
    2150                2155                2160

Met Ser  Ala Arg Gly Ile Gly  Lys Met Thr Leu Gly  Met Cys Cys
    2165                2170                2175

Ile Ile  Thr Ala Ser Ile Leu  Leu Trp Tyr Ala Gln  Ile Gln Pro
    2180                2185                2190

His Trp  Ile Ala Ala Ser Ile  Ile Leu Glu Phe Phe  Leu Ile Val
    2195                2200                2205

Leu Leu  Ile Pro Glu Pro Glu  Lys Gln Arg Thr Pro  Gln Asp Asn
    2210                2215                2220

Gln Leu  Thr Tyr Val Val Ile  Ala Ile Leu Thr Val  Val Ala Ala
    2225                2230                2235

Thr Met  Ala Asn Glu Met Gly  Phe Leu Glu Lys Thr  Lys Lys Asp
    2240                2245                2250

Leu Gly  Leu Gly Ser Ile Ala  Thr Gln Gln Pro Glu  Ser Asn Ile
    2255                2260                2265

Leu Asp  Ile Asp Leu Arg Pro  Ala Ser Ala Trp Thr  Leu Tyr Ala
    2270                2275                2280

Val Ala  Thr Thr Phe Val Thr  Pro Met Leu Arg His  Ser Ile Glu
    2285                2290                2295

Asn Ser  Ser Val Asn Val Ser  Leu Thr Ala Ile Ala  Asn Gln Ala
    2300                2305                2310

Thr Val  Leu Met Gly Leu Gly  Lys Gly Trp Pro Leu  Ser Lys Met
    2315                2320                2325

Asp Ile  Gly Val Pro Leu Leu  Ala Ile Gly Cys Tyr  Ser Gln Val
    2330                2335                2340

Asn Pro  Ile Thr Leu Thr Ala  Ala Leu Phe Leu Leu  Val Ala His
    2345                2350                2355

Tyr Ala  Ile Ile Gly Pro Gly  Leu Gln Ala Lys Ala  Thr Arg Glu
    2360                2365                2370

Ala Gln  Lys Arg Ala Ala Ala  Gly Ile Met Lys Asn  Pro Thr Val
    2375                2380                2385

Asp Gly  Ile Thr Val Ile Asp  Leu Asp Pro Ile Pro  Tyr Asp Pro
    2390                2395                2400

Lys Phe  Glu Lys Gln Leu Gly  Gln Val Met Leu Leu  Val Leu Cys
    2405                2410                2415

Val Thr  Gln Val Leu Met Met  Arg Thr Thr Trp Ala  Leu Cys Glu
    2420                2425                2430

Ala Leu  Thr Leu Ala Thr Gly  Pro Ile Ser Thr Leu  Trp Glu Gly
    2435                2440                2445

Asn Pro  Gly Arg Phe Trp Asn  Thr Thr Ile Ala Val  Ser Met Ala
    2450                2455                2460

Asn Ile  Phe Arg Gly Ser Tyr  Leu Ala Gly Ala Gly  Leu Leu Phe
    2465                2470                2475

Ser Ile  Met Lys Asn Thr Thr  Asn Thr Arg Arg Gly  Thr Gly Asn
    2480                2485                2490

Ile Gly  Glu Thr Leu Gly Glu  Lys Trp Lys Ser Arg  Leu Asn Ala
    2495                2500                2505

Leu Gly  Lys Ser Glu Phe Gln  Ile Tyr Lys Lys Ser  Gly Ile Gln
    2510                2515                2520

Glu Val  Asp Arg Thr Leu Ala  Lys Glu Gly Ile Lys  Arg Gly Glu
    2525                2530                2535

Thr Asp  His His Ala Val Ser  Arg Gly Ser Ala Lys  Leu Arg Trp
    2540                2545                2550
```

```
Phe Val  Glu Arg Asn Met Val  Thr Pro Glu Gly Lys  Val Val Asp
    2555                 2560                 2565

Leu Gly  Cys Gly Arg Gly Gly  Trp Ser Tyr Tyr Cys  Gly Gly Leu
    2570                 2575                 2580

Lys Asn  Val Arg Glu Val Lys  Gly Leu Thr Lys Gly  Gly Pro Gly
    2585                 2590                 2595

His Glu  Glu Pro Ile Pro Met  Ser Thr Tyr Gly Trp  Asn Leu Val
    2600                 2605                 2610

Arg Leu  Gln Ser Gly Val Asp  Val Phe Phe Ile Pro  Pro Glu Lys
    2615                 2620                 2625

Cys Asp  Thr Leu Leu Cys Asp  Ile Gly Glu Ser Ser  Pro Asn Pro
    2630                 2635                 2640

Thr Val  Glu Ala Gly Arg Thr  Leu Arg Val Leu Asn  Leu Val Glu
    2645                 2650                 2655

Asn Trp  Leu Asn Asn Asn Thr  Gln Phe Cys Ile Lys  Val Leu Asn
    2660                 2665                 2670

Pro Tyr  Met Pro Ser Val Ile  Glu Lys Met Glu Ala  Leu Gln Arg
    2675                 2680                 2685

Lys Tyr  Gly Gly Ala Leu Val  Arg Asn Pro Leu Ser  Arg Asn Ser
    2690                 2695                 2700

Thr His  Glu Met Tyr Trp Val  Ser Asn Ala Ser Gly  Asn Ile Val
    2705                 2710                 2715

Ser Ser  Val Asn Met Ile Ser  Arg Met Leu Ile Asn  Arg Phe Thr
    2720                 2725                 2730

Met Arg  Tyr Lys Lys Ala Thr  Tyr Glu Pro Asp Val  Asp Leu Gly
    2735                 2740                 2745

Ser Gly  Thr Arg Asn Ile Gly  Ile Glu Ser Glu Ile  Pro Asn Leu
    2750                 2755                 2760

Asp Ile  Ile Gly Lys Arg Ile  Glu Lys Ile Lys Gln  Glu His Glu
    2765                 2770                 2775

Thr Ser  Trp His Tyr Asp Gln  Asp His Pro Tyr Lys  Thr Trp Ala
    2780                 2785                 2790

Tyr His  Gly Ser Tyr Glu Thr  Lys Gln Thr Gly Ser  Ala Ser Ser
    2795                 2800                 2805

Met Val  Asn Gly Val Val Arg  Leu Leu Thr Lys Pro  Trp Asp Val
    2810                 2815                 2820

Val Pro  Met Val Thr Gln Met  Ala Met Thr Asp Thr  Thr Pro Phe
    2825                 2830                 2835

Gly Gln  Gln Arg Val Phe Lys  Glu Lys Val Asp Thr  Arg Thr Gln
    2840                 2845                 2850

Glu Pro  Lys Glu Gly Thr Lys  Lys Leu Met Lys Ile  Thr Ala Glu
    2855                 2860                 2865

Trp Leu  Trp Lys Glu Leu Gly  Lys Lys Lys Thr Pro  Arg Met Cys
    2870                 2875                 2880

Thr Arg  Glu Glu Phe Thr Arg  Lys Val Arg Ser Asn  Ala Ala Leu
    2885                 2890                 2895

Gly Ala  Ile Phe Thr Asp Glu  Asn Lys Trp Lys Ser  Ala Arg Glu
    2900                 2905                 2910

Ala Val  Glu Asp Ser Arg Phe  Trp Glu Leu Val Asp  Lys Glu Arg
    2915                 2920                 2925

Asn Leu  His Leu Glu Gly Lys  Cys Glu Thr Cys Val  Tyr Asn Met
    2930                 2935                 2940
```

-continued

```
Met Gly Lys Arg Glu Lys Lys Leu Gly Glu Phe Gly Lys Ala Lys
    2945                2950                2955

Gly Ser Arg Ala Ile Trp Tyr Met Trp Leu Gly Ala Arg Phe Leu
    2960                2965                2970

Glu Phe Glu Ala Leu Gly Phe Leu Asn Glu Asp His Trp Phe Ser
    2975                2980                2985

Arg Glu Asn Ser Leu Ser Gly Val Glu Gly Glu Gly Leu His Lys
    2990                2995                3000

Leu Gly Tyr Ile Leu Arg Asp Val Ser Lys Lys Glu Gly Gly Ala
    3005                3010                3015

Met Tyr Ala Asp Asp Thr Ala Gly Trp Asp Thr Arg Ile Thr Leu
    3020                3025                3030

Glu Asp Leu Lys Asn Glu Glu Met Val Thr Asn His Met Glu Gly
    3035                3040                3045

Glu His Lys Lys Leu Ala Glu Ala Ile Phe Lys Leu Thr Tyr Gln
    3050                3055                3060

Asn Lys Val Val Arg Val Gln Arg Pro Thr Pro Arg Gly Thr Val
    3065                3070                3075

Met Asp Ile Ile Ser Arg Arg Asp Gln Arg Gly Ser Gly Gln Val
    3080                3085                3090

Gly Thr Tyr Gly Leu Asn Thr Phe Thr Asn Met Glu Ala Gln Leu
    3095                3100                3105

Ile Arg Gln Met Glu Gly Glu Gly Val Phe Lys Ser Ile Gln His
    3110                3115                3120

Leu Thr Ile Thr Glu Glu Ile Ala Val Gln Asn Trp Leu Ala Arg
    3125                3130                3135

Val Gly Arg Glu Arg Leu Ser Arg Met Ala Ile Ser Gly Asp Asp
    3140                3145                3150

Cys Val Val Lys Pro Leu Asp Asp Arg Phe Ala Ser Ala Leu Thr
    3155                3160                3165

Ala Leu Asn Asp Met Gly Lys Ile Arg Lys Asp Ile Gln Gln Trp
    3170                3175                3180

Glu Pro Ser Arg Gly Trp Asn Asp Trp Thr Gln Val Pro Phe Cys
    3185                3190                3195

Ser His His Phe His Glu Leu Ile Met Lys Asp Gly Arg Val Leu
    3200                3205                3210

Val Val Pro Cys Arg Asn Gln Asp Glu Leu Ile Gly Arg Ala Arg
    3215                3220                3225

Ile Ser Gln Gly Ala Gly Trp Ser Leu Arg Glu Thr Ala Cys Leu
    3230                3235                3240

Gly Lys Ser Tyr Ala Gln Met Trp Ser Leu Met Tyr Phe His Arg
    3245                3250                3255

Arg Asp Leu Arg Leu Ala Ala Asn Ala Ile Cys Ser Ala Val Pro
    3260                3265                3270

Ser His Trp Val Pro Thr Ser Arg Thr Thr Trp Ser Ile His Ala
    3275                3280                3285

Lys His Glu Trp Met Thr Thr Glu Asp Met Leu Thr Val Trp Asn
    3290                3295                3300

Arg Val Trp Ile Gln Glu Asn Pro Trp Met Glu Asp Lys Thr Pro
    3305                3310                3315

Val Glu Ser Trp Glu Glu Ile Pro Tyr Leu Gly Lys Arg Glu Asp
    3320                3325                3330

Gln Trp Cys Gly Ser Leu Ile Gly Leu Thr Ser Arg Ala Thr Trp
```

```
    3335                3340                3345

Ala Lys  Asn Ile Gln Ala Ala  Ile Asn Gln Val Arg  Ser Leu Ile
    3350                3355                3360

Gly Asn  Glu Glu Tyr Thr Asp  Tyr Met Pro Ser Met  Lys Arg Phe
    3365                3370                3375

Arg Arg  Glu Glu Glu Glu Ala  Gly Val Leu Trp
    3380                3385
```

<210> SEQ ID NO 20
<211> LENGTH: 10723
<212> TYPE: DNA
<213> ORGANISM: Artificial Sequence
<220> FEATURE:
<223> OTHER INFORMATION: Derived from Dengue virus serotype 2/Dengue virus serotype 4, MVS

<400> SEQUENCE: 20

```
agttgttagt ctacgtggac cgacaaagac agattctttg agggagctaa gctcaatgta     60

gttctaacag ttttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gacctttaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagctctg caggcatgat cattatgctg    420

attccaacag tgatggcgtt ccatttaacc acgcgtgatg gcgaacccct catgatagtg    480

gcaaaacatg aaagggggag acctctcttg tttaagacaa cagaggggat caacaaatgc    540

actctcattg ccatggactt gggtgaaatg tgtgaggaca ctgtcacgta taaatgcccc    600

ttactggtca ataccgaacc tgaagacatt gattgctggt gcaatctcac gtctacctgg    660

gtcatgtatg ggacatgcac ccagagcgga gaacggagac gagagaagcg ctcagtagct    720

ttaacaccac attcaggaat gggattggaa acaagagctg agacatggat gtcatcggaa    780

ggggcttgga agcatgctca gagagtagag agctggatac tcagaaaccc aggattcgcg    840

ctcttggcag gatttatggc ttatatgatt gggcaaacag gaatccagcg aactgtcttc    900

tttgtcctaa tgatgctggt cgccccatcc tacggaatgc gatgcgtagg agtaggaaac    960

agagactttg tggaaggagt ctcaggtgga gcatgggtcg atctggtgct agaacatgga   1020

ggatgcgtca caaccatggc ccagggaaaa ccaaccttgg attttgaact gactaagaca   1080

acagccaagg aagtggctct gttaagaacc tattgcattg aagcctcaat atcaaacata   1140

accacggcaa caagatgtcc aacgcaagga gagccttatc taaaagagga acaagaccaa   1200

cagtacattt gccggagaga tgtggtagac agagggtggg gcaatggctg tggcttgttt   1260

ggaaaaggag gagttgtgac atgtgcgaag ttttcatgtt cggggaagat aacaggcaat   1320

ttggtccaaa ttgagaacct tgaatacaca gtggttgtaa cagtccacaa tggagacacc   1380

catgcagtag gaaatgacac gtccaatcat ggagttacag ccacgataac tcccaggtca   1440

ccatcggtgg aagtcaaatt gccggactat ggagaactaa cactcgattg tgaacccagg   1500

tctggaattg actttaatga gatgattctg atgaaaatga aaaagaaaac atggcttgtg   1560

cataagcaat ggtttttgga tctacctcta ccatggacag caggagcaga cacatcagag   1620

gttcactgga attacaaaga gagaatggtg acatttaagg ttcctcatgc caagagacag   1680

gatgtgacag tgctgggatc tcaggaagga gccatgcatt ctgccctcgc tggagccaca   1740
```

```
gaagtggact ccggtgatgg aaatcacatg tttgcaggac atctcaagtg caaagtccgt   1800
atggagaaat tgagaatcaa gggaatgtca tacacgatgt gttcaggaaa gttctcaatt   1860
gacaaagaga tggcagaaac acagcatggg acaacagtgg tgaaagtcaa gtatgaaggt   1920
gctggagctc cgtgtaaagt ccccatagag ataagagatg tgaacaagga aaaagtggtt   1980
gggcgtatca tctcatccac ccctttggct gagaatacca acagtgtaac caacatagag   2040
ttagaacccc cctttgggga cagctacata gtgataggtg ttggaaacag tgcattaaca   2100
ctccattggt tcaggaaagg gagttccatt ggcaagatgt ttgagtccac atacagaggt   2160
gcaaaacgaa tggccattct aggtgaaaca gcttgggatt ttggttccgt tggtggactg   2220
ttcacatcat tgggaaaggc tgtgcaccag gtttttggaa gtgtgtatac aaccctgttt   2280
ggaggagtct catggatgat tagaatccta attgggttcc tagtgttgtg gattggcacg   2340
aactcaagga acacttcaat ggctatgacg tgcatagctg ccggcattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cgggtgacat aggtatgggc gtgacttatc ttgccctact agcagccttc   3720
aaagtcagac caacttttgc agctggacta ctcttgagaa agctgacctc cagggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgttc   4020
ttaacatcct cacagcaaaa aacagattgg ataccattag cattgacgat caaaggtctc   4080
```

-continued

```
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga tccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggtaag agacgcactg gacaacttag cagtgctgca cacggctgag   6480
```

gcaggtggaa gggcgtacaa ccatgctctc agtgaactgc cggagaccct ggagacattg 6540
cttttactga cacttctggc tacagtcacg ggagggatct ttttattctt gatgagcgca 6600
aggggcatag ggaagatgac cctgggaatg tgctgcataa tcacggctag catcctccta 6660
tggtacgcac aaatacagcc acactggata gcagcttcaa taatactgga gtttttctc 6720
atagttttgc ttattccaga acctgaaaaa cagagaacac cccaagacaa ccaactgacc 6780
tacgttgtca tagccatcct cacagtggtg gccgcaacca tggcaaacga gatgggtttc 6840
ctagaaaaaa cgaagaaaga tctcggattg ggaagcattg caacccagca acccgagagc 6900
aacatcctgg acatagatct acgtcctgca tcagcatgga cgctgtatgc cgtggccaca 6960
acatttgtta caccaatgtt gagacatagc attgaaaatt cctcagtgaa tgtgtcccta 7020
acagccatag ccaaccaagc cacagtgtta atgggtctcg ggaaaggatg gccattgtca 7080
aagatggaca tcggagttcc ccttctcgcc attggatgct actcacaagt caacccccata 7140
actctcacag cagctctttt cttattggta gcacattatg ccatcatagg gccaggactc 7200
caagcaaaag caaccagaga agctcagaaa agagcagcgg cgggcatcat gaaaaaccca 7260
actgtcgatg gaataacagt gattgaccta gatccaatac cttatgatcc aaagtttgaa 7320
aagcagttgg gacaagtaat gctcctagtc ctctgcgtga ctcaagtatt gatgatgagg 7380
actacatggg ctctgtgtga ggctttaacc ttagctaccg ggcccatctc cacattgtgg 7440
gaaggaaatc cagggaggtt ttggaacact accattgcgg tgtcaatggc taacattttt 7500
agagggagtt acttggccgg agctggactt ctcttttcta ttatgaagaa cacaaccaac 7560
acaagaaggg gaactggcaa catagg agag acgcttggag agaaatggaa aagccgattg 7620
aacgcattgg gaaaaagtga attccagatc tacaagaaaa gtggaatcca ggaagtggat 7680
agaaccttag caaaagaagg cattaaaaga ggagaaacgg accatcacgc tgtgtcgcga 7740
ggctcagcaa aactgagatg gttcgttgag agaaacatgg tcacaccaga agggaaagta 7800
gtggacctcg gttgtggcag aggaggctgg tcatactatt gtggaggact aaagaatgta 7860
agagaagtca aaggcctaac aaaaggagga ccaggacacg aagaacccat ccccatgtca 7920
acatatgggt ggaatctagt gcgtcttcaa agtggagttg acgttttctt catcccgcca 7980
gaaaagtgtg acacattatt gtgtgacata ggggagtcat caccaaatcc cacagtggaa 8040
gcaggacgaa cactcagagt ccttaactta gtagaaaatt ggttgaacaa caacactcaa 8100
ttttgcataa aggttctcaa cccatatatg ccctcagtca tagaaaaaat ggaagcacta 8160
caaaggaaat atggaggagc cttagtgagg aatccactct cacgaaactc cacacatgag 8220
atgtactggg tatccaatgc ttccgggaac atagtgtcat cagtgaacat gatttcaagg 8280
atgttgatca acagatttac aatgagatac aagaaagcca cttacgagcc ggatgttgac 8340
ctcggaagcg gaacccgtaa catcgggatt gaaagtgaga taccaaacct agatataatt 8400
gggaaaagaa tagaaaaaat aaagcaagag catgaaacat catggcacta tgaccaagac 8460
cacccataca aaacgtgggc ataccatggt agctatgaaa caaaacagac tggatcagca 8520
tcatccatgg tcaacggagt ggtcaggctg ctgacaaaac cttgggacgt cgtccccatg 8580
gtgacacaga tggcaatgac agacacgact ccatttggac aacagcgcgt tttaaagag 8640
aaagtggaca cgagaaccca agaaccgaaa gaaggcacga agaaactaat gaaaataaca 8700
gcagagtggc tttggaaaga attagggaag aaaaagacac ccaggatgtg caccagagaa 8760
gaattcacaa gaaaggtgag aagcaatgca gccttggggg ccatattcac tgatgagaac 8820

```
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttccc tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agaagcagga  10260
gttctgtggt agaaagcaaa actaacatga aacaaggcta gaagtcaggt cggattaagc  10320
catagtacgg aaaaaactat gctacctgtg agccccgtcc aaggacgtta aaagaagtca  10380
ggccatcata aatgccatag cttgagtaaa ctatgcagcc tgtagctcca cctgagaagg  10440
tgtaaaaaat ccgggaggcc acaaaccatg gaagctgtac gcatggcgta gtggactagc  10500
ggttagagga gacccctccc ttacaaatcg cagcaacaat gggggcccaa ggcgagatga  10560
agctgtagtc tcgctggaag gactagaggt tagaggagac ccccccgaaa caaaaaacag  10620
catattgacg ctgggaaaga ccagagatcc tgctgtctcc tcagcatcat tccaggcaca  10680
gaacgccaga aaatggaatg gtgctgttga atcaacaggt tct                    10723
```

<210> SEQ ID NO 21
<211> LENGTH: 3391
<212> TYPE: PRT
<213> ORGANISM: Artificial Sequence
<220> FEATURE:
<223> OTHER INFORMATION: Derived from Dengue virus serotype 2/Dengue virus serotype 4, MVS

<400> SEQUENCE: 21

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
```

-continued

```
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Ser Ser Ala Gly Met Ile Ile Met Leu Ile Pro Thr Val
            100                 105                 110

Met Ala Phe His Leu Thr Thr Arg Asp Gly Glu Pro Leu Met Ile Val
        115                 120                 125

Ala Lys His Glu Arg Gly Arg Pro Leu Leu Phe Lys Thr Thr Glu Gly
    130                 135                 140

Ile Asn Lys Cys Thr Leu Ile Ala Met Asp Leu Gly Glu Met Cys Glu
145                 150                 155                 160

Asp Thr Val Thr Tyr Lys Cys Pro Leu Leu Val Asn Thr Glu Pro Glu
                165                 170                 175

Asp Ile Asp Cys Trp Cys Asn Leu Thr Ser Thr Trp Val Met Tyr Gly
            180                 185                 190

Thr Cys Thr Gln Ser Gly Glu Arg Arg Arg Glu Lys Arg Ser Val Ala
        195                 200                 205

Leu Thr Pro His Ser Gly Met Gly Leu Glu Thr Arg Ala Glu Thr Trp
    210                 215                 220

Met Ser Ser Glu Gly Ala Trp Lys His Ala Gln Arg Val Glu Ser Trp
225                 230                 235                 240

Ile Leu Arg Asn Pro Gly Phe Ala Leu Leu Ala Gly Phe Met Ala Tyr
                245                 250                 255

Met Ile Gly Gln Thr Gly Ile Gln Arg Thr Val Phe Phe Val Leu Met
            260                 265                 270

Met Leu Val Ala Pro Ser Tyr Gly Met Arg Cys Val Gly Val Gly Asn
        275                 280                 285

Arg Asp Phe Val Glu Gly Val Ser Gly Gly Ala Trp Val Asp Leu Val
    290                 295                 300

Leu Glu His Gly Gly Cys Val Thr Thr Met Ala Gln Gly Lys Pro Thr
305                 310                 315                 320

Leu Asp Phe Glu Leu Thr Lys Thr Thr Ala Lys Glu Val Ala Leu Leu
                325                 330                 335

Arg Thr Tyr Cys Ile Glu Ala Ser Ile Ser Asn Ile Thr Thr Ala Thr
            340                 345                 350

Arg Cys Pro Thr Gln Gly Glu Pro Tyr Leu Lys Glu Glu Gln Asp Gln
        355                 360                 365

Gln Tyr Ile Cys Arg Arg Asp Val Val Asp Arg Gly Trp Gly Asn Gly
    370                 375                 380

Cys Gly Leu Phe Gly Lys Gly Gly Val Val Thr Cys Ala Lys Phe Ser
385                 390                 395                 400

Cys Ser Gly Lys Ile Thr Gly Asn Leu Val Gln Ile Glu Asn Leu Glu
                405                 410                 415

Tyr Thr Val Val Val Thr Val His Asn Gly Asp Thr His Ala Val Gly
            420                 425                 430

Asn Asp Thr Ser Asn His Gly Val Thr Ala Thr Ile Thr Pro Arg Ser
        435                 440                 445
```

-continued

```
Pro Ser Val Glu Val Lys Leu Pro Asp Tyr Gly Glu Leu Thr Leu Asp
    450                 455                 460

Cys Glu Pro Arg Ser Gly Ile Asp Phe Asn Glu Met Ile Leu Met Lys
465                 470                 475                 480

Met Lys Lys Lys Thr Trp Leu Val His Lys Gln Trp Phe Leu Asp Leu
                485                 490                 495

Pro Leu Pro Trp Thr Ala Gly Ala Asp Thr Ser Glu Val His Trp Asn
            500                 505                 510

Tyr Lys Glu Arg Met Val Thr Phe Lys Val Pro His Ala Lys Arg Gln
        515                 520                 525

Asp Val Thr Val Leu Gly Ser Gln Glu Gly Ala Met His Ser Ala Leu
    530                 535                 540

Ala Gly Ala Thr Glu Val Asp Ser Gly Asp Gly Asn His Met Phe Ala
545                 550                 555                 560

Gly His Leu Lys Cys Lys Val Arg Met Glu Lys Leu Arg Ile Lys Gly
                565                 570                 575

Met Ser Tyr Thr Met Cys Ser Gly Lys Phe Ser Ile Asp Lys Glu Met
            580                 585                 590

Ala Glu Thr Gln His Gly Thr Thr Val Val Lys Val Lys Tyr Glu Gly
        595                 600                 605

Ala Gly Ala Pro Cys Lys Val Pro Ile Glu Ile Arg Asp Val Asn Lys
    610                 615                 620

Glu Lys Val Val Gly Arg Ile Ile Ser Ser Thr Pro Leu Ala Glu Asn
625                 630                 635                 640

Thr Asn Ser Val Thr Asn Ile Glu Leu Glu Pro Pro Phe Gly Asp Ser
                645                 650                 655

Tyr Ile Val Ile Gly Val Gly Asn Ser Ala Leu Thr Leu His Trp Phe
            660                 665                 670

Arg Lys Gly Ser Ser Ile Gly Lys Met Phe Glu Ser Thr Tyr Arg Gly
        675                 680                 685

Ala Lys Arg Met Ala Ile Leu Gly Glu Thr Ala Trp Asp Phe Gly Ser
    690                 695                 700

Val Gly Gly Leu Phe Thr Ser Leu Gly Lys Ala Val His Gln Val Phe
705                 710                 715                 720

Gly Ser Val Tyr Thr Thr Leu Phe Gly Gly Val Ser Trp Met Ile Arg
                725                 730                 735

Ile Leu Ile Gly Phe Leu Val Leu Trp Ile Gly Thr Asn Ser Arg Asn
            740                 745                 750

Thr Ser Met Ala Met Thr Cys Ile Ala Ala Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860
```

-continued

```
Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
        995                 1000                1005

Asn Gly  Val Leu Glu Ser Glu  Met Ile Ile Pro Lys  Asn Leu Ala
    1010                 1015                 1020

Gly Pro  Val Ser Gln His Asn  Tyr Arg Pro Gly Tyr  His Thr Gln
    1025                 1030                 1035

Ile Thr  Gly Pro Trp His Leu  Gly Lys Leu Glu Met  Asp Phe Asp
    1040                 1045                 1050

Phe Cys  Asp Gly Thr Thr Val  Val Val Thr Glu Asp  Cys Gly Asn
    1055                 1060                 1065

Arg Gly  Pro Ser Leu Arg Thr  Thr Thr Ala Ser Gly  Lys Leu Ile
    1070                 1075                 1080

Thr Glu  Trp Cys Cys Arg Ser  Cys Thr Leu Pro Pro  Leu Arg Tyr
    1085                 1090                 1095

Arg Gly  Glu Asp Gly Cys Trp  Tyr Gly Met Glu Ile  Arg Pro Leu
    1100                 1105                 1110

Lys Glu  Lys Glu Glu Asn Leu  Val Asn Ser Leu Val  Thr Ala Gly
    1115                 1120                 1125

His Gly  Gln Val Asp Asn Phe  Ser Leu Gly Val Leu  Gly Met Ala
    1130                 1135                 1140

Leu Phe  Leu Glu Glu Met Leu  Arg Thr Arg Val Gly  Thr Lys His
    1145                 1150                 1155

Ala Ile  Leu Leu Val Ala Val  Ser Phe Val Thr Leu  Ile Thr Gly
    1160                 1165                 1170

Asn Met  Ser Phe Arg Asp Leu  Gly Arg Val Met Val  Met Val Gly
    1175                 1180                 1185

Ala Thr  Met Thr Gly Asp Ile  Gly Met Gly Val Thr  Tyr Leu Ala
    1190                 1195                 1200

Leu Leu  Ala Ala Phe Lys Val  Arg Pro Thr Phe Ala  Ala Gly Leu
    1205                 1210                 1215

Leu Leu  Arg Lys Leu Thr Ser  Arg Glu Leu Met Met  Thr Thr Ile
    1220                 1225                 1230

Gly Ile  Val Leu Leu Ser Gln  Ser Thr Ile Pro Glu  Thr Ile Leu
    1235                 1240                 1245

Glu Leu  Thr Asp Ala Leu Ala  Leu Gly Met Met Val  Leu Lys Met
    1250                 1255                 1260

Val Arg  Asn Met Glu Lys Tyr  Gln Leu Ala Val Thr  Ile Met Ala
```

1265 1270 1275

Ile Leu Cys Val Pro Asn Ala Val Ile Leu Gln Asn Ala Trp Lys
1280 1285 1290

Val Ser Cys Thr Ile Leu Ala Val Val Ser Val Ser Pro Leu Phe
1295 1300 1305

Leu Thr Ser Ser Gln Gln Lys Thr Asp Trp Ile Pro Leu Ala Leu
1310 1315 1320

Thr Ile Lys Gly Leu Asn Pro Thr Ala Ile Phe Leu Thr Thr Leu
1325 1330 1335

Ser Arg Thr Ser Lys Lys Arg Ser Trp Pro Leu Asn Glu Ala Ile
1340 1345 1350

Met Ala Val Gly Met Val Ser Ile Leu Ala Ser Ser Leu Leu Lys
1355 1360 1365

Asn Asp Ile Pro Met Thr Gly Pro Leu Val Ala Gly Gly Leu Leu
1370 1375 1380

Thr Val Cys Tyr Val Leu Thr Gly Arg Ser Ala Asp Leu Glu Leu
1385 1390 1395

Glu Arg Ala Ala Asp Val Lys Trp Glu Asp Gln Ala Glu Ile Ser
1400 1405 1410

Gly Ser Ser Pro Ile Leu Ser Ile Thr Ile Ser Glu Asp Gly Ser
1415 1420 1425

Met Ser Ile Lys Asn Glu Glu Glu Glu Gln Thr Leu Thr Ile Leu
1430 1435 1440

Ile Arg Thr Gly Leu Leu Val Ile Ser Gly Leu Phe Pro Val Ser
1445 1450 1455

Ile Pro Ile Thr Ala Ala Ala Trp Tyr Leu Trp Glu Val Lys Lys
1460 1465 1470

Gln Arg Ala Gly Val Leu Trp Asp Val Pro Ser Pro Pro Pro Met
1475 1480 1485

Gly Lys Ala Glu Leu Glu Asp Gly Ala Tyr Arg Ile Lys Gln Lys
1490 1495 1500

Gly Ile Leu Gly Tyr Ser Gln Ile Gly Ala Gly Val Tyr Lys Glu
1505 1510 1515

Gly Thr Phe His Thr Met Trp His Val Thr Arg Gly Ala Val Leu
1520 1525 1530

Met His Lys Gly Lys Arg Ile Glu Pro Ser Trp Ala Asp Val Lys
1535 1540 1545

Lys Asp Leu Ile Ser Tyr Gly Gly Gly Trp Lys Leu Glu Gly Glu
1550 1555 1560

Trp Lys Glu Gly Glu Glu Val Gln Val Leu Ala Leu Glu Pro Gly
1565 1570 1575

Lys Asn Pro Arg Ala Val Gln Thr Lys Pro Gly Leu Phe Lys Thr
1580 1585 1590

Asn Ala Gly Thr Ile Gly Ala Val Ser Leu Asp Phe Ser Pro Gly
1595 1600 1605

Thr Ser Gly Ser Pro Ile Ile Asp Lys Lys Gly Lys Val Val Gly
1610 1615 1620

Leu Tyr Gly Asn Gly Val Val Thr Arg Ser Gly Ala Tyr Val Ser
1625 1630 1635

Ala Ile Ala Gln Thr Glu Lys Ser Ile Glu Asp Asn Pro Glu Ile
1640 1645 1650

Glu Asp Asp Ile Phe Arg Lys Arg Arg Leu Thr Ile Met Asp Leu
1655 1660 1665

-continued

```
His Pro  Gly Ala Gly Lys Thr  Lys Arg Tyr Leu Pro  Ala Ile Val
    1670                 1675                 1680

Arg Glu  Ala Ile Lys Arg Gly  Leu Arg Thr Leu Ile  Leu Ala Pro
    1685                 1690                 1695

Thr Arg  Val Val Ala Ala Glu  Met Glu Glu Ala Leu  Arg Gly Leu
    1700                 1705                 1710

Pro Ile  Arg Tyr Gln Thr Pro  Ala Ile Arg Ala Val  His Thr Gly
    1715                 1720                 1725

Arg Glu  Ile Val Asp Leu Met  Cys His Ala Thr Phe  Thr Met Arg
    1730                 1735                 1740

Leu Leu  Ser Pro Val Arg Val  Pro Asn Tyr Asn Leu  Ile Ile Met
    1745                 1750                 1755

Asp Glu  Ala His Phe Thr Asp  Pro Ala Ser Ile Ala  Ala Arg Gly
    1760                 1765                 1770

Tyr Ile  Ser Thr Arg Val Glu  Met Gly Glu Ala Ala  Gly Ile Phe
    1775                 1780                 1785

Met Thr  Ala Thr Pro Pro Gly  Ser Arg Asp Pro Phe  Pro Gln Ser
    1790                 1795                 1800

Asn Ala  Pro Ile Ile Asp Glu  Glu Arg Glu Ile Pro  Glu Arg Ser
    1805                 1810                 1815

Trp Asn  Ser Gly His Glu Trp  Val Thr Asp Phe Lys  Gly Lys Thr
    1820                 1825                 1830

Val Trp  Phe Val Pro Ser Ile  Lys Ala Gly Asn Asp  Ile Ala Ala
    1835                 1840                 1845

Cys Leu  Arg Lys Asn Gly Lys  Lys Val Ile Gln Leu  Ser Arg Lys
    1850                 1855                 1860

Thr Phe  Asp Ser Glu Tyr Val  Lys Thr Arg Thr Asn  Asp Trp Asp
    1865                 1870                 1875

Phe Val  Val Thr Thr Asp Ile  Ser Glu Met Gly Ala  Asn Phe Lys
    1880                 1885                 1890

Ala Glu  Arg Val Ile Asp Pro  Arg Arg Cys Met Lys  Pro Val Ile
    1895                 1900                 1905

Leu Thr  Asp Gly Glu Glu Arg  Val Ile Leu Ala Gly  Pro Met Pro
    1910                 1915                 1920

Val Thr  His Ser Ser Ala Ala  Gln Arg Arg Gly Arg  Ile Gly Arg
    1925                 1930                 1935

Asn Pro  Lys Asn Glu Asn Asp  Gln Tyr Ile Tyr Met  Gly Glu Pro
    1940                 1945                 1950

Leu Glu  Asn Asp Glu Asp Cys  Ala His Trp Lys Glu  Ala Lys Met
    1955                 1960                 1965

Leu Leu  Asp Asn Ile Asn Thr  Pro Glu Gly Ile Ile  Pro Ser Met
    1970                 1975                 1980

Phe Glu  Pro Glu Arg Glu Lys  Val Asp Ala Ile Asp  Gly Glu Tyr
    1985                 1990                 1995

Arg Leu  Arg Gly Glu Ala Arg  Lys Thr Phe Val Asp  Leu Met Arg
    2000                 2005                 2010

Arg Gly  Asp Leu Pro Val Trp  Leu Ala Tyr Arg Val  Ala Ala Glu
    2015                 2020                 2025

Gly Ile  Asn Tyr Ala Asp Arg  Arg Trp Cys Phe Asp  Gly Val Lys
    2030                 2035                 2040

Asn Asn  Gln Ile Leu Glu Glu  Asn Val Glu Val Glu  Ile Trp Thr
    2045                 2050                 2055
```

-continued

Lys Glu Gly Glu Arg Lys Lys Leu Lys Pro Arg Trp Leu Asp Ala
2060 2065 2070

Arg Ile Tyr Ser Asp Pro Leu Ala Leu Lys Glu Phe Lys Glu Phe
2075 2080 2085

Ala Ala Gly Arg Lys Ser Leu Thr Leu Asn Leu Ile Thr Glu Met
2090 2095 2100

Gly Arg Leu Pro Thr Phe Met Thr Gln Lys Val Arg Asp Ala Leu
2105 2110 2115

Asp Asn Leu Ala Val Leu His Thr Ala Glu Ala Gly Gly Arg Ala
2120 2125 2130

Tyr Asn His Ala Leu Ser Glu Leu Pro Glu Thr Leu Glu Thr Leu
2135 2140 2145

Leu Leu Leu Thr Leu Leu Ala Thr Val Thr Gly Gly Ile Phe Leu
2150 2155 2160

Phe Leu Met Ser Ala Arg Gly Ile Gly Lys Met Thr Leu Gly Met
2165 2170 2175

Cys Cys Ile Ile Thr Ala Ser Ile Leu Leu Trp Tyr Ala Gln Ile
2180 2185 2190

Gln Pro His Trp Ile Ala Ala Ser Ile Ile Leu Glu Phe Phe Leu
2195 2200 2205

Ile Val Leu Leu Ile Pro Glu Pro Glu Lys Gln Arg Thr Pro Gln
2210 2215 2220

Asp Asn Gln Leu Thr Tyr Val Val Ile Ala Ile Leu Thr Val Val
2225 2230 2235

Ala Ala Thr Met Ala Asn Glu Met Gly Phe Leu Glu Lys Thr Lys
2240 2245 2250

Lys Asp Leu Gly Leu Gly Ser Ile Ala Thr Gln Gln Pro Glu Ser
2255 2260 2265

Asn Ile Leu Asp Ile Asp Leu Arg Pro Ala Ser Ala Trp Thr Leu
2270 2275 2280

Tyr Ala Val Ala Thr Thr Phe Val Thr Pro Met Leu Arg His Ser
2285 2290 2295

Ile Glu Asn Ser Ser Val Asn Val Ser Leu Thr Ala Ile Ala Asn
2300 2305 2310

Gln Ala Thr Val Leu Met Gly Leu Gly Lys Gly Trp Pro Leu Ser
2315 2320 2325

Lys Met Asp Ile Gly Val Pro Leu Leu Ala Ile Gly Cys Tyr Ser
2330 2335 2340

Gln Val Asn Pro Ile Thr Leu Thr Ala Ala Leu Phe Leu Leu Val
2345 2350 2355

Ala His Tyr Ala Ile Ile Gly Pro Gly Leu Gln Ala Lys Ala Thr
2360 2365 2370

Arg Glu Ala Gln Lys Arg Ala Ala Ala Gly Ile Met Lys Asn Pro
2375 2380 2385

Thr Val Asp Gly Ile Thr Val Ile Asp Leu Asp Pro Ile Pro Tyr
2390 2395 2400

Asp Pro Lys Phe Glu Lys Gln Leu Gly Gln Val Met Leu Leu Val
2405 2410 2415

Leu Cys Val Thr Gln Val Leu Met Met Arg Thr Thr Trp Ala Leu
2420 2425 2430

Cys Glu Ala Leu Thr Leu Ala Thr Gly Pro Ile Ser Thr Leu Trp
2435 2440 2445

Glu Gly Asn Pro Gly Arg Phe Trp Asn Thr Thr Ile Ala Val Ser

```
    2450                2455                2460

Met Ala  Asn Ile Phe Arg Gly  Ser Tyr Leu Ala Gly  Ala Gly Leu
    2465                2470                2475

Leu Phe  Ser Ile Met Lys Asn  Thr Thr Asn Thr Arg  Arg Gly Thr
    2480                2485                2490

Gly Asn  Ile Gly Glu Thr Leu  Gly Glu Lys Trp Lys  Ser Arg Leu
    2495                2500                2505

Asn Ala  Leu Gly Lys Ser Glu  Phe Gln Ile Tyr Lys  Lys Ser Gly
    2510                2515                2520

Ile Gln  Glu Val Asp Arg Thr  Leu Ala Lys Glu Gly  Ile Lys Arg
    2525                2530                2535

Gly Glu  Thr Asp His His Ala  Val Ser Arg Gly Ser  Ala Lys Leu
    2540                2545                2550

Arg Trp  Phe Val Glu Arg Asn  Met Val Thr Pro Glu  Gly Lys Val
    2555                2560                2565

Val Asp  Leu Gly Cys Gly Arg  Gly Gly Trp Ser Tyr  Tyr Cys Gly
    2570                2575                2580

Gly Leu  Lys Asn Val Arg Glu  Val Lys Gly Leu Thr  Lys Gly Gly
    2585                2590                2595

Pro Gly  His Glu Glu Pro Ile  Pro Met Ser Thr Tyr  Gly Trp Asn
    2600                2605                2610

Leu Val  Arg Leu Gln Ser Gly  Val Asp Val Phe Phe  Ile Pro Pro
    2615                2620                2625

Glu Lys  Cys Asp Thr Leu Leu  Cys Asp Ile Gly Glu  Ser Ser Pro
    2630                2635                2640

Asn Pro  Thr Val Glu Ala Gly  Arg Thr Leu Arg Val  Leu Asn Leu
    2645                2650                2655

Val Glu  Asn Trp Leu Asn Asn  Asn Thr Gln Phe Cys  Ile Lys Val
    2660                2665                2670

Leu Asn  Pro Tyr Met Pro Ser  Val Ile Glu Lys Met  Glu Ala Leu
    2675                2680                2685

Gln Arg  Lys Tyr Gly Gly Ala  Leu Val Arg Asn Pro  Leu Ser Arg
    2690                2695                2700

Asn Ser  Thr His Glu Met Tyr  Trp Val Ser Asn Ala  Ser Gly Asn
    2705                2710                2715

Ile Val  Ser Ser Val Asn Met  Ile Ser Arg Met Leu  Ile Asn Arg
    2720                2725                2730

Phe Thr  Met Arg Tyr Lys Lys  Ala Thr Tyr Glu Pro  Asp Val Asp
    2735                2740                2745

Leu Gly  Ser Gly Thr Arg Asn  Ile Gly Ile Glu Ser  Glu Ile Pro
    2750                2755                2760

Asn Leu  Asp Ile Ile Gly Lys  Arg Ile Glu Lys Ile  Lys Gln Glu
    2765                2770                2775

His Glu  Thr Ser Trp His Tyr  Asp Gln Asp His Pro  Tyr Lys Thr
    2780                2785                2790

Trp Ala  Tyr His Gly Ser Tyr  Glu Thr Lys Gln Thr  Gly Ser Ala
    2795                2800                2805

Ser Ser  Met Val Asn Gly Val  Val Arg Leu Leu Thr  Lys Pro Trp
    2810                2815                2820

Asp Val  Val Pro Met Val Thr  Gln Met Ala Met Thr  Asp Thr Thr
    2825                2830                2835

Pro Phe  Gly Gln Gln Arg Val  Phe Lys Glu Lys Val  Asp Thr Arg
    2840                2845                2850
```

-continued

```
Thr Gln  Glu Pro Lys Glu Gly  Thr Lys Lys Leu Met  Lys Ile Thr
    2855                 2860                 2865

Ala Glu  Trp Leu Trp Lys Glu  Leu Gly Lys Lys Lys  Thr Pro Arg
    2870                 2875                 2880

Met Cys  Thr Arg Glu Glu Phe  Thr Arg Lys Val Arg  Ser Asn Ala
    2885                 2890                 2895

Ala Leu  Gly Ala Ile Phe Thr  Asp Glu Asn Lys Trp  Lys Ser Ala
    2900                 2905                 2910

Arg Glu  Ala Val Glu Asp Ser  Arg Phe Trp Glu Leu  Val Asp Lys
    2915                 2920                 2925

Glu Arg  Asn Leu His Leu Glu  Gly Lys Cys Glu Thr  Cys Val Tyr
    2930                 2935                 2940

Asn Met  Met Gly Lys Arg Glu  Lys Lys Leu Gly Glu  Phe Gly Lys
    2945                 2950                 2955

Ala Lys  Gly Ser Arg Ala Ile  Trp Tyr Met Trp Leu  Gly Ala Arg
    2960                 2965                 2970

Phe Leu  Glu Phe Glu Ala Leu  Gly Phe Leu Asn Glu  Asp His Trp
    2975                 2980                 2985

Phe Ser  Arg Glu Asn Ser Leu  Ser Gly Val Glu Gly  Glu Gly Leu
    2990                 2995                 3000

His Lys  Leu Gly Tyr Ile Leu  Arg Asp Val Ser Lys  Lys Glu Gly
    3005                 3010                 3015

Gly Ala  Met Tyr Ala Asp Asp  Thr Ala Gly Trp Asp  Thr Arg Ile
    3020                 3025                 3030

Thr Leu  Glu Asp Leu Lys Asn  Glu Glu Met Val Thr  Asn His Met
    3035                 3040                 3045

Glu Gly  Glu His Lys Lys Leu  Ala Glu Ala Ile Phe  Lys Leu Thr
    3050                 3055                 3060

Tyr Gln  Asn Lys Val Val Arg  Val Gln Arg Pro Thr  Pro Arg Gly
    3065                 3070                 3075

Thr Val  Met Asp Ile Ile Ser  Arg Arg Asp Gln Arg  Gly Ser Gly
    3080                 3085                 3090

Gln Val  Gly Thr Tyr Gly Leu  Asn Thr Phe Thr Asn  Met Glu Ala
    3095                 3100                 3105

Gln Leu  Ile Arg Gln Met Glu  Gly Glu Gly Val Phe  Lys Ser Ile
    3110                 3115                 3120

Gln His  Leu Thr Ile Thr Glu  Glu Ile Ala Val Gln  Asn Trp Leu
    3125                 3130                 3135

Ala Arg  Val Gly Arg Glu Arg  Leu Ser Arg Met Ala  Ile Ser Gly
    3140                 3145                 3150

Asp Asp  Cys Val Val Lys Pro  Leu Asp Asp Arg Phe  Ala Ser Ala
    3155                 3160                 3165

Leu Thr  Ala Leu Asn Asp Met  Gly Lys Ile Arg Lys  Asp Ile Gln
    3170                 3175                 3180

Gln Trp  Glu Pro Ser Arg Gly  Trp Asn Asp Trp Thr  Gln Val Pro
    3185                 3190                 3195

Phe Cys  Ser His His Phe His  Glu Leu Ile Met Lys  Asp Gly Arg
    3200                 3205                 3210

Val Leu  Val Val Pro Cys Arg  Asn Gln Asp Glu Leu  Ile Gly Arg
    3215                 3220                 3225

Ala Arg  Ile Ser Gln Gly Ala  Gly Trp Ser Leu Arg  Glu Thr Ala
    3230                 3235                 3240
```

-continued

```
Cys Leu  Gly Lys Ser Tyr Ala  Gln Met Trp Ser Leu  Met Tyr Phe
    3245                 3250                 3255

His Arg  Arg Asp Leu Arg Leu  Ala Ala Asn Ala Ile  Cys Ser Ala
    3260                 3265                 3270

Val Pro  Ser His Trp Val Pro  Thr Ser Arg Thr Thr  Trp Ser Ile
    3275                 3280                 3285

His Ala  Lys His Glu Trp Met  Thr Thr Glu Asp Met  Leu Thr Val
    3290                 3295                 3300

Trp Asn  Arg Val Trp Ile Gln  Glu Asn Pro Trp Met  Glu Asp Lys
    3305                 3310                 3315

Thr Pro  Val Glu Ser Trp Glu  Glu Ile Pro Tyr Leu  Gly Lys Arg
    3320                 3325                 3330

Glu Asp  Gln Trp Cys Gly Ser  Leu Ile Gly Leu Thr  Ser Arg Ala
    3335                 3340                 3345

Thr Trp  Ala Lys Asn Ile Gln  Ala Ala Ile Asn Gln  Val Arg Ser
    3350                 3355                 3360

Leu Ile  Gly Asn Glu Glu Tyr  Thr Asp Tyr Met Pro  Ser Met Lys
    3365                 3370                 3375

Arg Phe  Arg Arg Glu Glu Glu  Glu Ala Gly Val Leu  Trp
    3380                 3385                 3390


<210> SEQ ID NO 22
<211> LENGTH: 10723
<212> TYPE: DNA
<213> ORGANISM: Artificial Sequence
<220> FEATURE:
<223> OTHER INFORMATION: Derived from Dengue virus serotype 2/Dengue
      virus serotype 4, DENV-4e

<400> SEQUENCE: 22

agttgttagt ctacgtggac cgacaaagac agattctttg agggagctaa gctcaatgta      60

gttctaacag tttttttaatt agagagcaga tctctgatga ataaccaacg gaaaaaggcg    120

aaaaacacgc ctttcaatat gctgaaacgc gagagaaacc gcgtgtcgac tgtgcaacag     180

ctgacaaaga gattctcact tggaatgctg cagggacgag gaccattaaa actgttcatg     240

gccctggtgg cgttccttcg tttcctaaca atcccaccaa cagcagggat attgaagaga     300

tggggaacaa ttaaaaaatc aaaagctatt aatgttttga gagggttcag gaaagagatt     360

ggaaggatgc tgaacatctt gaataggaga cgcagctcaa cgataacatt gctgtacttg     420

attcccaccg taatggcgtt tcacttgtca acgcgtgatg gcgaacccct catgatagtg     480

gcaaaacatg aaagggggag acctctcttg tttaagacaa cagaggggat caacaaatgc     540

actctcattg ccatggactt gggtgaaatg tgtgaggaca ctgtcacgta taaatgcccc     600

ttactggtca ataccgaacc tgaagacatt gattgctggt gcaatctcac gtctacctgg     660

gtcatgtatg ggacatgcac ccagagcgga gaacggagac gagagaagcg ctcagtagct     720

ttaacaccac attcaggaat gggattggaa acaagagctg agacatggat gtcatcggaa     780

ggggcttgga agcatgctca gagagtagag agctggatac tcagaaaccc aggattcgcg     840

ctcttggcag gatttatggc ttatatgatt gggcaaacag gaatccagcg aactgtcttc     900

tttgtcctaa tgatgctggt cgccccatcc tacggaatgc gatgcgtagg agtaggaaac     960

agagactttg tggaaggagt ctcaggtgga gcatgggtcg atctggtgct agaacatgga    1020

ggatgcgtca caaccatggc ccagggaaaa ccaaccttgg attttgaact gactaagaca    1080

acagccaagg aagtggctct gttaagaacc tattgcattg aagcctcaat atcaaacata    1140
```

-continued

```
accacggcaa caagatgtcc aacgcaagga gagccttatc taaaagagga acaagaccaa   1200
cagtacattt gccggagaga tgtggtagac agagggtggg gcaatggctg tggcttgttt   1260
ggaaaaggag gagttgtgac atgtgcgaag ttttcatgtt cggggaagat aacaggcaat   1320
ttggtccaaa ttgagaacct tgaatacaca gtggttgtaa cagtccacaa tggagacacc   1380
catgcagtag gaaatgacac gtccaatcat ggagttacag ccacgataac tcccaggtca   1440
ccatcggtgg aagtcaaatt gccggactat ggagaactaa cactcgattg tgaacccagg   1500
tctggaattg actttaatga gatgattctg atgaaaatga aaaagaaaac atggcttgtg   1560
cataagcaat ggtttttgga tctacctcta ccatggacag caggagcaga cacatcagag   1620
gttcactgga attacaaaga gagaatggtg acatttaagg ttcctcatgc caagagacag   1680
gatgtgacag tgctgggatc tcaggaagga gccatgcatt ctgccctcgc tggagccaca   1740
gaagtggact ccggtgatgg aaatcacatg tttgcaggac atctcaagtg caaagtccgt   1800
atggagaaat tgagaatcaa gggaatgtca tacacgatgt gttcaggaaa gttctcaatt   1860
gacaaagaga tggcagaaac acagcatggg acaacagtgg tgaaagtcaa gtatgaaggt   1920
gctggagctc cgtgtaaagt ccccatagag ataagagatg tgaacaagga aaaagtggtt   1980
gggcgtatca tctcatccac ccctttggct gagaatacca acagtgtaac caacatagag   2040
ttagaacccc cctttgggga cagctacata gtgataggtg ttggaaacag tgcattaaca   2100
ctccattggt tcaggaaagg gagttccatt ggcaagatgt ttgagtccac atacagaggt   2160
gcaaaacgaa tggccattct aggtgaaaca gcttgggatt ttggttccgt tggtggactg   2220
ttcacatcat tgggaaaggc tgtgcaccag gtttttggaa gtgtgtatac aaccctgttt   2280
ggaggagtct catggatgat tagaatccta attgggttcc tagtgttgtg gattggcacg   2340
aactcaagga acacttcaat ggctatgacg tgcatagctg ccggcattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
```

```
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgttc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
```

-continued

```
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct ttttattctt gatgagcgca   6600
aggggcatag ggaagatgac cctgggaatg tgctgcataa tcacggctag catcctccta   6660
tggtacgcac aaatacagcc acactggata gcagcttcaa taatactgga gtttttctc    6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagagaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
```

-continued

```
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agaagcagga  10260
gttctgtggt agaaagcaaa actaacatga aacaaggcta gaagtcaggt cggattaagc  10320
catagtacgg aaaaaactat gctacctgtg agccccgtcc aaggacgtta aaagaagtca  10380
ggccatcata aatgccatag cttgagtaaa ctatgcagcc tgtagctcca cctgagaagg  10440
tgtaaaaaat ccgggaggcc acaaaccatg gaagctgtac gcatggcgta gtggactagc  10500
ggttagagga gacccctccc ttacaaatcg cagcaacaat gggggcccaa ggcgagatga  10560
agctgtagtc tcgctggaag gactagaggt tagaggagac ccccccgaaa caaaaaacag  10620
```

```
catattgacg ctgggaaaga ccagagatcc tgctgtctcc tcagcatcat tccaggcaca  10680

gaacgccaga aaatggaatg gtgctgttga atcaacaggt tct                     10723


<210> SEQ ID NO 23
<211> LENGTH: 3391
<212> TYPE: PRT
<213> ORGANISM: Artificial Sequence
<220> FEATURE:
<223> OTHER INFORMATION: Derived from Dengue virus serotype 2/Dengue
      virus serotype 4, DEN-4e

<400> SEQUENCE: 23

Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Ser Ser Thr Ile Thr Leu Leu Tyr Leu Ile Pro Thr Val
            100                 105                 110

Met Ala Phe His Leu Ser Thr Arg Asp Gly Glu Pro Leu Met Ile Val
        115                 120                 125

Ala Lys His Glu Arg Gly Arg Pro Leu Leu Phe Lys Thr Thr Glu Gly
    130                 135                 140

Ile Asn Lys Cys Thr Leu Ile Ala Met Asp Leu Gly Glu Met Cys Glu
145                 150                 155                 160

Asp Thr Val Thr Tyr Lys Cys Pro Leu Leu Val Asn Thr Glu Pro Glu
                165                 170                 175

Asp Ile Asp Cys Trp Cys Asn Leu Thr Ser Thr Trp Val Met Tyr Gly
            180                 185                 190

Thr Cys Thr Gln Ser Gly Glu Arg Arg Arg Glu Lys Arg Ser Val Ala
        195                 200                 205

Leu Thr Pro His Ser Gly Met Gly Leu Glu Thr Arg Ala Glu Thr Trp
    210                 215                 220

Met Ser Ser Glu Gly Ala Trp Lys His Ala Gln Arg Val Glu Ser Trp
225                 230                 235                 240

Ile Leu Arg Asn Pro Gly Phe Ala Leu Leu Ala Gly Phe Met Ala Tyr
                245                 250                 255

Met Ile Gly Gln Thr Gly Ile Gln Arg Thr Val Phe Phe Val Leu Met
            260                 265                 270

Met Leu Val Ala Pro Ser Tyr Gly Met Arg Cys Val Gly Val Gly Asn
        275                 280                 285

Arg Asp Phe Val Glu Gly Val Ser Gly Gly Ala Trp Val Asp Leu Val
    290                 295                 300

Leu Glu His Gly Gly Cys Val Thr Thr Met Ala Gln Gly Lys Pro Thr
305                 310                 315                 320

Leu Asp Phe Glu Leu Thr Lys Thr Thr Ala Lys Glu Val Ala Leu Leu
                325                 330                 335

Arg Thr Tyr Cys Ile Glu Ala Ser Ile Ser Asn Ile Thr Thr Ala Thr
```

```
            340                 345                 350

Arg Cys Pro Thr Gln Gly Glu Pro Tyr Leu Lys Glu Glu Gln Asp Gln
        355                 360                 365

Gln Tyr Ile Cys Arg Arg Asp Val Val Asp Arg Gly Trp Gly Asn Gly
    370                 375                 380

Cys Gly Leu Phe Gly Lys Gly Gly Val Val Thr Cys Ala Lys Phe Ser
385                 390                 395                 400

Cys Ser Gly Lys Ile Thr Gly Asn Leu Val Gln Ile Glu Asn Leu Glu
                405                 410                 415

Tyr Thr Val Val Val Thr Val His Asn Gly Asp Thr His Ala Val Gly
            420                 425                 430

Asn Asp Thr Ser Asn His Gly Val Thr Ala Thr Ile Thr Pro Arg Ser
        435                 440                 445

Pro Ser Val Glu Val Lys Leu Pro Asp Tyr Gly Glu Leu Thr Leu Asp
    450                 455                 460

Cys Glu Pro Arg Ser Gly Ile Asp Phe Asn Glu Met Ile Leu Met Lys
465                 470                 475                 480

Met Lys Lys Lys Thr Trp Leu Val His Lys Gln Trp Phe Leu Asp Leu
                485                 490                 495

Pro Leu Pro Trp Thr Ala Gly Ala Asp Thr Ser Glu Val His Trp Asn
            500                 505                 510

Tyr Lys Glu Arg Met Val Thr Phe Lys Val Pro His Ala Lys Arg Gln
        515                 520                 525

Asp Val Thr Val Leu Gly Ser Gln Glu Gly Ala Met His Ser Ala Leu
    530                 535                 540

Ala Gly Ala Thr Glu Val Asp Ser Gly Asp Gly Asn His Met Phe Ala
545                 550                 555                 560

Gly His Leu Lys Cys Lys Val Arg Met Glu Lys Leu Arg Ile Lys Gly
                565                 570                 575

Met Ser Tyr Thr Met Cys Ser Gly Lys Phe Ser Ile Asp Lys Glu Met
            580                 585                 590

Ala Glu Thr Gln His Gly Thr Thr Val Val Lys Val Lys Tyr Glu Gly
        595                 600                 605

Ala Gly Ala Pro Cys Lys Val Pro Ile Glu Ile Arg Asp Val Asn Lys
    610                 615                 620

Glu Lys Val Val Gly Arg Ile Ile Ser Ser Thr Pro Leu Ala Glu Asn
625                 630                 635                 640

Thr Asn Ser Val Thr Asn Ile Glu Leu Glu Pro Pro Phe Gly Asp Ser
                645                 650                 655

Tyr Ile Val Ile Gly Val Gly Asn Ser Ala Leu Thr Leu His Trp Phe
            660                 665                 670

Arg Lys Gly Ser Ser Ile Gly Lys Met Phe Glu Ser Thr Tyr Arg Gly
        675                 680                 685

Ala Lys Arg Met Ala Ile Leu Gly Glu Thr Ala Trp Asp Phe Gly Ser
    690                 695                 700

Val Gly Gly Leu Phe Thr Ser Leu Gly Lys Ala Val His Gln Val Phe
705                 710                 715                 720

Gly Ser Val Tyr Thr Thr Leu Phe Gly Gly Val Ser Trp Met Ile Arg
                725                 730                 735

Ile Leu Ile Gly Phe Leu Val Leu Trp Ile Gly Thr Asn Ser Arg Asn
            740                 745                 750

Thr Ser Met Ala Met Thr Cys Ile Ala Ala Gly Ile Val Thr Leu Tyr
        755                 760                 765
```

-continued

```
Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
        995                 1000                1005

Asn Gly  Val Leu Glu Ser Glu  Met Ile Ile Pro Lys  Asn Leu Ala
    1010                 1015                 1020

Gly Pro  Val Ser Gln His Asn  Tyr Arg Pro Gly Tyr  His Thr Gln
    1025                 1030                 1035

Ile Thr  Gly Pro Trp His Leu  Gly Lys Leu Glu Met  Asp Phe Asp
    1040                 1045                 1050

Phe Cys  Asp Gly Thr Thr Val  Val Val Thr Glu Asp  Cys Gly Asn
    1055                 1060                 1065

Arg Gly  Pro Ser Leu Arg Thr  Thr Thr Ala Ser Gly  Lys Leu Ile
    1070                 1075                 1080

Thr Glu  Trp Cys Cys Arg Ser  Cys Thr Leu Pro Pro  Leu Arg Tyr
    1085                 1090                 1095

Arg Gly  Glu Asp Gly Cys Trp  Tyr Gly Met Glu Ile  Arg Pro Leu
    1100                 1105                 1110

Lys Glu  Lys Glu Glu Asn Leu  Val Asn Ser Leu Val  Thr Ala Gly
    1115                 1120                 1125

His Gly  Gln Val Asp Asn Phe  Ser Leu Gly Val Leu  Gly Met Ala
    1130                 1135                 1140

Leu Phe  Leu Glu Glu Met Leu  Arg Thr Arg Val Gly  Thr Lys His
    1145                 1150                 1155

Ala Ile  Leu Leu Val Ala Val  Ser Phe Val Thr Leu  Ile Thr Gly
    1160                 1165                 1170
```

Asn Met Ser Phe Arg Asp Leu Gly Arg Val Met Val Met Val Gly
    1175 1180 1185

Ala Thr Met Thr Asp Asp Ile Gly Met Gly Val Thr Tyr Leu Ala
    1190 1195 1200

Leu Leu Ala Ala Phe Lys Val Arg Pro Thr Phe Ala Ala Gly Leu
    1205 1210 1215

Leu Leu Arg Lys Leu Thr Ser Lys Glu Leu Met Met Thr Thr Ile
    1220 1225 1230

Gly Ile Val Leu Leu Ser Gln Ser Thr Ile Pro Glu Thr Ile Leu
    1235 1240 1245

Glu Leu Thr Asp Ala Leu Ala Leu Gly Met Met Val Leu Lys Met
    1250 1255 1260

Val Arg Asn Met Glu Lys Tyr Gln Leu Ala Val Thr Ile Met Ala
    1265 1270 1275

Ile Leu Cys Val Pro Asn Ala Val Ile Leu Gln Asn Ala Trp Lys
    1280 1285 1290

Val Ser Cys Thr Ile Leu Ala Val Val Ser Val Ser Pro Leu Phe
    1295 1300 1305

Leu Thr Ser Ser Gln Gln Lys Thr Asp Trp Ile Pro Leu Ala Leu
    1310 1315 1320

Thr Ile Lys Gly Leu Asn Pro Thr Ala Ile Phe Leu Thr Thr Leu
    1325 1330 1335

Ser Arg Thr Ser Lys Lys Arg Ser Trp Pro Leu Asn Glu Ala Ile
    1340 1345 1350

Met Ala Val Gly Met Val Ser Ile Leu Ala Ser Ser Leu Leu Lys
    1355 1360 1365

Asn Asp Ile Pro Met Thr Gly Pro Leu Val Ala Gly Gly Leu Leu
    1370 1375 1380

Thr Val Cys Tyr Val Leu Thr Gly Arg Ser Ala Asp Leu Glu Leu
    1385 1390 1395

Glu Arg Ala Ala Asp Val Lys Trp Glu Asp Gln Ala Glu Ile Ser
    1400 1405 1410

Gly Ser Ser Pro Ile Leu Ser Ile Thr Ile Ser Glu Asp Gly Ser
    1415 1420 1425

Met Ser Ile Lys Asn Glu Glu Glu Glu Gln Thr Leu Thr Ile Leu
    1430 1435 1440

Ile Arg Thr Gly Leu Leu Val Ile Ser Gly Leu Phe Pro Val Ser
    1445 1450 1455

Ile Pro Ile Thr Ala Ala Ala Trp Tyr Leu Trp Glu Val Lys Lys
    1460 1465 1470

Gln Arg Ala Gly Val Leu Trp Asp Val Pro Ser Pro Pro Pro Met
    1475 1480 1485

Gly Lys Ala Glu Leu Glu Asp Gly Ala Tyr Arg Ile Lys Gln Lys
    1490 1495 1500

Gly Ile Leu Gly Tyr Ser Gln Ile Gly Ala Gly Val Tyr Lys Glu
    1505 1510 1515

Gly Thr Phe His Thr Met Trp His Val Thr Arg Gly Ala Val Leu
    1520 1525 1530

Met His Lys Gly Lys Arg Ile Glu Pro Ser Trp Ala Asp Val Lys
    1535 1540 1545

Lys Asp Leu Ile Ser Tyr Gly Gly Gly Trp Lys Leu Glu Gly Glu
    1550 1555 1560

Trp Lys Glu Gly Glu Glu Val Gln Val Leu Ala Leu Glu Pro Gly

-continued

```
    1565                1570                1575

Lys Asn  Pro Arg Ala Val Gln  Thr Lys Pro Gly Leu  Phe Lys Thr
    1580                1585                1590

Asn Ala  Gly Thr Ile Gly Ala  Val Ser Leu Asp Phe  Ser Pro Gly
    1595                1600                1605

Thr Ser  Gly Ser Pro Ile Ile  Asp Lys Lys Gly Lys  Val Val Gly
    1610                1615                1620

Leu Tyr  Gly Asn Gly Val Val  Thr Arg Ser Gly Ala  Tyr Val Ser
    1625                1630                1635

Ala Ile  Ala Gln Thr Glu Lys  Ser Ile Glu Asp Asn  Pro Glu Ile
    1640                1645                1650

Glu Asp  Asp Ile Phe Arg Lys  Arg Arg Leu Thr Ile  Met Asp Leu
    1655                1660                1665

His Pro  Gly Ala Gly Lys Thr  Lys Arg Tyr Leu Pro  Ala Ile Val
    1670                1675                1680

Arg Glu  Ala Ile Lys Arg Gly  Leu Arg Thr Leu Ile  Leu Ala Pro
    1685                1690                1695

Thr Arg  Val Val Ala Ala Glu  Met Glu Glu Ala Leu  Arg Gly Leu
    1700                1705                1710

Pro Ile  Arg Tyr Gln Thr Pro  Ala Ile Arg Ala Val  His Thr Gly
    1715                1720                1725

Arg Glu  Ile Val Asp Leu Met  Cys His Ala Thr Phe  Thr Met Arg
    1730                1735                1740

Leu Leu  Ser Pro Val Arg Val  Pro Asn Tyr Asn Leu  Ile Ile Met
    1745                1750                1755

Asp Glu  Ala His Phe Thr Asp  Pro Ala Ser Ile Ala  Ala Arg Gly
    1760                1765                1770

Tyr Ile  Ser Thr Arg Val Glu  Met Gly Glu Ala Ala  Gly Ile Phe
    1775                1780                1785

Met Thr  Ala Thr Pro Pro Gly  Ser Arg Asp Pro Phe  Pro Gln Ser
    1790                1795                1800

Asn Ala  Pro Ile Ile Asp Glu  Glu Arg Glu Ile Pro  Glu Arg Ser
    1805                1810                1815

Trp Asn  Ser Gly His Glu Trp  Val Thr Asp Phe Lys  Gly Lys Thr
    1820                1825                1830

Val Trp  Phe Val Pro Ser Ile  Lys Ala Gly Asn Asp  Ile Ala Ala
    1835                1840                1845

Cys Leu  Arg Lys Asn Gly Lys  Lys Val Ile Gln Leu  Ser Arg Lys
    1850                1855                1860

Thr Phe  Asp Ser Glu Tyr Val  Lys Thr Arg Thr Asn  Asp Trp Asp
    1865                1870                1875

Phe Val  Val Thr Thr Asp Ile  Ser Glu Met Gly Ala  Asn Phe Lys
    1880                1885                1890

Ala Glu  Arg Val Ile Asp Pro  Arg Arg Cys Met Lys  Pro Val Ile
    1895                1900                1905

Leu Thr  Asp Gly Glu Glu Arg  Val Ile Leu Ala Gly  Pro Met Pro
    1910                1915                1920

Val Thr  His Ser Ser Ala Ala  Gln Arg Arg Gly Arg  Ile Gly Arg
    1925                1930                1935

Asn Pro  Lys Asn Glu Asn Asp  Gln Tyr Ile Tyr Met  Gly Glu Pro
    1940                1945                1950

Leu Glu  Asn Asp Glu Asp Cys  Ala His Trp Lys Glu  Ala Lys Met
    1955                1960                1965
```

-continued

```
Leu Leu  Asp Asn Ile Asn Thr  Pro Glu Gly Ile Ile  Pro Ser Met
    1970                 1975                 1980

Phe Glu  Pro Glu Arg Glu Lys  Val Asp Ala Ile Asp  Gly Glu Tyr
    1985                 1990                 1995

Arg Leu  Arg Gly Glu Ala Arg  Lys Thr Phe Val Asp  Leu Met Arg
    2000                 2005                 2010

Arg Gly  Asp Leu Pro Val Trp  Leu Ala Tyr Arg Val  Ala Ala Glu
    2015                 2020                 2025

Gly Ile  Asn Tyr Ala Asp Arg  Arg Trp Cys Phe Asp  Gly Val Lys
    2030                 2035                 2040

Asn Asn  Gln Ile Leu Glu Glu  Asn Val Glu Val Glu  Ile Trp Thr
    2045                 2050                 2055

Lys Glu  Gly Glu Arg Lys Lys  Leu Lys Pro Arg Trp  Leu Asp Ala
    2060                 2065                 2070

Arg Ile  Tyr Ser Asp Pro Leu  Ala Leu Lys Glu Phe  Lys Glu Phe
    2075                 2080                 2085

Ala Ala  Gly Arg Lys Ser Leu  Thr Leu Asn Leu Ile  Thr Glu Met
    2090                 2095                 2100

Gly Arg  Leu Pro Thr Phe Met  Thr Gln Lys Ala Arg  Asp Ala Leu
    2105                 2110                 2115

Asp Asn  Leu Ala Val Leu His  Thr Ala Glu Ala Gly  Gly Arg Ala
    2120                 2125                 2130

Tyr Asn  His Ala Leu Ser Glu  Leu Pro Glu Thr Leu  Glu Thr Leu
    2135                 2140                 2145

Leu Leu  Leu Thr Leu Leu Ala  Thr Val Thr Gly Gly  Ile Phe Leu
    2150                 2155                 2160

Phe Leu  Met Ser Ala Arg Gly  Ile Gly Lys Met Thr  Leu Gly Met
    2165                 2170                 2175

Cys Cys  Ile Ile Thr Ala Ser  Ile Leu Leu Trp Tyr  Ala Gln Ile
    2180                 2185                 2190

Gln Pro  His Trp Ile Ala Ala  Ser Ile Ile Leu Glu  Phe Phe Leu
    2195                 2200                 2205

Ile Val  Leu Leu Ile Pro Glu  Pro Glu Lys Gln Arg  Thr Pro Gln
    2210                 2215                 2220

Asp Asn  Gln Leu Thr Tyr Val  Val Ile Ala Ile Leu  Thr Val Val
    2225                 2230                 2235

Ala Ala  Thr Met Ala Asn Glu  Met Gly Phe Leu Glu  Lys Thr Lys
    2240                 2245                 2250

Lys Asp  Leu Gly Leu Gly Ser  Ile Ala Thr Gln Gln  Pro Glu Ser
    2255                 2260                 2265

Asn Ile  Leu Asp Ile Asp Leu  Arg Pro Ala Ser Ala  Trp Thr Leu
    2270                 2275                 2280

Tyr Ala  Val Ala Thr Thr Phe  Val Thr Pro Met Leu  Arg His Ser
    2285                 2290                 2295

Ile Glu  Asn Ser Ser Val Asn  Val Ser Leu Thr Ala  Ile Ala Asn
    2300                 2305                 2310

Gln Ala  Thr Val Leu Met Gly  Leu Gly Lys Gly Trp  Pro Leu Ser
    2315                 2320                 2325

Lys Met  Asp Ile Gly Val Pro  Leu Leu Ala Ile Gly  Cys Tyr Ser
    2330                 2335                 2340

Gln Val  Asn Pro Ile Thr Leu  Thr Ala Ala Leu Phe  Leu Leu Val
    2345                 2350                 2355
```

```
Ala His  Tyr Ala Ile Ile Gly  Pro Gly Leu Gln Ala  Lys Ala Thr
    2360                 2365                 2370

Arg Glu  Ala Gln Lys Arg Ala  Ala Ala Gly Ile Met  Lys Asn Pro
    2375                 2380                 2385

Thr Val  Asp Gly Ile Thr Val  Ile Asp Leu Asp Pro  Ile Pro Tyr
    2390                 2395                 2400

Asp Pro  Lys Phe Glu Lys Gln  Leu Gly Gln Val Met  Leu Leu Val
    2405                 2410                 2415

Leu Cys  Val Thr Gln Val Leu  Met Met Arg Thr Thr  Trp Ala Leu
    2420                 2425                 2430

Cys Glu  Ala Leu Thr Leu Ala  Thr Gly Pro Ile Ser  Thr Leu Trp
    2435                 2440                 2445

Glu Gly  Asn Pro Gly Arg Phe  Trp Asn Thr Thr Ile  Ala Val Ser
    2450                 2455                 2460

Met Ala  Asn Ile Phe Arg Gly  Ser Tyr Leu Ala Gly  Ala Gly Leu
    2465                 2470                 2475

Leu Phe  Ser Ile Met Lys Asn  Thr Thr Asn Thr Arg  Arg Gly Thr
    2480                 2485                 2490

Gly Asn  Ile Gly Glu Thr Leu  Gly Glu Lys Trp Lys  Ser Arg Leu
    2495                 2500                 2505

Asn Ala  Leu Gly Lys Ser Glu  Phe Gln Ile Tyr Lys  Lys Ser Gly
    2510                 2515                 2520

Ile Gln  Glu Val Asp Arg Thr  Leu Ala Lys Glu Gly  Ile Lys Arg
    2525                 2530                 2535

Gly Glu  Thr Asp His His Ala  Val Ser Arg Gly Ser  Ala Lys Leu
    2540                 2545                 2550

Arg Trp  Phe Val Glu Arg Asn  Met Val Thr Pro Glu  Gly Lys Val
    2555                 2560                 2565

Val Asp  Leu Gly Cys Gly Arg  Gly Gly Trp Ser Tyr  Tyr Cys Gly
    2570                 2575                 2580

Gly Leu  Lys Asn Val Arg Glu  Val Lys Gly Leu Thr  Lys Gly Gly
    2585                 2590                 2595

Pro Gly  His Glu Glu Pro Ile  Pro Met Ser Thr Tyr  Gly Trp Asn
    2600                 2605                 2610

Leu Val  Arg Leu Gln Ser Gly  Val Asp Val Phe Phe  Ile Pro Pro
    2615                 2620                 2625

Glu Lys  Cys Asp Thr Leu Leu  Cys Asp Ile Gly Glu  Ser Ser Pro
    2630                 2635                 2640

Asn Pro  Thr Val Glu Ala Gly  Arg Thr Leu Arg Val  Leu Asn Leu
    2645                 2650                 2655

Val Glu  Asn Trp Leu Asn Asn  Asn Thr Gln Phe Cys  Ile Lys Val
    2660                 2665                 2670

Leu Asn  Pro Tyr Met Pro Ser  Val Ile Glu Lys Met  Glu Ala Leu
    2675                 2680                 2685

Gln Arg  Lys Tyr Gly Gly Ala  Leu Val Arg Asn Pro  Leu Ser Arg
    2690                 2695                 2700

Asn Ser  Thr His Glu Met Tyr  Trp Val Ser Asn Ala  Ser Gly Asn
    2705                 2710                 2715

Ile Val  Ser Ser Val Asn Met  Ile Ser Arg Met Leu  Ile Asn Arg
    2720                 2725                 2730

Phe Thr  Met Arg Tyr Lys Lys  Ala Thr Tyr Glu Pro  Asp Val Asp
    2735                 2740                 2745

Leu Gly  Ser Gly Thr Arg Asn  Ile Gly Ile Glu Ser  Glu Ile Pro
```

2750 2755 2760

Asn Leu Asp Ile Ile Gly Lys Arg Ile Glu Lys Ile Lys Gln Glu
2765 2770 2775

His Glu Thr Ser Trp His Tyr Asp Gln Asp His Pro Tyr Lys Thr
2780 2785 2790

Trp Ala Tyr His Gly Ser Tyr Glu Thr Lys Gln Thr Gly Ser Ala
2795 2800 2805

Ser Ser Met Val Asn Gly Val Val Arg Leu Leu Thr Lys Pro Trp
2810 2815 2820

Asp Val Val Pro Met Val Thr Gln Met Ala Met Thr Asp Thr Thr
2825 2830 2835

Pro Phe Gly Gln Gln Arg Val Phe Lys Glu Lys Val Asp Thr Arg
2840 2845 2850

Thr Gln Glu Pro Lys Glu Gly Thr Lys Lys Leu Met Lys Ile Thr
2855 2860 2865

Ala Glu Trp Leu Trp Lys Glu Leu Gly Lys Lys Lys Thr Pro Arg
2870 2875 2880

Met Cys Thr Arg Glu Glu Phe Thr Arg Lys Val Arg Ser Asn Ala
2885 2890 2895

Ala Leu Gly Ala Ile Phe Thr Asp Glu Asn Lys Trp Lys Ser Ala
2900 2905 2910

Arg Glu Ala Val Glu Asp Ser Arg Phe Trp Glu Leu Val Asp Lys
2915 2920 2925

Glu Arg Asn Leu His Leu Glu Gly Lys Cys Glu Thr Cys Val Tyr
2930 2935 2940

Asn Met Met Gly Lys Arg Glu Lys Lys Leu Gly Glu Phe Gly Lys
2945 2950 2955

Ala Lys Gly Ser Arg Ala Ile Trp Tyr Met Trp Leu Gly Ala Arg
2960 2965 2970

Phe Leu Glu Phe Glu Ala Leu Gly Phe Leu Asn Glu Asp His Trp
2975 2980 2985

Phe Ser Arg Glu Asn Ser Leu Ser Gly Val Glu Gly Glu Gly Leu
2990 2995 3000

His Lys Leu Gly Tyr Ile Leu Arg Asp Val Ser Lys Lys Glu Gly
3005 3010 3015

Gly Ala Met Tyr Ala Asp Asp Thr Ala Gly Trp Asp Thr Arg Ile
3020 3025 3030

Thr Leu Glu Asp Leu Lys Asn Glu Glu Met Val Thr Asn His Met
3035 3040 3045

Glu Gly Glu His Lys Lys Leu Ala Glu Ala Ile Phe Lys Leu Thr
3050 3055 3060

Tyr Gln Asn Lys Val Val Arg Val Gln Arg Pro Thr Pro Arg Gly
3065 3070 3075

Thr Val Met Asp Ile Ile Ser Arg Arg Asp Gln Arg Gly Ser Gly
3080 3085 3090

Gln Val Gly Thr Tyr Gly Leu Asn Thr Phe Thr Asn Met Glu Ala
3095 3100 3105

Gln Leu Ile Arg Gln Met Glu Gly Glu Gly Val Phe Lys Ser Ile
3110 3115 3120

Gln His Leu Thr Ile Thr Glu Glu Ile Ala Val Gln Asn Trp Leu
3125 3130 3135

Ala Arg Val Gly Arg Glu Arg Leu Ser Arg Met Ala Ile Ser Gly
3140 3145 3150

Asp Asp Cys Val Val Lys Pro Leu Asp Asp Arg Phe Ala Ser Ala
3155 3160 3165

Leu Thr Ala Leu Asn Asp Met Gly Lys Ile Arg Lys Asp Ile Gln
3170 3175 3180

Gln Trp Glu Pro Ser Arg Gly Trp Asn Asp Trp Thr Gln Val Pro
3185 3190 3195

Phe Cys Ser His His Phe His Glu Leu Ile Met Lys Asp Gly Arg
3200 3205 3210

Val Leu Val Val Pro Cys Arg Asn Gln Asp Glu Leu Ile Gly Arg
3215 3220 3225

Ala Arg Ile Ser Gln Gly Ala Gly Trp Ser Leu Arg Glu Thr Ala
3230 3235 3240

Cys Leu Gly Lys Ser Tyr Ala Gln Met Trp Ser Leu Met Tyr Phe
3245 3250 3255

His Arg Arg Asp Leu Arg Leu Ala Ala Asn Ala Ile Cys Ser Ala
3260 3265 3270

Val Pro Ser His Trp Val Pro Thr Ser Arg Thr Thr Trp Ser Ile
3275 3280 3285

His Ala Lys His Glu Trp Met Thr Thr Glu Asp Met Leu Thr Val
3290 3295 3300

Trp Asn Arg Val Trp Ile Gln Glu Asn Pro Trp Met Glu Asp Lys
3305 3310 3315

Thr Pro Val Glu Ser Trp Glu Glu Ile Pro Tyr Leu Gly Lys Arg
3320 3325 3330

Glu Asp Gln Trp Cys Gly Ser Leu Ile Gly Leu Thr Ser Arg Ala
3335 3340 3345

Thr Trp Ala Lys Asn Ile Gln Ala Ala Ile Asn Gln Val Arg Ser
3350 3355 3360

Leu Ile Gly Asn Glu Glu Tyr Thr Asp Tyr Met Pro Ser Met Lys
3365 3370 3375

Arg Phe Arg Arg Glu Glu Glu Glu Ala Gly Val Leu Trp
3380 3385 3390

<210> SEQ ID NO 24
<211> LENGTH: 10723
<212> TYPE: DNA
<213> ORGANISM: Artificial Sequence
<220> FEATURE:
<223> OTHER INFORMATION: Derived from Dengue virus serotype 2/Dengue
virus serotype 4, DEN, 4h

<400> SEQUENCE: 24
agttgttagt ctacgtggac cgacaaagac agattctttg agggagctaa gctcaatgta 60
gttctaacag tttttaatt agagagcaga tctctgatga ataaccaacg gaaaaaggcg 120
aaaaacacgc ctttcaatat gctgaaacgc gagagaaacc gcgtgtcgac tgtgcaacag 180
ctgacaaaga gattctcact tggaatgctg cagggacgag gaccattaaa actgttcatg 240
gccctggtgg cgttccttcg tttcctaaca atcccaccaa cagcagggat attgaagaga 300
tggggaacaa ttaaaaaatc aaaagctatt aatgttttga gagggttcag gaaagagatt 360
ggaaggatgc tgaacatctt gaataggaga cgcagctctg caggcatgat cattatgctg 420
attccaacag tgatggcgtt ccatttaacc acgcgtgatg gcgaacccct catgatagtg 480
gcaaaacatg aaagggggag acctctcttg tttaagacaa cagaggggat caacaaatgc 540
actctcattg ccatggactt gggtgaaatg tgtgaggaca ctgtcacgta taaatgcccc 600

-continued

```
ttactggtca ataccgaacc tgaagacatt gattgctggt gcaatctcac gtctacctgg    660
gtcatgtatg ggacatgcac ccagagcgga gaacggagac gagagaagcg ctcagtagct    720
ttaacaccac attcaggaat gggattggaa acaagagctg agacatggat gtcatcggaa    780
ggggcttgga agcatgctca gagagtagag agctggatac tcagaaaccc aggattcgcg    840
ctcttggcag gatttatggc ttatatgatt gggcaaacag gaatccagcg aactgtcttc    900
tttgtcctaa tgatgctggt cgccccatcc tacggaatgc gatgcgtagg agtaggaaac    960
agagactttg tggaaggagt ctcaggtgga gcatgggtcg atctggtgct agaacatgga   1020
ggatgcgtca caaccatggc ccagggaaaa ccaaccttgg attttgaact gactaagaca   1080
acagccaagg aagtggctct gttaagaacc tattgcattg aagcctcaat atcaaacata   1140
accacggcaa caagatgtcc aacgcaagga gagccttatc taaaagagga acaagaccaa   1200
cagtacattt gccggagaga tgtggtagac agagggtggg gcaatggctg tggcttgttt   1260
ggaaaaggag gagttgtgac atgtgcgaag ttttcatgtt cggggaagat aacaggcaat   1320
ttggtccaaa ttgagaacct tgaatacaca gtggttgtaa cagtccacaa tggagacacc   1380
catgcagtag gaaatgacac gtccaatcat ggagttacag ccacgataac tcccaggtca   1440
ccatcggtgg aagtcaaatt gccggactat ggagaactaa cactcgattg tgaacccagg   1500
tctggaattg actttaatga gatgattctg atgaaaatga aaaagaaaac atggcttgtg   1560
cataagcaat ggtttttgga tctacctcta ccatggacag caggagcaga cacatcagag   1620
gttcactgga attacaaaga gagaatggtg acatttaagg ttcctcatgc caagagacag   1680
gatgtgacag tgctgggatc tcaggaagga gccatgcatt ctgccctcgc tggagccaca   1740
gaagtggact ccggtgatgg aaatcacatg tttgcaggac atctcaagtg caaagtccgt   1800
atggagaaat tgagaatcaa gggaatgtca tacacgatgt gttcaggaaa gttctcaatt   1860
gacaaagaga tggcagaaac acagcatggg acaacagtgg tgaaagtcaa gtatgaaggt   1920
gctggagctc cgtgtaaagt ccccatagag ataagagatg tgaacaagga aaaagtggtt   1980
gggcgtatca tctcatccac ccctttggct gagaatacca acagtgtaac caacatagag   2040
ttagaacccc cctttgggga cagctacata gtgataggtg ttggaaacag tgcattaaca   2100
ctccattggt tcaggaaagg gagttccatt ggcaagatgt ttgagtccac atacagaggt   2160
gcaaaacgaa tggccattct aggtaaaaca gcttgggatt ttggttccgt tggtggactg   2220
ttcacatcat tgggaaaggc tgtgcaccag gtttttggaa gtgtgtatac aaccctgttt   2280
ggaggagtct catggatgat tagaatccta attgggttcc tagtgttgtg gattggcacg   2340
aactcaagga acacttcaat ggctatgacg tgcatagctg ccggcattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
```

-continued aaacaggatg tattctgcga ctcaaaactc atgtcagcgg ccataaaaga caacagagcc 3000
gtccatgccg atatgggtta ttggatagaa agtgcactca atgacacatg gaagatagag 3060
aaagcctctt tcattgaagt taaaaactgc cactggccaa aatcacacac cctctggagc 3120
aatggagtgc tagaaagtga gatgataatt ccaaagaatc tcgctggacc agtgtctcaa 3180
cacaactata gaccaggcta ccatacacaa ataacaggac catggcatct aggtaagctt 3240
gagatggact ttgatttctg tgatggaaca acagtggtag tgactgagga ctgcggaaat 3300
agaggaccct ctttgagaac aaccactgcc tctggaaaac tcataacaga atggtgctgc 3360
cgatcttgca cattaccacc gctaagatac agaggtgagg atgggtgctg gtacgggatg 3420
gaaatcagac cattgaagga gaaagaagag aatttggtca actccttggt cacagctgga 3480
catgggcagg tcgacaactt ttcactagga gtcttgggaa tggcattgtt cctggaggaa 3540
atgcttagga cccgagtagg aacgaaacat gcaatactac tagttgcagt ttcttttgtg 3600
acattgatca cagggaacat gtcctttaga gacctgggaa gagtgatggt tatggtaggc 3660
gccactatga cggatgacat aggtatgggc gtgacttatc ttgccctact agcagccttc 3720
aaagtcagac caacttttgc agctggacta ctcttgagaa agctgacctc caaggaattg 3780
atgatgacta ctataggaat tgtactcctc tcccagagca ccataccaga gaccattctt 3840
gagttgactg atgcgttagc cttaggcatg atggtcctca aaatggtgag aaatatggaa 3900
aagtatcaat tggcagtgac tatcatggct atcttgtgcg tcccaaacgc agtgatatta 3960
caaaacgcat ggaaagtgag ttgcacaata ttggcagtgg tgtccgtttc cccactgttc 4020
ttaacatcct cacagcaaaa aacagattgg ataccattag cattgacgat caaaggtctc 4080
aatccaacag ctatttttct aacaaccctc tcaagaacca gcaagaaaag gagctggcca 4140
ttaaatgagg ctatcatggc agtcgggatg gtgagcattt tagccagttc tctcctaaaa 4200
aatgatattc ccatgacagg accattagtg gctggagggc tcctcactgt gtgctacgtg 4260
ctcactggac gatcggccga tttggaactg gagagagcag ccgatgtcaa atgggaagac 4320
caggcagaga tatcaggaag cagtccaatc ctgtcaataa caatatcaga agatggtagc 4380
atgtcgataa aaaatgaaga ggaagaacaa acactgacca tactcattag aacaggattg 4440
ctggtgatct caggactttt tcctgtatca ataccaatca cggcagcagc atggtacctg 4500
tgggaagtga agaaacaacg ggccggagta ttgtgggatg ttccttcacc cccacccatg 4560
ggaaaggctg aactggaaga tggagcctat agaattaagc aaaaagggat tcttggatat 4620
tcccagatcg gagccggagt ttacaaagaa ggaacattcc atacaatgtg gcatgtcaca 4680
cgtggcgctg ttctaatgca taaaggaaag aggattgaac catcatgggc ggacgtcaag 4740
aaagacctaa tatcatatgg aggaggctgg aagttagaag gagaatggaa ggaaggagaa 4800
gaagtccagg tattggcact ggagcctgga aaaaatccaa gagccgtcca aacgaaacct 4860
ggtcttttca aaaccaacgc cggaacaata ggtgctgtat ctctggactt ttctcctgga 4920
acgtcaggat ctccaattat cgacaaaaaa ggaaaagttg tgggtcttta tggtaatggt 4980
gttgttacaa ggagtggagc atatgtgagt gctatagccc agactgaaaa aagcattgaa 5040
gacaacccag agatcgaaga tgacattttc cgaaagagaa gactgaccat catggacctc 5100
cacccaggag cgggaaagac gaagagatac cttccggcca tagtcagaga agctataaaa 5160
cggggtttga gaacattaat cttggccccc actagagttg tggcagctga aatggaggaa 5220
gcccttagag gacttccaat aagataccag accccagcca tcagagctgt gcacaccggg 5280
cgggagattg tggacctaat gtgtcatgcc acatttacca tgaggctgct atcaccagtt 5340

-continued agagtgccaa actacaacct gattatcatg gacgaagccc atttcacaga cccagcaagt 5400
atagcagcta gaggatacat ctcaactcga gtggagatgg gtgaggcagc tgggattttt 5460
atgacagcca ctcccccggg aagcagagac ccatttcctc agagcaatgc accaatcata 5520
gatgaagaaa gagaaatccc tgaacgctcg tggaattccg gacatgaatg ggtcacggat 5580
tttaaaggga agactgtttg gttcgttcca agtataaaag caggaaatga tatagcagct 5640
tgcctgagga aaaatggaaa gaaagtgata caactcagta ggaagacctt tgattctgag 5700
tatgtcaaga ctagaaccaa tgattgggac ttcgtggtta caactgacat ttcagaaatg 5760
ggtgccaatt tcaaggctga gagggttata gaccccagac gctgcatgaa accagtcata 5820
ctaacagatg gtgaagagcg ggtgattctg gcaggaccta tgccagtgac ccactctagt 5880
gcagcacaaa gaagagggag aataggaaga aatccaaaaa atgagaatga ccagtacata 5940
tacatggggg aacctctgga aaatgatgaa gactgtgcac actggaaaga agctaaaatg 6000
ctcctagata acatcaacac gccagaagga atcattccta gcatgttcga accagagcgt 6060
gaaaaggtgg atgccattga tggcgaatac cgcttgagag gagaagcaag gaaaaccttt 6120
gtagacttaa tgagaagagg agacctacca gtctggttgg cctacagagt ggcagctgaa 6180
ggcatcaact acgcagacag aaggtggtgt tttgatggag tcaagaacaa ccaaatccta 6240
gaagaaaacg tggaagttga aatctggaca aaagaagggg aaaggaagaa attgaaaccc 6300
agatggttgg atgctaggat ctattctgac ccactggcgc taaaagaatt taaggaattt 6360
gcagccggaa gaaagtctct gaccctgaac ctaatcacag aaatgggtag gctcccaacc 6420
ttcatgactc agaaggcaag agacgcactg gacaacttag cagtgctgca cacggctgag 6480
gcaggtggaa gggcgtacaa ccatgctctc agtgaactgc cggagaccct ggagacattg 6540
cttttactga cacttctggc tacagtcacg ggagggatct tttattcttt gatgagcgca 6600
aggggcatag ggaagatgac cctgggaatg tgctgcataa tcacggctag catcctccta 6660
tggtacgcac aaatacagcc acactggata gcagcttcaa taatactgga gtttttctc 6720
atagttttgc ttattccaga acctgaaaaa cagagaacac cccaagacaa ccaactgacc 6780
tacgttgtca tagccatcct cacagtggtg gccgcaacca tggcaaacga gatgggtttc 6840
ctagaaaaaa cgaagaaaga tctcggattg ggaagcattg caacccagca acccgagagc 6900
aacatcctgg acatagatct acgtcctgca tcagcatgga cgctgtatgc cgtggccaca 6960
acatttgtta caccaatgtt gagacatagc attgaaaatt cctcagtgaa tgtgtcccta 7020
acagctatag ccaaccaagc cacagtgtta atgggtctcg ggaaaggatg gccattgtca 7080
aagatggaca tcggagttcc ccttctcgcc attggatgct actcacaagt caaccccata 7140
actctcacag cagctctttt cttattggta gcacattatg ccatcatagg gccaggactc 7200
caagcaaaag caaccagaga agctcagaaa agagcagcgg cgggcatcat gaaaaaccca 7260
actgtcgatg gaataacagt gattgaccta gatccaatac cttatgatcc aaagtttgaa 7320
aagcagttgg gacaagtaat gctcctagtc ctctgcgtga ctcaagtatt gatgatgagg 7380
actacatggg ctctgtgtga ggctttaacc ttagctaccg ggcccatctc cacattgtgg 7440
gaaggaaatc cagggaggtt ttggaacact accattgcgg tgtcaatggc taacattttt 7500
agagggagtt acttggccgg agctggactt ctcttttcta ttatgaagaa cacaaccaac 7560
acaagaaggg gaactggcaa cataggagag acgcttggag agaaatggaa aagccgattg 7620
aacgcattgg gaaaaagtga attccagatc tacaagaaaa gtggaatcca ggaagtggat 7680

-continued

```
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
```

```
tacttgggga aaagagaaga ccaatggtgc ggctcattga ttgggttaac aagcagggcc  10140

acctgggcaa agaacatcca agcagcaata aatcaagtta gatcccttat aggcaatgaa  10200

gaatacacag attacatgcc atccatgaaa agattcagaa gagaagagga agaagcagga  10260

gttctgtggt agaaagcaaa actaacatga aacaaggcta gaagtcaggt cggattaagc  10320

catagtacgg aaaaaactat gctacctgtg agccccgtcc aaggacgtta aaagaagtca  10380

ggccatcata aatgccatag cttgagtaaa ctatgcagcc tgtagctcca cctgagaagg  10440

tgtaaaaaat ccgggaggcc acaaaccatg gaagctgtac gcatggcgta gtggactagc  10500

ggttagagga gacccctccc ttacaaatcg cagcaacaat gggggcccaa ggcgagatga  10560

agctgtagtc tcgctggaag gactagaggt tagaggagac ccccccgaaa caaaaaacag  10620

catattgacg ctgggaaaga ccagagatcc tgctgtctcc tcagcatcat tccaggcaca  10680

gaacgccaga aaatggaatg gtgctgttga atcaacaggt tct                    10723
```

<210> SEQ ID NO 25
<211> LENGTH: 3391
<212> TYPE: PRT
<213> ORGANISM: Artificial Sequence
<220> FEATURE:
<223> OTHER INFORMATION: Derived from Dengue virus serotype 2/Dengue
      virus serotype 4, DEN4h

<400> SEQUENCE: 25

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Ser Ser Ala Gly Met Ile Ile Met Leu Ile Pro Thr Val
            100                 105                 110

Met Ala Phe His Leu Thr Thr Arg Asp Gly Glu Pro Leu Met Ile Val
        115                 120                 125

Ala Lys His Glu Arg Gly Arg Pro Leu Leu Phe Lys Thr Thr Glu Gly
    130                 135                 140

Ile Asn Lys Cys Thr Leu Ile Ala Met Asp Leu Gly Glu Met Cys Glu
145                 150                 155                 160

Asp Thr Val Thr Tyr Lys Cys Pro Leu Leu Val Asn Thr Glu Pro Glu
                165                 170                 175

Asp Ile Asp Cys Trp Cys Asn Leu Thr Ser Thr Trp Val Met Tyr Gly
            180                 185                 190

Thr Cys Thr Gln Ser Gly Glu Arg Arg Arg Glu Lys Arg Ser Val Ala
        195                 200                 205

Leu Thr Pro His Ser Gly Met Gly Leu Glu Thr Arg Ala Glu Thr Trp
    210                 215                 220

Met Ser Ser Glu Gly Ala Trp Lys His Ala Gln Arg Val Glu Ser Trp
225                 230                 235                 240
```

```
Ile Leu Arg Asn Pro Gly Phe Ala Leu Leu Ala Gly Phe Met Ala Tyr
                245                 250                 255

Met Ile Gly Gln Thr Gly Ile Gln Arg Thr Val Phe Phe Val Leu Met
            260                 265                 270

Met Leu Val Ala Pro Ser Tyr Gly Met Arg Cys Val Gly Val Gly Asn
        275                 280                 285

Arg Asp Phe Val Glu Gly Val Ser Gly Gly Ala Trp Val Asp Leu Val
    290                 295                 300

Leu Glu His Gly Gly Cys Val Thr Thr Met Ala Gln Gly Lys Pro Thr
305                 310                 315                 320

Leu Asp Phe Glu Leu Thr Lys Thr Thr Ala Lys Glu Val Ala Leu Leu
                325                 330                 335

Arg Thr Tyr Cys Ile Glu Ala Ser Ile Ser Asn Ile Thr Thr Ala Thr
            340                 345                 350

Arg Cys Pro Thr Gln Gly Glu Pro Tyr Leu Lys Glu Glu Gln Asp Gln
        355                 360                 365

Gln Tyr Ile Cys Arg Arg Asp Val Val Asp Arg Gly Trp Gly Asn Gly
    370                 375                 380

Cys Gly Leu Phe Gly Lys Gly Gly Val Val Thr Cys Ala Lys Phe Ser
385                 390                 395                 400

Cys Ser Gly Lys Ile Thr Gly Asn Leu Val Gln Ile Glu Asn Leu Glu
                405                 410                 415

Tyr Thr Val Val Val Thr Val His Asn Gly Asp Thr His Ala Val Gly
            420                 425                 430

Asn Asp Thr Ser Asn His Gly Val Thr Ala Thr Ile Thr Pro Arg Ser
        435                 440                 445

Pro Ser Val Glu Val Lys Leu Pro Asp Tyr Gly Glu Leu Thr Leu Asp
    450                 455                 460

Cys Glu Pro Arg Ser Gly Ile Asp Phe Asn Glu Met Ile Leu Met Lys
465                 470                 475                 480

Met Lys Lys Lys Thr Trp Leu Val His Lys Gln Trp Phe Leu Asp Leu
                485                 490                 495

Pro Leu Pro Trp Thr Ala Gly Ala Asp Thr Ser Glu Val His Trp Asn
            500                 505                 510

Tyr Lys Glu Arg Met Val Thr Phe Lys Val Pro His Ala Lys Arg Gln
        515                 520                 525

Asp Val Thr Val Leu Gly Ser Gln Glu Gly Ala Met His Ser Ala Leu
    530                 535                 540

Ala Gly Ala Thr Glu Val Asp Ser Gly Asp Gly Asn His Met Phe Ala
545                 550                 555                 560

Gly His Leu Lys Cys Lys Val Arg Met Glu Lys Leu Arg Ile Lys Gly
                565                 570                 575

Met Ser Tyr Thr Met Cys Ser Gly Lys Phe Ser Ile Asp Lys Glu Met
            580                 585                 590

Ala Glu Thr Gln His Gly Thr Thr Val Val Lys Val Lys Tyr Glu Gly
        595                 600                 605

Ala Gly Ala Pro Cys Lys Val Pro Ile Glu Ile Arg Asp Val Asn Lys
    610                 615                 620

Glu Lys Val Val Gly Arg Ile Ile Ser Ser Thr Pro Leu Ala Glu Asn
625                 630                 635                 640

Thr Asn Ser Val Thr Asn Ile Glu Leu Glu Pro Pro Phe Gly Asp Ser
                645                 650                 655

Tyr Ile Val Ile Gly Val Gly Asn Ser Ala Leu Thr Leu His Trp Phe
```

-continued 660 665 670

Arg Lys Gly Ser Ser Ile Gly Lys Met Phe Glu Ser Thr Tyr Arg Gly
675 680 685

Ala Lys Arg Met Ala Ile Leu Gly Lys Thr Ala Trp Asp Phe Gly Ser
690 695 700

Val Gly Gly Leu Phe Thr Ser Leu Gly Lys Ala Val His Gln Val Phe
705 710 715 720

Gly Ser Val Tyr Thr Thr Leu Phe Gly Gly Val Ser Trp Met Ile Arg
725 730 735

Ile Leu Ile Gly Phe Leu Val Leu Trp Ile Gly Thr Asn Ser Arg Asn
740 745 750

Thr Ser Met Ala Met Thr Cys Ile Ala Ala Gly Ile Val Thr Leu Tyr
755 760 765

Leu Gly Val Met Val Gln Ala Asp Ser Gly Cys Val Val Ser Trp Lys
770 775 780

Asn Lys Glu Leu Lys Cys Gly Ser Gly Ile Phe Ile Thr Asp Asn Val
785 790 795 800

His Thr Trp Thr Glu Gln Tyr Lys Phe Gln Pro Glu Ser Pro Ser Lys
805 810 815

Leu Ala Ser Ala Ile Gln Lys Ala His Glu Glu Asp Ile Cys Gly Ile
820 825 830

Arg Ser Val Thr Arg Leu Glu Asn Leu Met Trp Lys Gln Ile Thr Pro
835 840 845

Glu Leu Asn His Ile Leu Ser Glu Asn Glu Val Lys Leu Thr Ile Met
850 855 860

Thr Gly Asp Ile Lys Gly Ile Met Gln Ala Gly Lys Arg Ser Leu Arg
865 870 875 880

Pro Gln Pro Thr Glu Leu Lys Tyr Ser Trp Lys Thr Trp Gly Lys Ala
885 890 895

Lys Met Leu Ser Thr Glu Ser His Asn Gln Thr Phe Leu Ile Asp Gly
900 905 910

Pro Glu Thr Ala Glu Cys Pro Asn Thr Asn Arg Ala Trp Asn Ser Leu
915 920 925

Glu Val Glu Asp Tyr Gly Phe Gly Val Phe Thr Thr Asn Ile Trp Leu
930 935 940

Lys Leu Lys Glu Lys Gln Asp Val Phe Cys Asp Ser Lys Leu Met Ser
945 950 955 960

Ala Ala Ile Lys Asp Asn Arg Ala Val His Ala Asp Met Gly Tyr Trp
965 970 975

Ile Glu Ser Ala Leu Asn Asp Thr Trp Lys Ile Glu Lys Ala Ser Phe
980 985 990

Ile Glu Val Lys Asn Cys His Trp Pro Lys Ser His Thr Leu Trp Ser
995 1000 1005

Asn Gly Val Leu Glu Ser Glu Met Ile Ile Pro Lys Asn Leu Ala
1010 1015 1020

Gly Pro Val Ser Gln His Asn Tyr Arg Pro Gly Tyr His Thr Gln
1025 1030 1035

Ile Thr Gly Pro Trp His Leu Gly Lys Leu Glu Met Asp Phe Asp
1040 1045 1050

Phe Cys Asp Gly Thr Thr Val Val Val Thr Glu Asp Cys Gly Asn
1055 1060 1065

Arg Gly Pro Ser Leu Arg Thr Thr Thr Ala Ser Gly Lys Leu Ile
1070 1075 1080

-continued

Thr Glu Trp Cys Cys Arg Ser Cys Thr Leu Pro Pro Leu Arg Tyr
1085 1090 1095

Arg Gly Glu Asp Gly Cys Trp Tyr Gly Met Glu Ile Arg Pro Leu
1100 1105 1110

Lys Glu Lys Glu Glu Asn Leu Val Asn Ser Leu Val Thr Ala Gly
1115 1120 1125

His Gly Gln Val Asp Asn Phe Ser Leu Gly Val Leu Gly Met Ala
1130 1135 1140

Leu Phe Leu Glu Glu Met Leu Arg Thr Arg Val Gly Thr Lys His
1145 1150 1155

Ala Ile Leu Leu Val Ala Val Ser Phe Val Thr Leu Ile Thr Gly
1160 1165 1170

Asn Met Ser Phe Arg Asp Leu Gly Arg Val Met Val Met Val Gly
1175 1180 1185

Ala Thr Met Thr Asp Asp Ile Gly Met Gly Val Thr Tyr Leu Ala
1190 1195 1200

Leu Leu Ala Ala Phe Lys Val Arg Pro Thr Phe Ala Ala Gly Leu
1205 1210 1215

Leu Leu Arg Lys Leu Thr Ser Lys Glu Leu Met Met Thr Thr Ile
1220 1225 1230

Gly Ile Val Leu Leu Ser Gln Ser Thr Ile Pro Glu Thr Ile Leu
1235 1240 1245

Glu Leu Thr Asp Ala Leu Ala Leu Gly Met Met Val Leu Lys Met
1250 1255 1260

Val Arg Asn Met Glu Lys Tyr Gln Leu Ala Val Thr Ile Met Ala
1265 1270 1275

Ile Leu Cys Val Pro Asn Ala Val Ile Leu Gln Asn Ala Trp Lys
1280 1285 1290

Val Ser Cys Thr Ile Leu Ala Val Val Ser Val Ser Pro Leu Phe
1295 1300 1305

Leu Thr Ser Ser Gln Gln Lys Thr Asp Trp Ile Pro Leu Ala Leu
1310 1315 1320

Thr Ile Lys Gly Leu Asn Pro Thr Ala Ile Phe Leu Thr Thr Leu
1325 1330 1335

Ser Arg Thr Ser Lys Lys Arg Ser Trp Pro Leu Asn Glu Ala Ile
1340 1345 1350

Met Ala Val Gly Met Val Ser Ile Leu Ala Ser Ser Leu Leu Lys
1355 1360 1365

Asn Asp Ile Pro Met Thr Gly Pro Leu Val Ala Gly Gly Leu Leu
1370 1375 1380

Thr Val Cys Tyr Val Leu Thr Gly Arg Ser Ala Asp Leu Glu Leu
1385 1390 1395

Glu Arg Ala Ala Asp Val Lys Trp Glu Asp Gln Ala Glu Ile Ser
1400 1405 1410

Gly Ser Ser Pro Ile Leu Ser Ile Thr Ile Ser Glu Asp Gly Ser
1415 1420 1425

Met Ser Ile Lys Asn Glu Glu Glu Glu Gln Thr Leu Thr Ile Leu
1430 1435 1440

Ile Arg Thr Gly Leu Leu Val Ile Ser Gly Leu Phe Pro Val Ser
1445 1450 1455

Ile Pro Ile Thr Ala Ala Ala Trp Tyr Leu Trp Glu Val Lys Lys
1460 1465 1470

-continued

```
Gln Arg  Ala Gly Val Leu Trp  Asp Val Pro Ser Pro  Pro Pro Met
    1475                 1480                 1485

Gly Lys  Ala Glu Leu Glu Asp  Gly Ala Tyr Arg Ile  Lys Gln Lys
    1490                 1495                 1500

Gly Ile  Leu Gly Tyr Ser Gln  Ile Gly Ala Gly Val  Tyr Lys Glu
    1505                 1510                 1515

Gly Thr  Phe His Thr Met Trp  His Val Thr Arg Gly  Ala Val Leu
    1520                 1525                 1530

Met His  Lys Gly Lys Arg Ile  Glu Pro Ser Trp Ala  Asp Val Lys
    1535                 1540                 1545

Lys Asp  Leu Ile Ser Tyr Gly  Gly Gly Trp Lys Leu  Glu Gly Glu
    1550                 1555                 1560

Trp Lys  Glu Gly Glu Glu Val  Gln Val Leu Ala Leu  Glu Pro Gly
    1565                 1570                 1575

Lys Asn  Pro Arg Ala Val Gln  Thr Lys Pro Gly Leu  Phe Lys Thr
    1580                 1585                 1590

Asn Ala  Gly Thr Ile Gly Ala  Val Ser Leu Asp Phe  Ser Pro Gly
    1595                 1600                 1605

Thr Ser  Gly Ser Pro Ile Ile  Asp Lys Lys Gly Lys  Val Val Gly
    1610                 1615                 1620

Leu Tyr  Gly Asn Gly Val Val  Thr Arg Ser Gly Ala  Tyr Val Ser
    1625                 1630                 1635

Ala Ile  Ala Gln Thr Glu Lys  Ser Ile Glu Asp Asn  Pro Glu Ile
    1640                 1645                 1650

Glu Asp  Asp Ile Phe Arg Lys  Arg Arg Leu Thr Ile  Met Asp Leu
    1655                 1660                 1665

His Pro  Gly Ala Gly Lys Thr  Lys Arg Tyr Leu Pro  Ala Ile Val
    1670                 1675                 1680

Arg Glu  Ala Ile Lys Arg Gly  Leu Arg Thr Leu Ile  Leu Ala Pro
    1685                 1690                 1695

Thr Arg  Val Val Ala Ala Glu  Met Glu Glu Ala Leu  Arg Gly Leu
    1700                 1705                 1710

Pro Ile  Arg Tyr Gln Thr Pro  Ala Ile Arg Ala Val  His Thr Gly
    1715                 1720                 1725

Arg Glu  Ile Val Asp Leu Met  Cys His Ala Thr Phe  Thr Met Arg
    1730                 1735                 1740

Leu Leu  Ser Pro Val Arg Val  Pro Asn Tyr Asn Leu  Ile Ile Met
    1745                 1750                 1755

Asp Glu  Ala His Phe Thr Asp  Pro Ala Ser Ile Ala  Ala Arg Gly
    1760                 1765                 1770

Tyr Ile  Ser Thr Arg Val Glu  Met Gly Glu Ala Ala  Gly Ile Phe
    1775                 1780                 1785

Met Thr  Ala Thr Pro Pro Gly  Ser Arg Asp Pro Phe  Pro Gln Ser
    1790                 1795                 1800

Asn Ala  Pro Ile Ile Asp Glu  Glu Arg Glu Ile Pro  Glu Arg Ser
    1805                 1810                 1815

Trp Asn  Ser Gly His Glu Trp  Val Thr Asp Phe Lys  Gly Lys Thr
    1820                 1825                 1830

Val Trp  Phe Val Pro Ser Ile  Lys Ala Gly Asn Asp  Ile Ala Ala
    1835                 1840                 1845

Cys Leu  Arg Lys Asn Gly Lys  Lys Val Ile Gln Leu  Ser Arg Lys
    1850                 1855                 1860

Thr Phe  Asp Ser Glu Tyr Val  Lys Thr Arg Thr Asn  Asp Trp Asp
```

```
    1865                1870                1875

Phe Val  Val Thr Thr Asp Ile  Ser Glu Met Gly Ala  Asn Phe Lys
    1880                1885                1890

Ala Glu  Arg Val Ile Asp Pro  Arg Arg Cys Met Lys  Pro Val Ile
    1895                1900                1905

Leu Thr  Asp Gly Glu Glu Arg  Val Ile Leu Ala Gly  Pro Met Pro
    1910                1915                1920

Val Thr  His Ser Ser Ala Ala  Gln Arg Arg Gly Arg  Ile Gly Arg
    1925                1930                1935

Asn Pro  Lys Asn Glu Asn Asp  Gln Tyr Ile Tyr Met  Gly Glu Pro
    1940                1945                1950

Leu Glu  Asn Asp Glu Asp Cys  Ala His Trp Lys Glu  Ala Lys Met
    1955                1960                1965

Leu Leu  Asp Asn Ile Asn Thr  Pro Glu Gly Ile Ile  Pro Ser Met
    1970                1975                1980

Phe Glu  Pro Glu Arg Glu Lys  Val Asp Ala Ile Asp  Gly Glu Tyr
    1985                1990                1995

Arg Leu  Arg Gly Glu Ala Arg  Lys Thr Phe Val Asp  Leu Met Arg
    2000                2005                2010

Arg Gly  Asp Leu Pro Val Trp  Leu Ala Tyr Arg Val  Ala Ala Glu
    2015                2020                2025

Gly Ile  Asn Tyr Ala Asp Arg  Arg Trp Cys Phe Asp  Gly Val Lys
    2030                2035                2040

Asn Asn  Gln Ile Leu Glu Glu  Asn Val Glu Val Glu  Ile Trp Thr
    2045                2050                2055

Lys Glu  Gly Glu Arg Lys Lys  Leu Lys Pro Arg Trp  Leu Asp Ala
    2060                2065                2070

Arg Ile  Tyr Ser Asp Pro Leu  Ala Leu Lys Glu Phe  Lys Glu Phe
    2075                2080                2085

Ala Ala  Gly Arg Lys Ser Leu  Thr Leu Asn Leu Ile  Thr Glu Met
    2090                2095                2100

Gly Arg  Leu Pro Thr Phe Met  Thr Gln Lys Ala Arg  Asp Ala Leu
    2105                2110                2115

Asp Asn  Leu Ala Val Leu His  Thr Ala Glu Ala Gly  Gly Arg Ala
    2120                2125                2130

Tyr Asn  His Ala Leu Ser Glu  Leu Pro Glu Thr Leu  Glu Thr Leu
    2135                2140                2145

Leu Leu  Leu Thr Leu Leu Ala  Thr Val Thr Gly Gly  Ile Phe Leu
    2150                2155                2160

Phe Leu  Met Ser Ala Arg Gly  Ile Gly Lys Met Thr  Leu Gly Met
    2165                2170                2175

Cys Cys  Ile Ile Thr Ala Ser  Ile Leu Leu Trp Tyr  Ala Gln Ile
    2180                2185                2190

Gln Pro  His Trp Ile Ala Ala  Ser Ile Ile Leu Glu  Phe Phe Leu
    2195                2200                2205

Ile Val  Leu Leu Ile Pro Glu  Pro Glu Lys Gln Arg  Thr Pro Gln
    2210                2215                2220

Asp Asn  Gln Leu Thr Tyr Val  Val Ile Ala Ile Leu  Thr Val Val
    2225                2230                2235

Ala Ala  Thr Met Ala Asn Glu  Met Gly Phe Leu Glu  Lys Thr Lys
    2240                2245                2250

Lys Asp  Leu Gly Leu Gly Ser  Ile Ala Thr Gln Gln  Pro Glu Ser
    2255                2260                2265
```

```
Asn Ile Leu Asp Ile Asp Leu Arg Pro Ala Ser Ala Trp Thr Leu
    2270                2275                2280

Tyr Ala Val Ala Thr Thr Phe Val Thr Pro Met Leu Arg His Ser
    2285                2290                2295

Ile Glu Asn Ser Ser Val Asn Val Ser Leu Thr Ala Ile Ala Asn
    2300                2305                2310

Gln Ala Thr Val Leu Met Gly Leu Gly Lys Gly Trp Pro Leu Ser
    2315                2320                2325

Lys Met Asp Ile Gly Val Pro Leu Leu Ala Ile Gly Cys Tyr Ser
    2330                2335                2340

Gln Val Asn Pro Ile Thr Leu Thr Ala Ala Leu Phe Leu Leu Val
    2345                2350                2355

Ala His Tyr Ala Ile Ile Gly Pro Gly Leu Gln Ala Lys Ala Thr
    2360                2365                2370

Arg Glu Ala Gln Lys Arg Ala Ala Ala Gly Ile Met Lys Asn Pro
    2375                2380                2385

Thr Val Asp Gly Ile Thr Val Ile Asp Leu Asp Pro Ile Pro Tyr
    2390                2395                2400

Asp Pro Lys Phe Glu Lys Gln Leu Gly Gln Val Met Leu Leu Val
    2405                2410                2415

Leu Cys Val Thr Gln Val Leu Met Met Arg Thr Thr Trp Ala Leu
    2420                2425                2430

Cys Glu Ala Leu Thr Leu Ala Thr Gly Pro Ile Ser Thr Leu Trp
    2435                2440                2445

Glu Gly Asn Pro Gly Arg Phe Trp Asn Thr Thr Ile Ala Val Ser
    2450                2455                2460

Met Ala Asn Ile Phe Arg Gly Ser Tyr Leu Ala Gly Ala Gly Leu
    2465                2470                2475

Leu Phe Ser Ile Met Lys Asn Thr Thr Asn Thr Arg Arg Gly Thr
    2480                2485                2490

Gly Asn Ile Gly Glu Thr Leu Gly Glu Lys Trp Lys Ser Arg Leu
    2495                2500                2505

Asn Ala Leu Gly Lys Ser Glu Phe Gln Ile Tyr Lys Lys Ser Gly
    2510                2515                2520

Ile Gln Glu Val Asp Arg Thr Leu Ala Lys Glu Gly Ile Lys Arg
    2525                2530                2535

Gly Glu Thr Asp His His Ala Val Ser Arg Gly Ser Ala Lys Leu
    2540                2545                2550

Arg Trp Phe Val Glu Arg Asn Met Val Thr Pro Glu Gly Lys Val
    2555                2560                2565

Val Asp Leu Gly Cys Gly Arg Gly Gly Trp Ser Tyr Tyr Cys Gly
    2570                2575                2580

Gly Leu Lys Asn Val Arg Glu Val Lys Gly Leu Thr Lys Gly Gly
    2585                2590                2595

Pro Gly His Glu Glu Pro Ile Pro Met Ser Thr Tyr Gly Trp Asn
    2600                2605                2610

Leu Val Arg Leu Gln Ser Gly Val Asp Val Phe Phe Ile Pro Pro
    2615                2620                2625

Glu Lys Cys Asp Thr Leu Leu Cys Asp Ile Gly Glu Ser Ser Pro
    2630                2635                2640

Asn Pro Thr Val Glu Ala Gly Arg Thr Leu Arg Val Leu Asn Leu
    2645                2650                2655
```

```
Val Glu Asn Trp Leu Asn Asn Asn Thr Gln Phe Cys Ile Lys Val
    2660                2665                2670

Leu Asn Pro Tyr Met Pro Ser Val Ile Glu Lys Met Glu Ala Leu
    2675                2680                2685

Gln Arg Lys Tyr Gly Gly Ala Leu Val Arg Asn Pro Leu Ser Arg
    2690                2695                2700

Asn Ser Thr His Glu Met Tyr Trp Val Ser Asn Ala Ser Gly Asn
    2705                2710                2715

Ile Val Ser Ser Val Asn Met Ile Ser Arg Met Leu Ile Asn Arg
    2720                2725                2730

Phe Thr Met Arg Tyr Lys Lys Ala Thr Tyr Glu Pro Asp Val Asp
    2735                2740                2745

Leu Gly Ser Gly Thr Arg Asn Ile Gly Ile Glu Ser Glu Ile Pro
    2750                2755                2760

Asn Leu Asp Ile Ile Gly Lys Arg Ile Glu Lys Ile Lys Gln Glu
    2765                2770                2775

His Glu Thr Ser Trp His Tyr Asp Gln Asp His Pro Tyr Lys Thr
    2780                2785                2790

Trp Ala Tyr His Gly Ser Tyr Glu Thr Lys Gln Thr Gly Ser Ala
    2795                2800                2805

Ser Ser Met Val Asn Gly Val Val Arg Leu Leu Thr Lys Pro Trp
    2810                2815                2820

Asp Val Val Pro Met Val Thr Gln Met Ala Met Thr Asp Thr Thr
    2825                2830                2835

Pro Phe Gly Gln Gln Arg Val Phe Lys Glu Lys Val Asp Thr Arg
    2840                2845                2850

Thr Gln Glu Pro Lys Glu Gly Thr Lys Lys Leu Met Lys Ile Thr
    2855                2860                2865

Ala Glu Trp Leu Trp Lys Glu Leu Gly Lys Lys Lys Thr Pro Arg
    2870                2875                2880

Met Cys Thr Arg Glu Glu Phe Thr Arg Lys Val Arg Ser Asn Ala
    2885                2890                2895

Ala Leu Gly Ala Ile Phe Thr Asp Glu Asn Lys Trp Lys Ser Ala
    2900                2905                2910

Arg Glu Ala Val Glu Asp Ser Arg Phe Trp Glu Leu Val Asp Lys
    2915                2920                2925

Glu Arg Asn Leu His Leu Glu Gly Lys Cys Glu Thr Cys Val Tyr
    2930                2935                2940

Asn Met Met Gly Lys Arg Glu Lys Lys Leu Gly Glu Phe Gly Lys
    2945                2950                2955

Ala Lys Gly Ser Arg Ala Ile Trp Tyr Met Trp Leu Gly Ala Arg
    2960                2965                2970

Phe Leu Glu Phe Glu Ala Leu Gly Phe Leu Asn Glu Asp His Trp
    2975                2980                2985

Phe Ser Arg Glu Asn Ser Leu Ser Gly Val Glu Gly Glu Gly Leu
    2990                2995                3000

His Lys Leu Gly Tyr Ile Leu Arg Asp Val Ser Lys Lys Glu Gly
    3005                3010                3015

Gly Ala Met Tyr Ala Asp Asp Thr Ala Gly Trp Asp Thr Arg Ile
    3020                3025                3030

Thr Leu Glu Asp Leu Lys Asn Glu Glu Met Val Thr Asn His Met
    3035                3040                3045

Glu Gly Glu His Lys Lys Leu Ala Glu Ala Ile Phe Lys Leu Thr
```

```
    3050                3055                3060

Tyr Gln  Asn Lys Val Val Arg  Val Gln Arg Pro Thr  Pro Arg Gly
    3065                3070                3075

Thr Val  Met Asp Ile Ile Ser  Arg Arg Asp Gln Arg  Gly Ser Gly
    3080                3085                3090

Gln Val  Gly Thr Tyr Gly Leu  Asn Thr Phe Thr Asn  Met Glu Ala
    3095                3100                3105

Gln Leu  Ile Arg Gln Met Glu  Gly Glu Gly Val Phe  Lys Ser Ile
    3110                3115                3120

Gln His  Leu Thr Ile Thr Glu  Glu Ile Ala Val Gln  Asn Trp Leu
    3125                3130                3135

Ala Arg  Val Gly Arg Glu Arg  Leu Ser Arg Met Ala  Ile Ser Gly
    3140                3145                3150

Asp Asp  Cys Val Val Lys Pro  Leu Asp Asp Arg Phe  Ala Ser Ala
    3155                3160                3165

Leu Thr  Ala Leu Asn Asp Met  Gly Lys Ile Arg Lys  Asp Ile Gln
    3170                3175                3180

Gln Trp  Glu Pro Ser Arg Gly  Trp Asn Asp Trp Thr  Gln Val Pro
    3185                3190                3195

Phe Cys  Ser His His Phe His  Glu Leu Ile Met Lys  Asp Gly Arg
    3200                3205                3210

Val Leu  Val Val Pro Cys Arg  Asn Gln Asp Glu Leu  Ile Gly Arg
    3215                3220                3225

Ala Arg  Ile Ser Gln Gly Ala  Gly Trp Ser Leu Arg  Glu Thr Ala
    3230                3235                3240

Cys Leu  Gly Lys Ser Tyr Ala  Gln Met Trp Ser Leu  Met Tyr Phe
    3245                3250                3255

His Arg  Arg Asp Leu Arg Leu  Ala Ala Asn Ala Ile  Cys Ser Ala
    3260                3265                3270

Val Pro  Ser His Trp Val Pro  Thr Ser Arg Thr Thr  Trp Ser Ile
    3275                3280                3285

His Ala  Lys His Glu Trp Met  Thr Thr Glu Asp Met  Leu Thr Val
    3290                3295                3300

Trp Asn  Arg Val Trp Ile Gln  Glu Asn Pro Trp Met  Glu Asp Lys
    3305                3310                3315

Thr Pro  Val Glu Ser Trp Glu  Glu Ile Pro Tyr Leu  Gly Lys Arg
    3320                3325                3330

Glu Asp  Gln Trp Cys Gly Ser  Leu Ile Gly Leu Thr  Ser Arg Ala
    3335                3340                3345

Thr Trp  Ala Lys Asn Ile Gln  Ala Ala Ile Asn Gln  Val Arg Ser
    3350                3355                3360

Leu Ile  Gly Asn Glu Glu Tyr  Thr Asp Tyr Met Pro  Ser Met Lys
    3365                3370                3375

Arg Phe  Arg Arg Glu Glu Glu  Glu Ala Gly Val Leu  Trp
    3380                3385                3390
```

<210> SEQ ID NO 26
<211> LENGTH: 5
<212> TYPE: PRT
<213> ORGANISM: Artificial Sequence
<220> FEATURE:
<223> OTHER INFORMATION: Derived from Dengue-2 virus

<400> SEQUENCE: 26

Gly Arg Ile Gly Arg 1 5

<210> SEQ ID NO 27
<211> LENGTH: 5
<212> TYPE: PRT
<213> ORGANISM: Artificial Sequence
<220> FEATURE:
<223> OTHER INFORMATION: Derived from Dengue-2 virus

<400> SEQUENCE: 27

Gly Ala Gly Lys Thr
1 5

<210> SEQ ID NO 28
<211> LENGTH: 10723
<212> TYPE: DNA
<213> ORGANISM: Artificial Sequence
<220> FEATURE:
<223> OTHER INFORMATION: Derived from Dengue virus serotype 2/Dengue virus serotype 4, DenVax-4g

<400> SEQUENCE: 28

```
agttgttagt ctacgtggac cgacaaagac agattctttg agggagctaa gctcaacgta     60

gttctaacag tttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagctctg caggcatgat cattatgctg    420

attccaacag tgatggcgtt ccatttaacc acgcgtgatg gcgaacccct catgatagtg    480

gcaaaacatg aaagggggag acctctcttg tttaagacaa cagaggggat caacaaatgc    540

actctcattg ccatggactt gggtgaaatg tgtgaggaca ctgtcacgta taaatgcccc    600

ttactggtca ataccgaacc tgaagacatt gattgctggt gcaatctcac gtctacctgg    660

gtcatgtatg ggacatgcac ccagagcgga gaacggagac gagagaagcg ctcagtagct    720

ttaacaccac attcaggaat gggattggaa acaagagctg agacatggat gtcatcggaa    780

ggggcttgga agcatgctca gagagtagag agctggatac tcagaaaccc aggattcgcg    840

ctcttggcag gatttatggc ttatatgatt gggcaaacag gaatccagcg aactgtcttc    900

tttgtcctaa tgatgctggt cgccccatcc tacggaatgc gatgcgtagg agtaggaaac    960

agagactttg tggaaggagt ctcaggtgga gcatgggtcg atctggtgct agaacatgga   1020

ggatgcgtca caaccatggc ccagggaaaa ccaaccttgg attttgaact gactaagaca   1080

acagccaagg aagtggctct gttaagaacc tattgcattg aagcctcaat atcaaacata   1140

accacggcaa caagatgtcc aacgcaagga gagccttatc taaaagagga acaagaccaa   1200

cagtacattt gccggagaga tgtggtagac agagggtggg gcaatggctg tggcttgttt   1260

ggaaaaggag gagttgtgac atgtgcgaag ttttcatgtt cggggaagat aacaggcaat   1320

ttggtccaaa ttgagaacct tgaatacaca gtggttgtaa cagtccacaa tggagacacc   1380

catgcagtag gaaatgacac gtccaatcat ggagttacag ccacgataac tcccaggtca   1440

ccatcggtgg aagtcaaatt gccggactat ggagaactaa cactcgattg tgaacccagg   1500

tctggaattg actttaatga gatgattctg atgaaaatga aaaagaaaac atggcttgtg   1560

cataagcaat ggtttttgga tctacctcta ccatggacag caggagcaga cacatcagag   1620
```

```
gttcactgga attacaaaga gagaatggtg acatttaagg ttcctcatgc caagagacag   1680
gatgtgacag tgctgggatc tcaggaagga gccatgcatt ctgccctcgc tggagccaca   1740
gaagtggact ccggtgatgg aaatcacatg tttgcaggac atctcaagtg caaagtccgt   1800
atggagaaat tgagaatcaa gggaatgtca tacacgatgt gttcaggaaa gttctcaatt   1860
gacaaagaga tggcagaaac acagcatggg acaacagtgg tgaaagtcaa gtatgaaggt   1920
gctggagctc cgtgtaaagt ccccatagag ataagagatg tgaacaagga aaaagtggtt   1980
gggcgtatca tctcatccac cccttttggct gagaatacca acagtgtaac caacatagag   2040
ttagaacccc cctttgggga cagctacata gtgataggtg ttggaaacag tgcattaaca   2100
ctccattggt tcaggaaagg gagttccatt ggcaagatgt ttgagtccac atacagaggt   2160
gcaaaacgaa tggccattct aggtgaaaca gcttgggatt ttggttccgt tggtggactg   2220
ttcacatcat tgggaaaggc tgtgcaccag gtttttggaa gtgtgtatac aaccctgttt   2280
ggaggagtct catggatgat tagaatccta attgggttcc tagtgttgtg gattggcacg   2340
aactcaagga acacttcaat ggctatgacg tgcatagctg ccggcattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
```

-continued

```
caaaacgcat ggaaagtgag ttgcacaata ttggcagtgg tgtccgtttc cccactgctc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
```

```
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct tttattcttt gatgagcgga   6600
aggggcatag ggaagatgac cctgggaatg tgctgcataa tcacggctag catcctccta   6660
tggtacgcac aaatacagcc acactggata gcagcttcaa taatactgga gtttttctc   6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag   8640
aaagtggaca cgagaaccca agaaccgaaa gaaggcacga agaaactaat gaaaataaca   8700
```

gcagagtggc tttggaaaga attagggaag aaaaagacac ccaggatgtg caccagagaa 8760
gaattcacaa gaaaggtgag aagcaatgca gccttggggg ccatattcac tgatgagaac 8820
aagtggaagt cggcacgtga ggctgttgaa gatagtaggt tttgggagct ggttgacaag 8880
gaaaggaatc tccatcttga aggaaagtgt gaaacatgtg tgtacaacat gatgggaaaa 8940
agagagaaga agctagggga attcggcaag gcaaaaggca gcagagccat atggtacatg 9000
tggcttggag cacgcttctt agagtttgaa gccctaggat tcttaaatga agatcactgg 9060
ttctccagag agaactccct gagtggagtg gaaggagaag ggctgcacaa gctaggttac 9120
attctaagag acgtgagcaa gaaagaggga ggagcaatgt atgccgatga caccgcagga 9180
tgggatacaa gaatcacact agaagaccta aaaaatgaag aaatggtaac aaaccacatg 9240
gaaggagaac acaagaaact agccgaggcc attttcaaac taacgtacca aaacaaggtg 9300
gtgcgtgtgc aaagaccaac accaagaggc acagtaatgg acatcatatc gagaagagac 9360
caaagaggta gtggacaagt tggcacctat ggactcaata ctttcaccaa tatggaagcc 9420
caactaatca gacagatgga gggagaagga gtctttaaaa gcattcagca cctaacaatc 9480
acagaagaaa tcgctgtgca aaactggtta gcaagagtgg ggcgcgaaag gttatcaaga 9540
atggccatca gtggagatga ttgtgttgtg aaacctttag atgacaggtt cgcaagcgct 9600
ttaacagctc taaatgacat gggaaagatt aggaaagaca tacaacaatg ggaaccttca 9660
agaggatgga atgattggac acaagtgccc ttctgttcac accatttcca tgagttaatc 9720
atgaaagacg gtcgcgtact cgttgttcca tgtagaaacc aagatgaact gattggcaga 9780
gcccgaatct cccaaggagc agggtggtct ttgcgggaga cggcctgttt ggggaagtct 9840
tacgcccaaa tgtggagctt gatgtacttc cacagacgcg acctcaggct ggcggcaaat 9900
gctatttgct cggcagtacc atcacattgg gttccaacaa gtcgaacaac ctggtccata 9960
catgctaaac atgaatggat gacaacggaa gacatgctga cagtctggaa cagggtgtgg 10020
attcaagaaa acccatggat ggaagacaaa actccagtgg aatcatggga ggaaatccca 10080
tacttgggga aaagagaaga ccaatggtgc ggctcattga ttgggttaac aagcagggcc 10140
acctgggcaa agaacatcca agcagcaata aatcaagtta gatcccttat aggcaatgaa 10200
gaatacacag attacatgcc atccatgaaa agattcagaa gagaagagga agaagcagga 10260
gttctgtggt agaaagcaaa actaacatga aacaaggcta gaagtcaggt cggattaagc 10320
catagtacgg aaaaaactat gctacctgtg agccccgtcc aaggacgtta aaagaagtca 10380
ggccatcata aatgccatag cttgagtaaa ctatgcagcc tgtagctcca cctgagaagg 10440
tgtaaaaaat ccgggaggcc acaaaccatg gaagctgtac gcatggcgta gtggactagc 10500
ggttagagga gacccctccc ttacaaatcg cagcaacaat gggggcccaa ggcgagatga 10560
agctgtagtc tcgctggaag gactagaggt tagaggagac ccccccgaaa caaaaaacag 10620
catattgacg ctgggaaaga ccagagatcc tgctgtctcc tcagcatcat tccaggcaca 10680
gaacgccaga aaatggaatg gtgctgttga atcaacaggt tct 10723

<210> SEQ ID NO 29
<211> LENGTH: 3391
<212> TYPE: PRT
<213> ORGANISM: Artificial Sequence
<220> FEATURE:
<223> OTHER INFORMATION: Derived from Dengue virus serotype 2/Dengue
virus serotype 4, DenVax-4g

<400> SEQUENCE: 29

-continued

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Ser Ser Ala Gly Met Ile Ile Met Leu Ile Pro Thr Val
            100                 105                 110

Met Ala Phe His Leu Thr Thr Arg Asp Gly Glu Pro Leu Met Ile Val
        115                 120                 125

Ala Lys His Glu Arg Gly Arg Pro Leu Leu Phe Lys Thr Thr Glu Gly
    130                 135                 140

Ile Asn Lys Cys Thr Leu Ile Ala Met Asp Leu Gly Glu Met Cys Glu
145                 150                 155                 160

Asp Thr Val Thr Tyr Lys Cys Pro Leu Leu Val Asn Thr Glu Pro Glu
                165                 170                 175

Asp Ile Asp Cys Trp Cys Asn Leu Thr Ser Thr Trp Val Met Tyr Gly
            180                 185                 190

Thr Cys Thr Gln Ser Gly Glu Arg Arg Arg Glu Lys Arg Ser Val Ala
        195                 200                 205

Leu Thr Pro His Ser Gly Met Gly Leu Glu Thr Arg Ala Glu Thr Trp
    210                 215                 220

Met Ser Ser Glu Gly Ala Trp Lys His Ala Gln Arg Val Glu Ser Trp
225                 230                 235                 240

Ile Leu Arg Asn Pro Gly Phe Ala Leu Leu Ala Gly Phe Met Ala Tyr
                245                 250                 255

Met Ile Gly Gln Thr Gly Ile Gln Arg Thr Val Phe Phe Val Leu Met
            260                 265                 270

Met Leu Val Ala Pro Ser Tyr Gly Met Arg Cys Val Gly Val Gly Asn
        275                 280                 285

Arg Asp Phe Val Glu Gly Val Ser Gly Gly Ala Trp Val Asp Leu Val
    290                 295                 300

Leu Glu His Gly Gly Cys Val Thr Thr Met Ala Gln Gly Lys Pro Thr
305                 310                 315                 320

Leu Asp Phe Glu Leu Thr Lys Thr Thr Ala Lys Glu Val Ala Leu Leu
                325                 330                 335

Arg Thr Tyr Cys Ile Glu Ala Ser Ile Ser Asn Ile Thr Thr Ala Thr
            340                 345                 350

Arg Cys Pro Thr Gln Gly Glu Pro Tyr Leu Lys Glu Glu Gln Asp Gln
        355                 360                 365

Gln Tyr Ile Cys Arg Arg Asp Val Val Asp Arg Gly Trp Gly Asn Gly
    370                 375                 380

Cys Gly Leu Phe Gly Lys Gly Gly Val Val Thr Cys Ala Lys Phe Ser
385                 390                 395                 400

Cys Ser Gly Lys Ile Thr Gly Asn Leu Val Gln Ile Glu Asn Leu Glu
                405                 410                 415

Tyr Thr Val Val Val Thr Val His Asn Gly Asp Thr His Ala Val Gly
```

-continued

```
            420                 425                 430

Asn Asp Thr Ser Asn His Gly Val Thr Ala Thr Ile Thr Pro Arg Ser
        435                 440                 445

Pro Ser Val Glu Val Lys Leu Pro Asp Tyr Gly Glu Leu Thr Leu Asp
    450                 455                 460

Cys Glu Pro Arg Ser Gly Ile Asp Phe Asn Glu Met Ile Leu Met Lys
465                 470                 475                 480

Met Lys Lys Lys Thr Trp Leu Val His Lys Gln Trp Phe Leu Asp Leu
                485                 490                 495

Pro Leu Pro Trp Thr Ala Gly Ala Asp Thr Ser Glu Val His Trp Asn
            500                 505                 510

Tyr Lys Glu Arg Met Val Thr Phe Lys Val Pro His Ala Lys Arg Gln
        515                 520                 525

Asp Val Thr Val Leu Gly Ser Gln Glu Gly Ala Met His Ser Ala Leu
    530                 535                 540

Ala Gly Ala Thr Glu Val Asp Ser Gly Asp Gly Asn His Met Phe Ala
545                 550                 555                 560

Gly His Leu Lys Cys Lys Val Arg Met Glu Lys Leu Arg Ile Lys Gly
                565                 570                 575

Met Ser Tyr Thr Met Cys Ser Gly Lys Phe Ser Ile Asp Lys Glu Met
            580                 585                 590

Ala Glu Thr Gln His Gly Thr Thr Val Val Lys Val Lys Tyr Glu Gly
        595                 600                 605

Ala Gly Ala Pro Cys Lys Val Pro Ile Glu Ile Arg Asp Val Asn Lys
    610                 615                 620

Glu Lys Val Val Gly Arg Ile Ile Ser Ser Thr Pro Leu Ala Glu Asn
625                 630                 635                 640

Thr Asn Ser Val Thr Asn Ile Glu Leu Glu Pro Pro Phe Gly Asp Ser
                645                 650                 655

Tyr Ile Val Ile Gly Val Gly Asn Ser Ala Leu Thr Leu His Trp Phe
            660                 665                 670

Arg Lys Gly Ser Ser Ile Gly Lys Met Phe Glu Ser Thr Tyr Arg Gly
        675                 680                 685

Ala Lys Arg Met Ala Ile Leu Gly Glu Thr Ala Trp Asp Phe Gly Ser
    690                 695                 700

Val Gly Gly Leu Phe Thr Ser Leu Gly Lys Ala Val His Gln Val Phe
705                 710                 715                 720

Gly Ser Val Tyr Thr Thr Leu Phe Gly Gly Val Ser Trp Met Ile Arg
                725                 730                 735

Ile Leu Ile Gly Phe Leu Val Leu Trp Ile Gly Thr Asn Ser Arg Asn
            740                 745                 750

Thr Ser Met Ala Met Thr Cys Ile Ala Ala Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845
```

```
Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
        995                 1000                1005

Asn Gly  Val Leu Glu Ser Glu  Met Ile Ile Pro Lys  Asn Leu Ala
    1010                1015                1020

Gly Pro  Val Ser Gln His Asn  Tyr Arg Pro Gly Tyr  His Thr Gln
    1025                1030                1035

Ile Thr  Gly Pro Trp His Leu  Gly Lys Leu Glu Met  Asp Phe Asp
    1040                1045                1050

Phe Cys  Asp Gly Thr Thr Val  Val Val Thr Glu Asp  Cys Gly Asn
    1055                1060                1065

Arg Gly  Pro Ser Leu Arg Thr  Thr Thr Ala Ser Gly  Lys Leu Ile
    1070                1075                1080

Thr Glu  Trp Cys Cys Arg Ser  Cys Thr Leu Pro Pro  Leu Arg Tyr
    1085                1090                1095

Arg Gly  Glu Asp Gly Cys Trp  Tyr Gly Met Glu Ile  Arg Pro Leu
    1100                1105                1110

Lys Glu  Lys Glu Glu Asn Leu  Val Asn Ser Leu Val  Thr Ala Gly
    1115                1120                1125

His Gly  Gln Val Asp Asn Phe  Ser Leu Gly Val Leu  Gly Met Ala
    1130                1135                1140

Leu Phe  Leu Glu Glu Met Leu  Arg Thr Arg Val Gly  Thr Lys His
    1145                1150                1155

Ala Ile  Leu Leu Val Ala Val  Ser Phe Val Thr Leu  Ile Thr Gly
    1160                1165                1170

Asn Met  Ser Phe Arg Asp Leu  Gly Arg Val Met Val  Met Val Gly
    1175                1180                1185

Ala Thr  Met Thr Asp Asp Ile  Gly Met Gly Val Thr  Tyr Leu Ala
    1190                1195                1200

Leu Leu  Ala Ala Phe Lys Val  Arg Pro Thr Phe Ala  Ala Gly Leu
    1205                1210                1215

Leu Leu  Arg Lys Leu Thr Ser  Lys Glu Leu Met Met  Thr Thr Ile
    1220                1225                1230

Gly Ile  Val Leu Leu Ser Gln  Ser Thr Ile Pro Glu  Thr Ile Leu
    1235                1240                1245
```

```
Glu Leu Thr Asp Ala Leu Ala Leu Gly Met Met Val Leu Lys Met
    1250                1255                1260

Val Arg Asn Met Glu Lys Tyr Gln Leu Ala Val Thr Ile Met Ala
    1265                1270                1275

Ile Leu Cys Val Pro Asn Ala Val Ile Leu Gln Asn Ala Trp Lys
    1280                1285                1290

Val Ser Cys Thr Ile Leu Ala Val Val Ser Val Ser Pro Leu Leu
    1295                1300                1305

Leu Thr Ser Ser Gln Gln Lys Thr Asp Trp Ile Pro Leu Ala Leu
    1310                1315                1320

Thr Ile Lys Gly Leu Asn Pro Thr Ala Ile Phe Leu Thr Thr Leu
    1325                1330                1335

Ser Arg Thr Ser Lys Lys Arg Ser Trp Pro Leu Asn Glu Ala Ile
    1340                1345                1350

Met Ala Val Gly Met Val Ser Ile Leu Ala Ser Ser Leu Leu Lys
    1355                1360                1365

Asn Asp Ile Pro Met Thr Gly Pro Leu Val Ala Gly Gly Leu Leu
    1370                1375                1380

Thr Val Cys Tyr Val Leu Thr Gly Arg Ser Ala Asp Leu Glu Leu
    1385                1390                1395

Glu Arg Ala Ala Asp Val Lys Trp Glu Asp Gln Ala Glu Ile Ser
    1400                1405                1410

Gly Ser Ser Pro Ile Leu Ser Ile Thr Ile Ser Glu Asp Gly Ser
    1415                1420                1425

Met Ser Ile Lys Asn Glu Glu Glu Glu Gln Thr Leu Thr Ile Leu
    1430                1435                1440

Ile Arg Thr Gly Leu Leu Val Ile Ser Gly Leu Phe Pro Val Ser
    1445                1450                1455

Ile Pro Ile Thr Ala Ala Ala Trp Tyr Leu Trp Glu Val Lys Lys
    1460                1465                1470

Gln Arg Ala Gly Val Leu Trp Asp Val Pro Ser Pro Pro Pro Met
    1475                1480                1485

Gly Lys Ala Glu Leu Glu Asp Gly Ala Tyr Arg Ile Lys Gln Lys
    1490                1495                1500

Gly Ile Leu Gly Tyr Ser Gln Ile Gly Ala Gly Val Tyr Lys Glu
    1505                1510                1515

Gly Thr Phe His Thr Met Trp His Val Thr Arg Gly Ala Val Leu
    1520                1525                1530

Met His Lys Gly Lys Arg Ile Glu Pro Ser Trp Ala Asp Val Lys
    1535                1540                1545

Lys Asp Leu Ile Ser Tyr Gly Gly Gly Trp Lys Leu Glu Gly Glu
    1550                1555                1560

Trp Lys Glu Gly Glu Glu Val Gln Val Leu Ala Leu Glu Pro Gly
    1565                1570                1575

Lys Asn Pro Arg Ala Val Gln Thr Lys Pro Gly Leu Phe Lys Thr
    1580                1585                1590

Asn Ala Gly Thr Ile Gly Ala Val Ser Leu Asp Phe Ser Pro Gly
    1595                1600                1605

Thr Ser Gly Ser Pro Ile Ile Asp Lys Lys Gly Lys Val Val Gly
    1610                1615                1620

Leu Tyr Gly Asn Gly Val Val Thr Arg Ser Gly Ala Tyr Val Ser
    1625                1630                1635

Ala Ile Ala Gln Thr Glu Lys Ser Ile Glu Asp Asn Pro Glu Ile
```

```
    1640                1645                1650

Glu Asp  Asp Ile Phe Arg Lys  Arg Arg Leu Thr Ile  Met Asp Leu
    1655                1660                1665

His Pro  Gly Ala Gly Lys Thr  Lys Arg Tyr Leu Pro  Ala Ile Val
    1670                1675                1680

Arg Glu  Ala Ile Lys Arg Gly  Leu Arg Thr Leu Ile  Leu Ala Pro
    1685                1690                1695

Thr Arg  Val Val Ala Ala Glu  Met Glu Glu Ala Leu  Arg Gly Leu
    1700                1705                1710

Pro Ile  Arg Tyr Gln Thr Pro  Ala Ile Arg Ala Val  His Thr Gly
    1715                1720                1725

Arg Glu  Ile Val Asp Leu Met  Cys His Ala Thr Phe  Thr Met Arg
    1730                1735                1740

Leu Leu  Ser Pro Val Arg Val  Pro Asn Tyr Asn Leu  Ile Ile Met
    1745                1750                1755

Asp Glu  Ala His Phe Thr Asp  Pro Ala Ser Ile Ala  Ala Arg Gly
    1760                1765                1770

Tyr Ile  Ser Thr Arg Val Glu  Met Gly Glu Ala Ala  Gly Ile Phe
    1775                1780                1785

Met Thr  Ala Thr Pro Pro Gly  Ser Arg Asp Pro Phe  Pro Gln Ser
    1790                1795                1800

Asn Ala  Pro Ile Ile Asp Glu  Glu Arg Glu Ile Pro  Glu Arg Ser
    1805                1810                1815

Trp Asn  Ser Gly His Glu Trp  Val Thr Asp Phe Lys  Gly Lys Thr
    1820                1825                1830

Val Trp  Phe Val Pro Ser Ile  Lys Ala Gly Asn Asp  Ile Ala Ala
    1835                1840                1845

Cys Leu  Arg Lys Asn Gly Lys  Lys Val Ile Gln Leu  Ser Arg Lys
    1850                1855                1860

Thr Phe  Asp Ser Glu Tyr Val  Lys Thr Arg Thr Asn  Asp Trp Asp
    1865                1870                1875

Phe Val  Val Thr Thr Asp Ile  Ser Glu Met Gly Ala  Asn Phe Lys
    1880                1885                1890

Ala Glu  Arg Val Ile Asp Pro  Arg Arg Cys Met Lys  Pro Val Ile
    1895                1900                1905

Leu Thr  Asp Gly Glu Glu Arg  Val Ile Leu Ala Gly  Pro Met Pro
    1910                1915                1920

Val Thr  His Ser Ser Ala Ala  Gln Arg Arg Gly Arg  Ile Gly Arg
    1925                1930                1935

Asn Pro  Lys Asn Glu Asn Asp  Gln Tyr Ile Tyr Met  Gly Glu Pro
    1940                1945                1950

Leu Glu  Asn Asp Glu Asp Cys  Ala His Trp Lys Glu  Ala Lys Met
    1955                1960                1965

Leu Leu  Asp Asn Ile Asn Thr  Pro Glu Gly Ile Ile  Pro Ser Met
    1970                1975                1980

Phe Glu  Pro Glu Arg Glu Lys  Val Asp Ala Ile Asp  Gly Glu Tyr
    1985                1990                1995

Arg Leu  Arg Gly Glu Ala Arg  Lys Thr Phe Val Asp  Leu Met Arg
    2000                2005                2010

Arg Gly  Asp Leu Pro Val Trp  Leu Ala Tyr Arg Val  Ala Ala Glu
    2015                2020                2025

Gly Ile  Asn Tyr Ala Asp Arg  Arg Trp Cys Phe Asp  Gly Val Lys
    2030                2035                2040
```

Asn Asn Gln Ile Leu Glu Glu Asn Val Glu Val Glu Ile Trp Thr
2045 2050 2055

Lys Glu Gly Glu Arg Lys Lys Leu Lys Pro Arg Trp Leu Asp Ala
2060 2065 2070

Arg Ile Tyr Ser Asp Pro Leu Ala Leu Lys Glu Phe Lys Glu Phe
2075 2080 2085

Ala Ala Gly Arg Lys Ser Leu Thr Leu Asn Leu Ile Thr Glu Met
2090 2095 2100

Gly Arg Leu Pro Thr Phe Met Thr Gln Lys Ala Arg Asp Ala Leu
2105 2110 2115

Asp Asn Leu Ala Val Leu His Thr Ala Glu Ala Gly Gly Arg Ala
2120 2125 2130

Tyr Asn His Ala Leu Ser Glu Leu Pro Glu Thr Leu Glu Thr Leu
2135 2140 2145

Leu Leu Leu Thr Leu Leu Ala Thr Val Thr Gly Gly Ile Phe Leu
2150 2155 2160

Phe Leu Met Ser Gly Arg Gly Ile Gly Lys Met Thr Leu Gly Met
2165 2170 2175

Cys Cys Ile Ile Thr Ala Ser Ile Leu Leu Trp Tyr Ala Gln Ile
2180 2185 2190

Gln Pro His Trp Ile Ala Ala Ser Ile Ile Leu Glu Phe Phe Leu
2195 2200 2205

Ile Val Leu Leu Ile Pro Glu Pro Glu Lys Gln Arg Thr Pro Gln
2210 2215 2220

Asp Asn Gln Leu Thr Tyr Val Val Ile Ala Ile Leu Thr Val Val
2225 2230 2235

Ala Ala Thr Met Ala Asn Glu Met Gly Phe Leu Glu Lys Thr Lys
2240 2245 2250

Lys Asp Leu Gly Leu Gly Ser Ile Ala Thr Gln Gln Pro Glu Ser
2255 2260 2265

Asn Ile Leu Asp Ile Asp Leu Arg Pro Ala Ser Ala Trp Thr Leu
2270 2275 2280

Tyr Ala Val Ala Thr Thr Phe Val Thr Pro Met Leu Arg His Ser
2285 2290 2295

Ile Glu Asn Ser Ser Val Asn Val Ser Leu Thr Ala Ile Ala Asn
2300 2305 2310

Gln Ala Thr Val Leu Met Gly Leu Gly Lys Gly Trp Pro Leu Ser
2315 2320 2325

Lys Met Asp Ile Gly Val Pro Leu Leu Ala Ile Gly Cys Tyr Ser
2330 2335 2340

Gln Val Asn Pro Ile Thr Leu Thr Ala Ala Leu Phe Leu Leu Val
2345 2350 2355

Ala His Tyr Ala Ile Ile Gly Pro Gly Leu Gln Ala Lys Ala Thr
2360 2365 2370

Arg Glu Ala Gln Lys Arg Ala Ala Ala Gly Ile Met Lys Asn Pro
2375 2380 2385

Thr Val Asp Gly Ile Thr Val Ile Asp Leu Asp Pro Ile Pro Tyr
2390 2395 2400

Asp Pro Lys Phe Glu Lys Gln Leu Gly Gln Val Met Leu Leu Val
2405 2410 2415

Leu Cys Val Thr Gln Val Leu Met Met Arg Thr Thr Trp Ala Leu
2420 2425 2430

Cys Glu Ala Leu Thr Leu Ala Thr Gly Pro Ile Ser Thr Leu Trp
2435 2440 2445

Glu Gly Asn Pro Gly Arg Phe Trp Asn Thr Thr Ile Ala Val Ser
2450 2455 2460

Met Ala Asn Ile Phe Arg Gly Ser Tyr Leu Ala Gly Ala Gly Leu
2465 2470 2475

Leu Phe Ser Ile Met Lys Asn Thr Thr Asn Thr Arg Arg Gly Thr
2480 2485 2490

Gly Asn Ile Gly Glu Thr Leu Gly Glu Lys Trp Lys Ser Arg Leu
2495 2500 2505

Asn Ala Leu Gly Lys Ser Glu Phe Gln Ile Tyr Lys Lys Ser Gly
2510 2515 2520

Ile Gln Glu Val Asp Arg Thr Leu Ala Lys Glu Gly Ile Lys Arg
2525 2530 2535

Gly Glu Thr Asp His His Ala Val Ser Arg Gly Ser Ala Lys Leu
2540 2545 2550

Arg Trp Phe Val Glu Arg Asn Met Val Thr Pro Glu Gly Lys Val
2555 2560 2565

Val Asp Leu Gly Cys Gly Arg Gly Gly Trp Ser Tyr Tyr Cys Gly
2570 2575 2580

Gly Leu Lys Asn Val Arg Glu Val Lys Gly Leu Thr Lys Gly Gly
2585 2590 2595

Pro Gly His Glu Glu Pro Ile Pro Met Ser Thr Tyr Gly Trp Asn
2600 2605 2610

Leu Val Arg Leu Gln Ser Gly Val Asp Val Phe Phe Ile Pro Pro
2615 2620 2625

Glu Lys Cys Asp Thr Leu Leu Cys Asp Ile Gly Glu Ser Ser Pro
2630 2635 2640

Asn Pro Thr Val Glu Ala Gly Arg Thr Leu Arg Val Leu Asn Leu
2645 2650 2655

Val Glu Asn Trp Leu Asn Asn Asn Thr Gln Phe Cys Ile Lys Val
2660 2665 2670

Leu Asn Pro Tyr Met Pro Ser Val Ile Glu Lys Met Glu Ala Leu
2675 2680 2685

Gln Arg Lys Tyr Gly Gly Ala Leu Val Arg Asn Pro Leu Ser Arg
2690 2695 2700

Asn Ser Thr His Glu Met Tyr Trp Val Ser Asn Ala Ser Gly Asn
2705 2710 2715

Ile Val Ser Ser Val Asn Met Ile Ser Arg Met Leu Ile Asn Arg
2720 2725 2730

Phe Thr Met Arg Tyr Lys Lys Ala Thr Tyr Glu Pro Asp Val Asp
2735 2740 2745

Leu Gly Ser Gly Thr Arg Asn Ile Gly Ile Glu Ser Glu Ile Pro
2750 2755 2760

Asn Leu Asp Ile Ile Gly Lys Arg Ile Glu Lys Ile Lys Gln Glu
2765 2770 2775

His Glu Thr Ser Trp His Tyr Asp Gln Asp His Pro Tyr Lys Thr
2780 2785 2790

Trp Ala Tyr His Gly Ser Tyr Glu Thr Lys Gln Thr Gly Ser Ala
2795 2800 2805

Ser Ser Met Val Asn Gly Val Val Arg Leu Leu Thr Lys Pro Trp
2810 2815 2820

Asp Val Val Pro Met Val Thr Gln Met Ala Met Thr Asp Thr Thr

-continued

```
    2825                2830                2835

Pro Phe  Gly Gln Gln Arg Val  Phe Lys Glu Lys Val  Asp Thr Arg
    2840                2845                2850

Thr Gln  Glu Pro Lys Glu Gly  Thr Lys Lys Leu Met  Lys Ile Thr
    2855                2860                2865

Ala Glu  Trp Leu Trp Lys Glu  Leu Gly Lys Lys Lys  Thr Pro Arg
    2870                2875                2880

Met Cys  Thr Arg Glu Glu Phe  Thr Arg Lys Val Arg  Ser Asn Ala
    2885                2890                2895

Ala Leu  Gly Ala Ile Phe Thr  Asp Glu Asn Lys Trp  Lys Ser Ala
    2900                2905                2910

Arg Glu  Ala Val Glu Asp Ser  Arg Phe Trp Glu Leu  Val Asp Lys
    2915                2920                2925

Glu Arg  Asn Leu His Leu Glu  Gly Lys Cys Glu Thr  Cys Val Tyr
    2930                2935                2940

Asn Met  Met Gly Lys Arg Glu  Lys Lys Leu Gly Glu  Phe Gly Lys
    2945                2950                2955

Ala Lys  Gly Ser Arg Ala Ile  Trp Tyr Met Trp Leu  Gly Ala Arg
    2960                2965                2970

Phe Leu  Glu Phe Glu Ala Leu  Gly Phe Leu Asn Glu  Asp His Trp
    2975                2980                2985

Phe Ser  Arg Glu Asn Ser Leu  Ser Gly Val Glu Gly  Glu Gly Leu
    2990                2995                3000

His Lys  Leu Gly Tyr Ile Leu  Arg Asp Val Ser Lys  Lys Glu Gly
    3005                3010                3015

Gly Ala  Met Tyr Ala Asp Asp  Thr Ala Gly Trp Asp  Thr Arg Ile
    3020                3025                3030

Thr Leu  Glu Asp Leu Lys Asn  Glu Glu Met Val Thr  Asn His Met
    3035                3040                3045

Glu Gly  Glu His Lys Lys Leu  Ala Glu Ala Ile Phe  Lys Leu Thr
    3050                3055                3060

Tyr Gln  Asn Lys Val Val Arg  Val Gln Arg Pro Thr  Pro Arg Gly
    3065                3070                3075

Thr Val  Met Asp Ile Ile Ser  Arg Arg Asp Gln Arg  Gly Ser Gly
    3080                3085                3090

Gln Val  Gly Thr Tyr Gly Leu  Asn Thr Phe Thr Asn  Met Glu Ala
    3095                3100                3105

Gln Leu  Ile Arg Gln Met Glu  Gly Glu Gly Val Phe  Lys Ser Ile
    3110                3115                3120

Gln His  Leu Thr Ile Thr Glu  Glu Ile Ala Val Gln  Asn Trp Leu
    3125                3130                3135

Ala Arg  Val Gly Arg Glu Arg  Leu Ser Arg Met Ala  Ile Ser Gly
    3140                3145                3150

Asp Asp  Cys Val Val Lys Pro  Leu Asp Asp Arg Phe  Ala Ser Ala
    3155                3160                3165

Leu Thr  Ala Leu Asn Asp Met  Gly Lys Ile Arg Lys  Asp Ile Gln
    3170                3175                3180

Gln Trp  Glu Pro Ser Arg Gly  Trp Asn Asp Trp Thr  Gln Val Pro
    3185                3190                3195

Phe Cys  Ser His His Phe His  Glu Leu Ile Met Lys  Asp Gly Arg
    3200                3205                3210

Val Leu  Val Val Pro Cys Arg  Asn Gln Asp Glu Leu  Ile Gly Arg
    3215                3220                3225
```

```
Ala Arg Ile Ser Gln Gly Ala Gly Trp Ser Leu Arg Glu Thr Ala
    3230                3235                3240

Cys Leu Gly Lys Ser Tyr Ala Gln Met Trp Ser Leu Met Tyr Phe
    3245                3250                3255

His Arg Arg Asp Leu Arg Leu Ala Ala Asn Ala Ile Cys Ser Ala
    3260                3265                3270

Val Pro Ser His Trp Val Pro Thr Ser Arg Thr Thr Trp Ser Ile
    3275                3280                3285

His Ala Lys His Glu Trp Met Thr Thr Glu Asp Met Leu Thr Val
    3290                3295                3300

Trp Asn Arg Val Trp Ile Gln Glu Asn Pro Trp Met Glu Asp Lys
    3305                3310                3315

Thr Pro Val Glu Ser Trp Glu Glu Ile Pro Tyr Leu Gly Lys Arg
    3320                3325                3330

Glu Asp Gln Trp Cys Gly Ser Leu Ile Gly Leu Thr Ser Arg Ala
    3335                3340                3345

Thr Trp Ala Lys Asn Ile Gln Ala Ala Ile Asn Gln Val Arg Ser
    3350                3355                3360

Leu Ile Gly Asn Glu Glu Tyr Thr Asp Tyr Met Pro Ser Met Lys
    3365                3370                3375

Arg Phe Arg Arg Glu Glu Glu Glu Ala Gly Val Leu Trp
    3380                3385                3390
```

<210> SEQ ID NO 30
<211> LENGTH: 10723
<212> TYPE: DNA
<213> ORGANISM: Artificial Sequence
<220> FEATURE:
<223> OTHER INFORMATION: Derived from Dengue virus serotype 2/Dengue virus serotype 4, Denvax-4f

<400> SEQUENCE: 30

```
agttgttagt ctacgtggac cgacaaagac agattctttg agggagctaa gctcaatgta     60

gttctaacag tttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagctctg caggcatgat cattatgctg    420

attccaacag tgatggcgtt ccatttaacc acgcgtgatg gcgaacccct catgatagtg    480

gcaaaacatg aaagggggag acctctcttg tttaagacaa cagaggggat caacaaatgc    540

actctcattg ccatggactt gggtgaaatg tgtgaggaca ctgtcacgta taaatgcccc    600

ttactggtca ataccgaacc tgaagacatt gattgctggt gcaatctcac gtctacctgg    660

gtcatgtatg ggacatgcac ccagagcgga gaacggagac gagagaagcg ctcagtagct    720

ttaacaccac attcaggaat gggattggaa acaagagctg agacatggat gtcatcggaa    780

ggggcttgga agcatgctca gagagtagag agctggatac tcagaaaccc aggattcgcg    840

ctcttggcag gatttatggc ttatatgatt gggcaaacag gaatccagcg aactgtcttc    900

tttgtcctaa tgatgctggt cgccccatcc tacggaatgc gatgcgtagg agtaggaaac    960

agagactttg tggaaggagt ctcaggtgga gcatgggtcg atctggtgct agaacatgga   1020
```

-continued

```
ggatgcgtca caaccatggc ccagggaaaa ccaaccttgg attttgaact gactaagaca   1080
acagccaagg aagtggctct gttaagaacc tattgcattg aagcctcaat atcaaacata   1140
accacggcaa caagatgtcc aacgcaagga gagccttatc taaaagagga acaagaccaa   1200
cagtacattt gccggagaga tgtggtagac agagggtggg gcaatggctg tggcttgttt   1260
ggaaaaggag gagttgtgac atgtgcgaag ttttcatgtt cggggaagat aacaggcaat   1320
ttggtccaaa ttgagaacct tgaatacaca gtggttgtaa cagtccacaa tggagacacc   1380
catgcagtag gaaatgacac gtccaatcat ggagttacag ccacgataac tcccaggtca   1440
ccatcggtgg aagtcaaatt gccggactat ggagaactaa cactcgattg tgaacccagg   1500
tctggaattg actttaatga gatgattctg atgaaaatga aaaagaaaac atggcttgtg   1560
cataagcaat ggtttttgga tctacctcta ccatggacag caggagcaga cacatcagag   1620
gttcactgga attacaaaga gagaatggtg acatttaagg ttcctcatgc caagagacag   1680
gatgtgacag tgctgggatc tcaggaagga gccatgcatt ctgccctcgc tggagccaca   1740
gaagtggact ccggtgatgg aaatcacatg tttgcaggac atctcaagtg caaagtccgt   1800
atggagaaat tgagaatcaa gggaatgtca tacacgatgt gttcaggaaa gttctcaatt   1860
gacaaagaga tggcagaaac acagcatggg acaacagtgg tgaaagtcaa gtatgaaggt   1920
gctggagctc cgtgtaaagt ccccatagag ataagagatg tgaacaagga aaaagtggtt   1980
gggcgtatca tctcatccac ccctttggct gagaatacca acagtgtaac caacatagag   2040
ttagaacccc cctttgggga cagctacata gtgataggtg ttggaaacag tgcattaaca   2100
ctccattggt tcaggaaagg gagttccatt ggcaagatgt ttgagtccac atacagaggt   2160
gcaaaacgaa tggccattct aggtgaaaca gcttgggatt ttggttccgt tggtggactg   2220
ttcacatcat tgggaaaggc tgtgcaccag gtttttggaa gtgtgtatac aaccctgttt   2280
ggaggagtct catggatgat tagaatccta attgggttcc tagtgttgtg gattggcacg   2340
aactcaagga acacttcaat ggctatgacg tgcatagctg ccggcattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
```

-continued gaaatcagac cattgaagga gaaagaagag aatttggtca actccttggt cacagctgga 3480
catgggcagg tcgacaactt ttcactagga gtcttgggaa tggcattgtt cctggaggaa 3540
atgcttagga cccgagtagg aacgaaacat gcaatactac tagttgcagt ttcttttgtg 3600
acattgatca cagggaacat gtcctttaga gacctgggaa gagtgatggt tatggtaggc 3660
gccactatga cggatgacat aggtatgggc gtgacttatc ttgccctact agcagccttc 3720
aaagtcagac caacttttgc agctggacta ctcttgagaa agctgacctc caaggaattg 3780
atgatgacta ctataggaat tgtactcctc tcccagagca ccataccaga gaccattctt 3840
gagttgactg atgcgttagc cttaggcatg atggtcctca aaatggtgag aaatatggaa 3900
aagtatcaat tggcagtgac tatcatggct atcttgtgcg tcccaaacgc agtgatatta 3960
caaaacgcat ggaaagtgag ttgcacaata ttggcagtgg tgtccgtttc ccccactgctc 4020
ttaacatcct cacagcaaaa aacagattgg ataccattag cattgacgat caaaggtctc 4080
aatccaacag ctatttttct aacaaccctc tcaagaacca gcaagaaaag gagctggcca 4140
ttaaatgagg ctatcatggc agtcgggatg gtgagcattt tagccagttc tctcctaaaa 4200
aatgatattc ccatgacagg accattagtg gctggagggc tcctcactgt gtgctacgtg 4260
ctcactggac gatcggccga tttggaactg gagagagcag ccgatgtcaa atgggaagac 4320
caggcagaga tatcaggaag cagtccaatc ctgtcaataa caatatcaga agatggtagc 4380
atgtcgataa aaaatgaaga ggaagaacaa acactgacca tactcattag aacaggattg 4440
ctggtgatct caggactttt tcctgtatca ataccaatca cggcagcagc atggtacctg 4500
tgggaagtga agaaacaacg ggccggagta ttgtgggatg ttccttcacc cccacccatg 4560
ggaaaggctg aactggaaga tggagcctat agaattaagc aaaaagggat tcttggatat 4620
tcccagatcg gagccggagt ttacaaagaa ggaacattcc atacaatgtg gcatgtcaca 4680
cgtggcgctg ttctaatgca taaaggaaag aggattgaac catcatgggc ggacgtcaag 4740
aaagacctaa tatcatatgg aggaggctgg aagttagaag gagaatggaa ggaaggagaa 4800
gaagtccagg tattggcact ggagcctgga aaaaatccaa gagccgtcca aacgaaacct 4860
ggtcttttca aaaccaacgc cggaacaata ggtgctgtat ctctggactt ttctcctgga 4920
acgtcaggat ctccaattat cgacaaaaaa ggaaaagttg tgggtcttta tggtaatggt 4980
gttgttacaa ggagtggagc atatgtgagt gctatagccc agactgaaaa aagcattgaa 5040
gacaacccag agatcgaaga tgacattttc cgaaagagaa gactgaccat catggacctc 5100
cacccaggag cgggaaagac gaagagatac cttccggcca tagtcagaga agctataaaa 5160
cggggtttga gaacattaat cttggccccc actagagttg tggcagctga aatggaggaa 5220
gcccttagag gacttccaat aagataccag accccagcca tcagagctgt gcacaccggg 5280
cgggagattg tggacctaat gtgtcatgcc acatttacca tgaggctgct atcaccagtt 5340
agagtgccaa actacaacct gattatcatg gacgaagccc atttcacaga cccagcaagt 5400
atagcagcta gaggatacat ctcaactcga gtggagatgg gtgaggcagc tgggattttt 5460
atgacagcca ctcccccggg aagcagagac ccatttcctc agagcaatgc accaatcata 5520
gatgaagaaa gagaaatccc tgaacgctcg tggaattccg gacatgaatg ggtcacggat 5580
tttaaaggga agactgtttg gttcgttcca agtataaaag caggaaatga tatagcagct 5640
tgcctgagga aaaatggaaa gaaagtgata caactcagta ggaagacctt tgattctgag 5700
tatgtcaaga ctagaaccaa tgattgggac ttcgtggtta caactgacat ttcagaaatg 5760
ggtgccaatt tcaaggctga gagggttata gaccccagac gctgcatgaa accagtcata 5820
ctaacagatg gtgaagagcg ggtgattctg gcaggaccta tgccagtgac ccactctagt 5880
gcagcacaaa gaagagggag aataggaaga aatccaaaaa atgagaatga ccagtacata 5940
tacatggggg aacctctgga aaatgatgaa gactgtgcac actggaaaga agctaaaatg 6000
ctcctagata acatcaacac gccagaagga atcattccta gcatgttcga accagagcgt 6060
gaaaaggtgg atgccattga tggcgaatac cgcttgagag gagaagcaag gaaaaccttt 6120
gtagacttaa tgagaagagg agacctacca gtctggttgg cctacagagt ggcagctgaa 6180
ggcatcaact acgcagacag aaggtggtgt tttgatggag tcaagaacaa ccaaatccta 6240
gaagaaaacg tggaagttga aatctggaca aaagaagggg aaaggaagaa attgaaaccc 6300
agatggttgg atgctaggat ctattctgac ccactggcgc taaaagaatt taaggaattt 6360
gcagccggaa gaaagtctct gaccctgaac ctaatcacag aaatgggtag gctcccaacc 6420
ttcatgactc agaaggcaag agacgcactg gacaacttag cagtgctgca cacggctgag 6480
gcaggtggaa gggcgtacaa ccatgctctc agtgaactgc cggagaccct ggagacattg 6540
cttttactga cacttctggc tacagtcacg ggagggatct tttattcttt gatgagcgga 6600
aggggcatag ggaagatgac cctgggaatg tgctgcataa tcacggctag catcctccta 6660
tggtacgcac aaatacagcc acactggata gcagcttcaa taatactgga gtttttttctc 6720
atagttttgc ttattccaga acctgaaaaa cagagaacac cccaagacaa ccaactgacc 6780
tacgttgtca tagccatcct cacagtggtg gccgcaacca tggcaaacga gatgggtttc 6840
ctagaaaaaa cgaagaaaga tctcggattg ggaagcattg caacccagca acccgagagc 6900
aacatcctgg acatagatct acgtcctgca tcagcatgga cgctgtatgc cgtggccaca 6960
acatttgtta caccaatgtt gagacatagc attgaaaatt cctcagtgaa tgtgtcccta 7020
acagctatag ccaaccaagc cacagtgtta atgggtctcg ggaaaggatg gccattgtca 7080
aagatggaca tcggagttcc ccttctcgcc attggatgct actcacaagt caaccccata 7140
actctcacag cagctctttt cttattggta gcacattatg ccatcatagg gccaggactc 7200
caagcaaaag caaccagaga agctcagaaa agagcagcgg cgggcatcat gaaaaaccca 7260
actgtcgatg gaataacagt gattgaccta gatccaatac cttatgatcc aaagtttgaa 7320
aagcagttgg gacaagtaat gctcctagtc ctctgcgtga ctcaagtatt gatgatgagg 7380
actacatggg ctctgtgtga ggctttaacc ttagctaccg ggcccatctc cacattgtgg 7440
gaaggaaatc cagggaggtt ttggaacact accattgcgg tgtcaatggc taacattttt 7500
agagggagtt acttggccgg agctggactt ctcttttcta ttatgaagaa cacaaccaac 7560
acaagaaggg gaactggcaa cataggagag acgcttggag agaaatggaa aagccgattg 7620
aacgcattgg gaaaaagtga attccagatc tacaagaaaa gtggaatcca ggaagtggat 7680
agaaccttag caaaagaagg cattaaaaga ggagaaacgg accatcacgc tgtgtcgcga 7740
ggctcagcaa aactgagatg gttcgttgag agaaacatgg tcacaccaga agggaaagta 7800
gtggacctcg gttgtggcag aggaggctgg tcatactatt gtggaggact aaagaatgta 7860
agagaagtca aaggcctaac aaaaggagga ccaggacacg aagaacccat ccccatgtca 7920
acatatgggt ggaatctagt gcgtcttcaa agtggagttg acgttttctt catcccgcca 7980
gaaaagtgtg acacattatt gtgtgacata ggggagtcat caccaaatcc cacagtggaa 8040
gcaggacgaa cactcagagt ccttaactta gtagaaaatt ggttgaacaa caacactcaa 8100
ttttgcataa aggttctcaa cccatatatg ccctcagtca tagaaaaaat ggaagcacta 8160
caaaggaaat atggaggagc cttagtgagg aatccactct cacgaaactc cacacatgag 8220
atgtactggg tatccaatgc ttccgggaac atagtgtcat cagtgaacat gatttcaagg 8280
atgttgatca acagatttac aatgagatac aagaaagcca cttacgagcc ggatgttgac 8340
ctcggaagcg gaacccgtaa catcgggatt gaaagtgaga taccaaacct agatataatt 8400
gggaaaagaa tagaaaaaat aaagcaagag catgaaacat catggcacta tgaccaagac 8460
cacccataca aaacgtgggc ataccatggt agctatgaaa caaaacagac tggatcagca 8520
tcatccatgg tcaacggagt ggtcaggctg ctgacaaaac cttgggacgt cgtccccatg 8580
gtgacacaga tggcaatgac agacacgact ccatttggac aacagcgcgt tttaaagag 8640
aaagtggaca cgagaaccca agaaccgaaa gaaggcacga agaaactaat gaaaataaca 8700
gcagagtggc tttggaaaga attagggaag aaaaagacac ccaggatgtg caccagagaa 8760
gaattcacaa gaaaggtgag aagcaatgca gccttggggg ccatattcac tgatgagaac 8820
aagtggaagt cggcacgtga ggctgttgaa gatagtaggt tttgggagct ggttgacaag 8880
gaaaggaatc tccatcttga aggaaagtgt gaaacatgtg tgtacaacat gatgggaaaa 8940
agagagaaga agctagggga attcggcaag gcaaaaggca gcagagccat atggtacatg 9000
tggcttggag cacgcttctt agagtttgaa gccctaggat tcttaaatga agatcactgg 9060
ttctccagag agaactccct gagtggagtg gaaggagaag ggctgcacaa gctaggttac 9120
attctaagag acgtgagcaa gaaagaggga ggagcaatgt atgccgatga caccgcagga 9180
tgggatacaa gaatcacact agaagaccta aaaaatgaag aaatggtaac aaaccacatg 9240
gaaggagaac acaagaaact agccgaggcc attttcaaac taacgtacca aaacaaggtg 9300
gtgcgtgtgc aaagaccaac accaagaggc acagtaatgg acatcatatc gagaagagac 9360
caaagaggta gtggacaagt tggcacctat ggactcaata ctttcaccaa tatggaagcc 9420
caactaatca gacagatgga gggagaagga gtctttaaaa gcattcagca cctaacaatc 9480
acagaagaaa tcgctgtgca aaactggtta gcaagagtgg ggcgcgaaag gttatcaaga 9540
atggccatca gtggagatga ttgtgttgtg aaacctttag atgacaggtt cgcaagcgct 9600
ttaacagctc taaatgacat gggaaagatt aggaaagaca tacaacaatg ggaaccttca 9660
agaggatgga atgattggac acaagtgccc ttctgttcac accatttcca tgagttaatc 9720
atgaaagacg gtcgcgtact cgttgttcca tgtagaaacc aagatgaact gattggcaga 9780
gcccgaatct cccaaggagc agggtggtct ttgcgggaga cggcctgttt ggggaagtct 9840
tacgcccaaa tgtggagctt gatgtacttc cacagacgcg acctcaggct ggcggcaaat 9900
gctatttgct cggcagtacc atcacattgg gttccaacaa gtcgaacaac ctggtccata 9960
catgctaaac atgaatggat gacaacggaa gacatgctga cagtctggaa cagggtgtgg 10020
attcaagaaa acccatggat ggaagacaaa actccagtgg aatcatggga ggaaatccca 10080
tacttgggga aaagagaaga ccaatggtgc ggctcattga ttgggttaac aagcagggcc 10140
acctgggcaa agaacatcca agcagcaata aatcaagtta gatcccttat aggcaatgaa 10200
gaatacacag attacatgcc atccatgaaa agattcagaa gagaagagga agaagcagga 10260
gttctgtggt agaaagcaaa actaacatga aacaaggcta gaagtcaggt cggattaagc 10320
catagtacgg aaaaaactat gctacctgtg agccccgtcc aaggacgtta aaagaagtca 10380
ggccatcata aatgccatag cttgagtaaa ctatgcagcc tgtagctcca cctgagaagg 10440
tgtaaaaaat ccgggaggcc acaaaccatg gaagctgtac gcatggcgta gtggactagc 10500

-continued ggttagagga gacccctccc ttacaaatcg cagcaacaat gggggcccaa ggcgagatga 10560
agctgtagtc tcgctggaag gactagaggt tagaggagac ccccccgaaa caaaaaacag 10620
catattgacg ctgggaaaga ccagagatcc tgctgtctcc tcagcatcat tccaggcaca 10680
gaacgccaga aaatggaatg gtgctgttga atcaacaggt tct 10723

<210> SEQ ID NO 31
<211> LENGTH: 3391
<212> TYPE: PRT
<213> ORGANISM: Artificial Sequence
<220> FEATURE:
<223> OTHER INFORMATION: Derived from Dengue virus serotype 2/Dengue
virus serotype 4, DenVax-4f

<400> SEQUENCE: 31

Met Asn Asn Gln Arg Lys Lys Ala Lys Asn Thr Pro Phe Asn Met Leu
1 5 10 15

Lys Arg Glu Arg Asn Arg Val Ser Thr Val Gln Gln Leu Thr Lys Arg
20 25 30

Phe Ser Leu Gly Met Leu Gln Gly Arg Gly Pro Leu Lys Leu Phe Met
35 40 45

Ala Leu Val Ala Phe Leu Arg Phe Leu Thr Ile Pro Pro Thr Ala Gly
50 55 60

Ile Leu Lys Arg Trp Gly Thr Ile Lys Lys Ser Lys Ala Ile Asn Val
65 70 75 80

Leu Arg Gly Phe Arg Lys Glu Ile Gly Arg Met Leu Asn Ile Leu Asn
85 90 95

Arg Arg Arg Ser Ser Ala Gly Met Ile Ile Met Leu Ile Pro Thr Val
100 105 110

Met Ala Phe His Leu Thr Thr Arg Asp Gly Glu Pro Leu Met Ile Val
115 120 125

Ala Lys His Glu Arg Gly Arg Pro Leu Leu Phe Lys Thr Thr Glu Gly
130 135 140

Ile Asn Lys Cys Thr Leu Ile Ala Met Asp Leu Gly Glu Met Cys Glu
145 150 155 160

Asp Thr Val Thr Tyr Lys Cys Pro Leu Leu Val Asn Thr Glu Pro Glu
165 170 175

Asp Ile Asp Cys Trp Cys Asn Leu Thr Ser Thr Trp Val Met Tyr Gly
180 185 190

Thr Cys Thr Gln Ser Gly Glu Arg Arg Arg Glu Lys Arg Ser Val Ala
195 200 205

Leu Thr Pro His Ser Gly Met Gly Leu Glu Thr Arg Ala Glu Thr Trp
210 215 220

Met Ser Ser Glu Gly Ala Trp Lys His Ala Gln Arg Val Glu Ser Trp
225 230 235 240

Ile Leu Arg Asn Pro Gly Phe Ala Leu Leu Ala Gly Phe Met Ala Tyr
245 250 255

Met Ile Gly Gln Thr Gly Ile Gln Arg Thr Val Phe Phe Val Leu Met
260 265 270

Met Leu Val Ala Pro Ser Tyr Gly Met Arg Cys Val Gly Val Gly Asn
275 280 285

Arg Asp Phe Val Glu Gly Val Ser Gly Gly Ala Trp Val Asp Leu Val
290 295 300

Leu Glu His Gly Gly Cys Val Thr Thr Met Ala Gln Gly Lys Pro Thr
305 310 315 320

```
Leu Asp Phe Glu Leu Thr Lys Thr Thr Ala Lys Glu Val Ala Leu Leu
                325                 330                 335

Arg Thr Tyr Cys Ile Glu Ala Ser Ile Ser Asn Ile Thr Thr Ala Thr
            340                 345                 350

Arg Cys Pro Thr Gln Gly Glu Pro Tyr Leu Lys Glu Glu Gln Asp Gln
        355                 360                 365

Gln Tyr Ile Cys Arg Arg Asp Val Val Asp Arg Gly Trp Gly Asn Gly
    370                 375                 380

Cys Gly Leu Phe Gly Lys Gly Gly Val Val Thr Cys Ala Lys Phe Ser
385                 390                 395                 400

Cys Ser Gly Lys Ile Thr Gly Asn Leu Val Gln Ile Glu Asn Leu Glu
                405                 410                 415

Tyr Thr Val Val Val Thr Val His Asn Gly Asp Thr His Ala Val Gly
            420                 425                 430

Asn Asp Thr Ser Asn His Gly Val Thr Ala Thr Ile Thr Pro Arg Ser
        435                 440                 445

Pro Ser Val Glu Val Lys Leu Pro Asp Tyr Gly Glu Leu Thr Leu Asp
    450                 455                 460

Cys Glu Pro Arg Ser Gly Ile Asp Phe Asn Glu Met Ile Leu Met Lys
465                 470                 475                 480

Met Lys Lys Lys Thr Trp Leu Val His Lys Gln Trp Phe Leu Asp Leu
                485                 490                 495

Pro Leu Pro Trp Thr Ala Gly Ala Asp Thr Ser Glu Val His Trp Asn
            500                 505                 510

Tyr Lys Glu Arg Met Val Thr Phe Lys Val Pro His Ala Lys Arg Gln
        515                 520                 525

Asp Val Thr Val Leu Gly Ser Gln Glu Gly Ala Met His Ser Ala Leu
    530                 535                 540

Ala Gly Ala Thr Glu Val Asp Ser Gly Asp Gly Asn His Met Phe Ala
545                 550                 555                 560

Gly His Leu Lys Cys Lys Val Arg Met Glu Lys Leu Arg Ile Lys Gly
                565                 570                 575

Met Ser Tyr Thr Met Cys Ser Gly Lys Phe Ser Ile Asp Lys Glu Met
            580                 585                 590

Ala Glu Thr Gln His Gly Thr Thr Val Val Lys Val Lys Tyr Glu Gly
        595                 600                 605

Ala Gly Ala Pro Cys Lys Val Pro Ile Glu Ile Arg Asp Val Asn Lys
    610                 615                 620

Glu Lys Val Val Gly Arg Ile Ile Ser Ser Thr Pro Leu Ala Glu Asn
625                 630                 635                 640

Thr Asn Ser Val Thr Asn Ile Glu Leu Glu Pro Pro Phe Gly Asp Ser
                645                 650                 655

Tyr Ile Val Ile Gly Val Gly Asn Ser Ala Leu Thr Leu His Trp Phe
            660                 665                 670

Arg Lys Gly Ser Ser Ile Gly Lys Met Phe Glu Ser Thr Tyr Arg Gly
        675                 680                 685

Ala Lys Arg Met Ala Ile Leu Gly Glu Thr Ala Trp Asp Phe Gly Ser
    690                 695                 700

Val Gly Gly Leu Phe Thr Ser Leu Gly Lys Ala Val His Gln Val Phe
705                 710                 715                 720

Gly Ser Val Tyr Thr Thr Leu Phe Gly Gly Val Ser Trp Met Ile Arg
                725                 730                 735

Ile Leu Ile Gly Phe Leu Val Leu Trp Ile Gly Thr Asn Ser Arg Asn
```

```
            740                 745                 750

Thr Ser Met Ala Met Thr Cys Ile Ala Ala Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
        995                 1000                1005

Asn Gly  Val Leu Glu Ser Glu  Met Ile Ile Pro Lys  Asn Leu Ala
    1010                1015                1020

Gly Pro  Val Ser Gln His Asn  Tyr Arg Pro Gly Tyr  His Thr Gln
    1025                1030                1035

Ile Thr  Gly Pro Trp His Leu  Gly Lys Leu Glu Met  Asp Phe Asp
    1040                1045                1050

Phe Cys  Asp Gly Thr Thr Val  Val Val Thr Glu Asp  Cys Gly Asn
    1055                1060                1065

Arg Gly  Pro Ser Leu Arg Thr  Thr Thr Ala Ser Gly  Lys Leu Ile
    1070                1075                1080

Thr Glu  Trp Cys Cys Arg Ser  Cys Thr Leu Pro Pro  Leu Arg Tyr
    1085                1090                1095

Arg Gly  Glu Asp Gly Cys Trp  Tyr Gly Met Glu Ile  Arg Pro Leu
    1100                1105                1110

Lys Glu  Lys Glu Glu Asn Leu  Val Asn Ser Leu Val  Thr Ala Gly
    1115                1120                1125

His Gly  Gln Val Asp Asn Phe  Ser Leu Gly Val Leu  Gly Met Ala
    1130                1135                1140

Leu Phe  Leu Glu Glu Met Leu  Arg Thr Arg Val Gly  Thr Lys His
    1145                1150                1155
```

```
Ala Ile Leu Leu Val Ala Val Ser Phe Val Thr Leu Ile Thr Gly
    1160                1165                1170

Asn Met Ser Phe Arg Asp Leu Gly Arg Val Met Val Met Val Gly
    1175                1180                1185

Ala Thr Met Thr Asp Asp Ile Gly Met Gly Val Thr Tyr Leu Ala
    1190                1195                1200

Leu Leu Ala Ala Phe Lys Val Arg Pro Thr Phe Ala Ala Gly Leu
    1205                1210                1215

Leu Leu Arg Lys Leu Thr Ser Lys Glu Leu Met Met Thr Thr Ile
    1220                1225                1230

Gly Ile Val Leu Leu Ser Gln Ser Thr Ile Pro Glu Thr Ile Leu
    1235                1240                1245

Glu Leu Thr Asp Ala Leu Ala Leu Gly Met Met Val Leu Lys Met
    1250                1255                1260

Val Arg Asn Met Glu Lys Tyr Gln Leu Ala Val Thr Ile Met Ala
    1265                1270                1275

Ile Leu Cys Val Pro Asn Ala Val Ile Leu Gln Asn Ala Trp Lys
    1280                1285                1290

Val Ser Cys Thr Ile Leu Ala Val Val Ser Val Ser Pro Leu Leu
    1295                1300                1305

Leu Thr Ser Ser Gln Gln Lys Thr Asp Trp Ile Pro Leu Ala Leu
    1310                1315                1320

Thr Ile Lys Gly Leu Asn Pro Thr Ala Ile Phe Leu Thr Thr Leu
    1325                1330                1335

Ser Arg Thr Ser Lys Lys Arg Ser Trp Pro Leu Asn Glu Ala Ile
    1340                1345                1350

Met Ala Val Gly Met Val Ser Ile Leu Ala Ser Ser Leu Leu Lys
    1355                1360                1365

Asn Asp Ile Pro Met Thr Gly Pro Leu Val Ala Gly Gly Leu Leu
    1370                1375                1380

Thr Val Cys Tyr Val Leu Thr Gly Arg Ser Ala Asp Leu Glu Leu
    1385                1390                1395

Glu Arg Ala Ala Asp Val Lys Trp Glu Asp Gln Ala Glu Ile Ser
    1400                1405                1410

Gly Ser Ser Pro Ile Leu Ser Ile Thr Ile Ser Glu Asp Gly Ser
    1415                1420                1425

Met Ser Ile Lys Asn Glu Glu Glu Glu Gln Thr Leu Thr Ile Leu
    1430                1435                1440

Ile Arg Thr Gly Leu Leu Val Ile Ser Gly Leu Phe Pro Val Ser
    1445                1450                1455

Ile Pro Ile Thr Ala Ala Ala Trp Tyr Leu Trp Glu Val Lys Lys
    1460                1465                1470

Gln Arg Ala Gly Val Leu Trp Asp Val Pro Ser Pro Pro Pro Met
    1475                1480                1485

Gly Lys Ala Glu Leu Glu Asp Gly Ala Tyr Arg Ile Lys Gln Lys
    1490                1495                1500

Gly Ile Leu Gly Tyr Ser Gln Ile Gly Ala Gly Val Tyr Lys Glu
    1505                1510                1515

Gly Thr Phe His Thr Met Trp His Val Thr Arg Gly Ala Val Leu
    1520                1525                1530

Met His Lys Gly Lys Arg Ile Glu Pro Ser Trp Ala Asp Val Lys
    1535                1540                1545
```

Lys Asp Leu Ile Ser Tyr Gly Gly Gly Trp Lys Leu Glu Gly Glu
1550 1555 1560

Trp Lys Glu Gly Glu Glu Val Gln Val Leu Ala Leu Glu Pro Gly
1565 1570 1575

Lys Asn Pro Arg Ala Val Gln Thr Lys Pro Gly Leu Phe Lys Thr
1580 1585 1590

Asn Ala Gly Thr Ile Gly Ala Val Ser Leu Asp Phe Ser Pro Gly
1595 1600 1605

Thr Ser Gly Ser Pro Ile Ile Asp Lys Lys Gly Lys Val Val Gly
1610 1615 1620

Leu Tyr Gly Asn Gly Val Val Thr Arg Ser Gly Ala Tyr Val Ser
1625 1630 1635

Ala Ile Ala Gln Thr Glu Lys Ser Ile Glu Asp Asn Pro Glu Ile
1640 1645 1650

Glu Asp Asp Ile Phe Arg Lys Arg Arg Leu Thr Ile Met Asp Leu
1655 1660 1665

His Pro Gly Ala Gly Lys Thr Lys Arg Tyr Leu Pro Ala Ile Val
1670 1675 1680

Arg Glu Ala Ile Lys Arg Gly Leu Arg Thr Leu Ile Leu Ala Pro
1685 1690 1695

Thr Arg Val Val Ala Ala Glu Met Glu Glu Ala Leu Arg Gly Leu
1700 1705 1710

Pro Ile Arg Tyr Gln Thr Pro Ala Ile Arg Ala Val His Thr Gly
1715 1720 1725

Arg Glu Ile Val Asp Leu Met Cys His Ala Thr Phe Thr Met Arg
1730 1735 1740

Leu Leu Ser Pro Val Arg Val Pro Asn Tyr Asn Leu Ile Ile Met
1745 1750 1755

Asp Glu Ala His Phe Thr Asp Pro Ala Ser Ile Ala Ala Arg Gly
1760 1765 1770

Tyr Ile Ser Thr Arg Val Glu Met Gly Glu Ala Ala Gly Ile Phe
1775 1780 1785

Met Thr Ala Thr Pro Pro Gly Ser Arg Asp Pro Phe Pro Gln Ser
1790 1795 1800

Asn Ala Pro Ile Ile Asp Glu Glu Arg Glu Ile Pro Glu Arg Ser
1805 1810 1815

Trp Asn Ser Gly His Glu Trp Val Thr Asp Phe Lys Gly Lys Thr
1820 1825 1830

Val Trp Phe Val Pro Ser Ile Lys Ala Gly Asn Asp Ile Ala Ala
1835 1840 1845

Cys Leu Arg Lys Asn Gly Lys Lys Val Ile Gln Leu Ser Arg Lys
1850 1855 1860

Thr Phe Asp Ser Glu Tyr Val Lys Thr Arg Thr Asn Asp Trp Asp
1865 1870 1875

Phe Val Val Thr Thr Asp Ile Ser Glu Met Gly Ala Asn Phe Lys
1880 1885 1890

Ala Glu Arg Val Ile Asp Pro Arg Arg Cys Met Lys Pro Val Ile
1895 1900 1905

Leu Thr Asp Gly Glu Glu Arg Val Ile Leu Ala Gly Pro Met Pro
1910 1915 1920

Val Thr His Ser Ser Ala Ala Gln Arg Arg Gly Arg Ile Gly Arg
1925 1930 1935

Asn Pro Lys Asn Glu Asn Asp Gln Tyr Ile Tyr Met Gly Glu Pro

-continued

```
    1940                 1945                 1950

Leu Glu  Asn Asp Glu Asp Cys  Ala His Trp Lys Glu  Ala Lys Met
    1955                 1960                 1965

Leu Leu  Asp Asn Ile Asn Thr  Pro Glu Gly Ile Ile  Pro Ser Met
    1970                 1975                 1980

Phe Glu  Pro Glu Arg Glu Lys  Val Asp Ala Ile Asp  Gly Glu Tyr
    1985                 1990                 1995

Arg Leu  Arg Gly Glu Ala Arg  Lys Thr Phe Val Asp  Leu Met Arg
    2000                 2005                 2010

Arg Gly  Asp Leu Pro Val Trp  Leu Ala Tyr Arg Val  Ala Ala Glu
    2015                 2020                 2025

Gly Ile  Asn Tyr Ala Asp Arg  Arg Trp Cys Phe Asp  Gly Val Lys
    2030                 2035                 2040

Asn Asn  Gln Ile Leu Glu Glu  Asn Val Glu Val Glu  Ile Trp Thr
    2045                 2050                 2055

Lys Glu  Gly Glu Arg Lys Lys  Leu Lys Pro Arg Trp  Leu Asp Ala
    2060                 2065                 2070

Arg Ile  Tyr Ser Asp Pro Leu  Ala Leu Lys Glu Phe  Lys Glu Phe
    2075                 2080                 2085

Ala Ala  Gly Arg Lys Ser Leu  Thr Leu Asn Leu Ile  Thr Glu Met
    2090                 2095                 2100

Gly Arg  Leu Pro Thr Phe Met  Thr Gln Lys Ala Arg  Asp Ala Leu
    2105                 2110                 2115

Asp Asn  Leu Ala Val Leu His  Thr Ala Glu Ala Gly  Gly Arg Ala
    2120                 2125                 2130

Tyr Asn  His Ala Leu Ser Glu  Leu Pro Glu Thr Leu  Glu Thr Leu
    2135                 2140                 2145

Leu Leu  Leu Thr Leu Leu Ala  Thr Val Thr Gly Gly  Ile Phe Leu
    2150                 2155                 2160

Phe Leu  Met Ser Gly Arg Gly  Ile Gly Lys Met Thr  Leu Gly Met
    2165                 2170                 2175

Cys Cys  Ile Ile Thr Ala Ser  Ile Leu Leu Trp Tyr  Ala Gln Ile
    2180                 2185                 2190

Gln Pro  His Trp Ile Ala Ala  Ser Ile Ile Leu Glu  Phe Phe Leu
    2195                 2200                 2205

Ile Val  Leu Leu Ile Pro Glu  Pro Glu Lys Gln Arg  Thr Pro Gln
    2210                 2215                 2220

Asp Asn  Gln Leu Thr Tyr Val  Val Ile Ala Ile Leu  Thr Val Val
    2225                 2230                 2235

Ala Ala  Thr Met Ala Asn Glu  Met Gly Phe Leu Glu  Lys Thr Lys
    2240                 2245                 2250

Lys Asp  Leu Gly Leu Gly Ser  Ile Ala Thr Gln Gln  Pro Glu Ser
    2255                 2260                 2265

Asn Ile  Leu Asp Ile Asp Leu  Arg Pro Ala Ser Ala  Trp Thr Leu
    2270                 2275                 2280

Tyr Ala  Val Ala Thr Thr Phe  Val Thr Pro Met Leu  Arg His Ser
    2285                 2290                 2295

Ile Glu  Asn Ser Ser Val Asn  Val Ser Leu Thr Ala  Ile Ala Asn
    2300                 2305                 2310

Gln Ala  Thr Val Leu Met Gly  Leu Gly Lys Gly Trp  Pro Leu Ser
    2315                 2320                 2325

Lys Met  Asp Ile Gly Val Pro  Leu Leu Ala Ile Gly  Cys Tyr Ser
    2330                 2335                 2340
```

```
Gln Val  Asn Pro Ile Thr Leu  Thr Ala Ala Leu Phe  Leu Leu Val
    2345                 2350                 2355

Ala His  Tyr Ala Ile Ile Gly  Pro Gly Leu Gln Ala  Lys Ala Thr
    2360                 2365                 2370

Arg Glu  Ala Gln Lys Arg Ala  Ala Ala Gly Ile Met  Lys Asn Pro
    2375                 2380                 2385

Thr Val  Asp Gly Ile Thr Val  Ile Asp Leu Asp Pro  Ile Pro Tyr
    2390                 2395                 2400

Asp Pro  Lys Phe Glu Lys Gln  Leu Gly Gln Val Met  Leu Leu Val
    2405                 2410                 2415

Leu Cys  Val Thr Gln Val Leu  Met Met Arg Thr Thr  Trp Ala Leu
    2420                 2425                 2430

Cys Glu  Ala Leu Thr Leu Ala  Thr Gly Pro Ile Ser  Thr Leu Trp
    2435                 2440                 2445

Glu Gly  Asn Pro Gly Arg Phe  Trp Asn Thr Thr Ile  Ala Val Ser
    2450                 2455                 2460

Met Ala  Asn Ile Phe Arg Gly  Ser Tyr Leu Ala Gly  Ala Gly Leu
    2465                 2470                 2475

Leu Phe  Ser Ile Met Lys Asn  Thr Thr Asn Thr Arg  Arg Gly Thr
    2480                 2485                 2490

Gly Asn  Ile Gly Glu Thr Leu  Gly Glu Lys Trp Lys  Ser Arg Leu
    2495                 2500                 2505

Asn Ala  Leu Gly Lys Ser Glu  Phe Gln Ile Tyr Lys  Lys Ser Gly
    2510                 2515                 2520

Ile Gln  Glu Val Asp Arg Thr  Leu Ala Lys Glu Gly  Ile Lys Arg
    2525                 2530                 2535

Gly Glu  Thr Asp His His Ala  Val Ser Arg Gly Ser  Ala Lys Leu
    2540                 2545                 2550

Arg Trp  Phe Val Glu Arg Asn  Met Val Thr Pro Glu  Gly Lys Val
    2555                 2560                 2565

Val Asp  Leu Gly Cys Gly Arg  Gly Gly Trp Ser Tyr  Tyr Cys Gly
    2570                 2575                 2580

Gly Leu  Lys Asn Val Arg Glu  Val Lys Gly Leu Thr  Lys Gly Gly
    2585                 2590                 2595

Pro Gly  His Glu Glu Pro Ile  Pro Met Ser Thr Tyr  Gly Trp Asn
    2600                 2605                 2610

Leu Val  Arg Leu Gln Ser Gly  Val Asp Val Phe Phe  Ile Pro Pro
    2615                 2620                 2625

Glu Lys  Cys Asp Thr Leu Leu  Cys Asp Ile Gly Glu  Ser Ser Pro
    2630                 2635                 2640

Asn Pro  Thr Val Glu Ala Gly  Arg Thr Leu Arg Val  Leu Asn Leu
    2645                 2650                 2655

Val Glu  Asn Trp Leu Asn Asn  Asn Thr Gln Phe Cys  Ile Lys Val
    2660                 2665                 2670

Leu Asn  Pro Tyr Met Pro Ser  Val Ile Glu Lys Met  Glu Ala Leu
    2675                 2680                 2685

Gln Arg  Lys Tyr Gly Gly Ala  Leu Val Arg Asn Pro  Leu Ser Arg
    2690                 2695                 2700

Asn Ser  Thr His Glu Met Tyr  Trp Val Ser Asn Ala  Ser Gly Asn
    2705                 2710                 2715

Ile Val  Ser Ser Val Asn Met  Ile Ser Arg Met Leu  Ile Asn Arg
    2720                 2725                 2730
```

-continued

```
Phe Thr Met Arg Tyr Lys Lys Ala Thr Tyr Glu Pro Asp Val Asp
    2735                2740                2745

Leu Gly Ser Gly Thr Arg Asn Ile Gly Ile Glu Ser Glu Ile Pro
    2750                2755                2760

Asn Leu Asp Ile Ile Gly Lys Arg Ile Glu Lys Ile Lys Gln Glu
    2765                2770                2775

His Glu Thr Ser Trp His Tyr Asp Gln Asp His Pro Tyr Lys Thr
    2780                2785                2790

Trp Ala Tyr His Gly Ser Tyr Glu Thr Lys Gln Thr Gly Ser Ala
    2795                2800                2805

Ser Ser Met Val Asn Gly Val Val Arg Leu Leu Thr Lys Pro Trp
    2810                2815                2820

Asp Val Val Pro Met Val Thr Gln Met Ala Met Thr Asp Thr Thr
    2825                2830                2835

Pro Phe Gly Gln Gln Arg Val Phe Lys Glu Lys Val Asp Thr Arg
    2840                2845                2850

Thr Gln Glu Pro Lys Glu Gly Thr Lys Lys Leu Met Lys Ile Thr
    2855                2860                2865

Ala Glu Trp Leu Trp Lys Glu Leu Gly Lys Lys Lys Thr Pro Arg
    2870                2875                2880

Met Cys Thr Arg Glu Glu Phe Thr Arg Lys Val Arg Ser Asn Ala
    2885                2890                2895

Ala Leu Gly Ala Ile Phe Thr Asp Glu Asn Lys Trp Lys Ser Ala
    2900                2905                2910

Arg Glu Ala Val Glu Asp Ser Arg Phe Trp Glu Leu Val Asp Lys
    2915                2920                2925

Glu Arg Asn Leu His Leu Glu Gly Lys Cys Glu Thr Cys Val Tyr
    2930                2935                2940

Asn Met Met Gly Lys Arg Glu Lys Lys Leu Gly Glu Phe Gly Lys
    2945                2950                2955

Ala Lys Gly Ser Arg Ala Ile Trp Tyr Met Trp Leu Gly Ala Arg
    2960                2965                2970

Phe Leu Glu Phe Glu Ala Leu Gly Phe Leu Asn Glu Asp His Trp
    2975                2980                2985

Phe Ser Arg Glu Asn Ser Leu Ser Gly Val Glu Gly Glu Gly Leu
    2990                2995                3000

His Lys Leu Gly Tyr Ile Leu Arg Asp Val Ser Lys Lys Glu Gly
    3005                3010                3015

Gly Ala Met Tyr Ala Asp Asp Thr Ala Gly Trp Asp Thr Arg Ile
    3020                3025                3030

Thr Leu Glu Asp Leu Lys Asn Glu Glu Met Val Thr Asn His Met
    3035                3040                3045

Glu Gly Glu His Lys Lys Leu Ala Glu Ala Ile Phe Lys Leu Thr
    3050                3055                3060

Tyr Gln Asn Lys Val Val Arg Val Gln Arg Pro Thr Pro Arg Gly
    3065                3070                3075

Thr Val Met Asp Ile Ile Ser Arg Arg Asp Gln Arg Gly Ser Gly
    3080                3085                3090

Gln Val Gly Thr Tyr Gly Leu Asn Thr Phe Thr Asn Met Glu Ala
    3095                3100                3105

Gln Leu Ile Arg Gln Met Glu Gly Glu Gly Val Phe Lys Ser Ile
    3110                3115                3120

Gln His Leu Thr Ile Thr Glu Glu Ile Ala Val Gln Asn Trp Leu
```

```
    3125                3130                3135

Ala Arg  Val Gly Arg Glu Arg  Leu Ser Arg Met Ala  Ile Ser Gly
    3140                3145                3150

Asp Asp  Cys Val Val Lys Pro  Leu Asp Asp Arg Phe  Ala Ser Ala
    3155                3160                3165

Leu Thr  Ala Leu Asn Asp Met  Gly Lys Ile Arg Lys  Asp Ile Gln
    3170                3175                3180

Gln Trp  Glu Pro Ser Arg Gly  Trp Asn Asp Trp Thr  Gln Val Pro
    3185                3190                3195

Phe Cys  Ser His His Phe His  Glu Leu Ile Met Lys  Asp Gly Arg
    3200                3205                3210

Val Leu  Val Val Pro Cys Arg  Asn Gln Asp Glu Leu  Ile Gly Arg
    3215                3220                3225

Ala Arg  Ile Ser Gln Gly Ala  Gly Trp Ser Leu Arg  Glu Thr Ala
    3230                3235                3240

Cys Leu  Gly Lys Ser Tyr Ala  Gln Met Trp Ser Leu  Met Tyr Phe
    3245                3250                3255

His Arg  Arg Asp Leu Arg Leu  Ala Ala Asn Ala Ile  Cys Ser Ala
    3260                3265                3270

Val Pro  Ser His Trp Val Pro  Thr Ser Arg Thr Thr  Trp Ser Ile
    3275                3280                3285

His Ala  Lys His Glu Trp Met  Thr Thr Glu Asp Met  Leu Thr Val
    3290                3295                3300

Trp Asn  Arg Val Trp Ile Gln  Glu Asn Pro Trp Met  Glu Asp Lys
    3305                3310                3315

Thr Pro  Val Glu Ser Trp Glu  Glu Ile Pro Tyr Leu  Gly Lys Arg
    3320                3325                3330

Glu Asp  Gln Trp Cys Gly Ser  Leu Ile Gly Leu Thr  Ser Arg Ala
    3335                3340                3345

Thr Trp  Ala Lys Asn Ile Gln  Ala Ala Ile Asn Gln  Val Arg Ser
    3350                3355                3360

Leu Ile  Gly Asn Glu Glu Tyr  Thr Asp Tyr Met Pro  Ser Met Lys
    3365                3370                3375

Arg Phe  Arg Arg Glu Glu Glu  Glu Ala Gly Val Leu  Trp
    3380                3385                3390
```

<210> SEQ ID NO 32
<211> LENGTH: 10723
<212> TYPE: DNA
<213> ORGANISM: Artificial Sequence
<220> FEATURE:
<223> OTHER INFORMATION: Derived from Dengue virus serotype 2/Dengue virus serotype 4, DenVax-4j

<400> SEQUENCE: 32

```
agttgttagt ctacgtggac cgacaaagac agattctttg agggagctaa gctcaacgta     60

gttctaacag ttttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagctctg caggcatgat cattatgctg    420

attccaacag tgatggcgtt ccatttaacc acgcgtgatg gcgaacccct catgatagtg    480
```

```
gcaaaacatg aaagggggag acctctcttg tttaagacaa cagaggggat caacaaatgc    540
actctcattg ccatggactt gggtgaaatg tgtgaggaca ctgtcacgta taaatgcccc    600
ttactggtca ataccgaacc tgaagacatt gattgctggt gcaatctcac gtctacctgg    660
gtcatgtatg ggacatgcac ccagagcgga gaacggagac gagagaagcg ctcagtagct    720
ttaacaccac attcaggaat gggattggaa acaagagctg agacatggat gtcatcggaa    780
ggggcttgga agcatgctca gagagtagag agctggatac tcagaaaccc aggattcgcg    840
ctcttggcag gatttatggc ttatatgatt gggcaaacag gaatccagcg aactgtcttc    900
tttgtcctaa tgatgctggt cgccccatcc tacggaatgc gatgcgtagg agtaggaaac    960
agagactttg tggaaggagt ctcaggtgga gcatgggtcg atctggtgct agaacatgga   1020
ggatgcgtca caaccatggc ccagggaaaa ccaaccttgg attttgaact gactaagaca   1080
acagccaagg aagtggctct gttaagaacc tattgcattg aagcctcaat atcaaacata   1140
accacggcaa caagatgtcc aacgcaagga gagccttatc taaaagagga acaagaccaa   1200
cagtacattt gccggagaga tgtggtagac agagggtggg gcaatggctg tggcttgttt   1260
ggaaaaggag gagttgtgac atgtgcgaag ttttcatgtt cggggaagat aacaggcaat   1320
ttggtccaaa ttgagaacct tgaatacaca gtggttgtaa cagtccacaa tggagacacc   1380
catgcagtag gaaatgacac gtccaatcat ggagttacag ccacgataac tcccaggtca   1440
ccatcggtgg aagtcaaatt gccggactat ggagaactaa cactcgattg tgaacccagg   1500
tctggaattg actttaatga gatgattctg atgaaaatga aaaagaaaac atggcttgtg   1560
cataagcaat ggtttttgga tctacctcta ccatggacag caggagcaga cacatcagag   1620
gttcactgga attacaaaga gagaatggtg acatttaagg ttcctcatgc caagagacag   1680
gatgtgacag tgctgggatc tcaggaagga gccatgcatt ctgccctcgc tggagccaca   1740
gaagtggact ccggtgatgg aaatcacatg tttgcaggac atctcaagtg caaagtccgt   1800
atggagaaat tgagaatcaa gggaatgtca tacacgatgt gttcaggaaa gttctcaatt   1860
gacaaagaga tggcagaaac acagcatggg acaacagtgg tgaaagtcaa gtatgaaggt   1920
gctggagctc cgtgtaaagt ccccatagag ataagagatg tgaacaagga aaaagtggtt   1980
gggcgtatca tctcatccac ccctttggct gagaatacca acagtgtaac caacatagag   2040
ttagaacccc cctttgggga cagctacata gtgataggtg ttggaaacag tgcattaaca   2100
ctccattggt tcaggaaagg gagttccatt ggcaagatgt ttgagtccac atacagaggt   2160
gcaaaacgaa tggccattct aggtgaaaca gcttgggatt ttggttccgt tggtggactg   2220
ttcacatcat tgggaaaggc tgtgcaccag gtttttggaa gtgtgtatac aaccctgttt   2280
ggaggagtct catggatgat tagaatccta attgggttcc tagtgttgtg gattggcacg   2340
aactcaagga acacttcaat ggctatgacg tgcatagctg ccggcattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
```

ctcattgatg gccccgaaac agcagaatgc cccaacacaa atagagcttg gaattcgttg 2880
gaagttgaag actatggctt tggagtattc accaccaata tatggctaaa attgaaagaa 2940
aaacaggatg tattctgcga ctcaaaactc atgtcagcgg ccataaaaga caacagagcc 3000
gtccatgccg atatgggtta ttggatagaa agtgcactca atgacacatg gaagatagag 3060
aaagcctctt tcattgaagt taaaaactgc cactggccaa aatcacacac cctctggagc 3120
aatggagtgc tagaaagtga gatgataatt ccaaagaatc tcgctggacc agtgtctcaa 3180
cacaactata gaccaggcta ccatacacaa ataacaggac catggcatct aggtaagctt 3240
gagatggact ttgatttctg tgatggaaca acagtggtag tgactgagga ctgcggaaat 3300
agaggaccct ctttgagaac aaccactgcc tctggaaaac tcataacaga atggtgctgc 3360
cgatcttgca cattaccacc gctaagatac agaggtgagg atgggtgctg gtacgggatg 3420
gaaatcagac cattgaagga gaaagaagag aatttggtca actccttggt cacagctgga 3480
catgggcagg tcgacaactt ttcactagga gtcttgggaa tggcattgtt cctggaggaa 3540
atgcttagga cccgagtagg aacgaaacat gcaatactac tagttgcagt ttcttttgtg 3600
acattgatca cagggaacat gtcctttaga gacctgggaa gagtgatggt tatggtaggc 3660
gccactatga cggatgacat aggtatgggc gtgacttatc ttgccctact agcagccttc 3720
aaagtcagac caacttttgc agctggacta ctcttgagaa agctgacctc caaggaattg 3780
atgatgacta ctataggaat tgtactcctc tcccagagca ccataccaga gaccattctt 3840
gagttgactg atgcgttagc cttaggcatg atggtcctca aaatggtgag aaatatggaa 3900
aagtatcaat tggcagtgac tatcatggct atcttgtgcg tcccaaacgc agtgatatta 3960
caaaacgcat ggaaagtgag ttgcacaata ttggcagtgg tgtccgtttc cccactgttc 4020
ttaacatcct cacagcaaaa aacagattgg ataccattag cattgacgat caaaggtctc 4080
aatccaacag ctatttttct aacaaccctc tcaagaacca gcaagaaaag gagctggcca 4140
ttaaatgagg ctatcatggc agtcgggatg gtgagcattt tagccagttc tctcctaaaa 4200
aatgatattc ccatgacagg accattagtg gctggagggc tcctcactgt gtgctacgtg 4260
ctcactggac gatcggccga tttggaactg gagagagcag ccgatgtcaa atgggaagac 4320
caggcagaga tatcaggaag cagtccaatc ctgtcaataa caatatcaga agatggtagc 4380
atgtcgataa aaaatgaaga ggaagaacaa acactgacca tactcattag aacaggattg 4440
ctggtgatct caggactttt tcctgtatca ataccaatca cggcagcagc atggtacctg 4500
tgggaagtga agaaacaacg ggccggagta ttgtgggatg ttccttcacc cccacccatg 4560
ggaaaggctg aactggaaga tggagcctat agaattaagc aaaaagggat tcttggatat 4620
tcccagatcg gagccggagt ttacaaagaa ggaacattcc atacaatgtg gcatgtcaca 4680
cgtggcgctg ttctaatgca taaaggaaag aggattgaac catcatgggc ggacgtcaag 4740
aaagacctaa tatcatatgg aggaggctgg aagttagaag gagaatggaa ggaaggagaa 4800
gaagtccagg tattggcact ggagcctgga aaaaatccaa gagccgtcca aacgaaacct 4860
ggtcttttca aaaccaacgc cggaacaata ggtgctgtat ctctggactt ttctcctgga 4920
acgtcaggat ctccaattat cgacaaaaaa ggaaaagttg tgggtcttta tggtaatggt 4980
gttgttacaa ggagtggagc atatgtgagt gctatagccc agactgaaaa aagcattgaa 5040
gacaacccag agatcgaaga tgacattttc cgaaagagaa gactgaccat catggacctc 5100
cacccaggag cgggaaagac gaagagatac cttccggcca tagtcagaga agctataaaa 5160
cggggtttga gaacattaat cttggccccc actagagttg tggcagctga aatggaggaa 5220
gcccttagag gacttccaat aagataccag accccagcca tcagagctgt gcacaccggg 5280
cgggagattg tggacctaat gtgtcatgcc acatttacca tgaggctgct atcaccagtt 5340
agagtgccaa actacaacct gattatcatg gacgaagccc atttcacaga cccagcaagt 5400
atagcagcta gaggatacat ctcaactcga gtggagatgg gtgaggcagc tgggattttt 5460
atgacagcca ctcccccggg aagcagagac ccatttcctc agagcaatgc accaatcata 5520
gatgaagaaa gagaaatccc tgaacgctcg tggaattccg gacatgaatg ggtcacggat 5580
tttaaaggga agactgtttg gttcgttcca agtataaaag caggaaatga tatagcagct 5640
tgcctgagga aaaatggaaa gaaagtgata caactcagta ggaagacctt tgattctgag 5700
tatgtcaaga ctagaaccaa tgattgggac ttcgtggtta caactgacat ttcagaaatg 5760
ggtgccaatt tcaaggctga gagggttata gaccccagac gctgcatgaa accagtcata 5820
ctaacagatg gtgaagagcg ggtgattctg gcaggaccta tgccagtgac ccactctagt 5880
gcagcacaaa gaagagggag aataggaaga aatccaaaaa atgagaatga ccagtacata 5940
tacatggggg aacctctgga aaatgatgaa gactgtgcac actggaaaga agctaaaatg 6000
ctcctagata acatcaacac gccagaagga atcattccta gcatgttcga accagagcgt 6060
gaaaaggtgg atgccattga tggcgaatac cgcttgagag gagaagcaag gaaaaccttt 6120
gtagacttaa tgagaagagg agacctacca gtctggttgg cctacagagt ggcagctgaa 6180
ggcatcaact acgcagacag aaggtggtgt tttgatggag tcaagaacaa ccaaatccta 6240
gaagaaaacg tggaagttga aatctggaca aaagaagggg aaaggaagaa attgaaaccc 6300
agatggttgg atgctaggat ctattctgac ccactggcgc taaaagaatt taaggaattt 6360
gcagccggaa gaaagtctct gaccctgaac ctaatcacag aaatgggtag gctcccaacc 6420
ttcatgactc agaaggcaag agacgcactg gacaacttag cagtgctgca cacggctgag 6480
gcaggtggaa gggcgtacaa ccatgctctc agtgaactgc cggagaccct ggagacattg 6540
cttttactga cacttctggc tacagtcacg ggagggatct ttttattctt gatgagcgca 6600
aggggcatag ggaagatgac cctgggaatg tgctgcataa tcacggctag catcctccta 6660
tggtacgcac aaatacagcc acactggata gcagcttcaa taatactgga gtttttctc 6720
atagttttgc ttattccaga acctgaaaaa cagagaacac cccaagacaa ccaactgacc 6780
tacgttgtca tagccatcct cacagtggtg gccgcaacca tggcaaacga gatgggtttc 6840
ctagaaaaaa cgaagaaaga tctcggattg ggaagcattg caacccagca acccgagagc 6900
aacatcctgg acatagatct acgtcctgca tcagcatgga cgctgtatgc cgtggccaca 6960
acatttgtta caccaatgtt gagacatagc attgaaaatt cctcagtgaa tgtgtcccta 7020
acagctatag ccaaccaagc cacagtgtta atgggtctcg ggaaaggatg gccattgtca 7080
aagatggaca tcggagttcc ccttctcgcc attggatgct actcacaagt caaccccata 7140
actctcacag cagctctttt cttattggta gcacattatg ccatcatagg gccaggactc 7200
caagcaaaag caaccagaga agctcagaaa agagcagcgg cgggcatcat gaaaaaccca 7260
actgtcgatg gaataacagt gattgaccta gatccaatac cttatgatcc aaagtttgaa 7320
aagcagttgg gacaagtaat gctcctagtc ctctgcgtga ctcaagtatt gatgatgagg 7380
actacatggg ctctgtgtga ggctttaacc ttagctaccg ggcccatctc cacattgtgg 7440
gaaggaaatc cagggaggtt ttggaacact accattgcgg tgtcaatggc taacattttt 7500
agagggagtt acttggccgg agctggactt ctcttttcta ttatgaagaa cacaaccaac 7560
acaagaaggg gaactggcaa cataggagag acgcttggag agaaatggaa aagccgattg 7620
aacgcattgg gaaaaagtga attccagatc tacaagaaaa gtggaatcca ggaagtggat 7680
agaaccttag caaaagaagg cattaaaaga ggagaaacgg accatcacgc tgtgtcgcga 7740
ggctcagcaa aactgagatg gttcgttgag agaaacatgg tcacaccaga agggaaagta 7800
gtggacctcg gttgtggcag aggaggctgg tcatactatt gtggaggact aaagaatgta 7860
agagaagtca aaggcctaac aaaaggagga ccaggacacg aagaacccat ccccatgtca 7920
acatatgggt ggaatctagt gcgtcttcaa agtggagttg acgttttctt catcccgcca 7980
gaaaagtgtg acacattatt gtgtgacata ggggagtcat caccaaatcc cacagtggaa 8040
gcaggacgaa cactcagagt ccttaactta gtagaaaatt ggttgaacaa caacactcaa 8100
ttttgcataa aggttctcaa cccatatatg ccctcagtca tagaaaaaat ggaagcacta 8160
caaaggaaat atggaggagc cttagtgagg aatccactct cacgaaactc cacacatgag 8220
atgtactggg tatccaatgc ttccgggaac atagtgtcat cagtgaacat gatttcaagg 8280
atgttgatca acagatttac aatgagatac aagaaagcca cttacgagcc ggatgttgac 8340
ctcggaagcg gaacccgtaa catcgggatt gaaagtgaga taccaaacct agatataatt 8400
gggaaaagaa tagaaaaaat aaagcaagag catgaaacat catggcacta tgaccaagac 8460
cacccataca aaacgtgggc ataccatggt agctatgaaa caaaacagac tggatcagca 8520
tcatccatgg tcaacggagt ggtcaggctg ctgacaaaac cttgggacgt cgtccccatg 8580
gtgacacaga tggcaatgac agacacgact ccatttggac aacagcgcgt tttaaagag 8640 aaagtggaca cgagaaccca agaaccgaaa gaaggcacga agaaactaat gaaaataaca 8700
gcagagtggc tttggaaaga attagggaag aaaaagacac ccaggatgtg caccagagaa 8760
gaattcacaa gaaaggtgag aagcaatgca gccttggggg ccatattcac tgatgagaac 8820
aagtggaagt cggcacgtga ggctgttgaa gatagtaggt tttgggagct ggttgacaag 8880
gaaaggaatc tccatcttga aggaaagtgt gaaacatgtg tgtacaacat gatgggaaaa 8940
agagagaaga agctagggga attcggcaag gcaaaaggca gcagagccat atggtacatg 9000
tggcttggag cacgcttctt agagtttgaa gccctaggat tcttaaatga agatcactgg 9060
ttctccagag agaactccct gagtggagtg gaaggagaag ggctgcacaa gctaggttac 9120
attctaagag acgtgagcaa gaaagaggga ggagcaatgt atgccgatga caccgcagga 9180
tgggatacaa gaatcacact agaagaccta aaaaatgaag aaatggtaac aaaccacatg 9240
gaaggagaac acaagaaact agccgaggcc attttcaaac taacgtacca aaacaaggtg 9300
gtgcgtgtgc aaagaccaac accaagaggc acagtaatgg acatcatatc gagaagagac 9360
caaagaggta gtggacaagt tggcacctat ggactcaata ctttcaccaa tatggaagcc 9420
caactaatca gacagatgga gggagaagga gtctttaaaa gcattcagca cctaacaatc 9480
acagaagaaa tcgctgtgca aaactggtta gcaagagtgg ggcgcgaaag gttatcaaga 9540
atggccatca gtggagatga ttgtgttgtg aaacctttag atgacaggtt cgcaagcgct 9600
ttaacagctc taaatgacat gggaaagatt aggaaagaca tacaacaatg ggaaccttca 9660
agaggatgga atgattggac acaagtgccc ttctgttcac accatttcca tgagttaatc 9720
atgaaagacg gtcgcgtact cgttgttcca tgtagaaacc aagatgaact gattggcaga 9780
gcccgaatct cccaaggagc agggtggtct ttgcgggaga cggcctgttt ggggaagtct 9840
tacgcccaaa tgtggagctt gatgtacttc cacagacgcg acctcaggct ggcggcaaat 9900
gctatttgct cggcagtacc atcacattgg gttccaacaa gtcgaacaac ctggtccata 9960

```
catgctaaac atgaatggat gacaacggaa gacatgctga cagtctggaa cagggtgtgg  10020

attcaagaaa acccatggat ggaagacaaa actccagtgg aatcatggga ggaaatccca  10080

tacttgggga aaagagaaga ccaatggtgc ggctcattga ttgggttaac aagcagggcc  10140

acctgggcaa agaacatcca agcagcaata aatcaagtta gatcccttat aggcaatgaa  10200

gaatacacag attacatgcc atccatgaaa agattcagaa gagaagagga agaagcagga  10260

gttctgtggt agaaagcaaa actaacatga aacaaggcta gaagtcaggt cggattaagc  10320

catagtacgg aaaaaactat gctacctgtg agccccgtcc aaggacgtta aaagaagtca  10380

ggccatcata aatgccatag cttgagtaaa ctatgcagcc tgtagctcca cctgagaagg  10440

tgtaaaaaat ccgggaggcc acaaaccatg gaagctgtac gcatggcgta gtggactagc  10500

ggttagagga gacccctccc ttacaaatcg cagcaacaat gggggcccaa ggcgagatga  10560

agctgtagtc tcgctggaag gactagaggt tagaggagac ccccccgaaa caaaaaacag  10620

catattgacg ctgggaaaga ccagagatcc tgctgtctcc tcagcatcat tccaggcaca  10680

gaacgccaga aaatggaatg gtgctgttga atcaacaggt tct                    10723
```

```
<210> SEQ ID NO 33
<211> LENGTH: 3391
<212> TYPE: PRT
<213> ORGANISM: Artificial Sequence
<220> FEATURE:
<223> OTHER INFORMATION: Derived from Dengue virus serotype 2/Dengue
      virus serotype 4, DenVax-4j

<400> SEQUENCE: 33

Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Ser Ser Ala Gly Met Ile Ile Met Leu Ile Pro Thr Val
            100                 105                 110

Met Ala Phe His Leu Thr Thr Arg Asp Gly Glu Pro Leu Met Ile Val
        115                 120                 125

Ala Lys His Glu Arg Gly Arg Pro Leu Leu Phe Lys Thr Thr Glu Gly
    130                 135                 140

Ile Asn Lys Cys Thr Leu Ile Ala Met Asp Leu Gly Glu Met Cys Glu
145                 150                 155                 160

Asp Thr Val Thr Tyr Lys Cys Pro Leu Leu Val Asn Thr Glu Pro Glu
                165                 170                 175

Asp Ile Asp Cys Trp Cys Asn Leu Thr Ser Thr Trp Val Met Tyr Gly
            180                 185                 190

Thr Cys Thr Gln Ser Gly Glu Arg Arg Arg Glu Lys Arg Ser Val Ala
        195                 200                 205

Leu Thr Pro His Ser Gly Met Gly Leu Glu Thr Arg Ala Glu Thr Trp
    210                 215                 220
```

Met Ser Ser Glu Gly Ala Trp Lys His Ala Gln Arg Val Glu Ser Trp
225 230 235 240

Ile Leu Arg Asn Pro Gly Phe Ala Leu Leu Ala Gly Phe Met Ala Tyr
245 250 255

Met Ile Gly Gln Thr Gly Ile Gln Arg Thr Val Phe Phe Val Leu Met
260 265 270

Met Leu Val Ala Pro Ser Tyr Gly Met Arg Cys Val Gly Val Gly Asn
275 280 285

Arg Asp Phe Val Glu Gly Val Ser Gly Gly Ala Trp Val Asp Leu Val
290 295 300

Leu Glu His Gly Gly Cys Val Thr Thr Met Ala Gln Gly Lys Pro Thr
305 310 315 320

Leu Asp Phe Glu Leu Thr Lys Thr Thr Ala Lys Glu Val Ala Leu Leu
325 330 335

Arg Thr Tyr Cys Ile Glu Ala Ser Ile Ser Asn Ile Thr Thr Ala Thr
340 345 350

Arg Cys Pro Thr Gln Gly Glu Pro Tyr Leu Lys Glu Glu Gln Asp Gln
355 360 365

Gln Tyr Ile Cys Arg Arg Asp Val Val Asp Arg Gly Trp Gly Asn Gly
370 375 380

Cys Gly Leu Phe Gly Lys Gly Gly Val Val Thr Cys Ala Lys Phe Ser
385 390 395 400

Cys Ser Gly Lys Ile Thr Gly Asn Leu Val Gln Ile Glu Asn Leu Glu
405 410 415

Tyr Thr Val Val Val Thr Val His Asn Gly Asp Thr His Ala Val Gly
420 425 430

Asn Asp Thr Ser Asn His Gly Val Thr Ala Thr Ile Thr Pro Arg Ser
435 440 445

Pro Ser Val Glu Val Lys Leu Pro Asp Tyr Gly Glu Leu Thr Leu Asp
450 455 460

Cys Glu Pro Arg Ser Gly Ile Asp Phe Asn Glu Met Ile Leu Met Lys
465 470 475 480

Met Lys Lys Lys Thr Trp Leu Val His Lys Gln Trp Phe Leu Asp Leu
485 490 495

Pro Leu Pro Trp Thr Ala Gly Ala Asp Thr Ser Glu Val His Trp Asn
500 505 510

Tyr Lys Glu Arg Met Val Thr Phe Lys Val Pro His Ala Lys Arg Gln
515 520 525

Asp Val Thr Val Leu Gly Ser Gln Glu Gly Ala Met His Ser Ala Leu
530 535 540

Ala Gly Ala Thr Glu Val Asp Ser Gly Asp Gly Asn His Met Phe Ala
545 550 555 560

Gly His Leu Lys Cys Lys Val Arg Met Glu Lys Leu Arg Ile Lys Gly
565 570 575

Met Ser Tyr Thr Met Cys Ser Gly Lys Phe Ser Ile Asp Lys Glu Met
580 585 590

Ala Glu Thr Gln His Gly Thr Thr Val Val Lys Val Lys Tyr Glu Gly
595 600 605

Ala Gly Ala Pro Cys Lys Val Pro Ile Glu Ile Arg Asp Val Asn Lys
610 615 620

Glu Lys Val Val Gly Arg Ile Ile Ser Ser Thr Pro Leu Ala Glu Asn
625 630 635 640

-continued

Thr Asn Ser Val Thr Asn Ile Glu Leu Glu Pro Pro Phe Gly Asp Ser
645 650 655

Tyr Ile Val Ile Gly Val Gly Asn Ser Ala Leu Thr Leu His Trp Phe
660 665 670

Arg Lys Gly Ser Ser Ile Gly Lys Met Phe Glu Ser Thr Tyr Arg Gly
675 680 685

Ala Lys Arg Met Ala Ile Leu Gly Glu Thr Ala Trp Asp Phe Gly Ser
690 695 700

Val Gly Gly Leu Phe Thr Ser Leu Gly Lys Ala Val His Gln Val Phe
705 710 715 720

Gly Ser Val Tyr Thr Thr Leu Phe Gly Gly Val Ser Trp Met Ile Arg
725 730 735

Ile Leu Ile Gly Phe Leu Val Leu Trp Ile Gly Thr Asn Ser Arg Asn
740 745 750

Thr Ser Met Ala Met Thr Cys Ile Ala Ala Gly Ile Val Thr Leu Tyr
755 760 765

Leu Gly Val Met Val Gln Ala Asp Ser Gly Cys Val Val Ser Trp Lys
770 775 780

Asn Lys Glu Leu Lys Cys Gly Ser Gly Ile Phe Ile Thr Asp Asn Val
785 790 795 800

His Thr Trp Thr Glu Gln Tyr Lys Phe Gln Pro Glu Ser Pro Ser Lys
805 810 815

Leu Ala Ser Ala Ile Gln Lys Ala His Glu Glu Asp Ile Cys Gly Ile
820 825 830

Arg Ser Val Thr Arg Leu Glu Asn Leu Met Trp Lys Gln Ile Thr Pro
835 840 845

Glu Leu Asn His Ile Leu Ser Glu Asn Glu Val Lys Leu Thr Ile Met
850 855 860

Thr Gly Asp Ile Lys Gly Ile Met Gln Ala Gly Lys Arg Ser Leu Arg
865 870 875 880

Pro Gln Pro Thr Glu Leu Lys Tyr Ser Trp Lys Thr Trp Gly Lys Ala
885 890 895

Lys Met Leu Ser Thr Glu Ser His Asn Gln Thr Phe Leu Ile Asp Gly
900 905 910

Pro Glu Thr Ala Glu Cys Pro Asn Thr Asn Arg Ala Trp Asn Ser Leu
915 920 925

Glu Val Glu Asp Tyr Gly Phe Gly Val Phe Thr Thr Asn Ile Trp Leu
930 935 940

Lys Leu Lys Glu Lys Gln Asp Val Phe Cys Asp Ser Lys Leu Met Ser
945 950 955 960

Ala Ala Ile Lys Asp Asn Arg Ala Val His Ala Asp Met Gly Tyr Trp
965 970 975

Ile Glu Ser Ala Leu Asn Asp Thr Trp Lys Ile Glu Lys Ala Ser Phe
980 985 990

Ile Glu Val Lys Asn Cys His Trp Pro Lys Ser His Thr Leu Trp Ser
995 1000 1005

Asn Gly Val Leu Glu Ser Glu Met Ile Ile Pro Lys Asn Leu Ala
1010 1015 1020

Gly Pro Val Ser Gln His Asn Tyr Arg Pro Gly Tyr His Thr Gln
1025 1030 1035

Ile Thr Gly Pro Trp His Leu Gly Lys Leu Glu Met Asp Phe Asp
1040 1045 1050

Phe Cys Asp Gly Thr Thr Val Val Val Thr Glu Asp Cys Gly Asn

```
    1055                1060                1065

Arg Gly  Pro Ser Leu Arg Thr  Thr Thr Ala Ser Gly  Lys Leu Ile
    1070                1075                1080

Thr Glu  Trp Cys Cys Arg Ser  Cys Thr Leu Pro Pro  Leu Arg Tyr
    1085                1090                1095

Arg Gly  Glu Asp Gly Cys Trp  Tyr Gly Met Glu Ile  Arg Pro Leu
    1100                1105                1110

Lys Glu  Lys Glu Glu Asn Leu  Val Asn Ser Leu Val  Thr Ala Gly
    1115                1120                1125

His Gly  Gln Val Asp Asn Phe  Ser Leu Gly Val Leu  Gly Met Ala
    1130                1135                1140

Leu Phe  Leu Glu Glu Met Leu  Arg Thr Arg Val Gly  Thr Lys His
    1145                1150                1155

Ala Ile  Leu Leu Val Ala Val  Ser Phe Val Thr Leu  Ile Thr Gly
    1160                1165                1170

Asn Met  Ser Phe Arg Asp Leu  Gly Arg Val Met Val  Met Val Gly
    1175                1180                1185

Ala Thr  Met Thr Asp Asp Ile  Gly Met Gly Val Thr  Tyr Leu Ala
    1190                1195                1200

Leu Leu  Ala Ala Phe Lys Val  Arg Pro Thr Phe Ala  Ala Gly Leu
    1205                1210                1215

Leu Leu  Arg Lys Leu Thr Ser  Lys Glu Leu Met Met  Thr Thr Ile
    1220                1225                1230

Gly Ile  Val Leu Leu Ser Gln  Ser Thr Ile Pro Glu  Thr Ile Leu
    1235                1240                1245

Glu Leu  Thr Asp Ala Leu Ala  Leu Gly Met Met Val  Leu Lys Met
    1250                1255                1260

Val Arg  Asn Met Glu Lys Tyr  Gln Leu Ala Val Thr  Ile Met Ala
    1265                1270                1275

Ile Leu  Cys Val Pro Asn Ala  Val Ile Leu Gln Asn  Ala Trp Lys
    1280                1285                1290

Val Ser  Cys Thr Ile Leu Ala  Val Val Ser Val Ser  Pro Leu Phe
    1295                1300                1305

Leu Thr  Ser Ser Gln Gln Lys  Thr Asp Trp Ile Pro  Leu Ala Leu
    1310                1315                1320

Thr Ile  Lys Gly Leu Asn Pro  Thr Ala Ile Phe Leu  Thr Thr Leu
    1325                1330                1335

Ser Arg  Thr Ser Lys Lys Arg  Ser Trp Pro Leu Asn  Glu Ala Ile
    1340                1345                1350

Met Ala  Val Gly Met Val Ser  Ile Leu Ala Ser Ser  Leu Leu Lys
    1355                1360                1365

Asn Asp  Ile Pro Met Thr Gly  Pro Leu Val Ala Gly  Gly Leu Leu
    1370                1375                1380

Thr Val  Cys Tyr Val Leu Thr  Gly Arg Ser Ala Asp  Leu Glu Leu
    1385                1390                1395

Glu Arg  Ala Ala Asp Val Lys  Trp Glu Asp Gln Ala  Glu Ile Ser
    1400                1405                1410

Gly Ser  Ser Pro Ile Leu Ser  Ile Thr Ile Ser Glu  Asp Gly Ser
    1415                1420                1425

Met Ser  Ile Lys Asn Glu Glu  Glu Glu Gln Thr Leu  Thr Ile Leu
    1430                1435                1440

Ile Arg  Thr Gly Leu Leu Val  Ile Ser Gly Leu Phe  Pro Val Ser
    1445                1450                1455
```

-continued

```
Ile Pro  Ile Thr Ala Ala Ala  Trp Tyr Leu Trp Glu  Val Lys Lys
    1460                 1465                 1470

Gln Arg  Ala Gly Val Leu Trp  Asp Val Pro Ser Pro  Pro Pro Met
    1475                 1480                 1485

Gly Lys  Ala Glu Leu Glu Asp  Gly Ala Tyr Arg Ile  Lys Gln Lys
    1490                 1495                 1500

Gly Ile  Leu Gly Tyr Ser Gln  Ile Gly Ala Gly Val  Tyr Lys Glu
    1505                 1510                 1515

Gly Thr  Phe His Thr Met Trp  His Val Thr Arg Gly  Ala Val Leu
    1520                 1525                 1530

Met His  Lys Gly Lys Arg Ile  Glu Pro Ser Trp Ala  Asp Val Lys
    1535                 1540                 1545

Lys Asp  Leu Ile Ser Tyr Gly  Gly Gly Trp Lys Leu  Glu Gly Glu
    1550                 1555                 1560

Trp Lys  Glu Gly Glu Glu Val  Gln Val Leu Ala Leu  Glu Pro Gly
    1565                 1570                 1575

Lys Asn  Pro Arg Ala Val Gln  Thr Lys Pro Gly Leu  Phe Lys Thr
    1580                 1585                 1590

Asn Ala  Gly Thr Ile Gly Ala  Val Ser Leu Asp Phe  Ser Pro Gly
    1595                 1600                 1605

Thr Ser  Gly Ser Pro Ile Ile  Asp Lys Lys Gly Lys  Val Val Gly
    1610                 1615                 1620

Leu Tyr  Gly Asn Gly Val Val  Thr Arg Ser Gly Ala  Tyr Val Ser
    1625                 1630                 1635

Ala Ile  Ala Gln Thr Glu Lys  Ser Ile Glu Asp Asn  Pro Glu Ile
    1640                 1645                 1650

Glu Asp  Asp Ile Phe Arg Lys  Arg Arg Leu Thr Ile  Met Asp Leu
    1655                 1660                 1665

His Pro  Gly Ala Gly Lys Thr  Lys Arg Tyr Leu Pro  Ala Ile Val
    1670                 1675                 1680

Arg Glu  Ala Ile Lys Arg Gly  Leu Arg Thr Leu Ile  Leu Ala Pro
    1685                 1690                 1695

Thr Arg  Val Val Ala Ala Glu  Met Glu Glu Ala Leu  Arg Gly Leu
    1700                 1705                 1710

Pro Ile  Arg Tyr Gln Thr Pro  Ala Ile Arg Ala Val  His Thr Gly
    1715                 1720                 1725

Arg Glu  Ile Val Asp Leu Met  Cys His Ala Thr Phe  Thr Met Arg
    1730                 1735                 1740

Leu Leu  Ser Pro Val Arg Val  Pro Asn Tyr Asn Leu  Ile Ile Met
    1745                 1750                 1755

Asp Glu  Ala His Phe Thr Asp  Pro Ala Ser Ile Ala  Ala Arg Gly
    1760                 1765                 1770

Tyr Ile  Ser Thr Arg Val Glu  Met Gly Glu Ala Ala  Gly Ile Phe
    1775                 1780                 1785

Met Thr  Ala Thr Pro Pro Gly  Ser Arg Asp Pro Phe  Pro Gln Ser
    1790                 1795                 1800

Asn Ala  Pro Ile Ile Asp Glu  Glu Arg Glu Ile Pro  Glu Arg Ser
    1805                 1810                 1815

Trp Asn  Ser Gly His Glu Trp  Val Thr Asp Phe Lys  Gly Lys Thr
    1820                 1825                 1830

Val Trp  Phe Val Pro Ser Ile  Lys Ala Gly Asn Asp  Ile Ala Ala
    1835                 1840                 1845
```

Cys Leu Arg Lys Asn Gly Lys Lys Val Ile Gln Leu Ser Arg Lys
1850 1855 1860

Thr Phe Asp Ser Glu Tyr Val Lys Thr Arg Thr Asn Asp Trp Asp
1865 1870 1875

Phe Val Val Thr Thr Asp Ile Ser Glu Met Gly Ala Asn Phe Lys
1880 1885 1890

Ala Glu Arg Val Ile Asp Pro Arg Arg Cys Met Lys Pro Val Ile
1895 1900 1905

Leu Thr Asp Gly Glu Glu Arg Val Ile Leu Ala Gly Pro Met Pro
1910 1915 1920

Val Thr His Ser Ser Ala Ala Gln Arg Arg Gly Arg Ile Gly Arg
1925 1930 1935

Asn Pro Lys Asn Glu Asn Asp Gln Tyr Ile Tyr Met Gly Glu Pro
1940 1945 1950

Leu Glu Asn Asp Glu Asp Cys Ala His Trp Lys Glu Ala Lys Met
1955 1960 1965

Leu Leu Asp Asn Ile Asn Thr Pro Glu Gly Ile Ile Pro Ser Met
1970 1975 1980

Phe Glu Pro Glu Arg Glu Lys Val Asp Ala Ile Asp Gly Glu Tyr
1985 1990 1995

Arg Leu Arg Gly Glu Ala Arg Lys Thr Phe Val Asp Leu Met Arg
2000 2005 2010

Arg Gly Asp Leu Pro Val Trp Leu Ala Tyr Arg Val Ala Ala Glu
2015 2020 2025

Gly Ile Asn Tyr Ala Asp Arg Arg Trp Cys Phe Asp Gly Val Lys
2030 2035 2040

Asn Asn Gln Ile Leu Glu Glu Asn Val Glu Val Glu Ile Trp Thr
2045 2050 2055

Lys Glu Gly Glu Arg Lys Lys Leu Lys Pro Arg Trp Leu Asp Ala
2060 2065 2070

Arg Ile Tyr Ser Asp Pro Leu Ala Leu Lys Glu Phe Lys Glu Phe
2075 2080 2085

Ala Ala Gly Arg Lys Ser Leu Thr Leu Asn Leu Ile Thr Glu Met
2090 2095 2100

Gly Arg Leu Pro Thr Phe Met Thr Gln Lys Ala Arg Asp Ala Leu
2105 2110 2115

Asp Asn Leu Ala Val Leu His Thr Ala Glu Ala Gly Gly Arg Ala
2120 2125 2130

Tyr Asn His Ala Leu Ser Glu Leu Pro Glu Thr Leu Glu Thr Leu
2135 2140 2145

Leu Leu Leu Thr Leu Leu Ala Thr Val Thr Gly Gly Ile Phe Leu
2150 2155 2160

Phe Leu Met Ser Ala Arg Gly Ile Gly Lys Met Thr Leu Gly Met
2165 2170 2175

Cys Cys Ile Ile Thr Ala Ser Ile Leu Leu Trp Tyr Ala Gln Ile
2180 2185 2190

Gln Pro His Trp Ile Ala Ala Ser Ile Ile Leu Glu Phe Phe Leu
2195 2200 2205

Ile Val Leu Leu Ile Pro Glu Pro Glu Lys Gln Arg Thr Pro Gln
2210 2215 2220

Asp Asn Gln Leu Thr Tyr Val Val Ile Ala Ile Leu Thr Val Val
2225 2230 2235

Ala Ala Thr Met Ala Asn Glu Met Gly Phe Leu Glu Lys Thr Lys

```
    2240                2245                2250

Lys Asp  Leu Gly Leu Gly Ser  Ile Ala Thr Gln Gln  Pro Glu Ser
    2255                2260                2265

Asn Ile  Leu Asp Ile Asp Leu  Arg Pro Ala Ser Ala  Trp Thr Leu
    2270                2275                2280

Tyr Ala  Val Ala Thr Thr Phe  Val Thr Pro Met Leu  Arg His Ser
    2285                2290                2295

Ile Glu  Asn Ser Ser Val Asn  Val Ser Leu Thr Ala  Ile Ala Asn
    2300                2305                2310

Gln Ala  Thr Val Leu Met Gly  Leu Gly Lys Gly Trp  Pro Leu Ser
    2315                2320                2325

Lys Met  Asp Ile Gly Val Pro  Leu Leu Ala Ile Gly  Cys Tyr Ser
    2330                2335                2340

Gln Val  Asn Pro Ile Thr Leu  Thr Ala Ala Leu Phe  Leu Leu Val
    2345                2350                2355

Ala His  Tyr Ala Ile Ile Gly  Pro Gly Leu Gln Ala  Lys Ala Thr
    2360                2365                2370

Arg Glu  Ala Gln Lys Arg Ala  Ala Ala Gly Ile Met  Lys Asn Pro
    2375                2380                2385

Thr Val  Asp Gly Ile Thr Val  Ile Asp Leu Asp Pro  Ile Pro Tyr
    2390                2395                2400

Asp Pro  Lys Phe Glu Lys Gln  Leu Gly Gln Val Met  Leu Leu Val
    2405                2410                2415

Leu Cys  Val Thr Gln Val Leu  Met Met Arg Thr Thr  Trp Ala Leu
    2420                2425                2430

Cys Glu  Ala Leu Thr Leu Ala  Thr Gly Pro Ile Ser  Thr Leu Trp
    2435                2440                2445

Glu Gly  Asn Pro Gly Arg Phe  Trp Asn Thr Thr Ile  Ala Val Ser
    2450                2455                2460

Met Ala  Asn Ile Phe Arg Gly  Ser Tyr Leu Ala Gly  Ala Gly Leu
    2465                2470                2475

Leu Phe  Ser Ile Met Lys Asn  Thr Thr Asn Thr Arg  Arg Gly Thr
    2480                2485                2490

Gly Asn  Ile Gly Glu Thr Leu  Gly Glu Lys Trp Lys  Ser Arg Leu
    2495                2500                2505

Asn Ala  Leu Gly Lys Ser Glu  Phe Gln Ile Tyr Lys  Lys Ser Gly
    2510                2515                2520

Ile Gln  Glu Val Asp Arg Thr  Leu Ala Lys Glu Gly  Ile Lys Arg
    2525                2530                2535

Gly Glu  Thr Asp His His Ala  Val Ser Arg Gly Ser  Ala Lys Leu
    2540                2545                2550

Arg Trp  Phe Val Glu Arg Asn  Met Val Thr Pro Glu  Gly Lys Val
    2555                2560                2565

Val Asp  Leu Gly Cys Gly Arg  Gly Gly Trp Ser Tyr  Tyr Cys Gly
    2570                2575                2580

Gly Leu  Lys Asn Val Arg Glu  Val Lys Gly Leu Thr  Lys Gly Gly
    2585                2590                2595

Pro Gly  His Glu Glu Pro Ile  Pro Met Ser Thr Tyr  Gly Trp Asn
    2600                2605                2610

Leu Val  Arg Leu Gln Ser Gly  Val Asp Val Phe Phe  Ile Pro Pro
    2615                2620                2625

Glu Lys  Cys Asp Thr Leu Leu  Cys Asp Ile Gly Glu  Ser Ser Pro
    2630                2635                2640
```

```
Asn Pro Thr Val Glu Ala Gly Arg Thr Leu Arg Val Leu Asn Leu
    2645                2650                2655

Val Glu Asn Trp Leu Asn Asn Asn Thr Gln Phe Cys Ile Lys Val
    2660                2665                2670

Leu Asn Pro Tyr Met Pro Ser Val Ile Glu Lys Met Glu Ala Leu
    2675                2680                2685

Gln Arg Lys Tyr Gly Gly Ala Leu Val Arg Asn Pro Leu Ser Arg
    2690                2695                2700

Asn Ser Thr His Glu Met Tyr Trp Val Ser Asn Ala Ser Gly Asn
    2705                2710                2715

Ile Val Ser Ser Val Asn Met Ile Ser Arg Met Leu Ile Asn Arg
    2720                2725                2730

Phe Thr Met Arg Tyr Lys Lys Ala Thr Tyr Glu Pro Asp Val Asp
    2735                2740                2745

Leu Gly Ser Gly Thr Arg Asn Ile Gly Ile Glu Ser Glu Ile Pro
    2750                2755                2760

Asn Leu Asp Ile Ile Gly Lys Arg Ile Glu Lys Ile Lys Gln Glu
    2765                2770                2775

His Glu Thr Ser Trp His Tyr Asp Gln Asp His Pro Tyr Lys Thr
    2780                2785                2790

Trp Ala Tyr His Gly Ser Tyr Glu Thr Lys Gln Thr Gly Ser Ala
    2795                2800                2805

Ser Ser Met Val Asn Gly Val Val Arg Leu Leu Thr Lys Pro Trp
    2810                2815                2820

Asp Val Val Pro Met Val Thr Gln Met Ala Met Thr Asp Thr Thr
    2825                2830                2835

Pro Phe Gly Gln Gln Arg Val Phe Lys Glu Lys Val Asp Thr Arg
    2840                2845                2850

Thr Gln Glu Pro Lys Glu Gly Thr Lys Lys Leu Met Lys Ile Thr
    2855                2860                2865

Ala Glu Trp Leu Trp Lys Glu Leu Gly Lys Lys Lys Thr Pro Arg
    2870                2875                2880

Met Cys Thr Arg Glu Glu Phe Thr Arg Lys Val Arg Ser Asn Ala
    2885                2890                2895

Ala Leu Gly Ala Ile Phe Thr Asp Glu Asn Lys Trp Lys Ser Ala
    2900                2905                2910

Arg Glu Ala Val Glu Asp Ser Arg Phe Trp Glu Leu Val Asp Lys
    2915                2920                2925

Glu Arg Asn Leu His Leu Glu Gly Lys Cys Glu Thr Cys Val Tyr
    2930                2935                2940

Asn Met Met Gly Lys Arg Glu Lys Lys Leu Gly Glu Phe Gly Lys
    2945                2950                2955

Ala Lys Gly Ser Arg Ala Ile Trp Tyr Met Trp Leu Gly Ala Arg
    2960                2965                2970

Phe Leu Glu Phe Glu Ala Leu Gly Phe Leu Asn Glu Asp His Trp
    2975                2980                2985

Phe Ser Arg Glu Asn Ser Leu Ser Gly Val Glu Gly Glu Gly Leu
    2990                2995                3000

His Lys Leu Gly Tyr Ile Leu Arg Asp Val Ser Lys Lys Glu Gly
    3005                3010                3015

Gly Ala Met Tyr Ala Asp Asp Thr Ala Gly Trp Asp Thr Arg Ile
    3020                3025                3030
```

Thr Leu Glu Asp Leu Lys Asn Glu Glu Met Val Thr Asn His Met
3035 3040 3045

Glu Gly Glu His Lys Lys Leu Ala Glu Ala Ile Phe Lys Leu Thr
3050 3055 3060

Tyr Gln Asn Lys Val Val Arg Val Gln Arg Pro Thr Pro Arg Gly
3065 3070 3075

Thr Val Met Asp Ile Ile Ser Arg Arg Asp Gln Arg Gly Ser Gly
3080 3085 3090

Gln Val Gly Thr Tyr Gly Leu Asn Thr Phe Thr Asn Met Glu Ala
3095 3100 3105

Gln Leu Ile Arg Gln Met Glu Gly Glu Gly Val Phe Lys Ser Ile
3110 3115 3120

Gln His Leu Thr Ile Thr Glu Glu Ile Ala Val Gln Asn Trp Leu
3125 3130 3135

Ala Arg Val Gly Arg Glu Arg Leu Ser Arg Met Ala Ile Ser Gly
3140 3145 3150

Asp Asp Cys Val Val Lys Pro Leu Asp Asp Arg Phe Ala Ser Ala
3155 3160 3165

Leu Thr Ala Leu Asn Asp Met Gly Lys Ile Arg Lys Asp Ile Gln
3170 3175 3180

Gln Trp Glu Pro Ser Arg Gly Trp Asn Asp Trp Thr Gln Val Pro
3185 3190 3195

Phe Cys Ser His His Phe His Glu Leu Ile Met Lys Asp Gly Arg
3200 3205 3210

Val Leu Val Val Pro Cys Arg Asn Gln Asp Glu Leu Ile Gly Arg
3215 3220 3225

Ala Arg Ile Ser Gln Gly Ala Gly Trp Ser Leu Arg Glu Thr Ala
3230 3235 3240

Cys Leu Gly Lys Ser Tyr Ala Gln Met Trp Ser Leu Met Tyr Phe
3245 3250 3255

His Arg Arg Asp Leu Arg Leu Ala Ala Asn Ala Ile Cys Ser Ala
3260 3265 3270

Val Pro Ser His Trp Val Pro Thr Ser Arg Thr Thr Trp Ser Ile
3275 3280 3285

His Ala Lys His Glu Trp Met Thr Thr Glu Asp Met Leu Thr Val
3290 3295 3300

Trp Asn Arg Val Trp Ile Gln Glu Asn Pro Trp Met Glu Asp Lys
3305 3310 3315

Thr Pro Val Glu Ser Trp Glu Glu Ile Pro Tyr Leu Gly Lys Arg
3320 3325 3330

Glu Asp Gln Trp Cys Gly Ser Leu Ile Gly Leu Thr Ser Arg Ala
3335 3340 3345

Thr Trp Ala Lys Asn Ile Gln Ala Ala Ile Asn Gln Val Arg Ser
3350 3355 3360

Leu Ile Gly Asn Glu Glu Tyr Thr Asp Tyr Met Pro Ser Met Lys
3365 3370 3375

Arg Phe Arg Arg Glu Glu Glu Glu Ala Gly Val Leu Trp
3380 3385 3390

<210> SEQ ID NO 34
<211> LENGTH: 3391
<212> TYPE: PRT
<213> ORGANISM: Artificial Sequence
<220> FEATURE:
<223> OTHER INFORMATION: Derived from Dengue virus serotype 2/Dengue virus serotype 4, DEN-4i

<400> SEQUENCE: 34

Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Ser Ser Ala Gly Met Ile Ile Met Leu Ile Pro Thr Val
            100                 105                 110

Met Ala Phe His Leu Thr Thr Arg Asp Gly Glu Pro Leu Met Ile Val
        115                 120                 125

Ala Lys His Glu Arg Gly Arg Pro Leu Leu Phe Lys Thr Thr Glu Gly
    130                 135                 140

Ile Asn Lys Cys Thr Leu Ile Ala Met Asp Leu Gly Glu Met Cys Glu
145                 150                 155                 160

Asp Thr Val Thr Tyr Lys Cys Pro Leu Leu Val Asn Thr Glu Pro Glu
                165                 170                 175

Asp Ile Asp Cys Trp Cys Asn Leu Thr Ser Thr Trp Val Met Tyr Gly
            180                 185                 190

Thr Cys Thr Gln Ser Gly Glu Arg Arg Arg Glu Lys Arg Ser Val Ala
        195                 200                 205

Leu Thr Pro His Ser Gly Met Gly Leu Glu Thr Arg Ala Glu Thr Trp
    210                 215                 220

Met Ser Ser Glu Gly Ala Trp Lys His Ala Gln Arg Val Glu Ser Trp
225                 230                 235                 240

Ile Leu Arg Asn Pro Gly Phe Ala Leu Leu Ala Gly Phe Met Ala Tyr
                245                 250                 255

Met Ile Gly Gln Thr Gly Ile Gln Arg Thr Val Phe Phe Val Leu Met
            260                 265                 270

Met Leu Val Ala Pro Ser Tyr Gly Met Arg Cys Val Gly Val Gly Asn
        275                 280                 285

Arg Asp Phe Val Glu Gly Val Ser Gly Gly Ala Trp Val Asp Leu Val
    290                 295                 300

Leu Glu His Gly Gly Cys Val Thr Thr Met Ala Gln Gly Lys Pro Thr
305                 310                 315                 320

Leu Asp Phe Glu Leu Thr Lys Thr Thr Ala Lys Glu Val Ala Leu Leu
                325                 330                 335

Arg Thr Tyr Cys Ile Glu Ala Ser Ile Ser Asn Ile Thr Thr Ala Thr
            340                 345                 350

Arg Cys Pro Thr Gln Gly Glu Pro Tyr Leu Lys Glu Glu Gln Asp Gln
        355                 360                 365

Gln Tyr Ile Cys Arg Arg Asp Val Val Asp Arg Gly Trp Gly Asn Gly
    370                 375                 380

Cys Gly Leu Phe Gly Lys Gly Gly Val Val Thr Cys Ala Lys Phe Ser
385                 390                 395                 400

-continued

```
Cys Ser Gly Lys Ile Thr Gly Asn Leu Val Gln Ile Glu Asn Leu Glu
                405                 410                 415

Tyr Thr Val Val Val Thr Val His Asn Gly Asp Thr His Ala Val Gly
            420                 425                 430

Asn Asp Thr Ser Asn His Gly Val Thr Ala Thr Ile Thr Pro Arg Ser
        435                 440                 445

Pro Ser Val Glu Val Lys Leu Pro Asp Tyr Gly Glu Leu Thr Leu Asp
    450                 455                 460

Cys Glu Pro Arg Ser Gly Ile Asp Phe Asn Glu Met Ile Leu Met Lys
465                 470                 475                 480

Met Lys Lys Lys Thr Trp Leu Val His Lys Gln Trp Phe Leu Asp Leu
                485                 490                 495

Pro Leu Pro Trp Thr Ala Gly Ala Asp Thr Ser Glu Val His Trp Asn
            500                 505                 510

Tyr Lys Glu Arg Met Val Thr Phe Lys Val Pro His Ala Lys Arg Gln
        515                 520                 525

Asp Val Thr Val Leu Gly Ser Gln Glu Gly Ala Met His Ser Ala Leu
    530                 535                 540

Ala Gly Ala Thr Glu Val Asp Ser Gly Asp Gly Asn His Met Phe Ala
545                 550                 555                 560

Gly His Leu Lys Cys Lys Val Arg Met Glu Lys Leu Arg Ile Lys Gly
                565                 570                 575

Met Ser Tyr Thr Met Cys Ser Gly Lys Phe Ser Ile Asp Lys Glu Met
            580                 585                 590

Ala Glu Thr Gln His Gly Thr Thr Val Val Lys Val Lys Tyr Glu Gly
        595                 600                 605

Ala Gly Ala Pro Cys Lys Val Pro Ile Glu Ile Arg Asp Val Asn Lys
    610                 615                 620

Glu Lys Val Val Gly Arg Ile Ile Ser Ser Thr Pro Leu Ala Glu Asn
625                 630                 635                 640

Thr Asn Ser Val Thr Asn Ile Glu Leu Glu Pro Pro Phe Gly Asp Ser
                645                 650                 655

Tyr Ile Val Ile Gly Val Gly Asn Ser Ala Leu Thr Leu His Trp Phe
            660                 665                 670

Arg Lys Gly Ser Ser Ile Gly Lys Met Phe Glu Ser Thr Tyr Arg Gly
        675                 680                 685

Ala Lys Arg Met Ala Ile Leu Gly Glu Thr Ala Trp Asp Phe Gly Ser
    690                 695                 700

Val Gly Gly Leu Phe Thr Ser Leu Gly Lys Ala Val His Gln Val Phe
705                 710                 715                 720

Gly Ser Val Tyr Thr Thr Leu Phe Gly Gly Val Ser Trp Met Ile Arg
                725                 730                 735

Ile Leu Ile Gly Phe Leu Val Leu Trp Ile Gly Thr Asn Ser Arg Asn
            740                 745                 750

Thr Ser Met Ala Met Thr Cys Ile Ala Ala Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
```

```
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
        995                 1000                1005

Asn Gly  Val Leu Glu Ser Glu  Met Ile Ile Pro Lys  Asn Leu Ala
    1010                1015                1020

Gly Pro  Val Ser Gln His Asn  Tyr Arg Pro Gly Tyr  His Thr Gln
    1025                1030                1035

Ile Thr  Gly Pro Trp His Leu  Gly Lys Leu Glu Met  Asp Phe Asp
    1040                1045                1050

Phe Cys  Asp Gly Thr Thr Val  Val Val Thr Glu Asp  Cys Gly Asn
    1055                1060                1065

Arg Gly  Pro Ser Leu Arg Thr  Thr Thr Ala Ser Gly  Lys Leu Ile
    1070                1075                1080

Thr Glu  Trp Cys Cys Arg Ser  Cys Thr Leu Pro Pro  Leu Arg Tyr
    1085                1090                1095

Arg Gly  Glu Asp Gly Cys Trp  Tyr Gly Met Glu Ile  Arg Pro Leu
    1100                1105                1110

Lys Glu  Lys Glu Glu Asn Leu  Val Asn Ser Leu Val  Thr Ala Gly
    1115                1120                1125

His Gly  Gln Val Asp Asn Phe  Ser Leu Gly Val Leu  Gly Met Ala
    1130                1135                1140

Leu Phe  Leu Glu Glu Met Leu  Arg Thr Arg Val Gly  Thr Lys His
    1145                1150                1155

Ala Ile  Leu Leu Val Ala Val  Ser Phe Val Thr Leu  Ile Thr Gly
    1160                1165                1170

Asn Met  Ser Phe Arg Asp Leu  Gly Arg Val Met Val  Met Val Gly
    1175                1180                1185

Ala Thr  Met Thr Asp Asp Ile  Gly Met Gly Val Thr  Tyr Leu Ala
    1190                1195                1200

Leu Leu  Ala Ala Phe Lys Val  Arg Pro Thr Phe Ala  Ala Gly Leu
    1205                1210                1215

Leu Leu  Arg Lys Leu Thr Ser  Lys Glu Leu Met Met  Thr Thr Ile
    1220                1225                1230
```

-continued

Gly Ile Val Leu Leu Ser Gln Ser Thr Ile Pro Glu Thr Ile Leu
1235 1240 1245

Glu Leu Thr Asp Ala Leu Ala Leu Gly Met Met Val Leu Lys Met
1250 1255 1260

Val Arg Asn Met Glu Lys Tyr Gln Leu Ala Val Thr Ile Met Ala
1265 1270 1275

Ile Leu Cys Val Pro Asn Ala Val Ile Leu Gln Asn Ala Trp Lys
1280 1285 1290

Val Ser Cys Thr Ile Leu Ala Val Val Ser Val Ser Pro Leu Phe
1295 1300 1305

Leu Thr Ser Ser Gln Gln Lys Thr Asp Trp Ile Pro Leu Ala Leu
1310 1315 1320

Thr Ile Lys Gly Leu Asn Pro Thr Ala Ile Phe Leu Thr Thr Leu
1325 1330 1335

Ser Arg Thr Ser Lys Lys Arg Ser Trp Pro Leu Asn Glu Ala Ile
1340 1345 1350

Met Ala Val Gly Met Val Ser Ile Leu Ala Ser Ser Leu Leu Lys
1355 1360 1365

Asn Asp Ile Pro Met Thr Gly Pro Leu Val Ala Gly Gly Leu Leu
1370 1375 1380

Thr Val Cys Tyr Val Leu Thr Gly Arg Ser Ala Asp Leu Glu Leu
1385 1390 1395

Glu Arg Ala Ala Asp Val Lys Trp Glu Asp Gln Ala Glu Ile Ser
1400 1405 1410

Gly Ser Ser Pro Ile Leu Ser Ile Thr Ile Ser Glu Asp Gly Ser
1415 1420 1425

Met Ser Ile Lys Asn Glu Glu Glu Glu Gln Thr Leu Thr Ile Leu
1430 1435 1440

Ile Arg Thr Gly Leu Leu Val Ile Ser Gly Leu Phe Pro Val Ser
1445 1450 1455

Ile Pro Ile Thr Ala Ala Ala Trp Tyr Leu Trp Glu Val Lys Lys
1460 1465 1470

Gln Arg Ala Gly Val Leu Trp Asp Val Pro Ser Pro Pro Pro Met
1475 1480 1485

Gly Lys Ala Glu Leu Glu Asp Gly Ala Tyr Arg Ile Lys Gln Lys
1490 1495 1500

Gly Ile Leu Gly Tyr Ser Gln Ile Gly Ala Gly Val Tyr Lys Glu
1505 1510 1515

Gly Thr Phe His Thr Met Trp His Val Thr Arg Gly Ala Val Leu
1520 1525 1530

Met His Lys Gly Lys Arg Ile Glu Pro Ser Trp Ala Asp Val Lys
1535 1540 1545

Lys Asp Leu Ile Ser Tyr Gly Gly Gly Trp Lys Leu Glu Gly Glu
1550 1555 1560

Trp Lys Glu Gly Glu Glu Val Gln Val Leu Ala Leu Glu Pro Gly
1565 1570 1575

Lys Asn Pro Arg Ala Val Gln Thr Lys Pro Gly Leu Phe Lys Thr
1580 1585 1590

Asn Ala Gly Thr Ile Gly Ala Val Ser Leu Asp Phe Ser Pro Gly
1595 1600 1605

Thr Ser Gly Ser Pro Ile Ile Asp Lys Lys Gly Lys Val Val Gly
1610 1615 1620

-continued

```
Leu Tyr  Gly Asn Gly Val Val  Thr Arg Ser Gly Ala  Tyr Val Ser
    1625                 1630                 1635

Ala Ile  Ala Gln Thr Glu Lys  Ser Ile Glu Asp Asn  Pro Glu Ile
    1640                 1645                 1650

Glu Asp  Asp Ile Phe Arg Lys  Arg Arg Leu Thr Ile  Met Asp Leu
    1655                 1660                 1665

His Pro  Gly Ala Gly Lys Thr  Lys Arg Tyr Leu Pro  Ala Ile Val
    1670                 1675                 1680

Arg Glu  Ala Ile Lys Arg Gly  Leu Arg Thr Leu Ile  Leu Ala Pro
    1685                 1690                 1695

Thr Arg  Val Val Ala Ala Glu  Met Glu Glu Ala Leu  Arg Gly Leu
    1700                 1705                 1710

Pro Ile  Arg Tyr Gln Thr Pro  Ala Ile Arg Ala Val  His Thr Gly
    1715                 1720                 1725

Arg Glu  Ile Val Asp Leu Met  Cys His Ala Thr Phe  Thr Met Arg
    1730                 1735                 1740

Leu Leu  Ser Pro Val Arg Val  Pro Asn Tyr Asn Leu  Ile Ile Met
    1745                 1750                 1755

Asp Glu  Ala His Phe Thr Asp  Pro Ala Ser Ile Ala  Ala Arg Gly
    1760                 1765                 1770

Tyr Ile  Ser Thr Arg Val Glu  Met Gly Glu Ala Ala  Gly Ile Phe
    1775                 1780                 1785

Met Thr  Ala Thr Pro Pro Gly  Ser Arg Asp Pro Phe  Pro Gln Ser
    1790                 1795                 1800

Asn Ala  Pro Ile Ile Asp Glu  Glu Arg Glu Ile Pro  Glu Arg Ser
    1805                 1810                 1815

Trp Asn  Ser Gly His Glu Trp  Val Thr Asp Phe Lys  Gly Lys Thr
    1820                 1825                 1830

Val Trp  Phe Val Pro Ser Ile  Lys Ala Gly Asn Asp  Ile Ala Ala
    1835                 1840                 1845

Cys Leu  Arg Lys Asn Gly Lys  Lys Val Ile Gln Leu  Ser Arg Lys
    1850                 1855                 1860

Thr Phe  Asp Ser Glu Tyr Val  Lys Thr Arg Thr Asn  Asp Trp Asp
    1865                 1870                 1875

Phe Val  Val Thr Thr Asp Ile  Ser Glu Met Gly Ala  Asn Phe Lys
    1880                 1885                 1890

Ala Glu  Arg Val Ile Asp Pro  Arg Arg Cys Met Lys  Pro Val Ile
    1895                 1900                 1905

Leu Thr  Asp Gly Glu Glu Arg  Val Ile Leu Ala Gly  Pro Met Pro
    1910                 1915                 1920

Val Thr  His Ser Ser Ala Ala  Gln Arg Arg Gly Arg  Ile Gly Arg
    1925                 1930                 1935

Asn Pro  Lys Asn Glu Asn Asp  Gln Tyr Ile Tyr Met  Gly Glu Pro
    1940                 1945                 1950

Leu Glu  Asn Asp Glu Asp Cys  Ala His Trp Lys Glu  Ala Lys Met
    1955                 1960                 1965

Leu Leu  Asp Asn Ile Asn Thr  Pro Glu Gly Ile Ile  Pro Ser Met
    1970                 1975                 1980

Phe Glu  Pro Glu Arg Glu Lys  Val Asp Ala Ile Asp  Gly Glu Tyr
    1985                 1990                 1995

Arg Leu  Arg Gly Glu Ala Arg  Lys Thr Phe Val Asp  Leu Met Arg
    2000                 2005                 2010

Arg Gly  Asp Leu Pro Val Trp  Leu Ala Tyr Arg Val  Ala Ala Glu
```

-continued

```
    2015                2020                2025

Gly Ile  Asn Tyr Ala Asp Arg  Arg Trp Cys Phe Asp  Gly Val Lys
    2030                2035                2040

Asn Asn  Gln Ile Leu Glu Glu  Asn Val Glu Val Glu  Ile Trp Thr
    2045                2050                2055

Lys Glu  Gly Glu Arg Lys Lys  Leu Lys Pro Arg Trp  Leu Asp Ala
    2060                2065                2070

Arg Ile  Tyr Ser Asp Pro Leu  Ala Leu Lys Glu Phe  Lys Glu Phe
    2075                2080                2085

Ala Ala  Gly Arg Lys Ser Leu  Thr Leu Asn Leu Ile  Thr Glu Met
    2090                2095                2100

Gly Arg  Leu Pro Thr Phe Leu  Thr Gln Lys Ala Arg  Asp Ala Leu
    2105                2110                2115

Asp Asn  Leu Ala Val Leu His  Thr Ala Glu Ala Gly  Gly Arg Ala
    2120                2125                2130

Tyr Asn  His Ala Leu Ser Glu  Leu Pro Glu Thr Leu  Glu Thr Leu
    2135                2140                2145

Leu Leu  Leu Thr Leu Leu Ala  Thr Val Thr Gly Gly  Ile Phe Leu
    2150                2155                2160

Phe Leu  Met Ser Ala Arg Gly  Ile Gly Lys Met Thr  Leu Gly Met
    2165                2170                2175

Cys Cys  Ile Ile Thr Ala Ser  Ile Leu Leu Trp Tyr  Ala Gln Ile
    2180                2185                2190

Gln Pro  His Trp Ile Ala Ala  Ser Ile Ile Leu Glu  Phe Phe Leu
    2195                2200                2205

Ile Val  Leu Leu Ile Pro Glu  Pro Glu Lys Gln Arg  Thr Pro Gln
    2210                2215                2220

Asp Asn  Gln Leu Thr Tyr Val  Val Ile Ala Ile Leu  Thr Val Val
    2225                2230                2235

Ala Ala  Thr Met Ala Asn Glu  Met Gly Phe Leu Glu  Lys Thr Lys
    2240                2245                2250

Lys Asp  Leu Gly Leu Gly Ser  Ile Ala Thr Gln Gln  Pro Glu Ser
    2255                2260                2265

Asn Ile  Leu Asp Ile Asp Leu  Arg Pro Ala Ser Ala  Trp Thr Leu
    2270                2275                2280

Tyr Ala  Val Ala Thr Thr Phe  Val Thr Pro Met Leu  Arg His Ser
    2285                2290                2295

Ile Glu  Asn Ser Ser Val Asn  Val Ser Leu Thr Ala  Ile Ala Asn
    2300                2305                2310

Gln Ala  Thr Val Leu Met Gly  Leu Gly Lys Gly Trp  Pro Leu Ser
    2315                2320                2325

Lys Met  Asp Ile Gly Val Pro  Leu Leu Ala Ile Gly  Cys Tyr Ser
    2330                2335                2340

Gln Val  Asn Pro Ile Thr Leu  Thr Ala Ala Leu Phe  Leu Leu Val
    2345                2350                2355

Ala His  Tyr Ala Ile Ile Gly  Pro Gly Leu Gln Ala  Lys Ala Thr
    2360                2365                2370

Arg Glu  Ala Gln Lys Arg Ala  Ala Ala Gly Ile Met  Lys Asn Pro
    2375                2380                2385

Thr Val  Asp Gly Ile Thr Val  Ile Asp Leu Asp Pro  Ile Pro Tyr
    2390                2395                2400

Asp Pro  Lys Phe Glu Lys Gln  Leu Gly Gln Val Met  Leu Leu Val
    2405                2410                2415
```

-continued

```
Leu Cys Val Thr Gln Val Leu Met Met Arg Thr Thr Trp Ala Leu
    2420                2425                2430

Cys Glu Ala Leu Thr Leu Ala Thr Gly Pro Ile Ser Thr Leu Trp
    2435                2440                2445

Glu Gly Asn Pro Gly Arg Phe Trp Asn Thr Thr Ile Ala Val Ser
    2450                2455                2460

Met Ala Asn Ile Phe Arg Gly Ser Tyr Leu Ala Gly Ala Gly Leu
    2465                2470                2475

Leu Phe Ser Ile Met Lys Asn Thr Thr Asn Thr Arg Arg Gly Thr
    2480                2485                2490

Gly Asn Ile Gly Glu Thr Leu Gly Glu Lys Trp Lys Ser Arg Leu
    2495                2500                2505

Asn Ala Leu Gly Lys Ser Glu Phe Gln Ile Tyr Lys Lys Ser Gly
    2510                2515                2520

Ile Gln Glu Val Asp Arg Thr Leu Ala Lys Glu Gly Ile Lys Arg
    2525                2530                2535

Gly Glu Thr Asp His His Ala Val Ser Arg Gly Ser Ala Lys Leu
    2540                2545                2550

Arg Trp Phe Val Glu Arg Asn Met Val Thr Pro Glu Gly Lys Val
    2555                2560                2565

Val Asp Leu Gly Cys Gly Arg Gly Gly Trp Ser Tyr Tyr Cys Gly
    2570                2575                2580

Gly Leu Lys Asn Val Arg Glu Val Lys Gly Leu Thr Lys Gly Gly
    2585                2590                2595

Pro Gly His Glu Glu Pro Ile Pro Met Ser Thr Tyr Gly Trp Asn
    2600                2605                2610

Leu Val Arg Leu Gln Ser Gly Val Asp Val Phe Phe Ile Pro Pro
    2615                2620                2625

Glu Lys Cys Asp Thr Leu Leu Cys Asp Ile Gly Glu Ser Ser Pro
    2630                2635                2640

Asn Pro Thr Val Glu Ala Gly Arg Thr Leu Arg Val Leu Asn Leu
    2645                2650                2655

Val Glu Asn Trp Leu Asn Asn Asn Thr Gln Phe Cys Ile Lys Val
    2660                2665                2670

Leu Asn Pro Tyr Met Pro Ser Val Ile Glu Lys Met Glu Ala Leu
    2675                2680                2685

Gln Arg Lys Tyr Gly Gly Ala Leu Val Arg Asn Pro Leu Ser Arg
    2690                2695                2700

Asn Ser Thr His Glu Met Tyr Trp Val Ser Asn Ala Ser Gly Asn
    2705                2710                2715

Ile Val Ser Ser Val Asn Met Ile Ser Arg Met Leu Ile Asn Arg
    2720                2725                2730

Phe Thr Met Arg Tyr Lys Lys Ala Thr Tyr Glu Pro Asp Val Asp
    2735                2740                2745

Leu Gly Ser Gly Thr Arg Asn Ile Gly Ile Glu Ser Glu Ile Pro
    2750                2755                2760

Asn Leu Asp Ile Ile Gly Lys Arg Ile Glu Lys Ile Lys Gln Glu
    2765                2770                2775

His Glu Thr Ser Trp His Tyr Asp Gln Asp His Pro Tyr Lys Thr
    2780                2785                2790

Trp Ala Tyr His Gly Ser Tyr Glu Thr Lys Gln Thr Gly Ser Ala
    2795                2800                2805
```

```
Ser Ser Met Val Asn Gly Val Val Arg Leu Leu Thr Lys Pro Trp
    2810                2815                2820

Asp Val Val Pro Met Val Thr Gln Met Ala Met Thr Asp Thr Thr
    2825                2830                2835

Pro Phe Gly Gln Gln Arg Val Phe Lys Glu Lys Val Asp Thr Arg
    2840                2845                2850

Thr Gln Glu Pro Lys Glu Gly Thr Lys Lys Leu Met Lys Ile Thr
    2855                2860                2865

Ala Glu Trp Leu Trp Lys Glu Leu Gly Lys Lys Lys Thr Pro Arg
    2870                2875                2880

Met Cys Thr Arg Glu Glu Phe Thr Arg Lys Val Arg Ser Asn Ala
    2885                2890                2895

Ala Leu Gly Ala Ile Phe Thr Asp Glu Asn Lys Trp Lys Ser Ala
    2900                2905                2910

Arg Glu Ala Val Glu Asp Ser Arg Phe Trp Glu Leu Val Asp Lys
    2915                2920                2925

Glu Arg Asn Leu His Leu Glu Gly Lys Cys Glu Thr Cys Val Tyr
    2930                2935                2940

Asn Met Met Gly Lys Arg Glu Lys Lys Leu Gly Glu Phe Gly Lys
    2945                2950                2955

Ala Lys Gly Ser Arg Ala Ile Trp Tyr Met Trp Leu Gly Ala Arg
    2960                2965                2970

Phe Leu Glu Phe Glu Ala Leu Gly Phe Leu Asn Glu Asp His Trp
    2975                2980                2985

Phe Ser Arg Glu Asn Ser Leu Ser Gly Val Glu Gly Glu Gly Leu
    2990                2995                3000

His Lys Leu Gly Tyr Ile Leu Arg Asp Val Ser Lys Lys Glu Gly
    3005                3010                3015

Gly Ala Met Tyr Ala Asp Asp Thr Ala Gly Trp Asp Thr Arg Ile
    3020                3025                3030

Thr Leu Glu Asp Leu Lys Asn Glu Glu Met Val Thr Asn His Met
    3035                3040                3045

Glu Gly Glu His Lys Lys Leu Ala Glu Ala Ile Phe Lys Leu Thr
    3050                3055                3060

Tyr Gln Asn Lys Val Val Arg Val Gln Arg Pro Thr Pro Arg Gly
    3065                3070                3075

Thr Val Met Asp Ile Ile Ser Arg Arg Asp Gln Arg Gly Ser Gly
    3080                3085                3090

Gln Val Gly Thr Tyr Gly Leu Asn Thr Phe Thr Asn Met Glu Ala
    3095                3100                3105

Gln Leu Ile Arg Gln Met Glu Gly Glu Gly Val Phe Lys Ser Ile
    3110                3115                3120

Gln His Leu Thr Ile Thr Glu Glu Ile Ala Val Gln Asn Trp Leu
    3125                3130                3135

Ala Arg Val Gly Arg Glu Arg Leu Ser Arg Met Ala Ile Ser Gly
    3140                3145                3150

Asp Asp Cys Val Val Lys Pro Leu Asp Asp Arg Phe Ala Ser Ala
    3155                3160                3165

Leu Thr Ala Leu Asn Asp Met Gly Lys Ile Arg Lys Asp Ile Gln
    3170                3175                3180

Gln Trp Glu Pro Ser Arg Gly Trp Asn Asp Trp Thr Gln Val Pro
    3185                3190                3195

Phe Cys Ser His His Phe His Glu Leu Ile Met Lys Asp Gly Arg
```

```
    3200                3205                3210

Val Leu  Val Val Pro Cys Arg  Asn Gln Asp Glu Leu  Ile Gly Arg
    3215                3220                3225

Ala Arg  Ile Ser Gln Gly Ala  Gly Trp Ser Leu Arg  Glu Thr Ala
    3230                3235                3240

Cys Leu  Gly Lys Ser Tyr Ala  Gln Met Trp Ser Leu  Met Tyr Phe
    3245                3250                3255

His Arg  Arg Asp Leu Arg Leu  Ala Ala Asn Ala Ile  Cys Ser Ala
    3260                3265                3270

Val Pro  Ser His Trp Val Pro  Thr Ser Arg Thr Thr  Trp Ser Ile
    3275                3280                3285

His Ala  Lys His Glu Trp Met  Thr Thr Glu Asp Met  Leu Thr Val
    3290                3295                3300

Trp Asn  Arg Val Trp Ile Gln  Glu Asn Pro Trp Met  Glu Asp Lys
    3305                3310                3315

Thr Pro  Val Glu Ser Trp Glu  Glu Ile Pro Tyr Leu  Gly Lys Arg
    3320                3325                3330

Glu Asp  Gln Trp Cys Gly Ser  Leu Ile Gly Leu Thr  Ser Arg Ala
    3335                3340                3345

Thr Trp  Ala Lys Asn Ile Gln  Ala Ala Ile Asn Gln  Val Arg Ser
    3350                3355                3360

Leu Ile  Gly Asn Glu Glu Tyr  Thr Asp Tyr Met Pro  Ser Met Lys
    3365                3370                3375

Arg Phe  Arg Arg Glu Glu Glu  Glu Ala Gly Val Leu  Trp
    3380                3385                3390
```

<210> SEQ ID NO 35
<211> LENGTH: 56
<212> TYPE: PRT
<213> ORGANISM: Artificial Sequence
<220> FEATURE:
<223> OTHER INFORMATION: Dengue serotype 1 virus-derived peptide

<400> SEQUENCE: 35

```
Lys Gly Ser Ser Ile Gly Lys Met Phe Glu Ala Thr Ala Arg Gly Ala
1               5                   10                  15

Arg Arg Met Ala Ile Leu Gly Asp Thr Ala Trp Asp Phe Gly Ser Ile
            20                  25                  30

Gly Gly Val Phe Thr Ser Val Gly Lys Leu Ile His Gln Ile Phe Gly
        35                  40                  45

Thr Ala Tyr Gly Val Leu Phe Ser
    50                  55
```

<210> SEQ ID NO 36
<211> LENGTH: 56
<212> TYPE: PRT
<213> ORGANISM: Artificial Sequence
<220> FEATURE:
<223> OTHER INFORMATION: Dengue serotype 2 virus-derived peptide

<400> SEQUENCE: 36

```
Lys Gly Ser Ser Ile Gly Gln Met Phe Glu Thr Thr Met Arg Gly Ala
1               5                   10                  15

Lys Arg Met Ala Ile Leu Gly Asp Thr Ala Trp Asp Phe Gly Ser Leu
            20                  25                  30

Gly Gly Val Phe Thr Ser Ile Gly Lys Ala Leu His Gln Val Phe Gly
        35                  40                  45
```

```
Ala Ile Tyr Gly Ala Ala Phe Ser
    50                  55


<210> SEQ ID NO 37
<211> LENGTH: 56
<212> TYPE: PRT
<213> ORGANISM: Artificial Sequence
<220> FEATURE:
<223> OTHER INFORMATION: Dengue serotype 3 virus-derived peptide

<400> SEQUENCE: 37

Lys Gly Ser Ser Ile Gly Lys Met Phe Glu Ala Thr Ala Arg Gly Ala
1               5                   10                  15

Arg Arg Met Ala Ile Leu Gly Asp Thr Ala Trp Asp Phe Gly Ser Val
            20                  25                  30

Gly Gly Val Leu Asn Ser Leu Gly Lys Met Val His Gln Ile Phe Gly
        35                  40                  45

Ser Ala Tyr Thr Ala Leu Phe Ser
    50                  55


<210> SEQ ID NO 38
<211> LENGTH: 56
<212> TYPE: PRT
<213> ORGANISM: Artificial Sequence
<220> FEATURE:
<223> OTHER INFORMATION: Dengue serotype 4 virus-derived peptide

<400> SEQUENCE: 38

Lys Gly Ser Ser Ile Gly Lys Met Phe Glu Ser Thr Tyr Arg Gly Ala
1               5                   10                  15

Lys Arg Met Ala Ile Leu Gly Glu Thr Ala Trp Asp Phe Gly Ser Val
            20                  25                  30

Gly Gly Leu Phe Thr Ser Leu Gly Lys Ala Val His Gln Val Phe Gly
        35                  40                  45

Ser Val Tyr Thr Thr Met Phe Gly
    50                  55


<210> SEQ ID NO 39
<211> LENGTH: 56
<212> TYPE: PRT
<213> ORGANISM: Artificial Sequence
<220> FEATURE:
<223> OTHER INFORMATION: West Nile virus-derived peptide

<400> SEQUENCE: 39

Ser Gly Ser Ser Ile Gly Lys Ala Phe Thr Thr Thr Leu Lys Gly Ala
1               5                   10                  15

Gln Arg Leu Ala Ala Leu Gly Asp Thr Ala Trp Asp Phe Gly Ser Val
            20                  25                  30

Gly Gly Val Phe Thr Ser Val Gly Lys Ala Val His Gln Val Phe Gly
        35                  40                  45

Gly Ala Phe Arg Ser Leu Phe Gly
    50                  55
```